(12) United States Patent
Tresch et al.

(10) Patent No.: US 12,203,089 B2
(45) Date of Patent: Jan. 21, 2025

(54) PLANTS HAVING INCREASED TOLERANCE TO HERBICIDES

(71) Applicant: BASF SE, Ludwigshafen am Rhein (DE)

(72) Inventors: Stefan Tresch, Ludwigshafen (DE); Mihiret Tekeste Sisay, Ludwigshafen (DE); Doreen Schachtschabel, Limburgerhof (DE); Kristin Hanzlik, Limburgerhof (DE); Brigitte Weston, Limburgerhof (DE); Florian Vogt, Ludwigshafen (DE); Danny Geerdink, Ludwigshafen (DE); Jens Lerchl, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 1273 days.

(21) Appl. No.: 15/769,969

(22) PCT Filed: Oct. 21, 2016

(86) PCT No.: PCT/IB2016/056348
§ 371 (c)(1),
(2) Date: Apr. 20, 2018

(87) PCT Pub. No.: WO2017/068543
PCT Pub. Date: Apr. 27, 2017

(65) Prior Publication Data
US 2019/0078114 A1    Mar. 14, 2019

(30) Foreign Application Priority Data

Oct. 22, 2015   (EP) ..................................... 15190979

(51) Int. Cl.
*C12N 15/82*    (2006.01)
*C12N 9/10*     (2006.01)

(52) U.S. Cl.
CPC ....... *C12N 15/8274* (2013.01); *C12N 9/1059* (2013.01); *C12Y 204/01012* (2013.01)

(58) Field of Classification Search
None
See application file for complete search history.

(56) References Cited

U.S. PATENT DOCUMENTS

| | | |
|---|---|---|
| 4,873,192 A | 10/1989 | Kunkel |
| 4,945,050 A | 7/1990 | Sanford et al. |
| 5,169,770 A | 12/1992 | Chee et al. |
| 5,240,855 A | 8/1993 | Tomes |
| 5,268,463 A | 12/1993 | Jefferson et al. |
| 5,316,931 A | 5/1994 | Donson et al. |
| 5,322,783 A | 6/1994 | Tomes et al. |
| 5,324,646 A | 6/1994 | Buising et al. |
| 5,366,892 A | 11/1994 | Foncerrada et al. |
| 5,376,543 A | 12/1994 | Chee et al. |
| 5,380,831 A | 1/1995 | Adang et al. |
| 5,399,680 A | 3/1995 | Zhu et al. |
| 5,405,765 A | 4/1995 | Vasil et al. |
| 5,424,412 A | 6/1995 | Brown et al. |
| 5,436,391 A | 7/1995 | Fujimoto et al. |
| 5,563,055 A | 10/1996 | Townsend et al. |
| 5,565,350 A | 10/1996 | Kmiec |
| 5,569,597 A | 10/1996 | Grimsley et al. |
| 5,589,367 A | 12/1996 | Donson et al. |
| 5,593,874 A | 1/1997 | Brown et al. |
| 5,593,881 A | 1/1997 | Thompson et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,659,026 A | 8/1997 | Baszczynski et al. |
| 5,723,756 A | 3/1998 | Peferoen et al. |
| 5,736,369 A | 4/1998 | Bowen et al. |
| 5,737,514 A | 4/1998 | Stiffler |
| 5,747,450 A | 5/1998 | Ohba et al. |
| 5,773,702 A | 6/1998 | Penner et al. |
| 5,859,348 A | 1/1999 | Penner et al. |
| 5,866,785 A | 2/1999 | Donson et al. |
| 5,879,918 A | 3/1999 | Tomes et al. |
| 5,886,244 A | 3/1999 | Tomes et al. |
| 5,889,190 A | 3/1999 | Donson et al. |
| 5,889,191 A | 3/1999 | Turpen |
| 5,932,782 A | 8/1999 | Bidney |
| 5,981,840 A | 11/1999 | Zhao et al. |
| 5,990,387 A | 11/1999 | Tomes et al. |
| 6,027,945 A | 2/2000 | Smith et al. |
| 6,072,050 A | 6/2000 | Bowen et al. |

(Continued)

FOREIGN PATENT DOCUMENTS

| | | |
|---|---|---|
| EP | 0242236 A1 | 10/1987 |
| EP | 0293356 A1 | 11/1988 |

(Continued)

OTHER PUBLICATIONS

Chalhoub et al. (2014) 345(6199):950-53.*
Whisstock & Lesk (2003) Q Rev Biophys. 36(3):307-40.*
Lehner & O'Farrell (1990) EMBO J 9(11)3573-81.*
Morelle (2016) BBC New Science Environment.*
Richmond (2001) Genome Biol 1(4):reviews3001.1-.6.*
Guo et al. (2004) Proc Natl Acad Sci USA 101:9205-10.*
"Method of the Year 2011", Nat. Methods, 9(1):1 (Jan. 2012).
Aldemita et al., "Agrobacterium tumefaciens-mediated transformation of japonica and indica rice varieties", Planta, vol. 199, Issue 4, Aug. 1996, pp. 612-617.

(Continued)

*Primary Examiner* — Russell T Boggs
(74) *Attorney, Agent, or Firm* — MARSHALL, GERSTEIN & BORUN LLP

(57) ABSTRACT

Provided is a plant or plant part comprising a polynucleotide encoding a mutated cellulose synthase (CESA) polypeptide, wherein the expression of said polynucleotide confers to the plant or plant part tolerance to CESA-inhibiting herbicides, such as azines.

5 Claims, 28 Drawing Sheets
Specification includes a Sequence Listing.

(56) References Cited

U.S. PATENT DOCUMENTS

| | | | |
|---|---|---|---|
| 6,177,611 | B1 | 1/2001 | Rice |
| 6,368,800 | B1 | 4/2002 | Smith et al. |
| 7,241,878 | B1 * | 7/2007 | Somervillle .......... C12N 9/2434 435/209 |
| 8,383,888 | B1 | 2/2013 | DeBolt et al. |

FOREIGN PATENT DOCUMENTS

| | | |
|---|---|---|
| EP | 0337899 A1 | 10/1989 |
| EP | 0374753 A2 | 6/1990 |
| EP | 0427529 A1 | 5/1991 |
| EP | 0451878 A1 | 10/1991 |
| EP | 0397687 B1 | 5/1994 |
| EP | 0424047 B1 | 7/1995 |
| EP | 1198985 A1 | 4/2002 |
| EP | 2930174 A1 | 10/2015 |
| WO | WO-93/07256 A1 | 4/1993 |
| WO | WO-93/07278 A1 | 4/1993 |
| WO | WO-93/22443 A1 | 11/1993 |
| WO | WO-95/34656 A1 | 12/1995 |
| WO | WO-99/43838 A1 | 9/1999 |
| WO | WO-00/15815 A1 | 3/2000 |
| WO | WO-00/28058 A2 | 5/2000 |
| WO | WO-02/15701 A2 | 2/2002 |
| WO | WO-02/068607 A2 | 9/2002 |
| WO | WO-03/018810 A2 | 3/2003 |
| WO | WO-03/052073 A2 | 6/2003 |
| WO | WO-2005/107437 A2 | 11/2005 |
| WO | WO-2006/024820 A1 | 3/2006 |
| WO | WO-2006/037945 A1 | 4/2006 |
| WO | WO-2007/071900 A1 | 6/2007 |
| WO | WO-2007/096576 A1 | 8/2007 |
| WO | WO-2008/124495 A2 | 10/2008 |
| WO | WO-2008/141154 A2 | 11/2008 |
| WO | WO-2010/049269 A1 | 5/2010 |
| WO | WO-2010/049270 A1 | 5/2010 |
| WO | WO 2013/142968 A1 * | 10/2013 |
| WO | WO-2014/064094 A1 | 5/2014 |
| WO | WO-2015/007711 A1 | 1/2015 |
| WO | WO-2015/059661 A1 | 4/2015 |
| WO | WO-2015/144881 A1 | 10/2015 |
| WO | WO-2015/150541 A1 | 10/2015 |
| WO | WO-2015/155119 A1 | 10/2015 |
| WO | WO-2015/155271 A1 | 10/2015 |
| WO | WO-2015/155272 A1 | 10/2015 |
| WO | WO-2015/155273 A1 | 10/2015 |
| WO | WO-2015/162143 A1 | 10/2015 |
| WO | WO-2015/162166 A1 | 10/2015 |
| WO | WO-2015/162169 A1 | 10/2015 |
| WO | WO-2017/068543 A1 | 4/2017 |
| WO | WO-2017/068544 A1 | 4/2017 |

OTHER PUBLICATIONS

Allison et al., "The nucleotide sequence of the coding region of tobacco etch virus genomic RNA: Evidence for the synthesis of a single polyprotein", Virology, vol. 154, Issue 1, Oct. 15, 1986, pp. 9-20.
Altschul et al., "Basic local alignment search tool", Journal of Molecular Biology, vol. 215, Issue 3, Oct. 1990, pp. 403-410.
An et al., "Transformation of Tobacco, Tomato, Potato, and *Arabidopsis thaliana* Using a Binary Ti Vector System", Plant Physiology, vol. 81, 1986, pp. 301-305.
Archer et al., "Current views on chloroplast protein import and hypotheses on the origin of the transport mechanism", Journal of Bioenergetics and Biomembranes, vol. 22, Issue 6, Dec. 1990, pp. 789-810.
Arias et al., "Molecular evolution of herbicide resistance to phytoene desaturase inhibitors in Hydrilla verticillata and its potential use to generate herbicide-resistant crops", Pest Management Science, vol. 61, Issue 3, Mar. 2005, pp. 258-268.

Asano, et al., "Transgenic plants of Agrostis alba obtained by electroporation-mediated direct gene transfer into protoplasts", Plant Cell Reports, Feb. 1994, vol. 13, Issue 5, pp. 243-246.
Ayres et al., "Genetic Transformation of Rice", Critical Reviews in Plant Sciences, vol. 13, Issue 3, 1994, pp. 219-239.
Baim et al., "A chimeric mammalian transactivator based on the lac repressor that is regulated by temperature and isopropyl beta-D-thiogalactopyranoside", Proceedings of the National Academy of Sciences, vol. 88, Issue 12, pp. 5072-5076.
Barcelo, et al., "Transgenic cereal (tritordeum) plants obtained at high efficiency by microprojectile bombardment of inflorescence tissue", The Plant Journal, vol. 5, Issue 4, Apr. 1994, pp. 583-592.
Barkley, "Repressor Recognition of Operator and Effectors", The Operon, 1980, pp. 177-220.
Bateman et al., "The Pfam Protein Families Database", Nucleic Acids Research, vol. 30, Issue 1, 2002, pp. 276-280.
Becker et al., "Fertile transgenic wheat from microprojectile bombardment of scutellar tissue", The Plant Journal, vol. 5, Issue 2, Feb. 1994, pp. 299-307.
Behrens et al., "Dicamba Resistance: Enlarging and Preserving Biotechnology-Based Weed Management Strategies", Science, May 2007, vol. 316, Issue 5828, pp. 1185-1188.
Bevan, "Binary Agrobacterium vectors for plant transformation", Nucleic Acids Research, vol. 12, Issue 22, Nov. 26, 1984, pp. 8711-8721.
Bilang, et al., "The 3?-terminal region of the hygromycin-B-resistance gene is important for its activity in *Escherichia coli* and Nicotiana tabacum", Gene, vol. 100, Apr. 1991, pp. 247-250.
Bock, "Transgenic Plastids in Basic Research and Plant Biotechnology", Journal of Molecular Biology, vol. 312, Issue 3, Sep. 2001, pp. 425-438.
Boglioli, et al., "Rewriting the book of life: a new era in precision genome editing", The Boston Consulting Group, Sep. 2015, 28 pages.
Brown et al., "Lac repressor can regulate expression from a hybrid SV40 early promoter containing a lac operator in animal cells", Cell, vol. 49, Issue 5, Jun. 5, 1987, pp. 603-612.
Buchman et al., "Comparison of intron-dependent and intron-independent gene expression", *Mol. Cell Biol.* 8(10): 4395-405 (1988).
Bytebier, et al., "T-DNA organization in tumor cultures and transgenic plants of the monocotyledon Asparagus officinalis", Proceedings of the National Academy of Sciences, vol. 84, Issue 15, Aug. 1, 1987, pp. 5345-5349.
Callis et al., "Introns increase gene expression in cultured maize cells", Genes & Development, vol. 1, Issue 10, 1988, pp. 1183-1200.
Campanella et al., "MatGAT: An application that generates similarity/identity matrices using protein or DNA sequences", BMC Tioinformatics, vol. 4, Issue 29, 2003, pp. 1-4.
Campbell, et al., "Codon Usage in Higher Plants, Green Algae, and Cyanobacteria", Plant Physiology, vol. 92, 1990, pp. 1-11.
Canevascini et al., "Tissue-Specific Expression and Promoter Analysis of the Tobacco ltp1 Gene", Plant Physiology, vol. 112, Issue 2, Oct. 1996, pp. 513-524.
Casas, et al., "Transgenic sorghum plants via microprojectile bombardment", Proceedings of the National Academy of Sciences, vol. 90, Issue 23, Dec. 1993. pp. 11212-11216.
Chalhoub et al., Plant genetics. Early allopolyploid evolution in the post-Neolithic *Brassica napus* oilseed genome, Science, 345(6199):950-3 (Aug. 2014).
Chan et al., Agrobacterium-mediated production of transgenic rice plants expressing a chimeric alpha-amylase promoter/beta-glucuronidase gene, Plant Mol. Biol., 22(3):491-506 (Jun. 1993).
Chang et al., "Stable genetic transformation of *Arabidopsis thaliana* by Agrobacterium inoculation in planta", The Plant Journal, vol. 5, Issue 4, Apr. 1994, pp. 551-558.
Chee, et al., "Transformation of cucumber tissues by microprojectile bombardment: identification of plants containing functional and non-functional transferred genes", Gene, vol. 118, Issue 2, Sep. 1992, pp. 255-260.
Christensen et al., "Sequence analysis and transcriptional regulation by heat shock of polyubiquitin transcripts from maize", Plant Molecular Biology, vol. 12, Issue 6, Jun. 1989, pp. 619-632.

(56) References Cited

OTHER PUBLICATIONS

Christopherson et al., "Ecdysteroid-dependent regulation of genes in mammalian cells by a *Drosophila ecdysone* receptor and chimeric transactivators", Proceedings of the National Academy of Sciences, vol. 89, Issue 14, 1992, pp. 6314-6318.

Christou, et al., "Parameters Influencing Stable Transformation of Rice Immature Embryos and Recovery of Transgenic Plants using Electric Discharge Particle Acceleration", Annals of Botany, vol. 75, Issue 4, Apr. 1, 1995, pp. 407-413.

Christou, et al., "Stable Transformation of Soybean Callus by DNA-Coated Gold Particles", Plant Physiology, vol. 87, 1988, pp. 671-674.

Christou, et al., "The development of a variety-independent gene-transfer method for rice", Trends in Biotechnology, vol. 10, 1992, pp. 239-246.

Clark et al., "Mutations at the transit peptide-mature protein junction separate two cleavage events during chloroplast import of the chlorophyll a/b-binding protein", The Journal of Biological Chemistry, vol. 264, 1989, pp. 17544-17550.

Clough et al., "Floral dip: a simplified method forAgrobacterium-mediated transformation of *Arabidopsis thaliana*", The Plant Journal, vol. 16, Issue 6, Dec. 1998, pp. 735-743.

Cousins, et al., "Transformation of an Australian Cotton Cultivar: Prospects for Cotton Improvement Through Genetic Engineering", Australian Journal of Plant Physiology, vol. 18, Issue 5, 1991, pp. 481-494.

D'Halluin, et al., "Transformation of Sugarbeet (*Beta vulgaris* L.) and Evaluation of Herbicide Resistance in Transgenic Plants", Bio/Technology, vol. 10, 1992 pp. 309-314.

Christou, "Philosophy and practice of variety-independent gene transfer into recalcitrant crops", In Vitro Cellular & Developmental Biology—Plant, Jul. 1993, vol. 29, Issue 3, pp. 119-124.

D'Halluin, et al., "Transgenic maize plants by tissue electroporation", The Plant Cell, vol. 4, 1992, pp. 1495-1505.

Datta, et al., "Genetically Engineered Fertile Indica-Rice Recovered from Protoplasts", Bio/Technology, 1990, vol. 8, pp. 736-740.

De Block et al., "Transformation of *Brassica napus* and *Brassica oleracea* Using Agrobacterium tumefaciens and the Expression of the bar and neo Genes in the Transgenic Plants", Plant Physiology, vol. 91, Issue 2, Oct. 1989, pp. 694-701.

De Block, "Genotype-independent leaf disc transformation of potato (*Solanum tuberosum*) using Agrobacterium tumefaciens", Theoretical and Applied Genetics, Nov. 1988, vol. 76, Issue 5, pp. 767-774.

Deblaere et al., "Efficient octopine Ti plasmid-derived vectors for Agrobacterium-mediated gene transfer to plants", Nucleic Acids Research, vol. 13, Issue 13, Jul. 11, 1985, pp. 4777-4788.

Degenkolb et al., "Structural requirements of tetracycline-Tet repressor interaction: determination of equilibrium binding constants for tetracycline analogs with the Tet repressor", Antimicrobial Agents and Chemotherapy, vol. 35, Issue 8, 1991, pp. 1591-1595.

Della-Cioppa et al., "Protein Trafficking in Plant Cells", Plant Physiology, vol. 84, Issue 4, Aug. 1987, pp. 965-968.

Deuschle et al., "Regulated expression of foreign genes in mammalian cells under the control of coliphage T3 RNA polymerase and lac repressor", Proceedings of the National Academy of Sciences, vol. 86, Issue 14, 1989, pp. 5400-5404.

Deuschle et al., "RNA polymerase II transcription blocked by *Escherichia coli* lac repressor", Science, vol. 248, Issue 4954, Apr. 27, 1990, pp. 480-483.

Dhir, et al., "Regeneration of Transgenic Soybean (*Glycine max*) Plants from Electroporated Protoplasts", Plant Physiology, vol. 99, 1992, pp. 81-88.

Dong, et al., "Transgenic flax plants from Agrobacterium mediated transformation: incidence of chimeric regenerants and inheritance of transgenic plants", Plant Science, vol. 91, Issue 2, 1993, pp. 139-148.

Eapen, et al., "Agrobacterium tumefaciens mediated gene transfer in peanut (*Arachis hypogaea* L.)", Plant Cell Reports, Jul. 1994, vol. 13, Issue 10, pp. 582-586.

Elroy-Stein et al., "Cap-independent translation of mRNA conferred by encephalomyocarditis virus 5' sequence improves the performance of the vaccinia virus/bacteriophage T7 hybrid expression system", Proceedings of the National Academy of Sciences, vol. 86, Issue 16, Aug. 1989, pp. 6126-6130.

Endler, et al., "Cellulose Synthases and Synthesis in *Arabidopsis*", Molecular Plant, vol. 4, Issue 2, Mar. 2011, pp. 199-211.

Esvelt, et al., "Genome?scale engineering for systems and synthetic biology", Molecular Systems Biology, vol. 9, 2013, pp. 1-17.

Feldmann et al., Agrobacterium-mediated transformation of germinating seeds of *Arabidopsis thaliana*: A non-tissue culture approach, Molecular Genetics and Genomics, vol. 208, Issue 1-2, 1987, pp. 1-9.

Figge et al., "Stringent regulation of stably integrated chloramphenicol acetyl transferase genes by *E. coli* lac repressor in monkey cells", Cell, vol. 52, Issue 5, Mar. 11, 1988, pp. 713-722.

Finer, et al., "Transformation of soybean via particle bombardment of embryogenic suspension culture tissue", In Vitro Cellular & Developmental Biology—Plant, Oct. 1991, vol. 27, Issue 4, pp. 175-182.

Frame et al., "Agrobacterium tumefaciens—Mediated Transformation of Maize Embryos Using a Standard Binary Vector System", Plant physiology, vol. 129, Issue 1, 2002, pp. 13-22.

Fromm, et al., "Inheritance and Expression of Chimeric Genes in the Progeny of Transgenic Maize Plants", Bio/Technology, vol. 8, 1990, pp. 833-839.

Fry, et al., "Transformation of *Brassica napus* with Agrobacterium tumefaciens based vectors", Plant Cell Reports, Oct. 1987, vol. 6, Issue 5, pp. 321-325.

Fuerst et al., "Transfer of the inducible lac repressor/operator system from *Escherichia coli* to a vaccinia virus expression vector", Proceedings of the National Academy of Sciences, vol. 86, Issue 8, pp. 2549-2553.

Gallie et al., "The Regulation of Gene Expression in Transformed Maize Aleurone and Endosperm Protoplasts (Analysis of Promoter Activity, Intron Enhancement, and mRNA Untranslated Regions on Expression)", Plant Physiology, vol. 106, Issue 3, Nov. 1994, pp. 929-939.

Gallie et al., "The tobacco etch viral 5? leader and poly(A) tail are functionally synergistic regulators of translation", Gene, vol. 165, Issue 2, 1995, pp. 233-238.

Gallie, et al., "A comparison of eukaryotic viral 5?-leader sequences as enhancers of mRNA expression in vivo", Nucleic Acids Research, vol. 15, Issue 21, Nov. 1987, pp. 8693-8711.

Gasteiger et al., "ExPASy: The proteomics server for in-depth protein knowledge and analysis", Nucleic Acids Research, vol. 31, Issue 13, 2003, pp. 3784-3788.

Geiser et al., "The hypervariable region in the genes coding for entomopathogenic crystal proteins of Bacillus thuringiensis: nucleotide sequence of the kurhd1 gene of subsp. *kurstaki* HD1", Gene, vol. 48, Isasue 1, 1986, pp. 109-118.

Gill et al., "Negative effect of the transcriptional activator GAL4", Nature, vol. 334, 1988, pp. 721-724.

Golovkin, et al., "Production of transgenic maize plants by direct DNA uptake into embryogenic protoplasts", Plant Science, vol. 90, Issue 1, 1993, pp. 41-52.

Gossen et al., "Tight control of gene expression in mammalian cells by tetracycline-responsive promoters", Proceedings of the National Academy of Sciences, vol. 89, Issue 12, 1992, pp. 5547-5551.

Green, "Evolution of Glyphosate-Resistant Crop Technology", Weed Science, vol. 57, Issue 1, 2009, pp. 108-117.

Green, et al., "New multiple-herbicide crop resistance and formulation technology to augment the utility of glyphosate", Pest Management Science, vol. 64, Issue 4, Apr. 2008, pp. 332-339.

Guerche, et al., "Direct gene transfer by electroporation in *Brassica napus*", Plant Science, vol. 52, Issues 1-2, 1987, pp. 111-116.

Guerineau, et al., "Effect of deletions in the cauliflower mosaic virus polyadenylation sequence on the choice of the polyadenylation sites in tobacco protoplasts", Molecular and General Genetics MGG, vol. 226, Issue 1-2, Apr. 1991, pp. 141-144.

Guevara-Garcia , et al., "Tissue specific and wound inducible pattern of expression of the mannopine synthase promoter is deter-

(56) References Cited

OTHER PUBLICATIONS mined by the interaction between positive and negative cis regulatory elements", The Plant Journal, vol. 4, Issue 3, Sep. 1993, pp. 495-505.
Guo, et al., "Transgenic Plants Obtained From Wheat Protoplasts Transformed by PEG-mediated Direct Gene Transfer", Chinese Science Bulletin, vol. 38, Issue 24, 1993, pp. 2072-2078.
Hansen, et al., "Wound-inducible and organ-specific expression of ORF13 from Agrobacterium rhizogenes; 8196 T-DNA in transgenic tobacco plants", Molecular and General Genetics MGG, vol. 254, Issue 3, Apr. 1997, pp. 337-343.
Hiei, et al., "Efficient transformation of rice (*Oryza sativa* L.) mediated by Agrobacterium and sequence analysis of the boundaries of the T-DNA", The Plant Journal, vol. 6, Issue 2, Aug. 1994, pp. 271-282.
Hofgen, et al., "Storage of competent cells for Agrobacterium transformation", Nucleic Acids Research, vol. 16, Issue 20, Oct. 25, 1988, p. 9877.
Horsch et al., "A Simple and General Method for Transferring Genes into Plants", Science, vol. 227, Issue 4691, 1985, pp. 1229-1231.
Howell, et al., "Cloned Cauliflower Mosaic Virus DNA Infects Turnips (*Brassica rapa*)", Science, vol. 208, Issue 4449, Jun. 1980, pp. 1265-1267.
Hu, et al., "The inducible lac operator-repressor system is functional in mammalian cells", Cell, vol. 48, Issue 4, Feb. 27, 1987, pp. 555-566.
Hulo, et al., "Recent improvements to the Prosite database", Nucleic Acids Research, vol. 32, Issue suppl. 1, 2004, D134-D137.
International Application No. PCT/IB2016/056348, International Preliminary Report on Patentability, dated Apr. 24, 2018.
International Application No. PCT/IB2016/056348, International Search Report and Written Opinion, dated Feb. 17, 2017.
Inui, et al., "Herbicide resistance in transgenic plants with mammalian P450 monooxygenase genes", Pest Management Science, vol. 61, Issue 3, Mar. 2005, pp. 286-291.
Jobling, et al., "Enhanced translation of chimaeric messenger RNAs containing a plant viral untranslated leader sequence", Nature, vol. 325, 1987, pp. 622-625.
Kaeppler, et al., "Silicon carbide fiber-mediated DNA delivery into plant cells", Plant Cell Reports, vol. 9, Issue 8, Dec. 1990, pp. 415-418.
Kaeppler, et al., "Silicon carbide fiber-mediated stable transformation of plant cells", Theoretical and Applied Genetics, vol. 84, Issues 5-6, Aug. 1992, pp. 560-566.
Katavic, et al., "In planta transformation of *Arabidopsis thaliana*", Molecular and General Genetics MGG, vol. 245, Issue 3, May 1994, pp. 363-370.
Kawamata, et al., "Temporal and Spatial Pattern of Expression of the Pea Phenylalanine Ammonia-Lyase Gene1 Promoter in Transgenic Tobacco", Plant and Cell Physiology, vol. 38, Issue 7, Jan. 1997, pp. 792-803.
Klaus, et al., "Generation of marker-free plastid transformants using a transiently cointegrated selection gene", Nature Biotechnology, vol. 22, 2004, pp. 225-229.
Klein, et al., "Factors Influencing Gene Delivery into *Zea mays* Cells by High-Velocity Microprojectiles", Bio/Technology, 1988, vol. 6, 1988, pp. 559-563.
Klein, et al., "Genetic Transformation of Maize Cells by Particle Bombardment", Plant Physiology, vol. 91, 1989, pp. 440-444.
Klein, et al., "High-velocity microprojectiles for delivering nucleic acids into living cells", Nature, May 1987, vol. 327, pp. 70-73.
Klein, et al., "Transfer of foreign genes into intact maize cells with high-velocity microprojectiles", Proceedings of the National Academy of Sciences, Jun. 1, 1988, vol. 85, Issue 12, pp. 4305-4309.
Kleinschmidt, et al., "Dynamics of repressor-operator recognition: Tn10-encoded tetracycline resistance control", Biochemistry, vol. 27, Issue 4, 1988, pp. 1094-1104.
Koncz, et al., "The promoter of TL-DNA gene 5 controls the tissue-specific expression of chimaeric genes carried by a novel type of Agrobacterium binary vector", Molecular and General Genetics, Sep. 1986, vol. 204, Issue 3, pp. 383-396.
Kunkel, "Rapid and efficient site-specific mutagenesis without phenotypic selection", Proceedings of the National Academy of Sciences, vol. 82, Issue 2, Jan. 1985. pp. 488-492.
Kunkel, et al., "Rapid and efficient site-specific mutagenesis without phenotypic selection", Methods in Enzymology, vol. 154, 1987, pp. 367-382.
Labow, et al., "Conversion of the lac repressor into an allosterically regulated transcriptional activator for mammalian cells", Molecular and Cellular Biollogy, vol. 10, Issue 7, Jul. 1990, pp. 3343-3356.
Lam, "Analysis of Tissue-Specific Elements in the CaMV 35S Promoter", Plant Promoters and Transcription Factors, 1994, pp. 181-196.
Lamppa, "The chlorophyll a/b-binding protein inserts into the thylakoids independent of its cognate transit peptide", The Journal of Biological Chemistry, Oct. 1988, vol. 263, pp. 14996-14999.
Larkin, et al., "Clustal W and Clustal X version 2.0", Bioinformatics, vol. 23, Issue 21, 2007, pp. 2947-2948.
Last, et al., "pEmu: an improved promoter for gene expression in cereal cells", Theoretical and Applied Genetics, vol. 81, Issue 5, May 1991, pp. 581-588.
Lawrence, et al., "Alterations in the Chlamydomonas Plastocyanin Transit Peptide Have Distinct Effects on in VitroImport and in Vivo Protein Accumulation", The Journal of Biological Chemistry, vol. 272, Issue 33, 1997, pp. 20357-20363.
Li, et al., "An improved rice transformation system using the biolistic method", Plant Cell Reports, Mar. 1993, vol. 12, Issue 5, pp. 250-255.
Li, et al., "Development of PPO inhibitor-resistant cultures and crops", Pest Management Science, vol. 61, Issue 3, Mar. 2005, pp. 277-285.
Lommel, et al., "Identification of the Maize chlorotic mottle virus capsid protein cistron and characterization of its subgenomic messenger RNA", Virology, vol. 181, Issue 1, Mar. 1991, pp. 382-385.
Macejak, et al., "Internal initiation of translation mediated by the 5? leader of a cellular mRNA", Nature, vol. 353, 1991, pp. 90-94.
Maliga, "Progress towards commercialization of plastid transformation technology", Trends in Biotechnology, vol. 21, Issue 1, Jan. 2003, pp. 20-28.
Matringe, et al., "p-Hydroxyphenylpyruvate dioxygenase inhibitor-resistant plants", Pest Management Science, vol. 61, Issue 3, Mar. 2005, pp. 269-276.
Matsuoka, et al., "Tissue-specific light-regulated expression directed by the promoter of a C4 gene, maize pyruvate,orthophosphate dikinase, in a C3 plant, rice", Proceedings of the National Academy of Sciences, vol. 90, Issue 20, 1993, pp. 9586-9590.
McBride, et al., "Controlled expression of plastid transgenes in plants based on a nuclear DNA-encoded and plastid-targeted T7 RNA polymerase", Proceedings of the National Academy of Sciences, vol. 91 Issue 15, 1994, pp. 7301-7305.
McCormick, et al., "Leaf disc transformation of cultivated tomato (*L. esculentum*) using Agrobacterium tumefaciens", Plant Cell Reports, Apr. 1986, vol. 5, Issue 2, pp. 81-84.
McElroy, et al., "Isolation of an efficient actin promoter for use in rice transformation", The Plant Cell, vol. 2, Issue 2, Feb. 1990, pp. 163-171.
Mlynarova, et al., "High efficiency Agrobacterium-mediated gene transfer to flax", Plant Cell Reports, vol. 13, Issue 5, Feb. 1994, pp. 282-285.
Mogen, et al., "Upstream sequences other than AAUAAA are required for efficient messenger RNA 3'-end formation in plants", The Plant Cell, vol. 2, Issue 12, Dec. 1990, pp. 1261-1272.
Moloney, et al., "High efficiency transformation of *Brassica napus* using Agrobacterium vectors", Plant Cell Reports, vol. 8, Issue 4, Apr. 1989, pp. 238-242.
Mulder, et al., "The InterPro Database, 2003 brings increased coverage and new features", Nucleic Acids Research, vol. 31, Issue 1, 2003, pp. 315-318.
Munroe, et al., "Tales of poly(A): a review", Gene, vol. 91, Issue 2, Jul. 16, 1990, pp. 151-158.

(56) References Cited

OTHER PUBLICATIONS

Murashige, et al., "A Revised Medium for Rapid Growth and Bio Assays with Tobacco Tissue Cultures", Physiologia Plantarum, vol. 15, Issue 3, Jul. 1962, pp. 473-497.
Needleman, et al., "A general method applicable to the search for similarities in the amino acid sequence of two proteins", Journal of Molecular Biology, vol. 48, issue 3, pp. 443-453.
Neuhaus, et al., "Transgenic rapeseed plants obtained by the microinjection of DNA into microspore-derived embryoids", Theoretical and Applied Genetics, Dec. 1987, vol. 75, Issue 1, pp. 30-36.
Odell, et al., "Identification of DNA sequences required for activity of the cauliflower mosaic virus 35S promoter", Nature, vol. 313, pp. 810-812.
Oliva, et al., "Evidence that tetracycline analogs whose primary target is not the bacterial ribosome cause lysis of *Escherichia coli*", Antimicrobial Agents and Chemotherapy, vol. 36, Issue 5, 1992, pp. 913-919.
Orozco, et al., "Localization of light-inducible and tissue-specific regions of the spinach ribulose bisphosphate carboxylase/oxygenase (rubisco) activase promoter in transgenic tobacco plants", Plant Molecular Biology, vol. 23, Issue 6, Dec. 1993, pp. 1129-1138.
Padgette, et al., "Site-directed Mutagenesis of a Conserved Region of the; 5-Enolpyruvylshikimate-3-phosphate Synthase Active Site", Journal of Biological Chemistry, vol. 266, Issue 33, 1991, pp. 22364-22369.
Paszkowski, et al., "Direct gene transfer to plants", The EMBO Journal, vol. 3, Issue 12, Dec. 1984, pp. 2717-2722.
Potrykus, "Gene Transfer to Plants: Assessment of Published Approaches and Results", Annual Review of Plant Physiology and Plant Molecular Biology, vol. 42, 1991, pp. 205-225.
Proudfoot, "Poly(A) signals", Cell, vol. 64, Issue 4, 1991, pp. 671-674.
Puchta, et al., "Gene targeting in plants: 25 years later", The International Journal of Developmental Biology vol. 57, 2013, pp. 629-637.
Reines, et al., "Elongation factor SII-dependent transcription by RNA polymerase II through a sequence-specific DNA-binding protein", Proceedings of the National Academy of Sciences, vol. 90, Issue 5, 1993, pp. 1917-1921.
Reznikoff, "The lactose operon controlling elements: a complex paradigm", vol. 6, Issue 17, Sep. 1992, pp. 2419-2422.
Richmond, et al., "The Cellulose Synthase Superfamily", Plant Physiology, vol. 124, Oct. 2000, pp. 495-498.
Riggs, et al., "Stable transformation of tobacco by electroporation: evidence for plasmid concatenation", Proceedings of the National Academy of Sciences, Aug. 1, 1986, vol. 83, Issue 15, pp. 5602-5606.
Rinehart, et al., "Tissue-Specific and Developmental Regulation of Cotton Gene FbL2A (Demonstration of Promoter Activity in Transgenic Plants)", Plant Physiology, vol. 112, Issue 3, Nov. 1996, pp. 1331-1341.
Ritala, et al., "Fertile transgenic barley by particle bombardment of immature embryos", Plant Molecular Biology, Jan. 1994, vol. 24, Issue 2, pp. 317-325.
Romer, et al., "Expression of the Genes Encoding the Early Carotenoid Biosynthetic-Enzymes in Capsicum annuum", Biochemical and Biophysical Research Communications, vol. 196, Issue 3, Nov. 15, 1993, pp. 1414-1421.
Sanfacon, et al., "A dissection of the cauliflower mosaic virus polyadenylation signal", Genes & Development, 1991, vol. 5, pp. 141-149.
Russell, et al., "Tissue-specific expression in transgenic maize of four endosperm promoters from maize and rice", Transgenic Research, Mar. 1997, vol. 6, Issue 2, pp. 157-168.
Sanford, et al., "Delivery of substances into cells and tissues using a particle bombardment process", Particulate Science and Technology, vol. 5, Issue 1, 1987, pp. 27-37.
Scheid, et al., "Reversible inactivation of a transgene in *Arabidopsis thaliana*", Molecular and General Genetics, Aug. 1991, vol. 228, Issue 1-2, pp. 104-112.

Schliep, et al., "Phangorn: phylogenetic analysis in R", Bioinformatics, vol. 27, Issue 4, Feb. 2011, pp. 592-593.
Schmidt, et al., "A novel operon organization involving the genes for chorismate synthase (aromatic biosynthesis pathway) and ribosomal GTPase center proteins (L11, L1, L10, L12: rpIKAJL) in cyanobacterium Synechocystis PCC 6803", The Journal of Biological Chemistry, vol. 268, Issue 36, 1993, p. 27447-27457.
Schnell, et al., "Signal peptide analogs derived from two chloroplast precursors interact with the signal recognition system of the chloroplast envelope", The Journal of Biological Chemistry, vol. 266, Issue 5, 1991, pp. 3335-3342.
Schultz, et al., "SMART, a simple modular architecture research tool: Identification of signaling domains", Proceedings of the National Academy of Sciences USA, vol. 95, Issue 11, May 1998, pp. 5857-5864.
Shah, et al., "Engineering Herbicide Tolerance in Transgenic Plants", Science, vol. 233, Issue 4762, Jul. 25, 1986, pp. 478-481.
Silva-Filho, et al., "Different in Vitro and in Vivo Targeting Properties of the Transit Peptide of a Chloroplast Envelope Inner Membrane Protein", The Journal of Biological Chemistry, vol. 272, Jun. 1997, pp. 15264-15269.
Skuzeski, et al., "Analysis of leaky viral translation termination codons in vivo by transient expression of improved ?-glucuronidase vectors", Plant Molecular Biology, vol. 15, Issue 1, Jul. 1990, pp. 65-79.
Slogteren, et al., "Expression of Ti plasmid genes in monocotyledonous plants infected with Agrobacterium tumefaciens", Nature, vol. 311, Oct. 1984, pp. 763-764.
Singh, et al., "Cytological characterization of transgenic soybean", Theoretical and Applied Genetics, Feb. 1998, vol. 96, Issue 2, pp. 319-324.
Smith, et al., "Identification of Common Molecular Subsequences", Journal of Molecular Biology, vol. 147, Issue 1, Mar. 1981, pp. 195-197.
Staub, et al., "Accumulation of D1 polypeptide in tobacco plastids is regulated via the untranslated region of the psbA mRNA", The EMBO Journal, vol. 12, Issue 2, Feb. 1993, pp. 601-606.
Svab, et al., "Stable transformation of plastids in higher plants", Proceedings of the National Academy of Sciences, vol. 87, Issue 21, 1990, pp. 8526-8530.
Svab, et al., "High-frequency plastid transformation in tobacco by selection for a chimeric aadA gene", Proceedings of the National Academy of Sciences, vol. 90, Issue 3, 1993, pp. 913-917.
Tan, et al., "Imidazolinone-tolerant crops: history, current status and future", Pest Management Science, vol. 61, Issue 3, Mar. 2005, pp. 246-257.
Tan, et al., "Precision Editing of Large Animal Genomes", Advances in Genetics, vol. 80, 2012, pp. 37-97.
Terpe, et al., "Overview of tag protein fusions: from molecular and biochemical fundamentals to commercial systems", Applied Microbiology and Biotechnology, vol. 60, Issue 5, 2003, pp. 523-533.
Tomes, et al., "Direct DNA Transfer into Intact Plant Cells Via Microprojectile Bombardment", Plant Cell, Tissue and Organ Culture, 1995, pp. 197-213.
Van Camp, et al., "Tissue-Specific Activity of Two Manganese Superoxide Dismutase Promoters in Transgenic Tobacco", Plant Physiology, vol. 112, Issue 2, Oct. 1996, pp. 525-535.
Velten, et al., "Isolation of a dual plant promoter fragment from the Ti plasmid of Agrobacterium tumefaciens", The EMBO Journal, vol. 3, Issue 12, Dec. 1984, pp. 2723-2730.
Von Heijne, et al., "CHLPEP—A database of chloroplast transit peptides", Plant Molecular Biology Reporter, vol. 9, Issue 2, May 1991, pp. 104-126.
Wan, et al., "Generation of Large Numbers of Independently Transformed Fertile Barley Plants", Plant Physiology, vol. 104, 1994, pp. 37-48.
Weising, et al., "Foreign Genes in Plants: Transfer, Structure, Expression, and Applications", Annual Review of Genetics, vol. 22, Dec. 1988, pp. 421-477.
Williams, et al., "Differences in zoospore germination and host penetration in response to temperature among Western Australian isolates of Plasmopara viticola", Australian Journal of Agricultural Research, vol. 58, Issue 7, pp. 702-710.

(56) References Cited

OTHER PUBLICATIONS

Wyborski, et al., "Analysis of inducers of the *E. coli* lac repressor system mammalian cells and whole animals", Nucleic Acids Research, vol. 19, Issue 17, Sep. 11, 1991, pp. 4647-4653.

Yamamoto, et al., "Light responsive elements of the tobacco PSI?D gene are located both upstream and within the transcribed region", The Plant Journal, vol. 12, Issue 2, Aug. 1997, pp. 255-265.

Yamamoto, et al., "The Promoter of a Pine Photosynthetic Gene Allows Expression of a ?-Glucuronidase Reporter Gene in Transgenic Rice Plants in a Light-Independent but Tissue-Specific Manner", Plant and Cell Physiology, vol. 35, Issue 5, Jan. 1, 1994, pp. 773-778.

Yao, et al., "*Drosophila ultraspiracle* modulates ecdysone receptor function via heterodimer formation", Cell, vol. 71, Issue 1, Oct. 1992, pp. 63-72.

Yarranton, "Inducible vectors for expression in mammalian cells", Current Opinion in Biotechnology, vol. 3, Issue 5, Oct. 1992, pp. 506-511.

Zambretti, et al., "A mutant p53 protein is required for maintenance of the transformed phenotype in cells transformed with p53 plus ras cDNAs", Proceedings of the National Academy of Sciences, vol. 89, Issue 9, pp. 3952-3956.

Murray, et al., "Codon usage in plant genes", Nucleic Acids Research, vol. 17, Issue 2, Jan. 25, 1989, pp. 477-498.

Zhao, et al., "Immunological Characterization and Chloroplast Localization of the Tryptophan Biosynthetic Enzymes of the Flowering Plant *Arabidopsis thaliana*", The Journal of Biological Chemistry, vol. 270, Issue 11, pp. 6081-6087.

Ballas et al., "Efficient functioning of plant promoters and poly(A) sites in Xenopus oocytes", Nucleic Acids Research, vol. 17, Issue 19, Oct. 11, 1989, pp. 7891-7903.

Joshi, "Putative polyadenylation signals in nuclear genes of higher plants: a compilation and analysis", Nucleic Acids Research, vol. 15, Issue 23, Dec. 10, 1987, pp. 9627-9640.

Christensen, et al., "Maize polyubiquitin genes: structure, thermal perturbation of expression and transcript splicing, and promoter activity following transfer to protoplasts by electroporation", Plant Molecular Biology, vol. 18, Issue 4, Feb. 1992, pp. 675-689.

Davies, et al., "Transformation of peas", Plant Cell Reports, Jan. 1993, vol. 12, Issue 3, pp. 180-183.

Dill et al., "Glyphosate-resistant crops: adoption, use and future considerations", Pest Management Science, vol. 64, Issue 4, Apr. 2008, pp. 326-331.

Hartman, et al., "Herbicide Resistant Turfgrass (*Agrostis palustris* Huds.) by Biolistic Transformation", Bio/Technology, vol. 12, 1994, pp. 919-923.

Ishida, et al., "High efficiency transformation of maize (*Zea mays* L.) mediated by Agrobacterium tumefaciens", Nature Biotechnology, vol. 14, Issue 6, pp. 745-750.

Letunic, et al., "Recent improvements to the SMART domain-based sequence annotition resource", Nucleic Acids Research, vol. 30, Issue 1, 2002, pp. 242-244.

McCabe, et al., "Stable Transformation of Soybean (*Glycine max*) by Particle Acceleration", Bio/Technology, vol. 6, 1988, pp. 923-926.

\* cited by examiner

Figure 2

| | | | | | | |
|---|---|---|---|---|---|---|
| | * | 20 | * | 40 | * | 60 | |
| At_CesA1 | : | MEASAGLVAGSYRNELVRIRHESDGGTKPLKNMNGQICQICGDDVGLAETGDVVACNE | : | 60 | SEQ ID NO: 1 |
| At_CesA10 | : | ------M.......V.F..N.BD..D.L....DL........TK..N........... | : | 54 | SEQ ID NO: 10 |
| BnaA01g04600D | : | ...............S..............DRE.......HA..T....L........ | : | 60 | SEQ ID NO: 21 |
| BnaC01g06090D | : | ...............S..............DRE.......HA..T....L........ | : | 60 | SEQ ID NO: 22 |
| BnaC07g43790D | : | .....................A...DPHT........NA..T....L........... | : | 60 | SEQ ID NO: 19 |
| BnaA03g52020D | : | ..................S.AM...DPHT........NA..T....L........... | : | 60 | SEQ ID NO:15 |
| Ha_Cesa1 | : | .Q.NG.......HK..........D....P....DL..T......T...T...I.... | : | 60 | SEQ ID NO: 25 |
| At_CesA3 | : | ------------MES.GETAG..M..IVP.T.......S..N..KTVD..R.....DI | : | 41 | SEQ ID NO: 3 |
| BnaAnng01240D | : | ------------MESDGETAG..MTSVG..........S..N..KTVD..R.....DI | : | 41 | SEQ ID NO: 20 |
| BnaC03g55200D | : | ------------MES.GETAG..MTSVG..........S..N..KTVD..R.....DV | : | 41 | SEQ ID NO: 12 |
| BnaC02g02440D | : | ------------MESDGETAG..MTSVG..........S..S..KTVD..R.....DI | : | 41 | SEQ ID NO: 16 |
| BnaC03g02050D | : | ------------MES.GETAG..MTSVG..........S..N..KTVD..W.....DV | : | 41 | SEQ ID NO: 23 |
| Ha_Cesa3 | : | ------------MES.GET.GTSM..VG..V.......T..TTAK..P.........DV | : | 41 | SEQ ID NO: 26 |
| Ha_Cesa3_fragm | : | ----------------------------------------------------------- | : | -  | SEQ ID NO: 28 |
| At_CesA2 | : | .NTGGR.I...HN...F.L.NADESARIRSVQELS..T........EIE.TVSSEL... | : | 60 | SEQ ID NO: 2 |
| At_CesA5 | : | .NTGGR.I...HN...F.L.NADESARIRSVEELS..T........EIE.SVD.ES... | : | 60 | SEQ ID NO: 5 |
| At_CesA6 | : | .NTGGR.I...HN...F.L.NADENARIRSVQELS..T........R.EIE.TVD.EP. | : | 60 | SEQ ID NO: 6 |
| At_CesA9 | : | .NTGGR.I...HN...F.L.NADDTARIRSAEELS..T.K...R.EIE.TDN.EP..I. | : | 60 | SEQ ID NO: 9 |
| BnaA02g34360D | : | .NTGGR.I...HN...F.L.NADENARIRSVQELR..T.E...R.EIESTVD.EP.... | : | 60 | SEQ ID NO: 14 |
| BnaA06g23700D | : | .NTGGR.I...HN...F.L.NADESARIRSVQELR..T.K...R.EIE.TVD.EP.... | : | 60 | SEQ ID NO: 11 |
| BnaA09g06990D | : | .NTGGR.I...HN...F.L.NADENARIRSVQELR..T.E...R.E.E.TVD.EP.... | : | 60 | SEQ ID NO: 13 |
| BnaC02g43280D | : | .NTGGR.....HN...F.L.NADENARIRSAEELS..T.K...R.EIE.TDN.EP.... | : | 60 | SEQ ID NO: 18 |
| BnaC03g49550D | : | .NTGGR.I...HN...F.L.NADESARIRSVQELR..T.E...R.EIESTVE.EP.... | : | 60 | SEQ ID NO: 17 |
| BnaC09g06600D | : | .NTGGR.I...HN...F.L.NADESARIRSVQELR..T.E...R.E.E.TVD.EP.... | : | 60 | SEQ ID NO: 24 |

From Figure 2A

| Name | Sequence | | SEQ ID NO |
|---|---|---|---|
| Ha_Cesa6_fragm | ------------------------------------ | - | SEQ ID NO: 29 |
| At_CesA4 | ------MEPNTMA.FDDEHRHSSFSAK.KV...E.KDDDN.QT....HV | 44 | SEQ ID NO: 4 |
| At_CesA7 | ...............HN...V.HNHEEP---....LD.F.E....QI..TVE..L...... | 58 | SEQ ID NO: 7 |
| At_CesA8 | --------------------MMESRSP..NT..EEI.VKSN.EF......H.. | 30 | SEQ ID NO: 8 |
| Ha_Cesa7 | ..Q............HN...V.HGHEEP---.....D.T.V.E....EI.TVD..L...... | 58 | SEQ ID NO: 27 |

| | * 80 * 100 * 120 | | |
|---|---|---|---|
| At_CesA1 | CAFPVCRPCYEYERKDGTQCCPQCKTRFRHRGSPRVEGDEDED-DVDDIENEPNYAQGA | 119 | SEQ ID NO: 1 |
| At_CesA10 | .G..L.QS.....D........S.....A....M......V..K..-....N......D.T..N | 113 | SEQ ID NO: 10 |
| BnaA01g04600D | .....................H....Y.L.H...................S....G | 119 | SEQ ID NO: 21 |
| BnaC01g06090D | .....................H....Y.L.H...................S....G | 119 | SEQ ID NO: 22 |
| BnaC07g43790D | ..........................Y.L..................T......... | 119 | SEQ ID NO: 19 |
| BnaA03g52020D | ..........................Y.L.H.......................... | 119 | SEQ ID NO: 15 |
| Ha_Cesa1 | ..........R..N.A........Y...K....D..E....-....L....S.P..N | 119 | SEQ ID NO: 25 |
| At_CesA3 | ..S............N.S....YK.LK....AIP..K....-GLA.EGTVEFNYPQK | 100 | SEQ ID NO: 3 |
| BnaAnng01240D | ..G............N.S....TYK..K....AIP..K....-VFA.EATVELNYPQK | 100 | SEQ ID NO: 20 |
| BnaA03g55200D | ..G.........F..N.S....TYK..K....AIP..K....-VFA.EATVELSYPQK | 100 | SEQ ID NO: 12 |
| BnaC02g02440D | ..G............H.N.S....TYK..K....AIP..K....-VFA.EATVELNYPQK | 100 | SEQ ID NO: 16 |
| BnaC03g02050D | ..G.........DF.N.S....YK.LK....AIP..K....-VFA.EATVELSYPQK | 100 | SEQ ID NO: 23 |
| Ha_Cesa3 | ...............N.S....YK.LK....AIP..RE...-IDG.D.TTNFPFSSQ | 100 | SEQ ID NO: 26 |
| Ha_Cesa3_fragm | ------------------------------------ | - | SEQ ID NO: 28 |
| At_CesA2 | ..RE.N.A........YK.IK..........D..DE.EE.I..L.Y..DHGMDP | 120 | SEQ ID NO: 2 |
| At_CesA5 | ..RE.N.S........YK.IK..............ED.-GI..LDF..D.SRSG | 119 | SEQ ID NO: 5 |

```
From
Figure 2B
At_CesA6        : ............................RE.N.A............K.LK.....E..-I.LD....E.GNNG : 119  SEQ ID NO: 6
At_CesA9        : ..........T.................RE.N.A.....G.YK.IK.....ED.-I.L.H.YGMDPE : 119  SEQ ID NO: 9
BnaA02g34360D   : ............................................YK.IK......D.-E.GGNG : 119  SEQ ID NO: 14
BnaA06g23700D   : ............................RE.N.A............YK.IK.....N.E.-I.LD....E.EN.G : 119  SEQ ID NO: 11
BnaA09g06990D   : ............................RE.N.A............YK.LK.....N.E.-I.D....D.MNNG : 119  SEQ ID NO: 13
BnaC02g43280D   : ............................RE.N.A............YK.IK.....N.E.-I.D....E.GGNG : 119  SEQ ID NO: 18
BnaC03g49550D   : ............................RE.N.A............YK.IK.....N.E.-I.LD....E.EN.G : 119  SEQ ID NO: 17
BnaC09g06600D   : ............................RE.N.A............YK.LK.....N.E.-I.D....D.MNNG : 119  SEQ ID NO: 24
Ha_Cesa6_fragm  : ----------------------------------------------------------------- :  -   SEQ ID NO: 29
At_CesA4        : .VY..K......SN.NK......M.LYK..K....KIA...ENN--------------------- : 88   SEQ ID NO: 4
At_CesA7        : .G.A........RE...N......YK.L.................E-.-.Y...IEHEQ : 117  SEQ ID NO: 7
At_CesA8        : .S..I.KA.L...F.E.RRI.LR.GNPYDEN---------------------------------- : 61   SEQ ID NO: 8
Ha_Cesa7        : .G..........RE.S.N......YK.LK.................D..E.-...H...IDDEH : 117  SEQ ID NO: 27

*         140         *         160         *         180
At_CesA1        : N-------KARHQR-HGEEFSSSSRHESQP----------IPLLTHGHVSGEIRTPDTQSV : 163  SEQ ID NO: 1
At_CesA10       : .-------..LPHRAE.FS...RHE..L..--------VS.........P.......RNAT : 158  SEQ ID NO: 10
BnaA01g04600D   : A-------NKPRR.-----D..........-..........G..................... : 161  SEQ ID NO: 21
BnaC01g06090D   : A-------NKPRR.-----D..........-..........G..................... : 161  SEQ ID NO: 22
BnaC07g43790D   : .-------..G.R.QR....................----........................ : 164  SEQ ID NO: 19
BnaA03g52020D   : .-------..G.R.QR....................----........................ : 164  SEQ ID NO:15
Ha_Cesa1        : .-------AR.WQG-DDANL..SARHD.---------L....N.QQ.....PSVRDNLS : 163  SEQ ID NO: 25
At_CesA3        : E-------.ISERMLGWHLTRGKGEEMGE.QYDKEVSHNHL.R..SRQDT...FSAASPERL : 155  SEQ ID NO: 3
To Figure 2D                           Figure 2C
```

From Figure 2C

| | | | |
|---|---|---|---|
| BnaAnng01240D | : E------.ISERMLGWHLTRGK.EEMG..EYDKEVSHNHL.R..SRQDT...FSAASPERL. | 155 | SEQ ID NO: 20 |
| BnaA03g55200D | : E------.ISERMLGWHLTRGK.EEMG..EYDKEVSHNHL.R..SRQET...FSAASPERL. | 155 | SEQ ID NO: 12 |
| BnaC02g02440D | : E------.ISERMLGWHLTRGK.EEMG..EYDKEVSHNHL.R..SRQDT...FSAASPERL. | 155 | SEQ ID NO: 16 |
| BnaC03g02050D | : E------.ISERMLGWHLTRGK.GEEMG..EYDKEVSHNHL.R..SRQET...FSAASPERL. | 155 | SEQ ID NO: 23 |
| Ha_Cesa3 | : TQNEKQ.TAERMLNWMHMTYGRGDDN.A.NVDKEVSHNH....G..E....LSAASP.RL. | 160 | SEQ ID NO: 26 |
| Ha_Cesa3_fragm | : ---------------------------------------------------------HAL. | 3 | SEQ ID NO: 28 |
| At_CesA2 | : E-------H.AEAALSSRINTGR-------GGLDSAPPGSQ......YCDEDADMYSDRHALI. | 169 | SEQ ID NO: 2 |
| At_CesA5 | : --------LES.T..RRNS----EFDLASAPPGSQ......Y.EEDVEISSDSHALI. | 164 | SEQ ID NO: 5 |
| At_CesA6 | : --------IGFD.VSE.MSI.RRNSGFP.SDLDSAPPGSQ......Y.DEDVEISSDRHALI. | 173 | SEQ ID NO: 6 |
| At_CesA9 | : H-------VTEAALYVMRLNTGRGTD-EVSHLYSASPGSEV.....YCDED.DMYSDRHALI. | 173 | SEQ ID NO: 9 |
| BnaA02g34360D | : --------IGFD.VSE.VSV.RRHS------GDLDSAPPGSQ......Y.DEDIEISSDRHALI. | 169 | SEQ ID NO: 14 |
| BnaA06g23700D | : --------VGFD.VSE.MSV.RRHSGFP.SDLDSAPPGSQ......Y.DEDIEISSDRHALI. | 173 | SEQ ID NO: 11 |
| BnaC09g06990D | : G-------IGFD.VSE.MSV.RRHSGFP.SDLDSAPPGSQ......Y.DEDIEISSDRHALI. | 174 | SEQ ID NO: 13 |
| BnaC02g43280D | : --------IGFD.VSE.VSV.RRHS------GDLDSAPPGSQ......Y.DEDIEISSDRHALI. | 169 | SEQ ID NO: 18 |
| BnaC03g49550D | : --------VGFD.VSE.MSV.RRHSGFP.SDLDSAPPGSQ......Y.DEDIEISSDRHALI. | 173 | SEQ ID NO: 17 |
| BnaC09g06600D | : G-------IGFD.VSE.MSV.RRHSGFP.SDLDSAPPGSQ......Y.DEDIEISSDRHALI. | 174 | SEQ ID NO: 24 |
| Ha_Cesa6_fragm | : ---------------------------------------------------------- | - | SEQ ID NO: 29 |
| At_CesA4 | : --------------GPDD-----------------------------SDDELN.KYRQDG.S | 107 | SEQ ID NO: 4 |
| At_CesA7 | : DKH--KHSAEAMLY.KMSYGR------G----PEDDENG--RFPPVI: | 150 | SEQ ID NO: 7 |
| At_CesA8 | : -----------------------------------VFDDV.TK.SK...I | 76 | SEQ ID NO: 8 |
| Ha_Cesa7 | : .KN--NNIAEAML..KMSYGR------G----PEDDDNMN.QYPPVI: | 152 | SEQ ID NO: 27 |

From Figure 2D

| | * | 200 | * | 220 | * | 240 | | |
|---|---|---|---|---|---|---|---|---|
| At_CesA1 | : | RTTSGPLGPSDRNAISSPYIDPRQPVPRIVDPSKDLNSY----GLGNVDWKERVEGWKLK | : | 220 | SEQ ID NO: 1 |
| At_CesA10 | : | LSPCIDP-------QLP-G.VQLLLL....L.......V......K.IQ....... | : | 207 | SEQ ID NO: 10 |
| BnaA01g04600D | : | ............GE...S.............................. | : | 218 | SEQ ID NO: 21 |
| BnaC01g06090D | : | ............G.................................. | : | 218 | SEQ ID NO: 22 |
| BnaC07g43790D | : | ............G.................................. | : | 221 | SEQ ID NO: 19 |
| BnaA03g52020D | : | ............G.................................. | : | 221 | SEQ ID NO:15 |
| Ha_CesA1 | : | VRSTSGPLG--PSDKQL.............................. | : | 218 | SEQ ID NO: 25 |
| At_CesA3 | : | SVS.TIA.GK----RLPYSS.VN.SPNR.....V---------A......D...M. | : | 202 | SEQ ID NO: 3 |
| BnaAnng01240D | : | SVS.TIA.GK----RLPYSS.IN.SPNR...S..V---------A......D...M. | : | 202 | SEQ ID NO: 20 |
| BnaA03g55200D | : | SVS.TIG.GK----RLPYSS.IN.SPHR..S..V---------A......D...M. | : | 202 | SEQ ID NO: 12 |
| BnaC02g02440D | : | SVS.TIA.GK----RLPYSC.IN.SPNR..S..V---------A......D...M. | : | 202 | SEQ ID NO: 16 |
| BnaC03g02050D | : | SVS.TIG.GK----RLPYSS.IN.SPHR..S..V---------A......D...M. | : | 202 | SEQ ID NO: 23 |
| Ha_Cesa3 | : | SVS.P.P.GERLTHSLPVSAVAN.SPNI.V..VREFG.T----LA......D...M. | : | 217 | SEQ ID NO: 26 |
| Ha_Cesa3_fragm | : | ITPPFMNRAKRVHPMFFSDTASSVSL.P.PM..K...AV.---Y.T.A..D.M.E.RRR | : | 60 | SEQ ID NO: 28 |
| At_CesA2 | : | PPST-GY.NRVYP.PFTDSSA.P.ARSMVPQKDIAEYGYG--------S.A..D.M.V..RR | : | 222 | SEQ ID NO: 2 |
| At_CesA5 | : | SPSP-GHIHRVHQPHFPDP--AAH.R.MVPQKDLAVYGYG--------S.A..D.M.E..R. | : | 215 | SEQ ID NO: 5 |
| At_CesA6 | : | PPSL.GH.NRVHPVSL.DPTTAAH.R.MVPQKDLAVYGYG--------S.A..D.M.E..R. | : | 227 | SEQ ID NO: 6 |
| At_CesA9 | : | PPST-G...NRVHHVPFTDSFBSIHTR.MVPQKDLTVYGYG--------S.A..D.M.V..KQ | : | 226 | SEQ ID NO: 9 |
| BnaC02g34360D | : | PPSLSGH.SRVHPVSL.DPTTAAH.R.MVPQKDLAVYGYG--------S.A..D.M.E..R. | : | 223 | SEQ ID NO: 14 |
| BnaA06g23700D | : | PPSI.GHSNKSHP.SL.DPTTAAH.R.MVPQKDLAVYGYG--------S.A..D.M.D..K. | : | 227 | SEQ ID NO: 11 |
| BnaC09g06990D | : | PPSLSGHSHRGHP.SL.DPTTAAH.R.MVPQKDLAVYGYG--------S.A..D.M.E..R. | : | 228 | SEQ ID NO: 13 |
| BnaC02g43280D | : | PPSLSGH.SKVHPVSL.DPTTAAH.R.MVPQKDLAVYGYG--------S.A..D.M.E..R. | : | 223 | SEQ ID NO: 18 |
| BnaC03g49550D | : | PPSI.GHSNKSHP.SL.DPTTAAH.R.MVPQKDLAVYGYG--------S.A..D.M.D..K. | : | 227 | SEQ ID NO: 17 |

| | | | |
|---|---|---|---|
| BnaC09g06600D | : PPSLSGHSHRGHP.SL.DPTIAAH.R.MVPQKDLAVYGYG------S.A..D.M.E.R. | : 228 | SEQ ID NO: 24 |
| Ha_Cesa6_fragm | : ------------------------------------------------------------ | : — | SEQ ID NO: 29 |
| At_CesA4 | : IHQNFAY.SENGDYN.KQQWR.NGRAFSSTGVLGKDFEAERD.YTDAE.....DK..AR | : 167 | SEQ ID NO: 4 |
| At_CesA7 | : AG---GHSGEFPVGGG-YGNGEHGLHKKVHPY..SEAG.......EGG.R..MDD...Q | : 199 | SEQ ID NO: 7 |
| At_CesA8 | : VP.QTNNTSQ.SGIHAR------HISTVST.DSELN.EYGNPIWKNRVES..DKKDKKSK. | : 131 | SEQ ID NO: 8 |
| Ha_Cesa7 | : AGR.AHVSDEFPISTQPHGEHLSSLHKRVHPYG.PEYG.GRWDDKKDGG.....M.E..MH | : 212 | SEQ ID NO 27 |

```
                  *       260         *       280         *       300
```

| | | | |
|---|---|---|---|
| At_CesA1 | : QEKN--MLQMTGKYHEGKG-GEIEGTGSNGEELQMADDTRLPMSRVVPIPSSRLTPYRVV | : 277 | SEQ ID NO: 1 |
| At_CesA10 | : .D..--.IH...........-.......F...........D....V.A.....HF..A.M....I. | : 264 | SEQ ID NO: 10 |
| BnaA01g04600D | : ....-............-.......................I....P.H.............. | : 275 | SEQ ID NO: 21 |
| BnaC01g06090D | : ....-............-.......S...............I....P.H.............. | : 275 | SEQ ID NO: 22 |
| BnaC07g43790D | : .....--V..........-.......................I....P.H.............. | : 278 | SEQ ID NO: 19 |
| BnaA03g52020D | : .....--V..........-.......S...............I....P.H.............. | : 278 | SEQ ID NO:15 |
| Ha_Cesa1 | : ....--QMTNRYGG....GD..R............A.Q.........S..AH......I. | : 276 | SEQ ID NO: 25 |
| At_CesA3 | : ....--TGPVS.QAAS.RG.VDIDAS.DILAD.ALIN.EA.Q.L..K.S.....IN...M. | : 261 | SEQ ID NO: 3 |
| BnaAnng01240D | : ....NGGPVS.QAAS.RG.GDIDAS.DILAD.ALIN.EA.Q.L..K.S.....IN...M. | : 262 | SEQ ID NO: 20 |
| BnaA03g55200D | : ....NGGPVS.QAAS.RG.GDIDAS.DILAD.ALIN.EA.Q.L..K.S.....IN...M. | : 262 | SEQ ID NO: 12 |
| BnaC02g02440D | : ....TGPVS.QAAS.RG.GDIDAS.DILAD.ALIN.EA.Q.L..K.S.....IN...M. | : 262 | SEQ ID NO: 16 |
| BnaC03g02050D | : ....NGGPVS.QAAS.RG.GDIDAS.DILAD.ALIN.EA.Q.L..K.S.....IN...M. | : 262 | SEQ ID NO: 23 |
| Ha_Cesa3 | : .D..VAPMTTSRAAS.RG--QD.DASTDVLDDALIN.EA.Q.L..K.S.....IN...M. | : 275 | SEQ ID NO: 26 |
| Ha_Cesa3_fragm | : .NDKLQ.VKHQ.DGGG--..---QNDGDVDBPDMPKM.EG.Q.L..KL..S..KIN...M. | : 115 | SEQ ID NO: 28 |
| At_CesA2 | : .GEKLQVIKHE.GNNGRGS---NDDDELDBPDMP.M.EG.Q.L..KL..R...IN...ML | : 279 | SEQ ID NO: 2 |

Figure 2F

From
Figure 2F

```
At_CesA5       : .NEKYQVVKHD.------------DSSLGDGDDADIP.M.EG.Q.L...K....K..KIN...ML. : 266  SEQ ID NO: 5
At_CesA6       : .NEKLQVVRHE.------------DPDFEDGDDADFP.M.EG.Q.L..KI.K..KIN...ML. : 278  SEQ ID NO: 6
At_CesA9       : IEKLQVVKNERVNDGDGD------GFIVDELDDPG.P.M.EG.Q.L..KL.R...IN...ML. : 284  SEQ ID NO: 9
BnaA02g34360D  : .NEKLQVVRHE.------------DPDFEBGD---DIP.M.EG.Q.L..KI..K..KIN...ML. : 272  SEQ ID NO: 14
BnaA06g23700D  : .NEKLQVVRHE.------------DPDFEDGD---DIP.M.EG.Q.L..KI.K..KIN...ML. : 276  SEQ ID NO: 11
BnaA09g06990D  : .NEKLQVVRHE.------------DPDFEDGD---DIP.M.EG.Q.L..KI.K..KIN...ML. : 277  SEQ ID NO: 13
BnaC02g43280D  : .NEKLQVVRHE.------------DPDFEDGD---DIP.M.EG.Q.L..KI.K..KIN...ML. : 272  SEQ ID NO: 18
BnaC03g49550D  : .NEKLQVVRHE.------------DPDFEDGD---DIP.M.EG.Q.L..KI.K..KIN...ML. : 276  SEQ ID NO: 17
BnaC09g06600D  : .NEKLEVVKHE.------------DPDFEBGD---DIP.M.EG.Q.L..KI.K..KIN...ML. : 277  SEQ ID NO: 24
Ha_Cesa6_fragm : ------------------------------------------------------------ : -    SEQ ID NO: 29
At_CesA4       : ...RGLVTKGEQ------------TNEDKEDD..EYLDAEA.Q.LW.K...S..KIS...I. : 217  SEQ ID NO: 4
At_CesA7       : HG----------------------NLGPEPDDDP.MGLI.EA.Q.L..K...A..KIN...M. : 240  SEQ ID NO: 7
At_CesA8       : KK.DPKATKAEQHEAQ--------IPTQQHMEDTPPNTESGATDVL.V.I..RTKI.S..I. : 186  SEQ ID NO: 8
Ha_Cesa7       : .QG---------------------NL--GA.IDD.VDPDMA.L.EA.Q.L..K...A..KIN...M. : 256  SEQ ID NO 27

*         320         *         340         *         360
At_CesA1       : IILRLIILCFFLQYRTTHPVKRNAYPLWLTSVICHIMFAFSWLLDQFPKWYPINRETYLDR. : 337  SEQ ID NO: 1
At_CesA10      : .V......GV..H.......D..A............................F....... : 324  SEQ ID NO: 10
BnaA01g04600D  : .........G........D.......................................... : 335  SEQ ID NO: 21
BnaC01g06090D  : .........G........D.......................................... : 335  SEQ ID NO: 22
BnaC07g43790D  : .........G........D.......................................... : 338  SEQ ID NO: 19
BnaA03g52020D  : .........G...CS...ND......V.....V....L............F.VE....... : 338  SEQ ID NO: 15
Ha_Cesa1       : .........G...CS...ND......V.....V....L............F.VE....... : 336  SEQ ID NO: 25
```

| From Figure 2G | | | | |
|---|---|---|---|---|
| At_CesA3 | : .M...V...L.H..I.N..P..FA...V..........L..I..........F.V. | 321 | SEQ ID NO: | 3 |
| BnaAnng01240D | : .M...V...L.H..I.N..P..FT...I..............I...........F.V. | 322 | SEQ ID NO: | 20 |
| BnaA03g55200D | : .M...V...L.H..I.N..P..FT...I..............I...........F.V. | 322 | SEQ ID NO: | 12 |
| BnaC02g02440D | : .M...V...L.H..I.N..P..FT...I..............I...........F.V. | 322 | SEQ ID NO: | 16 |
| BnaC03g02050D | : .M...V...L.H..I.N..P..FT...I..............I...........F.V. | 322 | SEQ ID NO: | 23 |
| Ha_Cesa3 | : .V...V...I.H..I.N..T......L..............I...........L.V. | 335 | SEQ ID NO: | 26 |
| Ha_Cesa3_fragm | : LI.MA..GL.FH..IL...ND..A...I........V..IF........F..E..... | 175 | SEQ ID NO: | 28 |
| At_CesA2 | : LC..A...GL.FH..IL...ND..G..........V..I.............F..E.. | 339 | SEQ ID NO: | 2 |
| At_CesA5 | : .V...V..GL.FH..IL...ND..A..I........V..V.............E.... | 326 | SEQ ID NO: | 5 |
| At_CesA6 | : .V...V..GL.FH..IL...D..A..I........V..V.............E.... | 338 | SEQ ID NO: | 6 |
| At_CesA9 | : .FC..A..GL.FH..IL...ND.FG..........V..I.............E.... | 344 | SEQ ID NO: | 9 |
| BnaA02g34360D | : .V...V..SL.FH..IL...D..A..........V..V.............E.... | 332 | SEQ ID NO: | 14 |
| BnaA06g23700D | : .V...V..GL.FH..IL...D..A..I........V..V.............E.... | 336 | SEQ ID NO: | 11 |
| BnaA09g06990D | : .V...V..GL.FH..IL...D..A..I........V..V.............E.... | 337 | SEQ ID NO: | 13 |
| BnaC02g43280D | : .V...V..SL.FH..IL...D..A..I........V..V.............E.... | 332 | SEQ ID NO: | 18 |
| BnaC03g49550D | : .V...V..GL.FH..IL...D..A..I........V..V.............E.... | 336 | SEQ ID NO: | 17 |
| BnaC09g06600D | : .V...V..GL.FH..IL...D..A..I........V..V.............E.... | 337 | SEQ ID NO: | 24 |
| Ha_Cesa6_fragm | : | - | SEQ ID NO: | 29 |
| At_CesA4 | : .V...V..V..FRF.ILT.A.D.....I..............t..I........F... | 277 | SEQ ID NO: | 4 |
| At_CesA7 | : VA..V..AV..R..LLN..HD.LG..........V..I.............F..E.. | 300 | SEQ ID NO: | 7 |
| At_CesA8 | : .M....AL.FN..I....DS..G...........V..V............S...I.. | 246 | SEQ ID NO: | 8 |
| Ha_Cesa7 | : VA..F..AI..R..LMN..QDGFG..........I..............F..D.. | 316 | SEQ ID NO 27 |

To Figure 2I

From Figure 2H

| | | 380 | | 400 | | 420 | | | |
|---|---|---|---|---|---|---|---|---|---|
| At_CesA1 | : | LAIRYDRDGEPSQLVPVDVFVSTVDPLKEPPLVTANTVLSILSVDYPVDKVACYVSDDGS | | | | | : | 397 | SEQ ID NO: 1 |
| At_CesA10 | : | .........L..........A............................A....... | | | | | : | 384 | SEQ ID NO: 10 |
| BnaA01g04600D | : | ............E........T...M.......A............A.......... | | | | | : | 395 | SEQ ID NO: 21 |
| BnaC01g06090D | : | ............E........T...........A............A.......... | | | | | : | 395 | SEQ ID NO: 22 |
| BnaC07g43790D | : | .....................T...........A............A.......... | | | | | : | 398 | SEQ ID NO: 19 |
| BnaA03g52020D | : | ..........................................................| | | | | : | 398 | SEQ ID NO: 15 |
| Ha_CesA1 | : | .........L..E........A..I........A............A......S... | | | | | : | 396 | SEQ ID NO: 25 |
| At_CesA3 | : | .........L..E.......AA..I........A............A......S... | | | | | : | 381 | SEQ ID NO: 3 |
| BnaAnng01240D | : | .........L..E.......AA..I........A............A......S... | | | | | : | 382 | SEQ ID NO: 20 |
| BnaA03g55200D | : | .........L..E.......AA..I........A............A......S... | | | | | : | 382 | SEQ ID NO: 12 |
| BnaC02g02440D | : | .........L..E.......AA..I........A............A......S... | | | | | : | 382 | SEQ ID NO: 16 |
| BnaC03g02050D | : | .........L..E.......AA..I........A............A......S... | | | | | : | 382 | SEQ ID NO: 23 |
| Ha_CesA3 | : | .........SL.E.E......A..I........A............A......S... | | | | | : | 395 | SEQ ID NO: 26 |
| Ha_CesA3_fragm | : | .........SL.EKE.K..E.A......M.....I........A............A......S... | | | | | : | 235 | SEQ ID NO: 28 |
| At_CesA2 | : | .........SL.EKE.K.G.A.............I........A............A......S... | | | | | : | 399 | SEQ ID NO: 2 |
| At_CesA5 | : | .........SL.EKE.K.E.AG....M.......I........A....R.......A......S... | | | | | : | 386 | SEQ ID NO: 5 |
| At_CesA6 | : | .........SL.EKE.K.G.S.............I........A............A......S... | | | | | : | 398 | SEQ ID NO: 6 |
| At_CesA9 | : | .........SL.EKE.K.E.A.............I........A....E.......A......S... | | | | | : | 404 | SEQ ID NO: 9 |
| BnaA02g34360D | : | .........SL.EKE.K.E.S.............I........A............A......S... | | | | | : | 392 | SEQ ID NO: 14 |
| BnaA06g23700D | : | .........SL.EKE.K.E.SA............I........A....R.......A......S... | | | | | : | 396 | SEQ ID NO: 11 |
| BnaA09g06990D | : | .........SL.EKE.K.E.A.............I........A....R.......A......S... | | | | | : | 397 | SEQ ID NO: 13 |
| BnaC02g43280D | : | .........SL.EKE.K.E.S.............I........A............A......S... | | | | | : | 392 | SEQ ID NO: 18 |
| BnaC03g49550D | : | .........SL.EKE.K.E.SA............I........A....R.......A......S... | | | | | : | 396 | SEQ ID NO: 17 |

From
Figure 2I

| | | | | |
|---|---|---|---|---|
| BnaC09g06600D | : ..SL..EKE.K..E.SA.................I.........A.....R.......A. : | 397 | SEQ ID NO: | 24 |
| Ha_Cesa6_fragm | : ------------------------------------------------------------ : | - | SEQ ID NO: | 29 |
| At_CesA4 | : ..SM.FE....KNK.A................II..I......A.....N.S.......A. : | 337 | SEQ ID NO: | 4 |
| At_CesA7 | : ..SL.E.E...NM.A.................S.........AM....E.IS........A. : | 360 | SEQ ID NO: | 7 |
| At_CesA8 | : ..SA.FE.E.Q..AA..F..............I..........AL....S..........A. : | 306 | SEQ ID NO: | 8 |
| Ha_CesA7 | : ..SL.E.E...NM.C.................AM.......IS.I........A. : | 376 | SEQ ID NO: | 27 |

```
                    *        440         *        460         *        480
```

| | | | | |
|---|---|---|---|---|
| At_CesA1 | : AMLTFESLSETAEFAKKWVPFCKKFNTEPRAPEFYFAQKIDYLKDKIQPSFVKERRAMKR : | 457 | SEQ ID NO: | 1 |
| At_CesA3 | : ...........A......S............S............................ : | 444 | SEQ ID NO: | 10 |
| At_CesA10 | : ...........S............Q................................... : | 455 | SEQ ID NO: | 21 |
| BnaA01g04600D | : ...S..A.A..S...R........S.................................... : | 455 | SEQ ID NO: | 22 |
| BnaC01g06090D | : ...S..A.A..S...R.......YS.................................... : | 458 | SEQ ID NO: | 19 |
| BnaC07g43790D | : ...S..A.A..S...R.......YS......W..A......V.T...D............. : | 458 | SEQ ID NO: | 15 |
| BnaA03g55200D | : ...S..A.A..S...R.......YS......W..A......V.T...D............. : | 456 | SEQ ID NO: | 25 |
| BnaC03g52020D | : ...S.....R.............HS...................................  : | 441 | SEQ ID NO: | 3 |
| Ha_Cesa1 | : ...S.....A..S..R.......YS......W..A......V.T...D............. : | 442 | SEQ ID NO: | 20 |
| At_CesA3 | : ...S.....A..S..R.......YS......W..A......V.T...D............. : | 442 | SEQ ID NO: | 12 |
| BnaAnng01240D | : ...S.....A..S..R.......YS......W..A......V.T...D............. : | 442 | SEQ ID NO: | 16 |
| BnaA03g55200D | : ...S.....S..R..........Y.......W.........T...D............... : | 442 | SEQ ID NO: | 23 |
| BnaC02g02440D | : ...S.....A..D..R...............W.E.V.........VH...R.......... : | 455 | SEQ ID NO: | 26 |
| BnaC03g02050D | : ..................................VH...R..................... : | 295 | SEQ ID NO: | 28 |
| Ha_Cesa3 | : .................S.M...N.VH.A..R............................. : | 459 | SEQ ID NO: | 2 |
| Ha_Cesa3_fragm | | | | |
| At_CesA2 | | | | |

From Figure 2J

```
At_CesA5         : .........A.......R..........YT.......W.CH.M.....N.VH.A..R..... : 446 SEQ ID NO: 5
At_CesA6         : .........A.......R..........YC.......W.CH.M.....N.VH.A..R..... : 458 SEQ ID NO: 6
At_CesA9         : .........A.Y.....R........S..........W.S.M.....H.VD.A..M....... : 464 SEQ ID NO: 9
BnaA02g34360D    : .........A.......R..........YC.......W.CH.M.....N.VH.A..R..... : 452 SEQ ID NO: 14
BnaA06g23700D    : .........A.......R..........YC.......W.CH.M.....N.VH.A..R..... : 456 SEQ ID NO: 11
BnaA09g06990D    : .........A.......R..........YC.......W.CH.M.....N.VH.A..R..... : 457 SEQ ID NO: 13
BnaC02g43280D    : .........A.......R..........YC.......W.CH.M.....N.VH.A..R..... : 452 SEQ ID NO: 18
BnaC03g49550D    : .........A.......R..........YC.......W.CH.M.....N.VH.A..R..... : 456 SEQ ID NO: 17
BnaC09g46600D    : .........A.......R..........YC.......W.CH.M.....N.VH.A..R..... : 457 SEQ ID NO: 24
Ha_CesA6_fragm   : ------------------------------------------------------------- :  -  SEQ ID NO: 29
At_CesA4         : S..L.DT....S...RR.........Y.V........SE........V.TT....D....... : 397 SEQ ID NO: 4
At_CesA7         : S................R............S......M.TL.V...Q..VH.T.......... : 420 SEQ ID NO: 7
At_CesA8         : ...S...V..D.R...........YS.......SL....R.V..................... : 366 SEQ ID NO: 8
Ha_CesA7         : S..S.............A.............M.SD..........V..T.............. : 436 SEQ ID NO: 27

*        500         *        520         *        540
At_CesA1         : EYEEFKVRINALVAKAQKIPEEGWTMQDGTPWPGNNTRDHPGMIQVFLGHSGGLDTDGNE : 517 SEQ ID NO: 1
At_CesA10        : ..................I......D..E..S....P...................... : 504 SEQ ID NO: 10
BnaA01g04600D    : ......................V..................................... : 515 SEQ ID NO: 21
BnaC01g06090D    : ............................................................ : 515 SEQ ID NO: 22
BnaC07g43790D    : ............................................................ : 518 SEQ ID NO: 19
BnaC03g52020D    : ............................................................ : 518 SEQ ID NO:15
Ha_Cesa1         : ..................M................P........................ : 516 SEQ ID NO: 25
```

From Figure 2K

| | | | | | |
|---|---|---|---|---|---|
| At_CesA3 | : | ........I.....S.L.C....V.................QN....AE... | 501 | SEQ ID NO: | 3 |
| BnaAnng01240D | : | ........I.....S.L.C....V.................QN....AE... | 502 | SEQ ID NO: | 20 |
| BnaA03g55200D | : | ........I.....S.L.C....V.................QN....AE... | 502 | SEQ ID NO: | 12 |
| BnaC02g02440D | : | ........I.....S.L.C....V.................QN....AE... | 502 | SEQ ID NO: | 16 |
| BnaC03g02050D | : | ........I.....S.L.C....V.................QN....AE... | 502 | SEQ ID NO: | 23 |
| Ha_CesA3 | : | ......I..G......V.D..I..................QN....SE... | 515 | SEQ ID NO: | 26 |
| Ha_CesA3_fragm | : | ......I..G..TM..V.................DV....Q.....SE... | 355 | SEQ ID NO: | 28 |
| At_CesA2 | : | .D.....K.....T..V........................VR........ | 519 | SEQ ID NO: | 2 |
| At_CesA5 | : | .D.....K.....T..V.....................NN.VR.VEN... | 506 | SEQ ID NO: | 5 |
| At_CesA6 | : | .D.....K.....T..V.D...................SD.VR.VEN... | 518 | SEQ ID NO: | 6 |
| At_CesA9 | : | .D.....K...SVS.V.D........................VC.M..... | 524 | SEQ ID NO: | 9 |
| BnaA02g34360D | : | .D.....K.....T..V......................S..TD.VR.VEN... | 512 | SEQ ID NO: | 14 |
| BnaA06g23700D | : | .D.....K.....T..V......................SV.SD.VR.VEN... | 516 | SEQ ID NO: | 11 |
| BnaA09g06990D | : | .D.....K.....T..V......................S..SD.VR.VEN... | 517 | SEQ ID NO: | 13 |
| BnaC02g43280D | : | .D.....K.....T..V......................S..SD.VR.VEN... | 512 | SEQ ID NO: | 18 |
| BnaC03g49550D | : | .D.....K.....T..V......................SV.SD.VR.VEN... | 516 | SEQ ID NO: | 17 |
| BnaC09g06600D | : | .D.....K.....T..V......................S..SD.VR.VEN... | 517 | SEQ ID NO: | 24 |
| Ha_Cesa6_fragm | : | -------MLQGIISILIRVHKITEICICSTC..NN.VQ.VE.K : | 39 | SEQ ID NO: | 29 |
| At_CesA4 | : | .........K.....V.................Y.KE.AF.I......... | 457 | SEQ ID NO: | 4 |
| At_CesA7 | : | .......Q...S.V.L..I........K.....................F.VE.H... | 480 | SEQ ID NO: | 7 |
| At_CesA8 | : | .D...I.M......T......S...........................Y.AR.IE... | 426 | SEQ ID NO: | 8 |
| Ha_Cesa7 | : | ........M.A.A..I........K..........Q...T.VE... | 496 | SEQ ID NO | 27 |

From Figure 2L

| | | 560 | * | 580 | * | 600 | | |
|---|---|---|---|---|---|---|---|---|
| At_CesA1 | : | LPRLLIVSREKRPGFQHHKKAGAMNALIRVSAVLTNGAYLLNVDCDHYFNNSKAIKEAMC | : | 577 | SEQ ID NO: | 1 |
| At_CesA10 | : | ............................................................ | : | 564 | SEQ ID NO: | 10 |
| BnaA01g04600D | : | ............................................................ | : | 575 | SEQ ID NO: | 21 |
| BnaC01g06090D | : | ............................................................ | : | 575 | SEQ ID NO: | 22 |
| BnaC07g43790D | : | ............................................................ | : | 578 | SEQ ID NO: | 19 |
| BnaA03g52020D | : | ............................................................ | : | 578 | SEQ ID NO:15 |
| Ha_CesA1 | : | ..........................................L............... | : | 576 | SEQ ID NO: | 25 |
| At_CesA3 | : | ....V....................................................... | : | 561 | SEQ ID NO: | 3 |
| BnaAnng01240D | : | ....V.........................V.........PFI..L......I......LR. | : | 562 | SEQ ID NO: | 20 |
| BnaA03g55200D | : | ....V.........................V.........PFI..L......I......LR. | : | 562 | SEQ ID NO: | 12 |
| BnaC02g02440D | : | ....V.........................V.........PFI..L......I......LR. | : | 562 | SEQ ID NO: | 16 |
| BnaC03g02050D | : | ....V.........................V.........PFI..L......I......LR. | : | 562 | SEQ ID NO: | 23 |
| Ha_Cesa3 | : | ....V.........................V.........PF...L......I......LR. | : | 575 | SEQ ID NO: | 26 |
| Ha_Cesa3_fragm | : | ....V.........................V.......N.PFI..L......I......LR. | : | 415 | SEQ ID NO: | 28 |
| At_CesA2 | : | ....V.................D.......S.........S.AP........I......R.S. | : | 579 | SEQ ID NO: | 2 |
| At_CesA5 | : | ....V.................D.......S....G....S.AP........I......LR. | : | 566 | SEQ ID NO: | 5 |
| At_CesA6 | : | ....V.................D.......S....G....S.AP........I......LR. | : | 578 | SEQ ID NO: | 6 |
| At_CesA9 | : | ....V.................D.......S....G....S.AP........I......R.. | : | 584 | SEQ ID NO: | 9 |
| BnaA02g34360D | : | ....V.................D.......S....G....S.AP........I......LR. | : | 572 | SEQ ID NO: | 14 |
| BnaA06g23700D | : | ....V.................D.......S....G....S.AP........I......LR. | : | 576 | SEQ ID NO: | 11 |
| BnaA09g06990D | : | ....V.................D.......S....G....S.AP........I......LR. | : | 578 | SEQ ID NO: | 13 |
| BnaC02g43280D | : | ....V.................D.......S....G....S.AP........I......LR. | : | 577 | SEQ ID NO: | 18 |
| BnaC03g49550D | : | ....V.................D.......S....G....S.AP........I......LR. | : | 576 | SEQ ID NO: | 17 |

| Name | Sequence | Position | SEQ ID |
|------|----------|----------|--------|
| BnaC09g06600D | .....V.........D......S.....G..S.AP..........I......LR.... | 577 | SEQ ID NO: 24 |
| Ha_Cesa6_fragm | ..Q..V.........D..........IS.AP.M..........I......LR.... | 99 | SEQ ID NO: 29 |
| At_CesA4 | .....V......YA...........MV......APFM.L......I......R.S.. | 517 | SEQ ID NO: 4 |
| At_CesA7 | .....V...............V..AG......APFM.L...V......VR.... | 540 | SEQ ID NO: 7 |
| At_CesA8 | .....V.........Y.....E..V.......APFI.L...V......VR.... | 486 | SEQ ID NO: 8 |
| Ha_Cesa7 | .....V...........V..G.........APFM.L......L......AR.... | 556 | SEQ ID NO: 27 |

```
                    *        620         *        640         *        660
At_CesA1  : FMMDPAIGKKCCYVQFPQRFDGIDLHDRYANRNIVFFDINMKGLDGIQPVVVGTGCCFN :  637  SEQ ID NO: 1
At_CesA10 : ..........................................................  :  624  SEQ ID NO: 10
BnaA01g04600D : .....L......Y..................T....L....................  :  635  SEQ ID NO: 21
BnaC01g06090D : .....L......Y........................L....................  :  635  SEQ ID NO: 22
BnaC07g43790D : .....L......Y........................L....................  :  638  SEQ ID NO: 19
BnaA03g52020D : .....L......Y........................L....................  :  638  SEQ ID NO: 15
Ha_Cesa1  : ............Y..T.....................L....................  :  636  SEQ ID NO: 25
At_CesA3  : .....L...NL..QV.........KN...........LR.................V.  :  621  SEQ ID NO: 3
BnaAnng01240D : .....L...NL..QV.........KN.....T......LR.................V.  :  622  SEQ ID NO: 20
BnaC03g55200D : .....L...NL..QV.........KN.....T......LR.................V.  :  622  SEQ ID NO: 12
BnaC02g02440D : .....L...NL..QV.........KN.....T......LR.................V.  :  622  SEQ ID NO: 16
BnaC03g02050D : .....L...NL..QV.........KN.....T......LR.................V.  :  622  SEQ ID NO: 23
Ha_Cesa3  : .........NL..YV.........RN.....T......LR.................V.  :  635  SEQ ID NO: 26
Ha_Cesa3_fragm : .........NL..YV.........RN.....T......LR.................V.  :  475  SEQ ID NO: 28
At_CesA2  : ........QS..V..........R..S..V........I..................V.R  :  639  SEQ ID NO: 2
```

From
Figure 2N

| | | | | | |
|---|---|---|---|---|---|
| At_CesA5 | : | ............................QS...I......KS...S...V.........L..I........V.R. | : | 626 | SEQ ID NO: 5 |
| At_CesA6 | : | ............................QS...I......R....S...V.........L..I........V.R. | : | 638 | SEQ ID NO: 6 |
| At_CesA9 | : | ............................QS...I......R....S...V............I........V.R. | : | 644 | SEQ ID NO: 9 |
| BnaA02g34360D | : | ............................QS...I......R....S...V.........L..I........V.R. | : | 632 | SEQ ID NO: 14 |
| BnaA06g23700D | : | ............................QS...i......R....S...V.........L..I........V.R. | : | 636 | SEQ ID NO: 11 |
| BnaA09g06990D | : | ............................QS...I......R....S...V.........L..I........V.R. | : | 637 | SEQ ID NO: 13 |
| BnaC02g43280D | : | ............................QS...I......R....S...V.........L..I........V.R. | : | 632 | SEQ ID NO: 18 |
| BnaC03g49550D | : | ............................QS...I......R....S...V.........L..I........V.R. | : | 636 | SEQ ID NO: 17 |
| BnaC09g06600D | : | ............................QS...I......R....S...V............I........V.R. | : | 637 | SEQ ID NO: 24 |
| Ha_Cesa6_fragm | : | ............................TS...I......R....S...V............I........V.R. | : | 159 | SEQ ID NO: 29 |
| At_CesA4 | : | ............................L..QL..L........N............R..............V.. | : | 577 | SEQ ID NO: 4 |
| At_CesA7 | : | ............................L..Q...V.....TN.....T.......................... | : | 600 | SEQ ID NO: 7 |
| At_CesA8 | : | ............................L..VV.QDV.F..KS...................V.R......TV.R. | : | 546 | SEQ ID NO: 8 |
| Ha_Cesa7 | : | ............................L..Q..R.V....R........T............I........V.R. | : | 616 | SEQ ID NO 27 |

```
                              *         680         *         700         *         720
```

| | | | | | |
|---|---|---|---|---|---|
| At_CesA1 | : | RQALYGYDPVLTEEDLEPNIIVKSCCGSRKKGKSSKK | : | 674 | SEQ ID NO: 1 |
| At_CesA10 | : | ---------------------------F-----R-- | : | 660 | SEQ ID NO: 10 |
| BnaA01g04600D | : | -----------------K---------------N-- | : | 672 | SEQ ID NO: 21 |
| BnaC01g06090D | : | -----------------Q---------------N-- | : | 672 | SEQ ID NO: 22 |
| BnaC07g43790D | : | ---------------------------------K-- | : | 675 | SEQ ID NO: 19 |
| BnaA03g52020D | : | ------------A----I---------------K-- | : | 675 | SEQ ID NO:15 |
| Ha_Cesa1 | : | ---------------------------------NS- | : | 671 | SEQ ID NO: 25 |

To Figure 2P          Figure 2O

| From Figure 2O | | | |
|---|---|---|---|
| At_CesA3 | ......T.....E.PIKVKHKK.S-LLSKL..GSR.KN.KA------------------------------ | 656 | SEQ ID NO: 3 |
| BnaAnng01240D | ......T.....E.PIKVKHKK.S-LLSKI..GSR.KN.KS------------------------------ | 657 | SEQ ID NO: 20 |
| BnaC03g55200D | ......T.....E.PIKVKHKK.S-LLSKI..GSR.KN.KS------------------------------ | 657 | SEQ ID NO: 12 |
| BnaC02g02440D | ......T.....E.PIKVKHKK.S-LLSKL..GSR.KN.KS------------------------------ | 657 | SEQ ID NO: 16 |
| BnaC03g02050D | ......T.....E.PIKVKHKK.S-LLSKL..GSR.KN.KS------------------------------ | 657 | SEQ ID NO: 23 |
| Ha_Cesa3 | ......T.....E.P.KPKKKREKGFFS..F.ESR.KS.KSS----------------------------- | 672 | SEQ ID NO: 26 |
| Ha_Cesa3_fragm | ......T.....E.PIKPKKKREKGVLS..F.ASRNKS.NSN----------------------------- | 512 | SEQ ID NO: 28 |
| At_CesA2 | ............F.APKKKKPPGKTONCWPKWCCLCC.LRK.S---------------------------- | 676 | SEQ ID NO: 2 |
| At_CesA5 | ............F.APKKKKTKRMTCNCWPKWCLFCC.LRKNR---------------------------- | 663 | SEQ ID NO: 5 |
| At_CesA6 | ............F.APKKKKGPRKTCNCWPKWCLICF.SRKNRK--------------------------- | 676 | SEQ ID NO: 6 |
| At_CesA9 | ............F.APKKKQPPGRTCNCWPKWCCLCC.MRK..---------------------------- | 681 | SEQ ID NO: 9 |
| BnaC02g34360D | ............F.APKKKKAPRKTCNCWPKWCFICC.SRKNRK--------------------------- | 670 | SEQ ID NO: 14 |
| BnaA06g23700D | ............F.APKKKKAPRKTCNCWPKWCFMCC.SRKNRQ--------------------------- | 674 | SEQ ID NO: 11 |
| BnaA09g06990D | ............F.APKKKKAPRKTCNCWPKWCFMCC.SRKNRK--------------------------- | 675 | SEQ ID NO: 13 |
| BnaC02g43280D | ............F.APKKKKAPRKTCNCWPKWCFICC.SRKNRK--------------------------- | 670 | SEQ ID NO: 18 |
| BnaC03g49550D | ............F.APKKKKAPRKTCNCWPKWCFMCC.SRKNRQ--------------------------- | 674 | SEQ ID NO: 17 |
| BnaC09g06600D | ............F.APKKKKAPRKTCNCWPKWCFICC.SRKNRK--------------------------- | 675 | SEQ ID NO: 24 |
| Ha_Cesa6_fragm | ............APTKKKKPPGKTCNCLPKWLLCCCSSRK..AK--------------------G------ | 199 | SEQ ID NO: 29 |
| At_CesA4 | ............P....E.PVS.KRKKMTCDCWPSWICCCC.GGNRNHKSDSSRKKKSGIKSLFSKLKKKT | 637 | SEQ ID NO: 4 |
| At_CesA7 | ............E.PKGPKRP----KMI..GCCPCF.RRR.N----------------------------- | 633 | SEQ ID NO: 7 |
| At_CesA8 | ............S.PS---KPR--ILPQS.SSSCCCIT.-----------------K------------- | 576 | SEQ ID NO: 8 |
| Ha_Cesa7 | ............PKGPKRP----KMV..DCCPCF.RRK.N----------------------------- | 649 | SEQ ID NO: 27 |

To Figure 2Q    Figure 2P

From Figure 2P

```
                        *         740         *         760         *         780
At_Cesa1       : ---YNVE-KRRGINRSDSNAPLFNMEDIDEGFEG----YDDERSILMSQRSVEKRFGQSPV..  727  SEQ ID NO: 1
At_CesA10      : ---IPNYEDN.S.K.....V........DV...----E..M.L.V..KRL...........:  714  SEQ ID NO: 10
BnaA01g04600D  : ---..S.DQ.....S..............D...----....K...................:  726  SEQ ID NO: 21
BnaC01g06090D  : ---..S.DQ.....S..............D...----....K...................:  726  SEQ ID NO: 22
BnaC07g43790D  : ---.....DQQ..................D.E.----...KR...................:  729  SEQ ID NO: 19
BnaA03g52020D  : ---.....DQQ..................D.E.----....K...................:  729  SEQ ID NO:15
Ha_Cesa1       : ---MK.TD.K.AVK..E..I.I..T.M..V..----..E.K.L........L.......S.:  725  SEQ ID NO: 25
At_CesA3       : ---KKESD.KKSGRHT..TV.V..LD.E.V..A-GF..KAL.........M.L........A:  712  SEQ ID NO: 3
BnaAnng01240D  : ---KKDSD.KKSGRHT..TV.V..LD.E.V..A-GF..KAL.........M.L........A:  713  SEQ ID NO: 20
BnaA03g55200D  : ---KKDSD.KKSGRHT..TV.V..LD.E.V..A-GF..KAL.........M.L........A:  713  SEQ ID NO: 12
BnaC02g02440D  : ---KKDSD.KKSGRHT..TV.V..LD.E.V..A-GF..KAL.........M.L........A:  713  SEQ ID NO: 16
BnaC03g02050D  : ---KKDSD.KKSGRHT..TV.V..LD.E.V..A-GF..KAL.........M.L........A:  713  SEQ ID NO: 23
Ha_Cesa3       : ---KKGSD.KKSSKPV.PTV.V.SL..E.V..A-GF....K.L.......K.L........A:  728  SEQ ID NO: 26
Ha_Cesa3_fragm : ---KKGSD.KKSSRHD.PTV.V.SL..E.V..V-GI....K.L.......MTL........A:  568  SEQ ID NO: 28
At_CesA2       : ---KTKAKDKKTN-TKETSKQIHAL.NV..VIVPVSNVEK-RSEAT.LKL..K.........:  731  SEQ ID NO: 2
At_CesA5       : ---KSKTTDKKKK-NREASKQIHAL.N.E.---TKGTN.AAK.PEAA.LKL..K........:  717  SEQ ID NO: 5
At_CesA6       : --AKTVAADKKKK-NREASKQIHAL.N.E.-RVTKGSNV.Q.TEAM.MKL..K.........:  732  SEQ ID NO: 6
At_CesA9       : --TGKVKDNQRKKPKETSKQIHAL.H.E.LQVTNAEN---NSETA.LKL..K..........:  735  SEQ ID NO: 9
BnaA02g34360D  : --AKTLAAADKKKKNREASKQIHAL.N.E.-PVTKGSNV.L.SEAM.LKL..K.........:  727  SEQ ID NO: 14
BnaA06g23700D  : --AKKVAADKKKK-NREASKQIHAL.N.E.-SVTKGSNV.Q.TEAM.LKL..K.........:  730  SEQ ID NO: 11
BnaA09g06990D  : --AKTAAADKKKK-NREASKQIHAL.N.E.RVTTKGSNV.L.TEAM.LKL..K.........:  732  SEQ ID NO: 13
BnaC02g43280D  : --AKTLAAADKKKKNREASKQIHAL.N.E.-PVSKGSNV.L.SEVM.LKL..K.........:  727  SEQ ID NO: 18
BnaC03g49550D  : --AKKVAADKKKK-NREASKQIHAL.N.E.-SVTKGSNV.Q.TEAM.LKL..K.........:  730  SEQ ID NO: 17
```

| Name | Sequence | Length | SEQ ID NO |
|---|---|---|---|
| BnaC09g06600D | --AKTAAADKKKK-NREASKQIHAL.N.E.RVTTKGSNV.L.TEAM.LKL..K......... | 732 | SEQ ID NO: 24 |
| Ha_Cesa6_fragm | KSKKSK.KSTK.KKSK.PPTQIHAL.N.E.I..I---.S.K.S..P.IKF..K......... | 256 | SEQ ID NO: 29 |
| At_CesA4 | KKKSDDKTMSSYSRKRS.TEAI.DL..E..L..-YDEL.K.S....KNF......M...... | 695 | SEQ ID NO: 4 |
| At_CesA7 | ---KKFSKNDMNGDVAALGGAEGDK.HIMSE------MN---------F..T....SI... | 673 | SEQ ID NO: 7 |
| At_CesA8 | KQPQDPSEIYKDAK.EELD.AI..LG.L.N------YDEYD..M.I..T.F..T.L.t... | 630 | SEQ ID NO: 8 |
| Ha_Cesa7 | ---PKF.KHGDVE.VQGY.--DDDK.LLKSQ----------MN-------F..K....AI. | 687 | SEQ ID NO: 27 |
|  |  *          800           *          820           *          840 |  |  |
| At_CesA1 | FIAATFMEQGIPPTTNPATLLKEAIHVISCGYEDKTEWGKREIGMTYGSVTEDILTGFKM | 787 | SEQ ID NO: 1 |
| At_CesA10 | ...................L.S..L............A..D................. | 774 | SEQ ID NO: 10 |
| BnaA01g04600D | .............................................................. | 786 | SEQ ID NO: 21 |
| BnaC01g06090D | .............................................................. | 786 | SEQ ID NO: 22 |
| BnaAnng01240D | .............................................................. | 789 | SEQ ID NO: 19 |
| BnaC07g43790D | .............................................................. | 789 | SEQ ID NO: 15 |
| BnaA03g52020D | .............................................................. | 785 | SEQ ID NO: 25 |
| Ha_Cesa1 | ....S........M....S........................................ | 772 | SEQ ID NO: 3 |
| At_CesA3 | .V.S.L.N..V..SAT.EN.....................SD..M.............. | 773 | SEQ ID NO: 20 |
| BnaA03g55200D | .V.S.L.N..V...ET.EN.....................SD..M.............. | 773 | SEQ ID NO: 12 |
| BnaC02g02440D | .V.S.L.N..V...ET.EN.....................SD..M.............. | 773 | SEQ ID NO: 16 |
| BnaC03g02050D | .V.S.L.N..V...ET.EN.....................SD..M.............. | 773 | SEQ ID NO: 23 |
| Ha_Cesa3 | .V.S.L.N..V.QSAA.E......................D..N............... | 788 | SEQ ID NO: 26 |
| Ha_Cesa3_fragm | .V.S.L.N..V.QSAA.E.........................D.S............. | 628 | SEQ ID NO: 28 |
| At_CesA2 | .V.SAVLQN..V.RNAS..C..R..Q.................................. | 791 | SEQ ID NO: 2 |

From Figure 2Q

To Figure 2S

From Figure 2R

| | | | |
|---|---|---|---|
| At_CesA5 | ..V.SAG..N..LARNAS..S..R..Q............ | 777 | SEQ ID NO: 5 |
| At_CesA6 | ..V.SAR..N..MARNAS..C.....Q............ | 792 | SEQ ID NO: 6 |
| At_CesA9 | LV.S.LLLN..V.SNV...S..R.S.Q............ | 795 | SEQ ID NO: 9 |
| BnaA02g34360D | ..V.SAR.QN..MARNAS..C.....E............ | 787 | SEQ ID NO: 14 |
| BnaA06g23700D | ..V.SAR.QN..MARNAS..C.....Q............ | 790 | SEQ ID NO: 11 |
| BnaA09g06990D | ..V.SAR..N..MARNAS..C.....Q............ | 792 | SEQ ID NO: 13 |
| BnaC02g43280D | ..V.SAR.QN..MARNAS..C.....Q............ | 787 | SEQ ID NO: 18 |
| BnaC03g49550D | ..V.SAR.QN..MARNAS..C.....Q............ | 790 | SEQ ID NO: 17 |
| BnaC09g06600D | ..V.SAR..N..MARNAS..C.....Q............ | 792 | SEQ ID NO: 24 |
| Ha_Cesa6_fragm | ...S.LL.D..V..GASS.S...........V........ | 316 | SEQ ID NO: 29 |
| At_CesA4 | ...S.L..N..L.EA.TSS.I..........E......R. | 755 | SEQ ID NO: 4 |
| At_CesA7 | VTS.L.E..V.SSS..V..................T.L..I | 733 | SEQ ID NO: 7 |
| At_CesA8 | ..ES.L..N..V.DSV..S..I.............E...I.. | 690 | SEQ ID NO: 8 |
| Ha_Cesa7 | VTS.L.VD..V..SSS..S................L.L..I | 747 | SEQ ID NO: 27 |

```
        *         860         *         880         *         900
```

| | | | |
|---|---|---|---|
| At_CesA1 | HARGWISTYCNPPRPAFKGSAPINLSDRLNQVLRWALGSIEILLSRHCPIWYGYHGR-LR | 846 | SEQ ID NO: 1 |
| At_CesA10 | ......................V.S.................................M.-.K | 833 | SEQ ID NO: 10 |
| BnaA01g04600D | .......M.................................................T.-.. | 845 | SEQ ID NO: 21 |
| BnaC01g06090D | .......M.................................................T.-.. | 845 | SEQ ID NO: 22 |
| BnaC07g43790D | .......M.................................................T.-.. | 848 | SEQ ID NO: 19 |
| BnaA03g52020D | .......M.................................................T.-.. | 848 | SEQ ID NO: 15 |
| Ha_Cesa1 | .................M..........................................N.K.-.K | 844 | SEQ ID NO: 25 |

| | | | | | | |
|---|---|---|---|---|---|---|
| At_CesA3 | : | ......R....M.KL.. | ........ | V..F.....N..-.K | : 831 | SEQ ID NO: 3 |
| BnaAnng01240D | : | ......R....M.KL.. | ........ | V..F.....S..-.K | : 832 | SEQ ID NO: 20 |
| BnaA03g55200D | : | ......R....M.KL.. | ........ | V..F.....S..-.K | : 832 | SEQ ID NO: 12 |
| BnaC02g02440D | : | ......R....M.KL.. | ........ | V..F.....S..-.K | : 832 | SEQ ID NO: 16 |
| BnaC03g02050D | : | ......R....M.KL.. | ........ | V..F.....S..-.K | : 832 | SEQ ID NO: 23 |
| Ha_Cesa3 | : | ......R....M..... | ........ | V..F.....S..-.K | : 847 | SEQ ID NO: 26 |
| Ha_Cesa3_fragm | : | ......R....M...A. | ........ | ...F.....S..-.K | : 687 | SEQ ID NO: 28 |
| At_CesA2 | : | ...CH..R.V..M.K.A | .....H.. | V..F.....G.G-.K | : 850 | SEQ ID NO: 2 |
| At_CesA5 | : | ...SH..R.V..T.KI. | .....H.. | V..F.....G.G-.K | : 836 | SEQ ID NO: 5 |
| At_CesA6 | : | ...SH..R.V..T.KlA | .....H.. | V..F.....G.G-.K | : 851 | SEQ ID NO: 6 |
| At_CesA9 | : | ...CH..R.V..M.K.A | .....H.. | V..F.....G.G-.K | : 854 | SEQ ID NO: 9 |
| BnaA02g34360D | : | ...SH..R.V..T.KL. | .....H.. | V..F.....G.G-.K | : 846 | SEQ ID NO: 14 |
| BnaA06g23700D | : | ...SH..R.V..T.KL. | .....H.. | V..F.....G.G-.K | : 849 | SEQ ID NO: 11 |
| BnaA09g06990D | : | ...SH..R.V..T.KL. | .....H.. | V..F.....G.G-.K | : 851 | SEQ ID NO: 13 |
| BnaC02g43280D | : | ...SH..R.V..M.K.A | .....H.. | V..F.....G.G-.K | : 846 | SEQ ID NO: 18 |
| BnaC03g49550D | : | ...SH..R.V..T.KL. | .....H.. | V..F.....G.G-.K | : 849 | SEQ ID NO: 17 |
| BnaC09g06600D | : | ...SH..R.V..T.KL. | .....H.. | V..F.....G.G-.K | : 851 | SEQ ID NO: 24 |
| Ha_Cesa6_fragm | : | ...CH..R.V..I.K.A | .....H.. | V........GCG-.K | : 375 | SEQ ID NO: 29 |
| At_CesA4 | : | ...C...K.V..M.K.. | ........ | V..FF...L.AWG.-K.K | : 814 | SEQ ID NO: 4 |
| At_CesA7 | : | ...C...R....M.K.. | ........ | V..FF..S.L...K.GK.K | : 793 | SEQ ID NO: 7 |
| At_CesA8 | : | ...C...R....M.L.. | ........ | V..F....L...CS.GR.K | : 750 | SEQ ID NO: 8 |
| Ha_Cesa7 | : | ...C...R....M.K.. | ........ | V..FF..S.LL..K.GN.K | : 807 | SEQ ID NO: 27 |

From Figure 2T

```
                        *         920         *         940         *         960
At_CesA1         : LLERIAYINTIVYPITSIPLIAYCILPAFCLITDRFITPEISNYASIWFILLFISIAVTG..    906  SEQ ID NO: 1
At_CesA10        : .................L....M.........NT......L..IC.M...A..YASA..    893  SEQ ID NO: 10
BnaA01g04600D    : .................L....AL.............K......................    905  SEQ ID NO: 21
BnaC01g06090D    : .................L....AL.............K......................    905  SEQ ID NO: 22
BnaC07g43790D    : .................L....AL.............K......................    908  SEQ ID NO: 19
BnaA03g52020D    : .................L....AL.............K......................    908  SEQ ID NO: 15
Ha_CesA1         : .................L..L..........V..V..L.GK........M......A..    904  SEQ ID NO: 25
At_CesA3         : E..F.V..TI......IM.T......V..F.NQ....Q...I.........LS..L..FA.    891  SEQ ID NO: 3
BnaAnng01240D    : E..F.V..TI..L..V.LF.T....V..F.NQ....Q...I.........LS..L..FA.    892  SEQ ID NO: 20
BnaA03g55200D    : E..F.V..TI..L..V.LL.T....V..F.NQ....Q...I.........LS..L..FA.    892  SEQ ID NO: 12
BnaC02g02440D    : E..F.V..TI..L..V.LL.T....V..F.NQ....Q...I.........LS..L..FA.    892  SEQ ID NO: 16
BnaC03g02050D    : E..F.V..TI..L..V.LL.T....V..F.NQ....Q...I.........LS..L..FA.    892  SEQ ID NO: 23
Ha_CesA3         : W..F.....TI.....IV.I.....IV.T..V..L.GK........Q...L..S..L..FA.    907  SEQ ID NO: 26
Ha_CesA3_fragm   : W..L.C...TI..VA..IV.T..V.S...V..L.GK....Q......L..L........    736  SEQ ID NO: 28
At_CesA2         : W..FS...SV...M.L...V..S...I..LGK..V.............G.L.M.M....    910  SEQ ID NO: 2
At_CesA5         : W...LS...SV...W...IV..S...I..LGK..V...............L.MA..G....    896  SEQ ID NO: 5
At_CesA6         : W...LS...SV...W.L..V.S...I..LGK..V...............L.MA..S..I.    911  SEQ ID NO: 6
At_CesA9         : W...FS...SV...M.L..LV.S...I..LGK..V...........G.L.L.M.M....    914  SEQ ID NO: 9
BnaA02g34360D    : W...LS...SV...M.L..M..S...I..LGK..V...............L.MA..S..I.    906  SEQ ID NO: 14
BnaA06g23700D    : W...LS...SV...W..L..V.S...I..LGK..V...............L.MA..S..I.    909  SEQ ID NO: 11
BnaA09g06990D    : W...LS...SV...M.L..V.S...I..LGK..V...............L.MA..S..I.    911  SEQ ID NO: 13
BnaC02g43280D    : W...LS...SV...M.L..V.S...I..LGK..V...............L.MA..S...    906  SEQ ID NO: 18
BnaC03g49550D    : W...LS...SV...M.L..V.S...I..LGK..V...............L.MA..S..I.    909  SEQ ID NO: 17
```

To Figure 2V

From Figure 2U

| Name | Sequence | Pos | SEQ ID |
|---|---|---|---|
| BnaC09g06600D | W..LS...SV....W..L..V..S....I..L.GK..V............LMA.S........ | 911 | SEQ ID NO: 24 |
| Ha_Cesa6_fragm | P...FS...SV..L.V..L...T.V.L.GK..V...........L.M.M.L.......S.. | 435 | SEQ ID NO: 29 |
| At_CesA4 | ....I..L....F.....L..TI..V.L.GK....T.N.F.....IA..L..IA.A.. | 874 | SEQ ID NO: 4 |
| At_CesA7 | W..F.A..TI.F.......I.L..K..M.P.TF..LF.S..M..I... | 853 | SEQ ID NO: 7 |
| At_CesA8 | ...Q.I.....F.I.V..T..I.L.GK...TL..L..ML.IG.........IL.S | 810 | SEQ ID NO: 8 |
| Ha_CesA7 | W..F..V..TI..F.AL..L.....I..L.GK..M...TL..LF..S..L..FA.. | 867 | SEQ ID NO: 27 |

|  | * 980 * 1000 * 1020 |  |  |
|---|---|---|---|
| At_CesA1 | ILELRWSGVSIEDWWRNEQFWVIGGTSAHLFAVEQGLIKVLAGIDTNFTVTSK-ATDEDG | 965 | SEQ ID NO: 1 |
| At_CesA10 | .....K..D.AL.......................F.....................-S........ | 952 | SEQ ID NO: 10 |
| BnaA01g04600D | ............................................................-S........ | 964 | SEQ ID NO: 21 |
| BnaC01g06090D | ............................................................-S........ | 964 | SEQ ID NO: 22 |
| BnaC07g43790D | V..............................................V............-S........ | 967 | SEQ ID NO: 19 |
| BnaA03g52020D | V..............................................V............-S........ | 967 | SEQ ID NO:15 |
| Ha_Cesa1 | ................................................V............-S........ | 963 | SEQ ID NO: 25 |
| At_CesA3 | ....M....G.DE...................................V............-S........ | 950 | SEQ ID NO: 3 |
| BnaAnng01240D | ....M....G.DE...................................V............-S........ | 951 | SEQ ID NO: 20 |
| BnaA03g55200D | ....M....G.DE...................................V............-S........ | 951 | SEQ ID NO: 12 |
| BnaC02g02440D | ....M....G.DE...................................V............-S........ | 951 | SEQ ID NO: 16 |
| BnaC03g02050D | ....M....G.DE..................................................-S........ | 951 | SEQ ID NO: 23 |
| Ha_Cesa3 | ................A.S....L..............................VN........-.A.DG- | 966 | SEQ ID NO: 26 |
| Ha_Cesa3_fragm | ------------------------------------------------------------ | - | SEQ ID NO: 28 |
| At_CesA2 | ...MQ.G..G.D................................................-.A.DG- | 968 | SEQ ID NO: 2 |

From
Figure 2V

```
At_CesA5        : .........MQ.GK.G.D.........V........................VE.........-.A.DG- :  954  SEQ ID NO: 5
At_CesA6        : .........MQ.GK.G.D.........V........L...............................A.DG- :  969  SEQ ID NO: 6
At_CesA9        : .........MQ.GKIG.D.........V.S......L...............VS.........-.A.DG- :  972  SEQ ID NO: 9
BnaA02g34360D   : .........MQ.GK.G.D.........V........L................V.........-.A.DG- :  964  SEQ ID NO: 14
BnaA06g23700D   : .........MQ.GK.G.D.........V........L................V.........-.A.DG- :  967  SEQ ID NO: 11
BnaA09g06990D   : .........MQ.GK.G.D.........V........L................V.........-.A.DG- :  969  SEQ ID NO: 13
BnaC02g43280D   : .........MQ.GK.G.D.........V........L................V.........-.A.DG- :  964  SEQ ID NO: 18
BnaC03g49550D   : .........MQ.GK.G.D.........V........L................V.........-.A.DG- :  967  SEQ ID NO: 17
BnaC09g06600D   : .........MQ.GK.G.D.........V........L................V.........-.A.DG- :  969  SEQ ID NO: 24
Ha_Cesa6_fragm  : .........IQ.G..G.D.L......N.I......V.....LV.........VN........--GGD.. :  493  SEQ ID NO: 29
At_CesA4        : .......................................V.........F.V........G.S..AD :  934  SEQ ID NO: 4
At_CesA7        : .........................E........i....V....I......D............ :  911  SEQ ID NO: 7
At_CesA8        : ...V.....................L.........V.....F.M.L...........--.AD.L : 868  SEQ ID NO: 8
Ha_Cesa7        : ..........................E.........V.....I.......DE-.......... :  925  SEQ ID NO: 27

*      1040       *       1060       *      1080
At_CesA1        : DFAELYIFKWTALLIPPTTVLLVNLIGIVAGVSYAVNSGYQSWGPLFGKLFFAIMWVIAHL : 1025  SEQ ID NO: 1
At_CesA10       : ............V..S....I..V......I..........M.L.F.V......... : 1012  SEQ ID NO: 10
BnaA01g04600D   : ................V.M.....I.........I.................... : 1024  SEQ ID NO: 21
BnaC01g06090D   : .......................V....................i.......... : 1024  SEQ ID NO: 22
BnaC07g43790D   : .......................V.............................. : 1027  SEQ ID NO: 19
BnaC03g52020D   : .......................V.............................. : 1027  SEQ ID NO:15
Ha_Cesa1        : .........................i..V..S..TI........i..V......... : 1023  SEQ ID NO: 25
```

From Figure 2W

| | | | | | |
|---|---|---|---|---|---|
| At_CesA3 | : | .................L...T........LI...VV.....I.........F..V.. | : | 1010 | SEQ ID NO: 3 |
| BnaAnng01240D | : | .................L...T........LI...VV...F..I........F..V.. | : | 1011 | SEQ ID NO: 20 |
| BnaC03g55200D | : | .................L...T........LI...VV...F..I........F..V.. | : | 1011 | SEQ ID NO: 12 |
| BnaC02g02440D | : | .................L...T........LI...VV...F..I........F..V.. | : | 1011 | SEQ ID NO: 16 |
| BnaC03g02050D | : | .................L...T........LI...VV...F..I........F..V.. | : | 1011 | SEQ ID NO: 23 |
| Ha_Cesa3 | : | .................L...T........LI...I....I...........F..V.. | : | 1026 | SEQ ID NO: 26 |
| Ha_Cesa3_fragm | : | ------------------------------------------------------------ | : | --- | SEQ ID NO: 28 |
| At_CesA2 | : | A.S..............T............L.II.I.VIV..D.ISN.D......R..V.. | : | 1028 | SEQ ID NO: 2 |
| At_CesA5 | : | E.S..............S............L.II.V.VIV.I.D.ISN.D......R..F..L.. | : | 1014 | SEQ ID NO: 5 |
| At_CesA6 | : | E.SD.L...........S.........M.L.II.V..VIV...D.ISN.D......R......I.. | : | 1029 | SEQ ID NO: 6 |
| At_CesA9 | : | E.S..............S............L.III.IV.VIV...D.I.N.D......R......V.. | : | 1032 | SEQ ID NO: 9 |
| BnaA02g34360D | : | E.SD.L...........S............L.II.V....V.I.D.ISN.D......R......VI.. | : | 1024 | SEQ ID NO: 14 |
| BnaA06g23700D | : | E.SD.L...........S............L.II.M.....V.I.D.ISN.D......R......VI.. | : | 1027 | SEQ ID NO: 11 |
| BnaA09g06990D | : | E.SD.L...........S............L.II.V.....V.I.D.ISN.D......R......VI.. | : | 1029 | SEQ ID NO: 13 |
| BnaC02g43280D | : | E.SD.L...........S............L.II.V.....V.I.D.ISN.D......R......VI.. | : | 1024 | SEQ ID NO: 18 |
| BnaC03g49550D | : | E.SD.L...........S............L.II.V.....V.I.D.ISN.D......R......VI.. | : | 1027 | SEQ ID NO: 17 |
| BnaC09g06600D | : | E.SD.L...........S............L.II.V.....V.I.D.ISN.D......R......VI.. | : | 1029 | SEQ ID NO: 24 |
| Ha_Cesa6_fragm | : | E.S...L...........T............LIIL.MV.V......D.I..G.........F..V.. | : | 509 | SEQ ID NO: 29 |
| At_CesA4 | : | E.GD.L...T................II.IV.V..I.D.I.N.........SF..V.. | : | 994 | SEQ ID NO: 4 |
| At_CesA7 | : | ..G..A...T................II.IV.V..I.D.I.N................ | : | 971 | SEQ ID NO: 7 |
| At_CesA8 | : | E.G...V...T.........SL.II..VV...F.D.L.K..EA......V..F..L.. | : | 928 | SEQ ID NO: 8 |
| Ha_Cesa7 | : | E.G...A...T............I.III.MV.V........I.D.I.N.........F..L.. | : | 985 | SEQ ID NO: 27 |

From Figure 2X

```
At_CesA1         : YPFLKGLIGRQNRTPTIVIWSVLLASIFSLLWVRINPFVDAN--PNANNFNGKGGVF---- : 1081  SEQ ID NO: 1
At_CesA10        : ...............A............................STT-GVMS.SFMGF---- : 1065  SEQ ID NO: 10
BnaA01g04600D    : ............................................SVT--A..PNAVP..... : 1080  SEQ ID NO: 21
BnaC01g06090D    : ............................................SVI--A..PNAVP..... : 1080  SEQ ID NO: 22
BnaC07g43790D    : ......M.....................................SVT--Q..PTAVP..... : 1083  SEQ ID NO: 19
BnaA03g52020D    : ......M.....................................SVT--E..PTAVP..... : 1083  SEQ ID NO:15
Ha_Cesa1         : .........................I.................D..TTDD--KLDSIRGQC.IDC- : 1079  SEQ ID NO: 25
At_CesA3         : ......M.......V.............................D..TSRV--TGPDILECGINC-- : 1065  SEQ ID NO: 3
BnaAnng01240D    : ......M.......V.............................D..TKRV--TGPDILECGINC-- : 1066  SEQ ID NO: 20
BnaC03g55200D    : ......M.......V.............................D..TKRV--TGPDILECGINC-- : 1066  SEQ ID NO: 12
BnaC02g02440D    : ......M.......V.............................D..TKRV--TGPDILECGINC-- : 1066  SEQ ID NO: 16
BnaC03g02050D    : ......M.......V.............................D..TKRV--TGPDILECGINC-- : 1066  SEQ ID NO: 23
Ha_Cesa3         : ......M.K.....V..I...........................D..TTKV--TGPDVKFCGINC-- : 1081  SEQ ID NO: 26
Ha_Cesa3_fragm   : ----------------------------------------------------------------- : -     SEQ ID NO: 28
```

From Figure 2Y

```
At_CesA2         : ........M..K.DKM...IV....I......LT.....V....AK---GGPVLEICGLNCGN : 1084   SEQ ID NO: 2
At_CesA5         : ...........K.D.M...IL....I......LT.....V....AK---GGPILEICGLDCL- : 1069   SEQ ID NO: 5
At_CesA6         : ...........K.D.M...IV....I......LT.....V....AK---GGPILEICGLDCL- : 1084   SEQ ID NO: 6
At_CesA9         : ...........K.D.V...IL....I......LT.....V....SK---DGPVLEICGLDCLK : 1088   SEQ ID NO: 9
BnaA02g34360D    : ...........K.D.M...IV....I......LT.....V....AK---GGPVLEICGLDCL- : 1079   SEQ ID NO: 14
BnaA06g23700D    : ...........K.D.M...I.I..I......LT.....V....AK---GGPILEICGLDCL- : 1082   SEQ ID NO: 11
BnaA09g06990D    : ...........K.D.M...IV....I......LT.....V....AK---GGPILEICGLDCL- : 1084   SEQ ID NO: 13
BnaC02g43280D    : ...........K.D.M...IV....I......LT.....V....AK---GGPILEICGLDCL- : 1079   SEQ ID NO: 18
BnaC03g49550D    : ...........K.D.M...IV....I......LT.....V....AK---GGPVLEICGLDCL- : 1082   SEQ ID NO: 17
BnaC09g06600D    : ...........K.D.M...IV....I......LT.....V....AK---GGPILEICGLDCL- : 1084   SEQ ID NO: 24
Ha_Cesa6_fragm   : ---------------------------------------------------------------- :    -   SEQ ID NO: 29
At_CesA4         : ........M........VL..I......V....D..LPK--QTGPLLKQCGVDC-- : 1049   SEQ ID NO: 4
At_CesA7         : ........M........VI..........V....D...LKT--KGPDTSKCGINC-- : 1026   SEQ ID NO: 7
At_CesA8         : ........M.........L..I..V..V.........SKTDTTSLSNCLLIDC-- :  985   SEQ ID NO: 8
Ha_Cesa7         : ........M.K.......VI..I........D...LKT--KGPDVKQCGINC-- : 1040   SEQ ID NO 27
```

Figure 2Z

PLANTS HAVING INCREASED TOLERANCE TO HERBICIDES

This application is a National Stage application of International Application No. PCT/IB2016/056348, filed Oct. 21, 2016, which claims priority to European Patent Application No. 15190979.3, filed on Oct. 22, 2015.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "150052_SubSeqlisting.txt", which was created on Sep. 27, 2018 and is 284,175 bytes in size. The subject matter of the Sequence Listing is incorporated herein in its entirety by reference.

FIELD OF THE INVENTION

The present invention relates in general to methods for conferring on plants agricultural level tolerance to herbicides. Particularly, the invention refers to plants having an increased tolerance to herbicides, more specifically to herbicides which inhibit the enzyme cellulose synthase (CESA), also known cellulose biosynthesis inhibitors (CBI). More specifically, the present invention relates to methods and plants obtained by mutagenesis and cross-breeding and transformation that have an increased tolerance to herbicides, particularly CESA-inhibiting herbicides.

BACKGROUND OF THE INVENTION

Plant cell walls are complex structures composed of high-molecular-weight polysaccharides, proteins, and lignins. Among the wall polysaccharides, cellulose, a hydrogen-bonded β-1,4-linked glucan microfibril, is the main load-bearing wall component and a key precursor for industrial applications. Cellulose is synthesized by large multimeric cellulose synthase (CESA) complexes (E.C.2.4.1.12), tracking along cortical microtubules at the plasma membrane. The only known components of these complexes are the cellulose synthase proteins. Recent studies have identified tentative interaction partners for the CESAs and shown that the migratory patterns of the CESA complexes depend on phosphorylation status (for review see Endler and Persson, Molecular Plant, 2011, Volume 4, Number 2, Pages 199-211, and references contained therein). For example, cotton cellulose synthase genes, termed CESA1 and CESA2, were identified in a collection of expressed sequence tag (EST) sequences on the basis of weak sequence similarity to genes for cellulose synthase from bacteria (Richmond and Somerville. Plant Physiology, 2000, Vol. 124, 495-498; and references contained therein) In addition, the genes were expressed at high levels in cotton fibers at the onset of secondary wall synthesis and a purified fragment of one of the corresponding proteins as shown to bind UDP-Glc, the proposed substrate for cellulose biosynthesis. The conclusion that the cotton CESA genes are cellulose synthases is supported by results obtained with two cellulose-deficient *Arabidopsis* mutants, rsw1 and irx3 (Richmond and Somerville. Plant Physiology, Vol. 124, 2000, 495-498; and references contained therein). The genes corresponding to the RSW1 and IRX3 loci exhibit a high degree of sequence similarity to the cotton CESA genes and are considered orthologs. Ten full-length CESA genes have been sequenced from *Arabidopsis*, and there is a genome survey sequence that may indicate one additional family member. Reiterative database searches using the *Arabidopsis* Rsw1 (AtCESA1) and the cotton CESA polypeptide sequences as the initial query sequences revealed a large superfamily of at least 41 CESA-like genes in *Arabidopsis*. Based on predicted protein sequences, these genes were grouped into seven clearly distinguishable families (Richmond and Somerville. Plant Physiology, Vol. 124, 2000, 495-498; and references contained therein): the CESA family, which includes RSW1 and IRX3 (AtCESA7), and six families of structurally related genes of unknown function designated as the "cellulose synthase-like" genes (CslA, CslB, CslC, CslD, CslE, and CslG).

WO 2013/142968 describes plant cellulose synthase (CESA) alleles identified by mutagenizing plants and screening said plants with a cellulose biosynthetic inhibitor (CBI). CBIs employed in WO 2013/142968 include dichlobenil, chlorthiamid, isoxaben, flupoxam, and quinclorac, particularly isoxaben or flupoxam (named fpx1-1 to fpx1-3 [CESA3], fxp2-1 to fxp2-3 [CESA1] and ixr1-1 to ixr1-7 [CESA3], ixr2-1 to ixr2-2 [CESA6] mutants of *Arabidopsis* CESA wildtype enzymes)

The inventors of the present invention have now surprisingly found that over-expression of mutated variants of the *Brassica napus* and *Helianthus annuus* orthologues cellulose synthase forms disclosed in WO 2013/142968 confers in plants tolerance/resistance to particular classes of CESA-inhibiting herbicides (cellulose biosynthesis inhibitors; CBIs) as compared to the non-transformed and/or non-mutagenized plants or plant cells, respectively. More specifically, the inventors of the present invention have found that mutated *Brassica napus* and *Helianthus annuus* CESA expression confers tolerance/resistance to azines. More specifically, the inventors of the present invention have found that modifications of the C-terminal part of the *Brassica napus* CESA proteins confer tolerance/resistance to azines. In addition, the inventors of the present invention have now surprisingly found that the combination of two amino acid substitutions which were described in WO 2013/142968 confers in plants tolerance/resistance to particular classes of CESA-inhibiting herbicides (cellulose biosynthesis inhibitors; CBIs) as compared to the non-transformed and/or non-mutagenized plants or plant cells, respectively.

The problem of the present invention can be seen as to the provision of novel traits by identifying target polypeptides, the manipulation of which makes plants tolerant to herbicides.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor.

The problem is solved by the subject-matter of the present invention.

SUMMARY OF THE INVENTION

Accordingly, in one aspect, the present invention provides a plant or plant part comprising a polynucleotide encoding a mutated CESA polypeptide, the expression of said polynucleotide confers to the plant or plant part tolerance to CESA-inhibiting herbicides.

In some aspects, the present invention provides a seed capable of germination into a plant comprising in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides.

In one aspect, the present invention provides a plant cell of or capable of regenerating a plant comprising in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides, wherein the plant cell comprises the polynucleotide operably linked to a promoter.

In another aspect, the present invention provides a plant cell comprising a polynucleotide operably linked to a promoter operable in a cell, the promoter capable of expressing a mutated CESA polypeptide encoded by the polynucleotide, the expression of the mutated CESA polypeptide conferring to the plant tolerance to CESA-inhibiting herbicides.

In other aspects, the present invention provides a plant product prepared from a plant or plant part comprising in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides.

In some aspects, the present invention provides a progeny or descendant plant derived from a plant comprising in at least some of its cells a polynucleotide operably linked to a promoter operable in plant cells, the promoter capable of expressing a mutated CESA polypeptide encoded by the polynucleotide, wherein the progeny or descendant plant comprises in at least some of its cells the recombinant polynucleotide operably linked to the promoter, the expression of the mutated CESA polypeptide conferring to the progeny or descendant plant tolerance to the CESA-inhibiting herbicides.

In other aspects, the present invention provides a method for controlling weeds at a locus for growth of a plant, the method comprising: (a) applying an herbicide composition comprising CESA-inhibiting herbicides to the locus; and (b) planting a seed at the locus, wherein the seed is capable of producing a plant that comprises in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides.

In some aspects, the present invention provides a method for controlling weeds at a locus for growth of a plant, the method comprising: applying an herbicidal composition comprising CESA-inhibiting herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides.

In one aspect, step (a) occurs before, after, or concurrently with step (b).

In other aspects, the present invention provides a method of producing a plant having tolerance to CESA-inhibiting herbicides, the method comprising regenerating a plant from a plant cell transformed with a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides.

In one aspect, the present invention provides a method of producing a progeny plant having tolerance to CESA-inhibiting herbicides, the method comprising: crossing a first CESA-inhibiting herbicides-tolerant plant with a second plant to produce a CESA-inhibiting herbicides-tolerant progeny plant, wherein the first plant and the progeny plant comprise in at least some of their cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides.

In addition, the present invention refers to a method for identifying a CESA-inhibiting herbicide by using a mutated CESA of the present invention encoded by a nucleic acid which comprises the nucleotide sequence of SEQ ID NO: 36, 37, 38, or 39, or a variant, homologue, paralogue or orthologue thereof.

Said method comprises the steps of:
a) generating a transgenic cell or plant comprising a nucleic acid encoding a mutated CESA of the present invention, wherein the mutated CESA of the present invention is expressed;
b) applying a CESA-inhibiting herbicide to the transgenic cell or plant of a) and to a control cell or plant of the same variety;
c) determining the growth or the viability of the transgenic cell or plant and the control cell or plant after application of said test compound, and
d) selecting test compounds which confer reduced growth to the control cell or plant as compared to the growth of the transgenic cell or plant.

Another object refers to a method of identifying a nucleotide sequence encoding a mutated CESA which is resistant or tolerant to a CESA-inhibiting herbicide, the method comprising:
a) generating a library of mutated CESA-encoding nucleic acids,
b) screening a population of the resulting mutated CESA-encoding nucleic acids by expressing each of said nucleic acids in a cell or plant and treating said cell or plant with a CESA-inhibiting herbicide,
c) comparing the CESA-inhibiting herbicide-tolerance levels provided by said population of mutated CESA encoding nucleic acids with the CESA-inhibiting herbicide-tolerance level provided by a control CESA-encoding nucleic acid,
d) selecting at least one mutated CESA-encoding nucleic acid that provides a significantly increased level of tolerance to a CESA-inhibiting herbicide as compared to that provided by the control CESA-encoding nucleic acid.

In a preferred embodiment, the mutated CESA-encoding nucleic acid selected in step d) provides at least 2-fold as much tolerance to a CESA-inhibiting herbicide as compared to that provided by the control CESA-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a mutated CESA which is resistant or tolerant to a CESA-inhibiting herbicide, the method comprising:
a) identifying an effective amount of a CESA-inhibiting herbicide in a culture of plant cells or green algae.
b) treating said plant cells or green algae with a mutagenizing agent,
c) contacting said mutagenized cells population with an effective amount of CESA-inhibiting herbicide, identified in a),
d) selecting at least one cell surviving these test conditions,
e) PCR-amplification and sequencing of CESA genes from cells selected in d) and comparing such sequences to wild-type CESA gene sequences, respectively.

In a preferred embodiment, the mutagenizing agent is ethylmethanesulfonate.

Another object refers to an isolated recombinantly produced, and/or chemically synthesized nucleic acid encoding a mutated CESA, the nucleic acid comprising the sequence of SEQ ID NO: 36, 37, 38, or 39, or a variant thereof, as defined hereinafter.

In a preferred embodiment, the nucleic acid being identifiable by a method as defined above.

Another object refers to an isolated, recombinantly produced, and/or chemically synthesized mutated CESA polypeptide, the polypeptide comprising the sequence set forth in SEQ ID NO: 1, 3, 11, 12, 13, 14, 15, 16, 17, 18, 19, 20, 21, 22, 23, 24, 25, 26, 27, 28, or 29, a variant, derivative, orthologue, paralogue or homologue thereof, as defined hereinafter.

In still further aspects, the present invention provides a plant or plant part comprising in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides, wherein the plant or plant part further exhibits a second or third herbicide-tolerant trait.

In another embodiment, the invention refers to a plant cell transformed by and expressing a a mutated CESA nucleic acid according to the present invention or a plant which has been mutated to obtain a plant expressing, preferably overexpressing a a mutated CESA nucleic acid according to the present invention, wherein expression of said nucleic acid in the plant cell results in increased resistance or tolerance to a CESA-inhibiting herbicide as compared to a wild type variety of the plant cell In another embodiment, the invention refers to a plant comprising a plant cell according to the present invention, wherein expression of the nucleic acid in the plant results in the plant's increased resistance to CESA-inhibiting herbicide as compared to a wild type variety of the plant.

The plants of the present invention can be transgenic or non-transgenic.

Preferably, the expression of the nucleic acid of the invention in the plant results in the plant's increased resistance to CESA-inhibiting herbicides as compared to a wild type variety of the plant. In another embodiment, the invention refers to a seed produced by a transgenic plant comprising a plant cell of the present invention, wherein the seed is true breeding for an increased resistance to a CESA-inhibiting herbicide as compared to a wild type variety of the seed.

In another embodiment, the invention refers to a method of producing a transgenic plant cell with an increased resistance to a CESA-inhibiting herbicide as compared to a wild type variety of the plant cell comprising, transforming the plant cell with an expression cassette comprising a a polynucleotide operably linked to a promoter operable in plant cells, the promoter capable of expressing a mutated CESA polypeptide encoded by the polynucleotide.

In another embodiment, the invention refers to a method of producing a transgenic plant comprising, (a) transforming a plant cell with an expression cassette comprising a a polynucleotide operably linked to a promoter operable in plant cells, the promoter capable of expressing a mutated CESA polypeptide encoded by the polynucleotide, and (b) generating a plant with an increased resistance to CESA-inhibiting herbicide from the plant cell.

Preferably, the expression cassette further comprises a transcription initiation regulatory region and a translation initiation regulatory region that are functional in the plant.

BRIEF DESCRIPTION OF THE DRAWINGS

Figure 2:
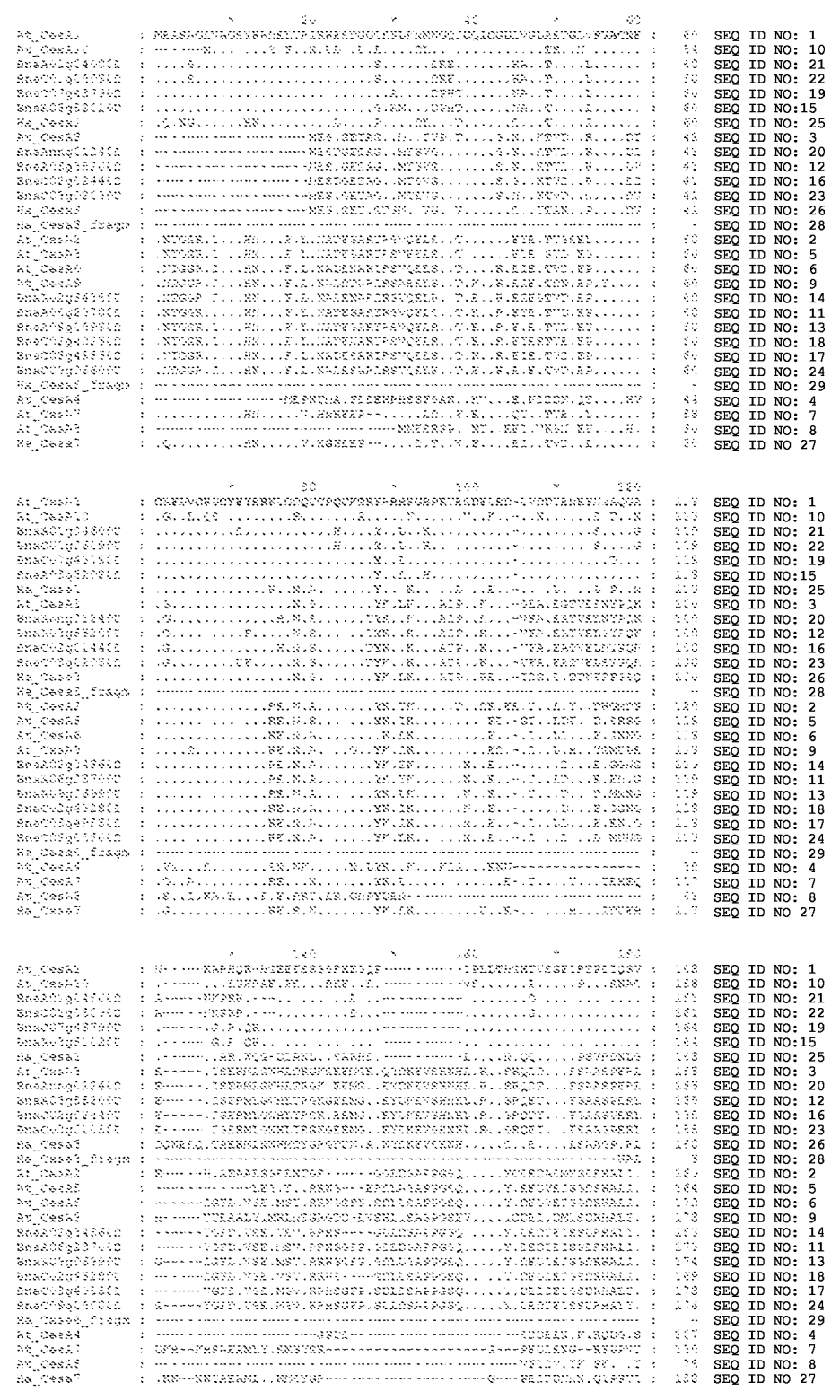

FIGS. 2A-2Z show alignment of all *Brassica napus* and *Helianthus annuus* cellulose synthase homologues to *Arabidopsis thaliana* CESA1, CESA3 and CESA 6.

FIG. 3 shows Transgenic T1 *Brassica* plants which were sprayed pre emergent in the greenhouse with the indicated amounts of 6-cyclopentyl-N4-(2,3,4,5,6-pentafluorophenyl)-1,3,5-triazine-2,4-diamine. Picture taken 21 days after treatment. 1=non-transgenic; 2=SEQ ID NO: 20—variant S1041L; 3=SEQ ID NO: 20—variant S1038F.

KEY TO SEQUENCE LISTING

TABLE 1

Figure 1A:
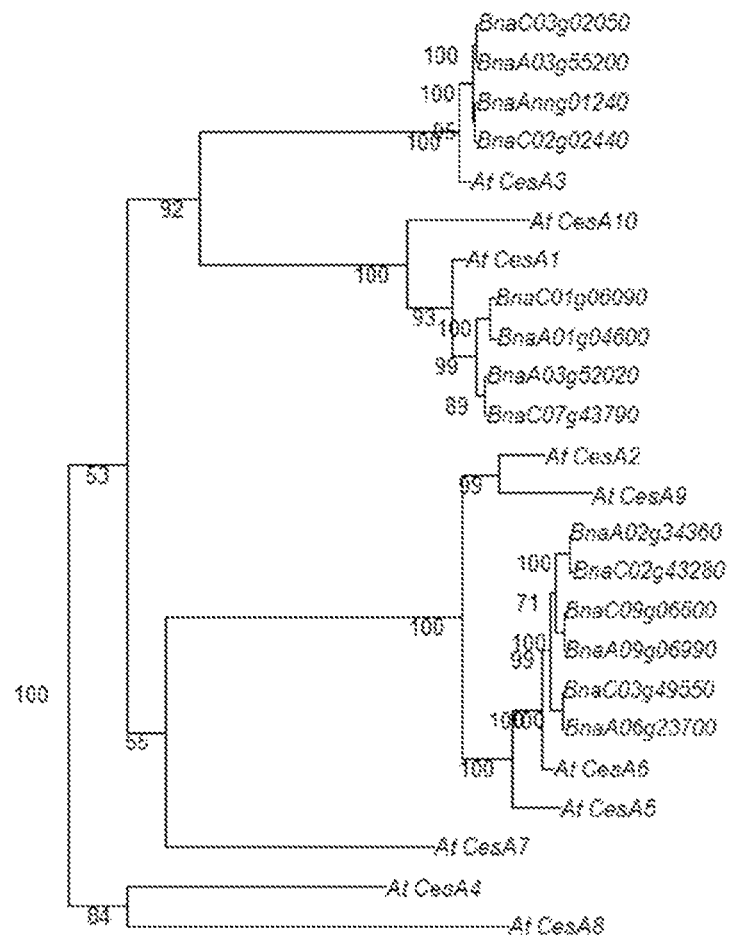
FIG. 1A shows phylogenetic tree of cellulose synthase homologues in *Brassica napus*.

| SEQ ID NO | Type | Sequence/Origin |
| --- | --- | --- |
| 1 | Amino acid | At_CESA1 |
| 2 | Amino acid | At_CESA2 |
| 3 | Amino acid | At_CESA3 |
| 4 | Amino acid | At_CESA4 |
| 5 | Amino acid | At_CESA5 |
| 6 | Amino acid | At_CESA6 |
| 7 | Amino acid | At_CESA7 |
| 8 | Amino acid | At_CESA8 |
| 9 | Amino acid | At_CESA9 |
| 10 | Amino acid | At_CESA10 |
| 11 | Amino acid | BnaA06g23700D |
| 12 | Amino acid | BnaA03g55200D_CesA3 |
| 13 | Amino acid | BnaA09g06990D |
| 14 | Amino acid | BnaA02g34360D |
| 15 | Amino acid | BnaA03g52020D_CesA1 |
| 16 | Amino acid | BnaC02g02440D |
| 17 | Amino acid | BnaC03g49550D |
| 18 | Amino acid | BnaC02g43280D |
| 19 | Amino acid | BnaC07g43790D |
| 20 | Amino acid | BnaAnng01240D_CesA3 |
| 21 | Amino acid | BnaA01g04600D_CesA1 |

TABLE 1-continued

| SEQ ID NO | Type | Sequence/Origin |
|---|---|---|
| 22 | Amino acid | BnaC01g06090D |
| 23 | Amino acid | BnaC03g02050D |
| 24 | Amino acid | BnaC09g06600D |
| 25 | Amino acid | Ha_Cesa1 |
| 26 | Amino acid | Ha_Cesa3 |
| 27 | Amino acid | Ha_Cesa7 |
| 28 | Amino acid | Ha_Cesa3b_fragment |
| 29 | Amino acid | Ha_Cesa6_fragment |
| 36 | Nucleic acid | BnaA03g55200D_CesA3 |
| 37 | Nucleic acid | BnaA03g52020D_CesA1 |
| 38 | Nucleic acid | BnaAnng01240D_CesA3 |
| 39 | Nucleic acid | BnaA01g04600D_CesA1 |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The term "control of undesired vegetation or weeds" is to be understood as meaning the killing of weeds and/or otherwise retarding or inhibiting the normal growth of the weeds. Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp.

(e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope. As used herein, in regard to an herbicidal composition useful in various embodiments hereof, terms such as CESA-inhibiting herbicides, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide-tolerant and herbicide-tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. For example, when used specifically in regard to a CESA enzyme, it refers specifically to the ability to tolerate a CESA-inhibitor. By "herbicide-tolerant mutated CESA protein" or "herbicide-resistant mutated CESA protein", it is intended that such a CESA protein displays higher CESA activity, relative to the CESA activity of a wild-type CESA protein, when in the presence of at least one herbicide that is known to interfere with CESA activity and at a concentration or level of the herbicide that is known to inhibit the CESA activity of the wild-type CESA protein. Furthermore, the CESA activity of such a herbicide-tolerant or herbicide-resistant mutated CESA protein may be referred to herein as "herbicide-tolerant" or "herbicide-resistant" CESA activity.

As used herein, "recombinant," when referring to nucleic acid or polypeptide, indicates that such material has been altered as a result of human application of a recombinant technique, such as by polynucleotide restriction and ligation, by polynucleotide overlap-extension, or by genomic insertion or transformation. A gene sequence open reading frame is recombinant if that nucleotide sequence has been removed from it natural text and cloned into any type of artificial nucleic acid vector. The term recombinant also can refer to an organism having a recombinant material, e.g., a plant that comprises a recombinant nucleic acid can be considered a recombinant plant.

The term "transgenic plant" refers to a plant that comprises a heterologous polynucleotide. Preferably, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been so altered by the presence of heterologous nucleic acid including those transgenic organisms or cells initially so altered, as well as those created by crosses or asexual propagation from the initial transgenic organism or cell. In some embodiments, a "recombinant" organism is a "transgenic" organism. The term "transgenic" as used herein is not intended to encompass the alteration of the genome (chromosomal or extra-chromosomal) by conventional plant breeding methods (e.g., crosses) or by naturally occurring events such as, e.g., self-fertilization, random cross-fertilization, non-recombinant viral infection, non-recombinant bacterial transformation, non-recombinant transposition, or spontaneous mutation.

As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induced and/or selected by human action. Examples of human action that can be used to produce a mutagenized organism or DNA include, but are not limited to, as illustrated in regard to herbicide tolerance: tissue culture of plant cells (e.g., calli) and selection thereof with herbicides (e.g., CESA-inhibiting herbicides), treatment of plant cells with a chemical mutagen such as EMS and subsequent selection with herbicide(s); or by treatment of plant cells with x-rays and subsequent selection with herbicide(s). Any method known in the art can be used to induce mutations. Methods of inducing mutations can induce mutations in random positions in the genetic material or can induce mutations in specific locations in the genetic material (i.e., can be directed mutagenesis techniques), such as by use of a genoplasty technique.

As used herein, a "genetically modified organism" (GMO) is an organism whose genetic characteristics contain alteration(s) that were produced by human effort causing transfection that results in transformation of a target organism with genetic material from another or "source" organism, or with synthetic or modified-native genetic material, or an organism that is a descendant thereof that retains the inserted genetic material. The source organism can be of a different type of organism (e.g., a GMO plant can contain bacterial genetic material) or from the same type of organism (e.g., a GMO plant can contain genetic material from another plant). As used herein in regard to plants and other organisms, "recombinant," "transgenic," and "GMO" are considered synonyms and indicate the presence of genetic material from a different source; in contrast, "mutagenized" is used to refer to a plant or other organism, or the DNA thereof, in which no such transgenic material is present, but in which the native genetic material has become mutated so as to differ from a corresponding wild-type organism or DNA.

As used herein, "wild-type" or "corresponding wild-type plant" means the typical form of an organism or its genetic material, as it normally occurs, as distinguished from, e.g., mutagenized and/or recombinant forms. Similarly, by "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

As used herein, "descendant" refers to any generation plant. In some embodiments, a descendant is a first, second, third, fourth, fifth, sixth, seventh, eight, ninth, or tenth generation plant.

As used herein, "progeny" refers to a first generation plant.

The term "seed" comprises seeds of all types, such as, for example, true seeds, caryopses, achenes, fruits, tubers, seedlings and similar forms. In the context of Brassica and Sinapis species, "seed" refers to true seed(s) unless otherwise specified. For example, the seed can be seed of transgenic plants or plants obtained by traditional breeding methods. Examples of traditional breeding methods can include cross-breeding, selfing, backcrossing, embryo rescue, in-crossing, out-crossing, inbreeding, selection, asexual propagation, and other traditional techniques as are known in the art.

Although exemplified with reference to specific plants or plant varieties and their hybrids, in various embodiments, the presently described methods using CESA-inhibiting herbicides can be employed with a variety of commercially valuable plants. CESA-inhibiting herbicides-tolerant plant lines described as useful herein can be employed in weed control methods either directly or indirectly, i. e. either as crops for herbicide treatment or as CESA-inhibiting herbicides-tolerance trait donor lines for development, as by traditional plant breeding, to produce other varietal and/or hybrid crops containing such trait or traits. All such resulting variety or hybrids crops, containing the ancestral CESA-inhibiting herbicides-tolerance trait or traits can be referred to herein as progeny or descendant of the ancestral, CESA-inhibiting herbicides-tolerant line(s). Such resulting plants can be said to retain the "herbicide tolerance characteristic(s)" of the ancestral plant, i.e. meaning that they possess and express the ancestral genetic molecular components responsible for the trait.

In one aspect, the present invention provides a plant or plant part comprising a polynucleotide encoding a mutated CESA polypeptide, the expression of said polynucleotide confers to the plant or plant part tolerance to CESA-inhibiting herbicides.

In a preferred embodiment, the plant has been previously produced by a process comprising recombinantly preparing a plant by introducing and over-expressing a mutated CESA transgene according to the present invention, as described in greater detail hereinafter.

In another preferred embodiment, the plant has been previously produced by a process comprising in situ mutagenizing plant cells or seeds, to obtain plant cells or plants which express a mutated CESA.

In another embodiment, the polynucleotide encoding the mutated CESA polypeptide polypeptide comprises the nucleic acid sequence set forth in SEQ ID NO: 36, 37, 38, or 39, or a variant or derivative thereof.

In other embodiments, the mutated CESA polypeptide for use according to the present invention is a functional variant having, over the full-length of the variant, at least about 80%, illustratively, at least about 80%, 90%, 95%, 98%, 99% or more amino acid sequence identity to SEQ ID NO: 1, 3, 11, 12, 13, 14, 15, 16, 17, 18, 19, 20, 21, 22, 23, 24, 25, 26, 27, 28, or 29.

In another embodiment, the mutated CESA polypeptide for use according to the present invention is a functional fragment of a polypeptide having the amino acid sequence set forth in SEQ ID NO: 1, 3, 11, 12, 13, 14, 15, 16, 17, 18, 19, 20, 21, 22, 23, 24, 25, 26, 27, 28, or 29.

It is recognized that the CESA polynucleotide molecules and CESA polypeptides of the invention encompass polynucleotide molecules and polypeptides comprising a nucleotide or an amino acid sequence that is sufficiently identical to nucleotide sequences set forth in SEQ ID Nos: 36, 37, 38, or 39, or to the amino acid sequences set forth in SEQ ID Nos: 1, 3, 11, 12, 13, 14, 15, 16, 17, 18, 19, 20, 21, 22, 23, 24, 25, 26, 27, 28, or 29. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mutated CESA nucleic acid" refers to a CESA nucleic acid having a sequence that is mutated from a wild-type CESA nucleic acid and that confers increased CESA-inhibiting herbicide tolerance to a plant in which it is expressed. Furthermore, the term "mutated cellulose synthase (mutated CESA)" refers to the replacement of an amino acid of the wild-type primary sequences of SEQ ID NO: 1, 3, 11, 12, 13, 14, 15, 16, 17, 18, 19, 20, 21, 22, 23, 24, 25, 26, 27, 28, or 29, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the CESA nucleotide sequence encoding a mutated CESA comprises the sequence of SEQ ID NO: 36, 37, 38, or 39, or a variant or derivative thereof.

Furthermore, it will be understood by the person skilled in the art that the CESA nucleotide sequences encompasse homologues, paralogues and orthologues of SEQ ID NO: 36, 37, 38, or 39, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein comprising the sequence of SEQ ID NO: 1, 3, 11, 12, 13, 14, 15, 16, 17, 18, 19, 20, 21, 22, 23, 24, 25, 26, 27, 28, or 29, as well as those that encode a polypeptide having amino acid substitutions relative to the native protein, e.g. the mutated CESA according to the present invention as disclosed herein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO: 36, 37, 38, or 39. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the CESA polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 1, 3, 11, 12, 13, 14, 15, 16, 17, 18, 19, 20, 21, 22, 23, 24, 25, 26, 27, 28, or 29.

By "variant" polypeptide is intended a polypeptide derived from the protein of SEQ ID NO: 1, 3, 11, 12, 13, 14, 15, 16, 17, 18, 19, 20, 21, 22, 23, 24, 25, 26, 27, 28, or 29, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. Thus, functional variants and fragments of the CESA polypeptides, and nucleic acid molecules encoding them, also are within the scope of the present invention, and unless specifically described otherwise, irrespective of the origin of said polypeptide and irrespective of whether it occurs naturally. Various assays for functionality of a CESA polypeptide can be employed. For example, a functional variant or fragment of the CESA polypeptide can be assayed to determine its ability to confer CESA-inhibiting herbicides tolerance. By way of illustration, a CESA-inhibiting herbicides tolerance can be defined as insensitivity to CESA inhibiting herbicides sufficient to provide a determinable increase in tolerance to CESA-inhibiting herbicides in a plant or plant part comprising a recombinant polynucleotide encoding the variant or fragment of the CESA polypeptide, wherein the plant or plant part expresses the variant or fragment at up to about 0.5%, illustratively, about 0.05 to about 0.5%, about 0.1 to about 0.4%, and about 0.2 to about 0.3%, of the total cellular protein relative to a similarly treated control plant that does not express the variant or fragment.

In a preferred embodiment, the mutated CESA polypeptide is a functional variant or fragment of a cellulose synthase having the amino acid sequence set forth in SEQ ID NO: 12, 15, 20, 21, 25, or 26 wherein the functional variant or fragment has at least about 80% amino acid sequence identity to SEQ ID NO: 12, 15, 20, 21, 25 or 26.

In other embodiments, the functional variant or fragment further has a CESA-inhibiting herbicides tolerance defined as insensitivity to CESA inhibiting herbicides sufficient to provide a determinable increase in tolerance to CESA-inhibiting herbicides in a plant or plant part comprising a recombinant polynucleotide encoding the variant or fragment, wherein the plant or plant part expresses the variant or fragment at up to about 0.5% of the total cellular protein to a similarly treated control plant that does not express the variant or fragment.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

In addition, one of ordinary skill in the art will further appreciate that changes can be introduced by mutation into the nucleotide sequences of the invention thereby leading to changes in the amino acid sequence of the encoded proteins without altering the biological activity of the proteins. Thus, for example, an isolated polynucleotide molecule encoding a mutated CESA polypeptide having an amino acid sequence that differs from that of SEQ ID NO: 1, 3, 11, 12, 13, 14, 15, 16, 17, 18, 19, 20, 21, 22, 23, 24, 25, 26, 27, 28, or 29, can be created by introducing one or more nucleotide substitutions, additions, or deletions into the corresponding nucleotide sequence, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention. For example, preferably, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid residue is required for biological activity.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione 5-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif. Conservative substitution tables are well known in the art (see for example Creighton (1984) Proteins. W.H. Freeman and Company (Eds).

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, OH), Quick-Change Site Directed mutagenesis (Stratagene, San Diego, CA), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. A non-limiting list of examples of such orthologues is shown in Table 1. It will be understood by the person skilled in the art that the sequences of SEQ ID NOs: 1, 2, 3, 4, 5, 6, 7, 8, 9, 10, 12, 13, 14, 15, 16, 17, 18, 19, 20, 21, 22, 23, 24, 25, 26, 27, 28, or 29, as listed in Table 1 represent orthologues and paralogues to SEQ ID NO: 12, 15, 20, 21, 25 or 26.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

In a preferred embodiment, the CESA polypeptide useful for the present invention, comprises one or more of the following motifs:

i) Motif 1a:
(SEQ ID NO: 30)
[V/I][A/V/S]G[V/I/F]S[Y/D/T]A[V/I/L][N/S][S/N/K]GY

[Q/D/G/E][S/A]WGPL[F/M]G[K/R][L/V][F/L]F.

Preferably said motif is
(motif 1b; SEQ ID NO: 31)
[V/I][A/V/S]G[V/I/F]S[Y/D/T]A[V/I][N/S][S/N]GY

[Q/D]SWGPL[F/M]G[K/R]L[F/L]F.

More preferably said motif is
(motif 1c; SEQ ID NO: 32)
V[A/S]G[V/I/F]S[Y/T]A[V/I]NSGYQSWGPL[F/M]GKL[F/L]F ii) Motif 2a:
(SEQ ID NO: 33)
[V/L/I]WS[V/A/I]L[L/I]AS[IV][F/L][S/T]L[L/V]WVR

[I/V][N/D]PF

Preferably, said motif is
(motif 2b; SEQ ID NO: 34)
VWS[V/A/I]L[L/I]ASI[F/L][S/T]LLWVR[I/V][N/D]PF;

More preferably said motif is
(motif 2c; SEQ ID NO: 35)
VWS[V/A/I]LLASIFSLLWVRI[N/D]PF Motifs 1a-c, 2a-c, given above were derived using the ClustalW algorithm to generate the alignments of cellulose synthase sequences (FIGS. 2A-2Z) (Larkin et al., Bioinformatics 23:21 (2007) 2947-2948 pp. 28-36,). The motifs were essentially derived based on sequence alignment; highly conserved regions were identified that contain the site of mutations conferring azine-herbicide tolerance. Residues within square brackets represent alternatives.

In a preferred embodiment, a CESA polypeptide as applied herein comprises, at least 1, at least 2, selected from the group comprising motifs 1a, 2a, as given above. Alternatively or in addition, in another preferred embodiment, a CESA polypeptide as applied herein comprises at least 1, at least 2, motifs selected from the group comprising motifs 1b, 2b, as given above. Alternatively or in addition, in another preferred embodiment, a CESA polypeptide as applied herein comprises at least 1, at least 2, motifs selected from the group comprising motifs 1c, 2c, as given above.

Additionally or alternatively, the homologue of a CESA protein has in increasing order of preference at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 1, 3, 11, 12, 13, 14, 15, 16, 17, 18, 19, 20, 21, 22, 23, 24, 25, 26, 27, 28, or 29, provided that the homologous protein comprises any one or more of the conserved motifs 1 and/or 2 as outlined above. The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides). Compared to overall sequence identity, the sequence identity will generally be higher when only conserved domains or motifs are considered. Preferably the motifs in a CESA polypeptide have, in increasing order of preference, at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one or more of the motifs represented by SEQ ID NO: 30, 31, 32, 33, 34, and 35, (Motifs 1a, 1b, 1c, 2a, 2b, 2c).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Figure 1B:
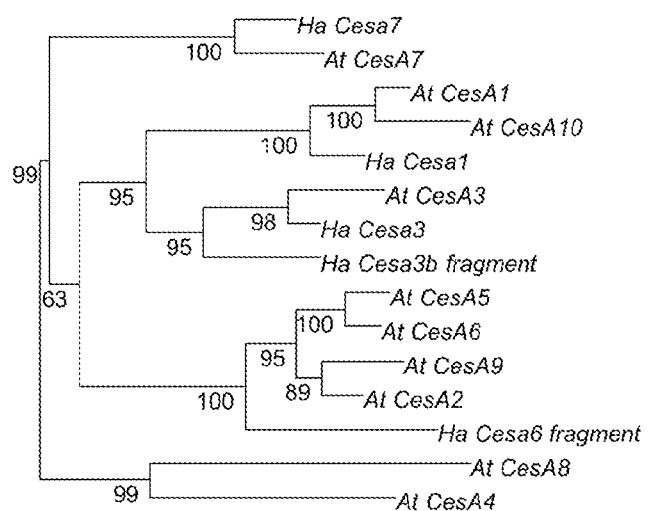
FIG. 1B shows phylogenetic tree of cellulose synthase homologues in *Helianthus annuus*.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage (See FIG. 1). Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The proteins of the invention may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. See, for example, Kunkel (1985) PNAS, 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D. C), herein incorporated by reference. Conservative substitutions, such as exchanging one amino acid with another having similar properties, may be preferable.

Alternatively, variant nucleotide sequences can be made by introducing mutations randomly along all or part of a coding sequence, such as by saturation mutagenesis, and the resultant mutants can be screened to identify mutants that encode proteins that retain activity. For example, following mutagenesis, the encoded protein can be expressed recombinantly, and the activity of the protein can be determined using standard assay techniques.

The inventors of the present invention have found that by substituting one or more of the key amino acid residues of the CESA enzyme of SEQ ID NO: 12, 15, 20, 21, 25, or 26, e.g. by employing one of the above described methods to mutate the CESA encoding nucleic acids, the tolerance or resistance to particular CESA-inhibiting herbicides, collectively named azines, and described in greater detail herein below, could be remarkably increased Preferred substitutions of mutated CESA are those that increase the herbicide tolerance of the plant, but leave the biological activity of the cellulose synthase activity substantially unaffected.

Accordingly, in another object of the present invention refers to a CESA polypeptide, comprising the sequence of SEQ ID NO: 1, 3, 11, 12, 13, 14, 15, 16, 17, 18, 19, 20, 21, 22, 23, 24, 25, 26, 27, 28, or 29, a variant, derivative, orthologue, paralogue or homologue thereof, the key amino acid residues of which is substituted by any other amino acid.

It will be understood by the person skilled in the art that amino acids located in a close proximity to the positions of amino acids mentioned below may also be substituted. Thus, in another embodiment the variant of SEQ ID NO: 1, 3, 11, 12, 13, 14, 15, 16, 17, 18, 19, 20, 21, 22, 23, 24, 25, 26, 27, 28, or 29, a variant, derivative, orthologue, paralogue or homologue thereof comprises a mutated CESA, wherein an amino acid ±3, ±2 or ±1 amino acid positions from a key amino acid is substituted by any other amino acid.

Based on techniques well-known in the art, a highly characteristic sequence pattern can be developed, by means of which further of mutated CESA candidates with the desired activity may be searched.

Searching for further mutated CESA candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, in particular saturation mutagenes (see e.g. Schenk et al., Biospektrum 03/2006, pages 277-279) PCR based site-directed mutagenesis (e.g. directed mutagenesis kit, Stratagene, California, USA or GeneArt Mutagenesis Service, ThermoFisher Scientific Inc., Massachusetts, USA) or systematic mutagenesis (GeneArt Systematic Mutagenesis Service, ThermoFisher Scientific Inc., Massachusetts, USA), the inventors of the present invention have identified and generated specific amino acid substitutions and combinations thereof, which—when introduced into a plant by transforming and expressing the respective mutated CESA encoding nucleic acid—confer increased herbicide resistance or tolerance to a CESA inhibiting herbicide to said plant.

Thus, in preferred embodiment, the variant or derivative of the CESA polypeptide refers to a mutated CESA polypeptide which comprises one or more of the following motifs:

i) Motif 1a:
(SEQ ID NO: 30)
[V/I][A/V/S]G[V/I/F]S[Y/D/T]A[V/I/L][N/S][S/N/K]GY

[Q/D/G/E][S/A]WGPL[F/M]G[K/R][L/V][F/L]F.

Preferably said motif is
(motif 1b; SEQ ID NO: 31)
[V/I][A/V/S]G[V/I/F]S[Y/D/T]A[V/I][N/S][S/N]GY

[Q/D]SWGPL[F/M]G[K/R]L[F/L]F.

More preferably said motif is
(motif 1c; SEQ ID NO: 32)
V[A/S]G[V/I/F]S[Y/T]A[V/I]NSGYQSWGPL[F/M]GKL[F/L]F Wherein the amino acid at position 5, 16, 17, and/or 20 within said motif is substituted by any other amino acid.

iii) Motif 2a:
(SEQ ID NO: 33)
[V/L/I]WS[V/A/I]L[L/I]AS[IV][F/L][S/T]L[L/V]WVR

[I/V][N/D]PF

Preferably, said motif is
(motif 2b; SEQ ID NO: 34)
VWS[V/A/I]L[L/I]ASI[F/L][S/T]LLWVR[I/V][N/D]PF;

More preferably said motif is
(motif 2c; SEQ ID NO: 35)
VWS[V/A/I]LLASIFSLLWVRI[N/D]PF Wherein the amino acid at position 8, and/or 11 within said motif is substituted by any other amino acid.

In a more preferred embodiment, the amino acid corresponding to position 5 of motif 1a, 1b, or 1c is:
Arg, His, Lys, Asp, Glu, Thr, Asn, Gln, Cys, Gly, Pro, Ala, Val, Leu, Ile, Met, Phe, Tyr, or Trp;
And/or
the amino acid corresponding to position 16 of motif 1a, 1b, or 1c is
Arg, His, Lys, Asp, Glu, Ser, Thr, Asn, Gln, Cys, Pro, Ala, Val, Leu, Ile, Met, Phe, Tyr, or Trp,
And/or
the amino acid corresponding to position 17 of motif 1a, 1b, or 1c is
Arg, His, Lys, Asp, Glu, Ser, Thr, Asn, Gln, Cys, Gly, Ala, Val, Leu, Ile, Met, Phe, Tyr, or Trp,
And/or
the amino acid corresponding to position 20 of motif 1a, 1b, or 1c is
Arg, His, Lys, Asp, Glu, Ser, Thr, Asn, Gln, Cys, Pro, Ala, Val, Leu, Ile, Met, Phe, Tyr, or Trp,
In another more preferred embodiment, the amino acid corresponding to position 8 of motif 2a, 2b, or 2c is:
Arg, His, Lys, Asp, Glu, Thr, Asn, Gln, Cys, Gly, Pro, Ala, Val, Leu, Ile, Met, Phe, Tyr, or Trp;
And/or
the amino acid corresponding to position 11 of motif 2a, 2b, or 2c is
Arg, His, Lys, Asp, Glu, Thr, Asn, Gln, Cys, Gly, Pro, Ala, Val, Leu, Ile, Met, Phe, Tyr, or Trp,
In a particularly preferred embodiment,
the amino acid corresponding to position 5 of motif 1a, 1b, or 1c is Phe,
And/or
the amino acid corresponding to position 16 of motif 1a, 1b, or 1c is Asp,
And/or
the amino acid corresponding to position 17 of motif 1a, 1b, or 1c is Leu,
And/or
the amino acid corresponding to position 20 of motif 1a, 1b, or 1c is
Arg.
In another particularly preferred embodiment,
the amino acid corresponding to position 16 of motif 1a, 1b, or 1c is other than Gly, preferably Asp, and the amino acid corresponding to position 20 of motif 1a, 1b, or 1c is other than Gly, preferably Arg.
In another particularly preferred embodiment,
the amino acid corresponding to position 17 of motif 1a, 1b, or 1c is other than Pro, preferably Leu, and the amino acid corresponding to position 20 of motif 1a, 1b, or 1c is other than Gly, preferably Arg.
In another particularly preferred embodiment,
the amino acid corresponding to position 5 of motif 1a, 1b, or 1c is other than Ser, preferably Phe, and the amino acid corresponding to position 8 of motif 2a, 2b, or 2c is other than Ser, preferably Phe.
In another particularly preferred embodiment,
the amino acid corresponding to position 5 of motif 1a, 1b, or 1c is other than Ser, preferably Phe, and the amino acid corresponding to position 11 of motif 2a, 2b, or 2c is other than Ser, preferably Leu.

In another more preferred embodiment,
the amino acid corresponding to position 8 of motif 2a, 2b, or 2c is Phe,
And/or
the amino acid corresponding to position 11 of motif 2a, 2b, or 2c is Leu, In another preferred embodiment, the variant or derivative of the CESA polypeptide refers to a CESA polypeptide comprising SEQ ID NO: 12, or SEQ ID NO:20, an orthologue, paralogue, or homologue thereof, wherein the amino acid sequence differs from the wildtype amino acid sequence of a CESA polypeptide at one or more positions corresponding to the following positions of SEQ ID NO:12, or SEQ ID NO:20: S984, G995, P996, G999, S1038, S1041

Examples of differences at these amino acid positions include, but are not limited to, one or more of the following:
the amino acid at or corresponding to position 984 is other than serine;
the amino acid at or corresponding to position 995 is other than glycine;
the amino acid at or corresponding to position 996 is other than proline;
the amino acid at or corresponding to position 999 is other than glycine,
the amino acid at or corresponding to position 1038 is other than serine,
the amino acid at or corresponding to position 1041 is other than serine, In some embodiments, the mutated CESA enzyme comprising SEQ ID NO:12, or SEQ ID NO:20, a orthologue, paralogue, or homologue thereof, comprises one or more of the following:
the amino acid at or corresponding to position 984 of SEQ ID NO:12, or SEQ ID NO:20 is Arg, His, Lys, Asp, Glu, Thr, Asn, Gln, Cys, Gly, Pro, Ala, Val, Leu, Ile, Met, Phe, Tyr, or Trp;
the amino acid at or corresponding to position 995 of SEQ ID NO:12, or SEQ ID NO:20 is Arg, His, Lys, Asp, Glu, Ser, Thr, Asn, Gln, Cys, Pro, Ala, Val, Leu, Ile, Met, Phe, Tyr, or Trp,
the amino acid at or corresponding to position 996 of SEQ ID NO:12, or SEQ ID NO:20 is Arg, His, Lys, Asp, Glu, Ser, Thr, Asn, Gln, Cys, Gly, Ala, Val, Leu, Ile, Met, Phe, Tyr, or Trp,
the amino acid at or corresponding to position 999 of SEQ ID NO:12, or SEQ ID NO:20 is Arg, His, Lys, Asp, Glu, Ser, Thr, Asn, Gln, Cys, Pro, Ala, Val, Leu, Ile, Met, Phe, Tyr, or Trp,
the amino acid at or corresponding to position 1038 of SEQ ID NO:12, or SEQ ID NO:20 is Arg, His, Lys, Asp, Glu, Thr, Asn, Gln, Cys, Gly, Pro, Ala, Val, Leu, Ile, Met, Phe, Tyr, or Trp,
the amino acid at or corresponding to position 1041 of SEQ ID NO:12, or SEQ ID NO:20 is Arg, His, Lys, Asp, Glu, Thr, Asn, Gln, Cys, Gly, Pro, Ala, Val, Leu, Ile, Met, Phe, Tyr, or Trp.

In a particularly preferred embodiment, the amino acid at or corresponding to position 984 of SEQ ID NO:12, or SEQ ID NO:20 is Phe.

In another particularly preferred embodiment, the amino acid at or corresponding to position 1038 of SEQ ID NO:12, or SEQ ID NO:20 is Phe.

In another particularly preferred embodiment, the amino acid at or corresponding to position 1041 of SEQ ID NO:12, or SEQ ID NO:20 is Leu.

In a particularly preferred embodiment, the amino acid at or corresponding to position 1011 of SEQ ID NO:15 is Asp.

In another particularly preferred embodiment, the amino acid at or corresponding to position 1012 of SEQ ID NO:15 is Leu.

In another particularly preferred embodiment, the amino acid at or corresponding to position 1015 of SEQ ID NO:15 is Arg.

In a particularly preferred embodiment, the amino acid at or corresponding to position 1008 of SEQ ID NO:21 is Asp.

In another particularly preferred embodiment, the amino acid at or corresponding to position 1009 of SEQ ID NO:21 is Leu.

In another particularly preferred embodiment, the amino acid at or corresponding to position 1012 of SEQ ID NO: 21 is Arg.

In another particularly preferred embodiment, the amino acid at or corresponding to position 1009 of SEQ ID NO:1 is other than Gly, preferably Asp, and the amino acid corresponding to position 1013 of SEQ ID NO:1 is other than Gly, preferably Arg.

In another particularly preferred embodiment, the amino acid at or corresponding to position 1010 of SEQ ID NO:1 is other than Pro, preferably Leu, and the amino acid corresponding to position 1013 of SEQ ID NO:1 is other than Gly, preferably Arg.

In another particularly preferred embodiment, the amino acid at or corresponding to position 983 of SEQ ID NO:3 is other than Ser, preferably Phe, and the amino acid corresponding to position 1037 of SEQ ID NO:3 is other than Ser, preferably Phe.

In another particularly preferred embodiment, the amino acid at or corresponding to position 983 of SEQ ID NO:3 is other than Ser, preferably Phe, and the amino acid corresponding to position 1040 of SEQ ID NO:3 is other than Ser, preferably Leu.

It will be within the knowledge of the skilled artisan to identify conserved regions and motifs shared between the homologues, orthologues and paralogues encoded by SEQ ID NO: 36, 37, 38, or 39, such as those depicted in Table 1. Having identified such conserved regions that may represent suitable binding motifs, amino acids corresponding to the amino acids listed below in Table 2, can be chosen to be substituted by any other amino acid, for example by conserved amino acids, preferably by the amino acid substitutions described SUPRA using SEQ ID NO: 1, 3, 12, 15, 20, 21, 25 or 26 as reference.

Table 2 provides an overview of positions in the orthologues and homologues to SEQ ID NO:1, i.e. the corresponding positions in SEQ ID NOs: 1 to 27.

TABLE 2

| ID | Pos 1 | Pos 2 | Pos 3 | Pos 4 | Pos 5 | Pos 6 |
|---|---|---|---|---|---|---|
| 1 | S998 | G1009 | P1010 | G1013 | S1052 | S1055 |
| 2 | S1001 | G1012 | P1013 | G1016 | S1055 | T1058 |
| 3 | S983 | G994 | P995 | G998 | S1037 | S1040 |
| 4 | S967 | G978 | P979 | G982 | S1021 | S1024 |
| 5 | S987 | G998 | P999 | G1002 | S1041 | T1044 |
| 6 | S1002 | G1013 | P1014 | G1017 | S1056 | T1059 |
| 7 | S944 | G955 | P956 | G959 | S998 | S1001 |
| 8 | S901 | G912 | P913 | G916 | S955 | S958 |
| 9 | S1005 | G1016 | P1017 | G1020 | S1059 | T1062 |
| 10 | S985 | G996 | P997 | G1000 | S1039 | S1042 |
| 11 | S1000 | G1011 | P1012 | G1015 | S1054 | T1057 |
| 12 | S984 | G995 | P996 | G999 | S1038 | S1041 |
| 13 | S1002 | G1013 | P1014 | G1017 | S1056 | T1059 |
| 14 | S997 | G1008 | P1009 | G1012 | S1051 | T1054 |
| 15 | S1000 | G1011 | P1012 | G1015 | S1054 | S1057 |
| 16 | S984 | G995 | P996 | G999 | S1038 | S1041 |
| 17 | S1000 | G1011 | P1012 | G1015 | S1054 | T1057 |

TABLE 2-continued

| ID | Pos 1 | Pos 2 | Pos 3 | Pos 4 | Pos 5 | Pos 6 |
|----|-------|-------|-------|-------|-------|-------|
| 18 | S997  | G1008 | P1009 | G1012 | S1051 | T1054 |
| 19 | S1000 | G1011 | P1012 | G1015 | S1054 | S1057 |
| 20 | S984  | G995  | P996  | G999  | S1038 | S1041 |
| 21 | S997  | G1008 | P1009 | G1012 | S1051 | S1054 |
| 22 | S997  | G1008 | P1009 | G1012 | S1051 | S1054 |
| 23 | S984  | G995  | P996  | G999  | S1038 | S1041 |
| 24 | S1002 | G1013 | P1014 | G1017 | S1056 | T1059 |
| 25 | S996  | G1007 | P1008 | G1011 | S1050 | S1053 |
| 26 | S999  | G1010 | P1011 | G1014 | S1053 | S1056 |
| 27 | S958  | G969  | P970  | G973  | S1012 | S1015 |
| 28 | —     | —     | —     | —     | —     | —     |
| 29 | —     | —     | —     | —     | —     | —     |

Another object refers to a method of identifying a nucleotide sequence encoding a mutated CESA which is resistant or tolerant to a CESA-inhibiting herbicide, the method comprising:
- a) generating a library of mutated CESA-encoding nucleic acids,
- b) screening a population of the resulting mutated CESA-encoding nucleic acids by expressing each of said nucleic acids in a cell or plant and treating said cell or plant with a CESA-inhibiting herbicide,
- c) comparing the CESA-inhibiting herbicide-tolerance levels provided by said population of mutated CESA encoding nucleic acids with the CESA-inhibiting herbicide-tolerance level provided by a control CESA-encoding nucleic acid,
- d) selecting at least one mutated CESA-encoding nucleic acid that provides a significantly increased level of tolerance to a CESA-inhibiting herbicide as compared to that provided by the control CESA-encoding nucleic acid.

In a preferred embodiment, the mutated CESA-encoding nucleic acid selected in step d) provides at least 2-fold as much resistance or tolerance of a cell or plant to a CESA-inhibiting herbicide as compared to that provided by the control CESA-encoding nucleic acid.

In a further preferred embodiment, the mutated CESA-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a CESA-inhibiting herbicide as compared to that provided by the control CESA-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a mutated CESA which is resistant or tolerant to a CESA-inhibiting herbicide, the method comprising:
- a) identifying an effective amount of a CESA-inhibiting herbicide in a culture of plant cells or green algae that leads to death of said cells.
- b) treating said plant cells or green algae with a mutagenizing agent,
- c) contacting said mutagenized cells population with an effective amount of CESA-inhibiting herbicide, identified in a),
- d) selecting at least one cell surviving these test conditions,
- e) PCR-amplification and sequencing of CESA genes from cells selected in d) and comparing such sequences to wild-type CESA gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a mutated CESA from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled mutated CESA-encoding sequences.

Nucleic acids comprising candidate and control CESA encoding sequences can be expressed in yeast, in a bacterial host strain, in an alga or in a higher plant such as tobacco or Arabidopsis and the relative levels of inherent tolerance of the CESA encoding sequences screened according to a visible indicator phenotype of the transformed strain or plant in the presence of different concentrations of the selected CESA-inhibiting herbicide. Dose responses and relative shifts in dose responses associated with these indicator phenotypes (formation of necrosis, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed CESA. For example, in a relatively rapid assay system based upon transformation of Arabidopsis each mutated CESA encoding sequence may be expressed, for example, as a DNA sequence under expression control of a suitable promoter and T1 plants can be selected for differential tolerance to selected CESA-inhibiting herbicides, measured by growth.

In another embodiment, candidate nucleic acids are transformed into plant material to generate a transgenic plant, regenerated into morphologically normal fertile plants which are then measured for differential tolerance to selected CESA-inhibiting herbicides as described in the Example section hereinafter. Many suitable methods for transformation using suitable selection markers such as kanamycin, binary vectors such as from Agrobacterium and plant regeneration as, for example, from tobacco leaf discs are well known in the art. Optionally, a control population of plants is likewise transformed with a nucleic acid expressing the control CESA. Alternatively, an untransformed dicot plant such as Arabidopsis or Tobacco can be used as a control since this, in any case, expresses its own endogenous CESA. The average, and distribution, of herbicide tolerance levels of a range of primary plant transformation events or their progeny to CESA-inhibiting herbicides described supra are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed CESA. Herbicides can suitably be applied pre-emergence or post-emergence.

Another object of the present invention refers to an isolated and or recombinantly produced and/or synthetic nucleic acid encoding a mutated CESA as disclosed SUPRA, wherein the nucleic acid comprises the nucleotide sequence of SEQ ID NO: 36, 37, 38, or 39, or a variant or derivative thereof.

In one embodiment, the nucleic acid is identifiable by a method as defined above.

For the purposes of the invention "recombinant" means with regard for example to a nucleic acid sequence, an expression cassette (=gene construct, nucleic acid construct) or a vector containing the nucleic acid sequence according to the invention or an organism transformed by said nucleic acid sequences, expression cassette or vector according to the invention all those constructions produced by genetic engineering methods in which either
  (a) the nucleic acid sequence comprising the sequence of SEQ ID NO: 36, 37, 38, or 39, or a homolog thereof, or its derivatives or parts thereof; or
  (b) a genetic control sequence functionally linked to the nucleic acid sequence described under (a), for example a 3'- and/or 5'-genetic control sequence such as a promoter or terminator, or
  (c) (a) and (b);
  are not found in their natural, genetic environment or have been modified by genetic engineering methods, wherein the modification may by way of example be a substitution, addition, deletion, inversion or insertion of one or more nucleotide residues.

"Natural genetic environment" means the natural genomic or chromosomal locus in the organism of origin or inside the host organism or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette—for example the naturally occurring combination of the natural promoter of the nucleic acid sequence according to the invention with the corresponding gene—turns into a transgenic expression cassette when the latter is modified by unnatural, synthetic ("artificial") methods such as by way of example a mutagenation. Appropriate methods are described by way of example in U.S. Pat. No. 5,565,350 or WO 00/15815

In a preferred embodiment, the encoded mutated CESA is a variant of SEQ ID NO:12, or SEQ ID NO:20, which includes one or more of the following:
  the amino acid at or corresponding to position 984 of SEQ ID NO:12, or SEQ ID NO:20 is Arg, His, Lys, Asp, Glu, Thr, Asn, Gln, Cys, Gly, Pro, Ala, Val, Leu, Ile, Met, Phe, Tyr, or Trp;
  the amino acid at or corresponding to position 995 of SEQ ID NO:12, or SEQ ID NO:20 is Arg, His, Lys, Asp, Glu, Ser, Thr, Asn, Gln, Cys, Pro, Ala, Val, Leu, Ile, Met, Phe, Tyr, or Trp,
  the amino acid at or corresponding to position 996 of SEQ ID NO:12, or SEQ ID NO:20 is Arg, His, Lys, Asp, Glu, Ser, Thr, Asn, Gln, Cys, Gly, Ala, Val, Leu, Ile, Met, Phe, Tyr, or Trp,
  the amino acid at or corresponding to position 999 of SEQ ID NO:12, or SEQ ID NO:20 is Arg, His, Lys, Asp, Glu, Ser, Thr, Asn, Gln, Cys, Pro, Ala, Val, Leu, Ile, Met, Phe, Tyr, or Trp,
  the amino acid at or corresponding to position 1038 of SEQ ID NO:12, or SEQ ID NO:20 is Arg, His, Lys, Asp, Glu, Thr, Asn, Gln, Cys, Gly, Pro, Ala, Val, Leu, Ile, Met, Phe, Tyr, or Trp,
  the amino acid at or corresponding to position 1041 of SEQ ID NO:12, or SEQ ID NO:20 is Arg, His, Lys, Asp, Glu, Thr, Asn, Gln, Cys, Gly, Pro, Ala, Val, Leu, Ile, Met, Phe, Tyr, or Trp.

In a particularly preferred embodiment, the amino acid at or corresponding to position 984 of SEQ ID NO:12, or SEQ ID NO:20 is Phe.

In another particularly preferred embodiment, the amino acid at or corresponding to position 1038 of SEQ ID NO:12, or SEQ ID NO:20 is Phe.

In another particularly preferred embodiment, the amino acid at or corresponding to position 1041 of SEQ ID NO:12, or SEQ ID NO:20 is Leu.

In a particularly preferred embodiment, the amino acid at or corresponding to position 1011 of SEQ ID NO:15 is Asp.

In another particularly preferred embodiment, the amino acid at or corresponding to position 1012 of SEQ ID NO:15 is Leu.

In another particularly preferred embodiment, the amino acid at or corresponding to position 1015 of SEQ ID NO:15 is Arg.

In a particularly preferred embodiment, the amino acid at or corresponding to position 1008 of SEQ ID NO:21 is Asp.

In another particularly preferred embodiment, the amino acid at or corresponding to position 1009 of SEQ ID NO:21 is Leu.

In another particularly preferred embodiment, the amino acid at or corresponding to position 1012 of SEQ ID 21 is Arg.

In another preferred embodiment, the encoded mutated CESA is a variant of SEQ ID NO:1, or SEQ ID NO:3, which includes one or more of the following:
  the amino acid at or corresponding to position 1009 of SEQ ID NO:1 is other than Gly, preferably Asp, and the amino acid corresponding to position 1013 of SEQ ID NO:1 is other than Gly, preferably Arg;
  the amino acid at or corresponding to position 1010 of SEQ ID NO:1 is other than Pro, preferably Leu, and the amino acid corresponding to position 1013 of SEQ ID NO:1 is other than Gly, preferably Arg;
  the amino acid at or corresponding to position 983 of SEQ ID NO:3 is other than Ser, preferably Phe, and the amino acid corresponding to position 1037 of SEQ ID NO:3 is other than Ser, preferably Phe;
  the amino acid at or corresponding to position 983 of SEQ ID NO:3 is other than Ser, preferably Phe, and the amino acid corresponding to position 1040 of SEQ ID NO:3 is other than Ser, preferably Leu.

In other aspects, the present invention encompasses a progeny or a descendant of a CESA-inhibiting herbicides-tolerant plant of the present invention as well as seeds derived from the CESA-inhibiting herbicides-tolerant plants of the invention and cells derived from the CESA-inhibiting herbicides-tolerant plants of the invention.

In some embodiments, the present invention provides a progeny or descendant plant derived from a plant comprising in at least some of its cells a polynucleotide operably linked to a promoter operable in plant cells, the promoter capable of expressing a mutated CESA polypeptide encoded by the polynucleotide, wherein the progeny or descendant plant comprises in at least some of its cells the recombinant polynucleotide operably linked to the promoter, the expression of the mutated CESA polypeptide conferring to the progeny or descendant plant tolerance to the CESA-inhibiting herbicides.

In one embodiment, seeds of the present invention preferably comprise the CESA-inhibiting herbicides-tolerance characteristics of the CESA-inhibiting herbicides-tolerant plant. In other embodiments, a seed is capable of germination into a plant comprising in at least some of its cells a polynucleotide operably linked to a promoter operable in plant cells, the promoter capable of expressing a mutated CESA polypeptide encoded by the polynucleotide, the expression of the mutated CESA polypeptide conferring to the progeny or descendant plant tolerance to the CESA-inhibiting herbicides.

In some embodiments, plant cells of the present invention are capable of regenerating a plant or plant part. In other embodiments, plant cells are not capable of regenerating a plant or plant part. Examples of cells not capable of regenerating a plant include, but are not limited to, endosperm, seed coat (testa & pericarp), and root cap.

In another embodiment, the present invention provides a plant cell of or capable of regenerating a plant comprising in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to the CESA-inhibiting herbicides, wherein the plant cell comprises the recombinant polynucleotide operably linked to a promoter.

In other embodiments, the present invention provides a plant cell comprising a polynucleotide operably linked to a promoter operable in plant cells, the promoter capable of expressing a mutated CESA polypeptide encoded by the polynucleotide, the expression of the mutated CESA polypeptide conferring to the cell tolerance to the CESA-inhibiting herbicides.

In another embodiment, the invention refers to a plant cell transformed by a nucleic acid encoding a mutated CESA polypeptide according to the present invention or to a plant cell which has been mutated to obtain a plant expressing a nucleic acid encoding a mutated CESA polypeptide according to the present invention, wherein expression of the nucleic acid in the plant cell results in increased resistance or tolerance to a CESA-inhibiting herbicide as compared to a wild type variety of the plant cell. Preferably, the mutated CESA polypeptide encoding nucleic acid comprises a polynucleotide sequence selected from the group consisting of: a) a polynucleotide as shown in SEQ ID NO: 36, 37, 38, or 39, or a variant or derivative thereof; b) a polynucleotide encoding a polypeptide as shown in SEQ ID NO: 1, 3, 11, 12, 13, 14, 15, 16, 17, 18, 19, 20, 21, 22, 23, 24, 25, 26, 27, 28, or 29, or a variant or derivative thereof; c) a polynucleotide comprising at least 60 consecutive nucleotides of any of a) or b); and d) a polynucleotide complementary to the polynucleotide of any of a) through c).

In some aspects, the present invention provides a plant product prepared from the CESA-inhibiting herbicides-tolerant plants hereof. In some embodiments, examples of plant products include, without limitation, grain, oil, and meal. In one embodiment, a plant product is plant grain (e.g., grain suitable for use as feed or for processing), plant oil (e.g., oil suitable for use as food or biodiesel), or plant meal (e.g., meal suitable for use as feed).

In one embodiment, a plant product prepared from a plant or plant part is provided, wherein the plant or plant part comprises in at least some of its cells a polynucleotide operably linked to a promoter operable in plant cells, the promoter capable of expressing a mutated CESA polypeptide encoded by the polynucleotide, the expression of the mutated CESA polypeptide conferring to the a plant or plant part tolerance to the CESA-inhibiting herbicides.

In another embodiment, the invention refers to a method of producing a transgenic plant cell with an increased resistance to a CESA-inhibiting herbicide as compared to a wild type variety of the plant cell comprising, transforming the plant cell with an expression cassette comprising a polynucleotide operably linked to a promoter operable in plant cells, the promoter capable of expressing a mutated CESA polypeptide encoded by the polynucleotide.

In another embodiment, the invention refers to a method of producing a transgenic plant comprising, (a) transforming a plant cell with an expression cassette comprising a a polynucleotide operably linked to a promoter operable in plant cells, the promoter capable of expressing a mutated CESA polypeptide encoded by the polynucleotide, and (b) generating a plant with an increased resistance to CESA-inhibiting herbicide from the plant cell.

In some aspects, the present invention provides a method for producing a CESA-inhibiting herbicides-tolerant plant. In one embodiment, the method comprises: regenerating a plant from a plant cell transformed with a polynucleotide operably linked to a promoter operable in plant cells, the promoter capable of expressing a mutated CESA polypeptide encoded by the polynucleotide, the expression of the mutated CESA polypeptide conferring to the plant tolerance to the CESA-inhibiting herbicides.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the CESA-inhibiting herbicide derivative herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene. An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Where appropriate, nucleic acid sequences may be optimized for increased expression in a transformed plant. For example, coding sequences that comprise plant-preferred codons for improved expression in a plant can be provided. See, for example, Campbell and Gowri (1990) Plant Physiol., 92: 1-11 fora discussion of host-preferred codon usage. Methods also are known in the art for preparing plant-preferred genes. See, for example, U.S. Pat. Nos. 5,380,831, and 5,436,391, and Murray et al. (1989) Nucleic Acids Res. 17:477-498, herein incorporated by reference.

Consequently, mutated CESA nucleic acids of the invention are provided in expression cassettes for expression in the plant of interest. The cassette will include regulatory sequences operably linked to a mutated CESA nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the mutated CESA nucleic acid sequence to be under the transcriptional regulation of the regulatory regions. The expression cassette may additionally contain selectable marker genes. The expression cassette of the present invention will include in the 5'-3' direction of transcription, a transcriptional and translational initiation region (i.e., a promoter), a mutated CESA encoding nucleic acid sequence of the invention, and a transcriptional and translational termination region (i.e., termination region) functional in plants. The promoter may be native or analogous, or foreign or heterologous, to the plant host and/or to the mutated CESA nucleic acid sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the mutated CESA nucleic acid sequence of the invention, it is intended that the promoter is not the native or naturally occurring promoter for the operably linked mutated CESA nucleic acid sequence of the invention. As used herein, a chimeric gene comprises a coding sequence operably linked to a transcription initiation region that is heterologous to the coding sequence. While it may be preferable to express the mutated CESA nucleic acids of the invention using heterologous promoters, the native promoter sequences may be used. Such constructs would change expression levels of the mutated CESA protein in the plant or plant cell. Thus, the phenotype of the plant or plant cell is altered.

The termination region may be native with the transcriptional initiation region, may be native with the operably linked mutated CESA sequence of interest, may be native with the plant host, or may be derived from another source (i.e., foreign or heterologous to the promoter, the mutated CESA nucleic acid sequence of interest, the plant host, or any combination thereof). Convenient termination regions are available from the Ti-plasmid of A. tumefaciens, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gown (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

While the polynucleotides of the invention may find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551;

Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention. Further, additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. Also, if desired, sequences can be readily modified to avoid predicted hairpin secondary mRNA structures. Nucleotide sequences for enhancing gene expression can also be used in the plant expression vectors. These include, for example, introns of the maize Adh gene Adh1-S intron 1, 2, and 6 (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize gene expression, the plant expression vectors of the invention also may contain DNA sequences containing matrix attachment regions (MARs). Plant cells transformed with such modified expression systems, then, may exhibit overexpression or constitutive expression of a nucleotide sequence of the invention.

The invention further provides an isolated recombinant expression vector comprising the expression cassette containing a mutated CESA nucleic acid nucleic acid as described above, wherein expression of the vector in a host cell results in increased tolerance to a CESA-inhibiting herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., mutated CESA polypeptides, fusion polypeptides, etc.)

Expression vectors may additionally contain 5' leader sequences in the expression construct. Such leader sequences can act to enhance translation. Translation leaders are known in the art and include: picornavirus leaders, for example, EMCV leader (Encephalomyo carditis 5' noncoding region) (Elroy-Stein et al. (1989) PNAS, 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

Other methods known to enhance translation also can be utilized, for example, introns, and the like. In preparing an expression vector, the various nucleic acid fragments may be manipulated, so as to provide for the nucleic acid sequences in the proper orientation and, as appropriate, in the proper reading frame. Toward this end, adapters or linkers may be employed to join the nucleic acid fragments or other manipulations may be involved to provide for convenient restriction sites, removal of superfluous nucleic acid, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor.

Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression within a particular plant tissue. Such tissue-preferred promoters include, but are not limited to, leaf-preferred promoters, root-preferred promoters, seed-preferred promoters, and stem-preferred promoters. Some examples of tissue-preferred promoters are described by, e.g., Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco of al. (1993) Plant Mol Biol. 23(6): 1 129-1138; Matsuoka et al. (1993) Voc Natl. Acad. ScL USA 90(20):9586-9590; and Guevara-Garcia et al. (1993) Plant J 4(3):495-505. Promoters can be modified, if necessary, for weak expression.

In some embodiments, the nucleic acids of interest can be targeted to the chloroplast for expression. In this manner, where the nucleic acid of interest is not directly inserted into the chloroplast, the expression vector will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the desired coding sequence of the invention such that the two sequences are contiguous and in the same reading frame. See, for example, Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481. For example, a chloroplast transit peptide known in the art can be fused to the amino acid sequence of a CESA polypeptide of the invention by operably linking a chloroplast-targeting sequence to the 5'-end of a nucleotide sequence encoding the CESA polypeptide.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J Biol. Chem. 266(5):3335-3342); EPSPS (Archer et al. (1990) J Bioenerg. Biomemb. 22(6):789-810); tryptophan synthase (Zhao et al. (1995) J Biol. Chem. 270(11):6081-6087); plastocyanin (Lawrence et al. (1997) J Biol. Chem. 272(33):20357-20363); chorismate synthase (Schmidt et al. (1993) J Biol. Chem. 268(36):27447-27457); and the light harvesting chlorophyll a/b binding protein (LHBP) (Lamppa et al. (1988) J Biol. Chem. 263: 14996-14999). See also Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Numerous plant transformation vectors and methods for transforming plants are available. See, for example, An, G. et al. (1986) Plant PysioL, 81:301-305; Fry, J., et al. (1987) Plant Cell Rep. 6:321-325; Block, M. (1988) Theor. Appl. Genet 0.16: 161-11 A; Hinchee, et al. (1990) Stadler. Genet. Symp. 2032\2.203-2\2; Cousins, et al. (1991) Aust. J. Plant Physiol. 18:481-494; Chee, P. P. and Slightom, J. L. (1992) Gene. II 8:255-260; Christou, et al. (1992) Trends. Biotechnol. 10:239-246; Halluin, et al. (1992) Bio/Technol. 10:309-314; Dhir, et al. (1992) Plant Physiol. 99:81-88; Casas et al. (1993) Proc. Nat. Acad Sd. USA 90: 1 1212-11216; Christou, P. (1993) In Vitro Cell. Dev. Biol.-Plant; 29P. 119-124; Davies, et al. (1993) Plant Cell Rep. 12: 180-183; Dong, J. A. and Mchughen, A. (1993) Plant ScL 91: 139-148; Franklin, C. I. and Trieu, T. N. (1993) Plant. Physiol. 102: 167; Golovkin, et al. (1993) Plant ScL 90:41-52; Guo Chin ScL Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

In some embodiments, the methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods. The term "introduction" or "transformation" as referred to herein further means the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

By "stable transformation" is intended that the polynucleotide construct introduced into a plant integrates into the genome of the plant and is capable of being inherited by descendent thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, the encoding nucleotide sequence is operably linked to a plant promoter, e.g. a promoter known in the art for high-level expression in a plant cell, and this construct is then introduced into a plant cell that is susceptible to CESA-inhibiting herbicides; and a transformed plant is regenerated. In some embodiments, the transformed plant is tolerant to exposure to a level of CESA-inhibiting herbicides that would kill or significantly injure a plant regenerated from an untransformed cell. This method can be applied to any plant species or crops.

Methodologies for constructing plant expression vectors and introducing foreign nucleic acids into plants are generally known in the art. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) Gene 100: 247-250; Scheid et al., (1991) MoL Gen. Genet., 228: 104-112; Guerche et al., (1987) Plant Science 52: 111-116; Neuhause et al., (1987) Theor. Appl Genet. 75: 30-36; Klein et al., (1987) Nature 327: 70-73; Howell et al., (1980) Science 208: 1265; Horsch et al., (1985) Science 227: 1229-1231; DeBlock et al., (1989) Plant Physiology 91: 694-701; Methods for Plant Molecular Biology (Weissbach and Weissbach, eds.) Academic Press, Inc. (1988) and Methods in Plant Molecular Biology (Schuler and Zielinski, eds.) Academic Press, Inc. (1989).

Other suitable methods of introducing nucleotide sequences into plant cells include microinjection as described by e.g., Crossway et al. (1986) Biotechniques 4:320-334, electroporation as described by e.g., Riggs et al. (1986) Proc. Natl. Acad. ScL USA 83:5602-5606, *Agrobacterium*-mediated transformation as described by e.g., Townsend et al., U.S. Pat. No. 5,563,055, Zhao et al., U.S. Pat. No. 5,981,840, direct gene transfer as described by, e.g., Paszkowski et al. (1984) EMBO J. 3:2717-2722, and ballistic particle acceleration as described by, e.g., U.S. Pat. Nos. 4,945,050; 5,879,918; 5,886,244; and 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) Biotechnology 6:923-926); and Led transformation (WO 00/28058). Also see, Weissinger et al., (1988) Ann. Rev. Genet. 22:421-477; Sanford et al, (1987) Particulate Science and Technology 5:27-37 (onion); Christou et al, (1988) Plant Physiol. 87:671-674 (soybean); McCabe et al., (1988) Bio/Technology 6:923-926 (soybean); Finer and McMullen (1991) In Vitro Cell Dev. Biol. 27P: 175-182 (soybean); Singh et al, (1998) Theor. Appl. Genet. 96:319-324 (soybean); Datta et al., (1990) Biotechnology 8:736-740 (rice); Klein et al., (1988) PNAS, 85:4305-4309 (maize); Klein et al., (1988) Biotechnology 6:559-563 (maize); U.S. Pat. Nos. 5,240,855; 5,322,783; and 5,324,646; Tomes et al., (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al., (1988) Plant Physiol. 91:440-444 (maize); Fromm et al., (1990) Biotechnology 8:833-839 (maize); Hooykaas-Van Slogteren et al., (1984) Nature (London) 311:763-764; Bowen et al, U.S. Pat. No. 5,736,369 (cereals); Bytebier et al, (1987) PNAS 84:5345-5349 (Liliaceae); De Wet et al., (1985) in The Experimental Manipulation of Ovule Tissues, ed. Chapman et al, (Longman, New York), pp. 197-209 (pollen); Kaeppler et al., (1990) Plant Cell Reports 9:415-418 and Kaeppler et al., (1992) Theor. Apph Genet. 84:560-566 (whisker-mediated transformation); D'Halluin et al., (1992) Plant Cell 4: 1495-1505 (electroporation); Li et al., (1993) Plant Cell Reports 12:250-255 and Christou and Ford (1995) Annals of Botany 75:407-413 (rice); Osjoda et al, (1996) Nature Biotechnology 14:745-750 (maize via *Agrobacterium tumefaciens*); each of which is herein incorporated by reference.

Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

One transformation method known to those of skill in the art is the dipping of a flowering plant into an Agrobacteria solution, wherein the Agrobacteria contains the CESA nucleic acid, followed by breeding of the transformed gametes. *Agrobacterium* mediated plant transformation can be performed using for example the GV3101(pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

In some embodiments, polynucleotides of the present invention may be introduced into plants by contacting plants with a virus or viral nucleic acids. Generally, such methods involve incorporating a polynucleotide construct of the invention within a viral DNA or RNA molecule. It is recognized that the polypeptides of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference. The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet e.g., pearl millet (*Pennisetum glaucum*), proso millet (*Panicum miliaceum*), foxtail millet (*Setaria italica*), finger millet (*Eleusine coracana*)), sunflower (*Helianthus annu*), safflower (*Carthamus tinctorius*), wheat (*Triticum aestivum*, T. *Turgidum* ssp. *durum*), soybean (*Glycine max*), tobacco (*Nicotiana tabacum*), potato (*Solarium tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (Macadamia integrifolia), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, Eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Aced Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the expression of the nucleic acid in the plant results in the plant's increased tolerance to CESA-inhibiting herbicide as compared to a wild type variety of the plant.

In another embodiment, the invention refers to a plant, comprising a plant cell according to the present invention, wherein expression of the nucleic acid in the plant results in the plant's increased resistance to CESA-inhibiting herbicide as compared to a wild type variety of the plant.

The plants described herein can be either transgenic crop plants or non-transgenic plants.

In addition to the general definition, give SUPRA, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues in order to allow for the expression of the mutated CESA of the present invention. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mutated CESA nucleic acids, the nucleic acids can be derived from different genomes or from the same genome. Alternatively, in embodiments wherein the plant is non-transgenic and comprises multiple mutated CESA nucleic acids, the nucleic acids are located on different genomes or on the same genome.

In certain embodiments, the present invention involves herbicide-resistant plants that are produced by mutation breeding. Such plants comprise a polynucleotide encoding a mutated CESA and are tolerant to one or more CESA-inhibiting herbicides. Such methods can involve, for example, exposing the plants or seeds to a mutagen, particularly a chemical mutagen such as, for example, ethyl methanesulfonate (EMS) and selecting for plants that have enhanced tolerance to at least one or more CESA-inhibiting herbicide [see Example 1].

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 250 to 290 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference.

Alternatively, herbicide-resistant plants according to the present invention can also be produced by using genome editing methods to select for plant cells comprising herbicide-resistance mutations and then regenerating herbicide-resistant plants therefrom. "Genome Editing" refers to a type of genetic engineering in which DNA is inserted, deleted or replaced in the genome of an organism using engineered nucleases. These nucleases are known to the skilled artisan to create site-specific double-strand breaks at desired locations in the genome. The induced double-strand breaks are repaired through nonhomologous end-joining or homologous recombination, resulting in targeted mutations. Known in the art are currently four families of engineered nucleases which can be used for the purposes of the present invention: meganucleases, zinc finger nucleases (ZFNs), transcription activator-like effector-based nucleases (TALEN), and the CRISPR-Cas system. For references, see, for example, Esvelt, K M. and Wang, H H. (2013) "Genome-scale engineering for systems and synthetic biology", Mol Syst Biol. 9 (1): 641; Tan, W S. et al., (2012) "Precision editing of large animal genomes", Adv Genet. 80: 37-97; Puchta, H. and Fauser, F. (2013) "Gene targeting in plants: 25 years later", Int. J. Dev. Biol. 57: 629-637; Boglioli, Elsy and Richard, Magali "Rewriting the book of life: a new era in precision genome editing", Boston Consulting Group, Retrieved Nov. 30, 2015; Method of the Year 2011. Nat Meth 9 (1), 1-1.

The plant of the present invention comprises at least one mutated CESA nucleic acid or over-expressed wild-type CESA nucleic acid, and has increased tolerance to a CESA-inhibiting herbicide as compared to a wild-type variety of the plant. It is possible for the plants of the present invention to have multiple mutated CESA nucleic acids from different genomes since these plants can contain more than one genome. For example, a plant contains two genomes, usually referred to as the A and B genomes. Because CESA is a required metabolic enzyme, it is assumed that each genome has at least one gene coding for the CESA enzyme (i.e. at least one CESA gene). As used herein, the term "CESA gene locus" refers to the position of a CESA gene on a genome, and the terms "CESA gene" and "CESA nucleic acid" refer to a nucleic acid encoding the CESA enzyme. The CESA nucleic acid on each genome differs in its nucleotide sequence from a CESA nucleic acid on another genome. One of skill in the art can determine the genome of origin of each CESA nucleic acid through genetic crossing and/or either sequencing methods or exonuclease digestion methods known to those of skill in the art.

The present invention includes plants comprising one, two, three, or more mutated CESA alleles, wherein the plant has increased tolerance to a CESA-inhibiting herbicide as compared to a wild-type variety of the plant. The mutated CESA alleles can comprise a nucleotide sequence selected from the group consisting of a polynucleotide as defined in SEQ ID NO: 36, 37, 38, or 39, or a variant or derivative thereof, a polynucleotide encoding a polypeptide as defined in SEQ ID NO: 1, 3, 11, 12, 13, 14, 15, 16, 17, 18, 19, 20, 21, 22, 23, 24, 25, 26, 27, 28, or 29, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a CESA gene of the plant or seed.

The herbicide-resistant plants of the invention that comprise polynucleotides encoding mutated CESA polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mutated CESA polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

It is to be understood that the plant of the present invention can comprise a wild type CESA nucleic acid in addition to a mutated CESA nucleic acid. It is contemplated that the CESA-inhibiting herbicide tolerant lines may contain a mutation in only one of multiple CESA isoenzymes. Therefore, the present invention includes a plant comprising one or more mutated CESA nucleic acids in addition to one or more wild type CESA nucleic acids.

In another embodiment, the invention refers to a seed produced by a transgenic plant comprising a plant cell of the present invention, wherein the seed is true breeding for an increased resistance to a CESA-inhibiting herbicide as compared to a wild type variety of the seed.

In other aspects, CESA-inhibiting herbicides-tolerant plants of the present invention can be employed as CESA-inhibiting herbicides-tolerance trait donor lines for development, as by traditional plant breeding, to produce other varietal and/or hybrid crops containing such trait or traits. All such resulting variety or hybrids crops, containing the ancestral CESA-inhibiting herbicides-tolerance trait or traits can be referred to herein as progeny or descendant of the ancestral, CESA-inhibiting herbicides-tolerant line(s).

In other embodiments, the present invention provides a method for producing a CESA-inhibiting herbicides-tolerant plant. The method comprises: crossing a first CESA-inhibiting herbicides-tolerant plant with a second plant to produce a CESA-inhibiting herbicides-tolerant progeny plant, wherein the first plant and the progeny plant comprise in at least some of their cells a polynucleotide operably linked to a promoter operable in plant cells, the recombinant polynucleotide being effective in the cells of the first plant to express a mutated CESA polypeptide encoded by the polynucleotide, the expression of the mutated CESA polypeptide conferring to the plant tolerance to CESA-inhibiting herbicides.

In some embodiments, traditional plant breeding is employed whereby the CESA-inhibiting herbicides-tolerant trait is introduced in the progeny plant resulting therefrom. In one embodiment, the present invention provides a method for producing a CESA-inhibiting herbicides-tolerant progeny plant, the method comprising: crossing a parent plant with a CESA-inhibiting herbicides-tolerant plant to introduce the CESA-inhibiting herbicides-tolerance characteristics of the CESA-inhibiting herbicides-tolerant plant into the germplasm of the progeny plant, wherein the progeny plant has increased tolerance to the CESA-inhibiting herbicides relative to the parent plant. In other embodiments, the method further comprises the step of introgressing the CESA-inhibiting herbicides-tolerance characteristics through traditional plant breeding techniques to obtain a descendent plant having the CESA-inhibiting herbicides-tolerance characteristics.

In other aspects, plants of the invention include those plants which, in addition to being CESA-inhibiting herbicides-tolerant, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, CESA-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, CESA-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other CESA inhibitors; and to GS inhibitors, such as glufosinate.

In addition to these classes of inhibitors, CESA-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype HPPD proteins, as mutant or wildtype PPO proteins, as mutant AHASL proteins, mutant ACCase proteins, mutant EPSPS proteins, or mutant glutamine synthetase proteins; or as mutant native, inbred, or transgenic aryloxy-alkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity. CESA-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, CESA-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB(bI) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or Xenorhabdus spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the CESA-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil Callosobruchus maculates; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil

*Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle Niptus hololeuc s; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear *Psylla Cacopsylla pyricola*; the currant aphid *Cryptomyzus ribis*; the grape *Phylloxera Daktulosphaira vitifoliae*; the citrus *psylla Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis* vires cens (tobacco budworm), *Homeosoma electellum* (sunflower moth); *Homona magnanima* (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armywonn); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculate*; Thysanoptera such as the tobacco *thrips Frankliniella fusca*, the flower *thrips Frankliniella intonsa*, the western flower *thrips Frankliniella* occidentalism the cotton bud *thrips Frankliniella schultzei*, the banded greenhouse *thrips Hercinothrips femoralis*, the soybean *thrips* Neohydatothrips *variabilis*, Kelly's citrus *thrips Pezothrips kellyanus*, the avocado *thrips Scirtothrips perseae*, the melon *thrips Thrips palmi*, and the onion *thrips Thrips tabaci*; and the like, and combinations comprising one or more of the foregoing organisms.

In some embodiments, expression of one or more protein toxins (e.g., insecticidal proteins) in the CESA-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the CESA-inhibiting herbicides-tolerant plants is effective for controlling cabbage seedpod weevil, the Bertha armyworm, *Lygus* bugs, or the diamondback moth.

Furthermore, in one embodiment, CESA-inhibiting herbicides-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, CESA-inhibiting herbicides-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, CESA-inhibiting herbicides-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, CESA-inhibiting herbicides-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, CESA-inhibiting herbicides-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, I,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, CESA-inhibiting herbicides-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla.

In other embodiments, CESA-inhibiting herbicides-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

In other aspects, a method for treating a plant of the present invention is provided.

In some embodiments, the method comprises contacting the plant with an agronomically acceptable composition. In one embodiment, the agronomically acceptable composition comprises a CESA inhibiting herbicide A. I, such as an azine as described herein.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a CESA-inhibiting herbicides herbicidal composition to the descendent plant.

In another embodiment, the invention refers to harvestable parts of the plant according to the present invention. Preferably, the harvestable parts comprise the CESA nucleic acid or CESA protein of the present invention. The harvestable parts may be seeds, roots, leaves and/or flowers comprising the CESA nucleic acid or CESA protein or parts thereof. Preferred parts of soy plants are soy beans comprising the CESA nucleic acid or CESA protein.

In another embodiment, the invention refers to products derived from a plant according to the present invention, parts thereof or harvestable parts thereof. A preferred plant product is fodder, seed meal, oil, or seed-treatment-coated seeds. Preferably, the meal and/or oil comprise the CESA nucleic acids or CESA proteins.

In another embodiment, the invention refers to a method for the production of a product, which method comprises
a) growing the plants of the invention or obtainable by the methods of invention and
b) producing said product from or by the plants of the invention and/or parts, e.g. seeds, of these plants.
In a further embodiment the method comprises the steps
a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Herbicides

As described above, the present invention provides nucleic acids, polypeptides, conferring tolerance of plants to compounds/herbicides interfering or inhibiting cell wall (cellulose) biosynthesis by interfering with the activity of cellulose synthase ("CESA-inhibiting herbicides"), also known to the person skilled in the art as Cellulose Biosynthesis Inhibitors (CBI).

Examples of herbicides which can be used according to the present invention, i.e. to which the plants according to the present invention are tolerant/resistant to, are compounds known to the skilled artisan as azines. Examples of Azines are described in detail in the following patent applications depicted in the following Table 1, which are incorporated by reference in its entirety.

TABLE 1

| No.: | Structural Formula | Publication or Application number/Internal reference |
|---|---|---|
| 1 | 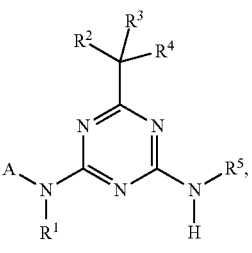 | WO 2014/064094 PF74283 |

TABLE 1-continued
| No.: | Structural Formula | Publication or Application number/Internal reference |
|---|---|---|
| 2 | 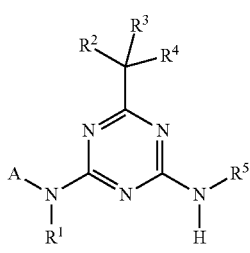 (I) | WO 2015/007711 PF75365 |
| 3 | 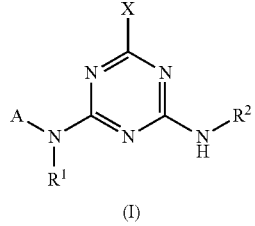 (I) | WO 2015/144881 PF76068 |
| 4 | 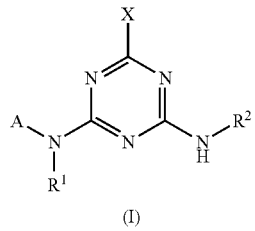 (I) | WO 2015/150541 PF76069 |
| 5 | 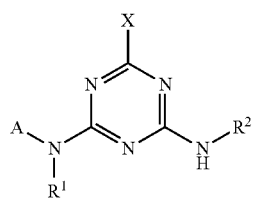 (I) | EP 14163742.1 PF76635 |
| 6 | 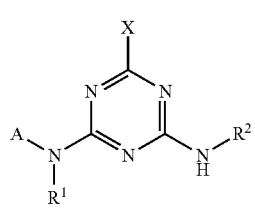 (I) | EP 14163743.9 PF76636 |
| 7 | 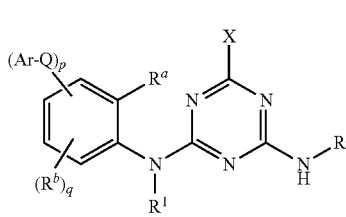 (I) | WO 2015/162166 PF76857 |

TABLE 1-continued

| No.: | Structural Formula | Publication or Application number/Internal reference |
|---|---|---|
| 8 | | WO 2015/162169 PF76888 |
| 9 | | WO 2015/155271 PF76890 |
| 10 | | WO 2015/155272 PF76930 |
| 11 | (I) | WO 2015/155273 PF77027 |
| 12 | | Indaziflam |
| 13 | | Triazofenamid |

TABLE 1-continued

| No.: | Structural Formula | Publication or Application number/Internal reference |
|---|---|---|
| 14 | 1-[4-chloro-3-(2,2,3,3,3-pentafluoropropoxymethyl)phenyl]-5-phenyl-1,2,4-triazole-3-carboxamide | Flupoxam |

Examples of preferred CESA inhibiting herbicides from the group of so-called azines which can be used according to the present invention are compounds having the Formula (I), known to the skilled artisan as azines.

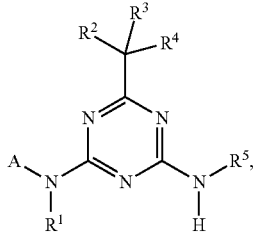

wherein
A is phenyl, which is substituted by two to five substituents selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_6$-haloalkynyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
  wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

Preferably the present invention provides azines of formula (I), wherein

A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)-carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
  wherein the $C_3$-$C_6$-cycloalkyl, $C_3$-$C_6$-cycloalkenyl or and three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

Useful for the present invention are also agrochemical compositions comprising at least one azines of formula (I) and auxiliaries customary for formulating crop protection agents.

The present invention also provides the use of azines of formula (I) as herbicides, i.e. for controlling harmful plants.

If the azines of formula (I) as described herein are capable of forming geometrical isomers, for example E/Z isomers, it is possible to use both, the pure isomers and mixtures thereof, in the compositions according to the invention.

If the azines of formula (I) as described herein have one or more centres of chirality and, as a consequence, are present as enantiomers or diastereomers, it is possible to use both, the pure enantiomers and diastereomers and their mixtures, in the compositions according to the invention.

If the azines of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

The organic moieties mentioned in the definition of the variables, e.g. $R^1$ to $R^5$, are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkylthio, alkylsulfinyl, alkylsulfonyl, (alkyl)amino, di(alkyl)amino chains can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$, n-butyl, $CH(CH_3)$—$C_2H_5$, $CH_2$—CH$(CH_3)_2$ and $C(CH_3)_3$;

$C_1$-$C_6$-alkyl and also the $C_1$-$C_6$-alkyl moieties of ($C_1$-$C_6$-alkyl)carbonyl, $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl: monocyclic saturated hydrocarbons having 3 to 6 ring members, such as cyclopropyl, cyclobutyl, cyclopentyl and cyclohexyl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-hexenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of ($C_1$-$C_6$-alkoxy)carbonyl, $C_1$-$C_6$-alkoxy-$C_1$-$C_6$-alkyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-di methylbutoxy, 2,2-di methylbutoxy, 2,3-di methylbutoxy, 3,3-di methylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-di-methylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutyl-sulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-di methyl propylsulfonyl, 1-ethylpropylsulfonyl, hexylsulfonyl, 1-methyl pentylsulfonyl, 2-methyl pentylsulfonyl, 3-methyl pentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino: for example methylamino, ethylamino, propylamino, 1-methylethyl-amino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutyl-amino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)

amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethyl-butyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)-amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

three- to six-membered heterocyclyl: monocyclic saturated or partially unsaturated hydrocarbon having three to six ring members as mentioned above which, in addition to carbon atoms, contains one or two heteroatoms selected from O, S and N;

for example 2-oxiranyl, 2-oxetanyl, 3-oxetanyl, 2-aziridinyl, 3-thietanyl, 1-azetidinyl, 2-azetidinyl, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl;

for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

for example 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl;

for example 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

The preferred embodiments of the invention mentioned herein below have to be understood as being preferred either independently from each other or in combination with one another.

According to a preferred embodiment of the invention preference is also given to those azines of formula (I), wherein the variables, either independently of one another or in combination with one another, have the following meanings:

Preferred are the azines of formula (I), wherein

A is phenyl, which is substituted by two to five substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

particularly preferred phenyl, which is substituted by two to five substituents selected from the group consisting of halogen, CN, $C_1$-$C_6$-alkyl and $C_1$-$C_6$-alkoxy;

particularly preferred selected from halogen and CN;

also particularly preferred selected from the group consisting of F, Cl, CN and $CH_3$;

especially preferred selected from the group consisting of F, Cl and CN;

especially preferred phenyl, which is substituted by two to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-

C$_6$-alkyl)amino, di(C$_1$-C$_6$-alkyl)amino, (C$_1$-C$_6$-alkyl)-carbonyl, (C$_1$-C$_6$-alkoxy)carbonyl;
  particularly preferred selected from the group consisting of halogen, CN, C$_1$-C$_6$-alkyl and C$_1$-C$_6$-alkoxy;
  especially preferred selected from halogen and CN;
  also especially preferred selected from the group consisting of F, Cl, CN and CH$_3$;
  more preferred selected from the group consisting of F, Cl and CN;
more preferred phenyl, which is substituted by two substituents selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)-carbonyl, (C$_1$-C$_6$-alkoxy)carbonyl;
  particularly preferred selected from the group consisting of halogen, CN, C$_1$-C$_6$-alkyl and C$_1$-C$_6$-alkoxy;
  especially preferred selected from halogen and CN;
  also especially preferred selected from the group consisting of F, Cl, CN and CH$_3$;
  more preferred selected from the group consisting of F, Cl and CN;
also more preferred phenyl, which is substituted by three substituents selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)-carbonyl, (C$_1$-C$_6$-alkoxy)carbonyl;
  particularly preferred selected from the group consisting of halogen, CN, C$_1$-C$_6$-alkyl and C$_1$-C$_6$-alkoxy;
  especially preferred selected from halogen and CN;
  also especially preferred selected from the group consisting of F, Cl, CN and CH$_3$;
  more preferred selected from the group consisting of F, Cl and CN;
also more preferred phenyl, which is substituted by four substituents selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)-carbonyl, (C$_1$-C$_6$-alkoxy)carbonyl;
  particularly preferred selected from the group consisting of halogen, CN, C$_1$-C$_6$-alkyl and C$_1$-C$_6$-alkoxy;
  especially preferred selected from halogen and CN;
  also especially preferred selected from the group consisting of F, Cl, CN and CH$_3$;
  more preferred selected from the group consisting of F, Cl and CN.
Also preferred are the azines of formula (I), wherein A is

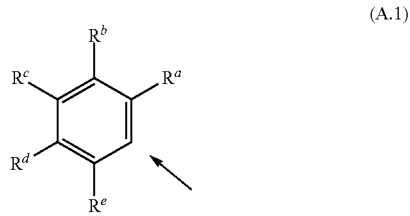

(A.1)

wherein
R$^a$ and R$^e$ independently of one another are halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)-carbonyl, (C$_1$-C$_6$-alkoxy)carbonyl; and
R$^b$, R$^c$ and R$^d$ independently of one another are hydrogen, halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;
particularly preferred R$^a$ and R$^e$ independently of one another are halogen, CN, C$_1$-C$_6$-alkyl or C$_1$-C$_6$-alkoxy; and
  R$^b$, R$^c$ and R$^d$ independently of one another are hydrogen, halogen, CN, NO$_2$, C$_1$-C$_6$-alkyl, C$_1$-C$_6$-haloalkyl or C$_1$-C$_6$-alkoxy;
especially preferred R$^a$ and R$^e$ independently of one another are halogen or CN; and
  R$^b$, R$^c$ and R$^d$ independently of one another are hydrogen, halogen, CN, C$_1$-C$_6$-alkyl or C$_1$-C$_6$-alkoxy;
more preferred R$^a$ and R$^e$ are halogen; and
  R$^b$, R$^c$ and R$^d$ independently of one another are hydrogen, halogen or CN;
most preferred R$^a$ and R$^e$ are halogen; and
  R$^b$, R$^c$ and R$^d$ are hydrogen;
also most preferred R$^a$, R$^b$, R$^d$ and R$^e$ are halogen; and
  R$^c$ hydrogen;
also most preferred R$^a$, R$^b$, R$^c$, R$^d$ and R$^e$ are halogen.
Also preferred are the azines of formula (I), wherein
A is

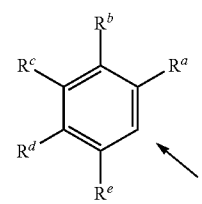

(A.1)

wherein R$^a$ is halogen or CN;
  R$^b$ and R$^d$ are H, halogen or CN;
  R$^c$ is H or halogen;
  R$^e$ is halogen, CN or C$_1$-C$_6$-alkyl;
particularly preferred R$^a$ is halogen;
  R$^b$, R$^c$ and R$^d$ are H or halogen; and
  R$^e$ is halogen or CN;
especially preferred R$^a$, R$^b$, R$^d$ and R$^e$ are halogen; and
  R$^c$ is H or halogen;
more preferred R$^a$, R$^b$, R$^d$ and R$^e$ are F; and
  R$^c$ is H or F.
Especially preferred are the azines of formula (I), wherein A is selected from the group consisting of (A.1.1), (A.1.2) and (A.1.3);

more preferred selected from the group consisting of (A.1.2) and (A.1.3);

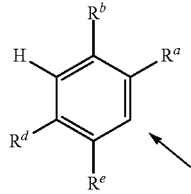
(A.1.1)

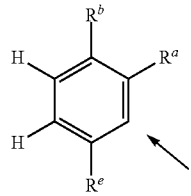
(A.1.2)

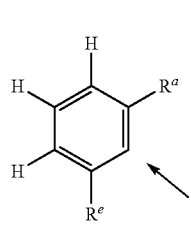
(A.1.3)

wherein $R^a$ and $R^e$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl; and $R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred $R^a$ and $R^e$ independently of one another are halogen, CN, $C_1$-$C_6$-alkyl or $C_1$-$C_6$-alkoxy; and $R^b$ and $R^d$ independently of one another are halogen, CN, $NO_2$, $C_1$-$C_6$-alkyl, $C_1$-$C_6$-haloalkyl or $C_1$-$C_6$-alkoxy;

especially preferred $R^a$ and $R^e$ independently of one another halogen or CN; and $R^b$ and $R^d$ independently of one another are halogen, CN, $C_1$-$C_6$-alkyl or $C_1$-$C_6$-alkoxy;

more preferred $R^a$ and $R^e$ are halogen; and $R^b$ and $R^d$ independently of one another are halogen or CN;

most preferred $R^a$, $R^b$, $R^d$ and $R^e$ are halogen.

Also especially preferred are the azines of formula (I), wherein

A is

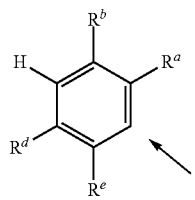
(A.1.1)

wherein $R^a$, $R^b$, $R^d$ and $R^e$ have the meanings, in particular the preferred meanings, as defined above.

Also especially preferred are the azines of formula (I), wherein

A is

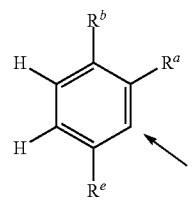
(A.1.2)

wherein $R^a$, $R^b$ and $R^e$ have the meanings, in particular the preferred meanings, as defined above.

Also especially preferred are the azines of formula (I), wherein

A is

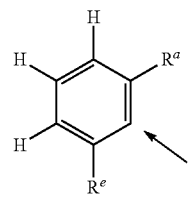
(A.1.3)

wherein $R^a$ and $R^e$ have the meanings, in particular the preferred meanings, as defined above.

Also preferred are the azines of formula (I), wherein

A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)carbonyl;

particularly preferred 2-fluoro-phenyl, which is substituted by one to four substituents selected from the group consisting of halogen, CN, $C_1$-$C_6$-alkyl and $C_1$-$C_6$-alkoxy;

particularly preferred selected from halogen and CN;

also particularly preferred selected from the group consisting of F, Cl, CN and $CH_3$;

especially preferred selected from the group consisting of F, Cl and CN;

especially preferred 2-fluoro-phenyl, which is substituted by one to three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
- particularly preferred selected from the group consisting of halogen, CN, $C_1$-$C_6$-alkyl and $C_1$-$C_6$-alkoxy;
- especially preferred selected from halogen and CN;
- also especially preferred selected from the group consisting of F, Cl, CN and $CH_3$;
- more preferred selected from the group consisting of F, Cl and CN;

more preferred 2-fluoro-phenyl, which is substituted by one substituent selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
- particularly preferred selected from the group consisting of halogen, CN, $C_1$-$C_6$-alkyl and $C_1$-$C_6$-alkoxy;
- especially preferred selected from halogen and CN;
- also especially preferred selected from the group consisting of F, Cl, CN and $CH_3$;
- more preferred selected from the group consisting of F, Cl and CN;

also more preferred 2-fluoro-phenyl, which is substituted by two substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
- particularly preferred selected from the group consisting of halogen, CN, $C_1$-$C_6$-alkyl and $C_1$-$C_6$-alkoxy;
- especially preferred selected from halogen and CN;
- also especially preferred selected from the group consisting of F, Cl, CN and $CH_3$;
- more preferred selected from the group consisting of F, Cl and CN;

also more preferred 2-fluoro-phenyl, which is substituted by three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;
- particularly preferred selected from the group consisting of halogen, CN, $C_1$-$C_6$-alkyl and $C_1$-$C_6$-alkoxy;
- especially preferred selected from halogen and CN;
- also especially preferred selected from the group consisting of F, Cl, CN and $CH_3$;
- more preferred selected from the group consisting of F, Cl and CN.

Also preferred are the azines of formula (I), wherein A is

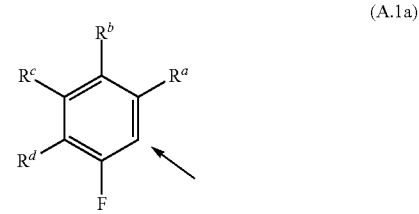

(A.1a)

wherein
$R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and
$R^b$, $R^b$ and $R^d$ independently of one another are hydrogen, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred $R^a$ is halogen, CN, $C_1$-$C_6$-alkyl or $C_1$-$C_6$-alkoxy; and
$R^b$, $R^c$ and $R^d$ independently of one another are hydrogen, halogen, CN, $NO_2$, $C_1$-$C_6$-alkyl, $C_1$-$C_6$-haloalkyl or $C_1$-$C_6$-alkoxy;
especially preferred $R^a$ is halogen or CN; and
$R^b$, $R^c$ and $R^d$ independently of one another are hydrogen, halogen, CN, $C_1$-$C_6$-alkyl or $C_1$-$C_6$-alkoxy;
more preferred $R^a$ is halogen; and
$R^b$, $R^c$ and $R^d$ independently of one another are hydrogen, halogen or CN;
most preferred $R^a$ is halogen; and
$R^b$, $R^c$ and $R^d$ are hydrogen;
also most preferred $R^a$, $R^b$ and $R^d$ are halogen; and
$R^c$ is hydrogen;
also most preferred $R^a$, $R^b$, $R^c$ and $R^d$ are halogen.

Also preferred are the azines of formula (I), wherein A is

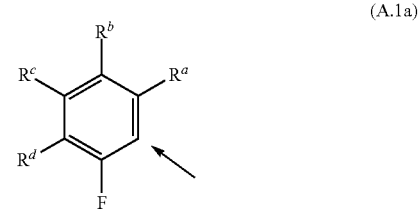

(A.1a)

wherein $R^a$ is halogen, CN or $C_1$-$C_6$-alkyl;
$R^b$ and $R^d$ are H, halogen or CN; and
$R^c$ is H or halogen;
particularly preferred $R^a$ is halogen or CN; and
$R^b$, $R^c$ and $R^d$ are H or halogen;
especially preferred $R^a$, $R^b$ and $R^d$ are halogen; and
$R^c$ is H or halogen;
Also especially preferred $R^a$, $R^b$ and $R^d$ are halogen; and
$R^c$ is H, F, Br or I;
more preferred $R^a$, $R^b$ and $R^d$ are F; and
$R^c$ is F, Br or I;
also more preferred $R^a$, $R^b$ and $R^d$ are F; and
$R^c$ is H or F.

Especially preferred are the azines of formula (I), wherein A is selected from the group consisting of (A.1a.1), (A.1a.2) and (A.1a.3);

more preferred selected from the group consisting of (A.1.2) and (A.1.3);

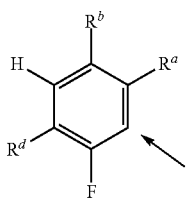
(A.1a.1)

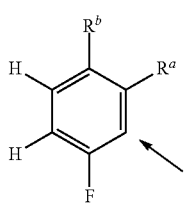
(A.1a.2)

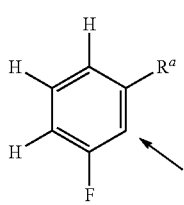
(A.1a.3)

wherein $R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and $R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred $R^a$ is halogen, CN, $C_1$-$C_6$-alkyl or $C_1$-$C_6$-alkoxy; and $R^b$ and $R^d$ independently of one another are halogen, CN, $NO_2$, $C_1$-$C_6$-alkyl, $C_1$-$C_6$-haloalkyl or $C_1$-$C_6$-alkoxy;

especially preferred $R^a$ is halogen or CN; and $R^b$ and $R^d$ independently of one another are halogen, CN, $C_1$-$C_6$-alkyl or $C_1$-$C_6$-alkoxy;

more preferred $R^a$ is halogen; and $R^b$ and $R^d$ independently of one another are halogen or CN;

most preferred $R^a$, $R^b$ and $R^d$ are halogen.

Also especially preferred are the azines of formula (I), wherein
A is

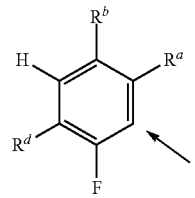
(A.1a.1)

wherein $R^a$, $R^b$ and $R^d$ have the meanings, in particular the preferred meanings, as defined above.

Also especially preferred are the azines of formula (I), wherein
A is

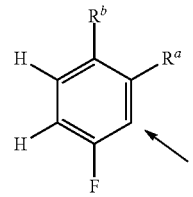
(A.1a.2)

wherein $R^a$ and $R^b$ have the meanings, in particular the preferred meanings, as defined above.

Also especially preferred are the azines of formula (I), wherein
A is

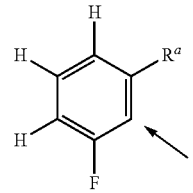
(A.1a.3)

wherein $R^a$ has the meanings, in particular the preferred meanings, as defined above.

Also preferred are the azines of formula (I), wherein $R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

especially preferred H, CN, $CH_3$, $CH_2OCH_3$, $OCH_3$, $COCH_3$ or $SO_2CH_3$;

more preferred hydrogen.

Also preferred are the azines of formula (I), wherein $R^2$ is H, halogen, $C_1$-$C_6$-alkyl or $C_1$-$C_6$-haloalkyl;

particularly preferred halogen, $C_1$-$C_6$-alkyl or $C_1$-$C_6$-haloalkyl;

also particularly preferred H, F, Cl, $CH_3$ or $CF_3$.

Also preferred are the azines of formula (I), wherein
$R^3$ and $R^4$ are
  independently of one another H, halogen, $C_1$-$C_6$-alkyl or $C_1$-$C_6$-haloalkyl; or
  together with the carbon atom to which they are attached form a moiety selected from the group consisting of $C_3$-$C_6$-cycloalkyl, $C_3$-$C_6$-cycloalkenyl and three- to six-membered heterocyclyl,
    wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;
  independently of one another particularly preferred H, halogen, $C_1$-$C_6$-alkyl or $C_1$-$C_6$-haloalkyl; or
  together with the carbon atom to which they are attached form a moiety selected from the group consisting of $C_3$-$C_6$-cycloalkyl and $C_3$-$C_6$-cycloalkenyl,
    wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;
  independently of one another especially preferred H, halogen, $C_1$-$C_6$-alkyl or $C_1$-$C_6$-haloalkyl;
  independently of one another more preferred H, halogen or $C_1$-$C_6$-alkyl.
Also preferred are the azines of formula (I), wherein
$R^2$ is H, halogen, $C_1$-$C_6$-alkyl; and
$R^3$ and $R^4$ are independently of one another H, halogen, $C_1$-$C_6$-alkyl, or together with the carbon atom to which they are attached form a $C_3$-$C_6$-cycloalkyl;
particularly preferred $R^2$ is H, halogen or $C_1$-$C_6$-alkyl;
  $R^3$ is $C_1$-$C_6$-alkyl;
  $R^4$ is H, halogen or $C_1$-$C_6$-alkyl;
  $R^3$ and $R^4$ together with the carbon atom to which they are attached form a $C_3$-$C_6$-cycloalkyl;
especially preferred $R^2$ is halogen or $C_1$-$C_6$-alkyl;
  $R^3$ is $C_1$-$C_6$-alkyl;
  $R^4$ is H or $C_1$-$C_6$-alkyl;
more preferred $R^2$ is halogen; and
  $R^3$ and $R^4$ are $C_1$-$C_6$-alkyl.
Also preferred are the azines of formula (I), wherein
$R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  especially preferred H, CN, $CH_3$, $CH_2OCH_3$, $OCH_3$, $COCH_3$ or $SO_2CH_3$;
  more preferred hydrogen.
Also preferred are the azines of formula (I), wherein
A is phenyl, which is substituted by two to five substituents
  selected from the group consisting of halogen, CN, $C_1$-$C_6$-alkyl and $C_1$-$C_6$-alkoxy;
  particularly preferred selected from halogen and CN;
  also particularly preferred selected from the group consisting of F, Cl, CN and $CH_3$;
  especially preferred selected from the group consisting of F, Cl and CN;
particularly preferred phenyl, which is substituted by two to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
  particularly preferred selected from the group consisting of halogen, CN, $C_1$-$C_6$-alkyl and $C_1$-$C_6$-alkoxy;
  especially preferred selected from halogen and CN;
  also especially preferred selected from the group consisting of F, Cl, CN and $CH_3$;
  more preferred selected from the group consisting of F, Cl and CN;
especially preferred phenyl, which is substituted by two substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
  particularly preferred selected from the group consisting of halogen, CN, $C_1$-$C_6$-alkyl and $C_1$-$C_6$-alkoxy;
  especially preferred selected from halogen and CN;
  also especially preferred selected from the group consisting of F, Cl, CN and $CH_3$;
  more preferred selected from the group consisting of F, Cl and CN;
also especially preferred phenyl, which is substituted by three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
  particularly preferred selected from the group consisting of halogen, CN, $C_1$-$C_6$-alkyl and $C_1$-$C_6$-alkoxy;
  especially preferred selected from halogen and CN;
  also especially preferred selected from the group consisting of F, Cl, CN and $CH_3$;
  more preferred selected from the group consisting of F, Cl and CN;
also specially preferred phenyl, which is substituted by four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
  particularly preferred selected from the group consisting of halogen, CN, $C_1$-$C_6$-alkyl and $C_1$-$C_6$-alkoxy;
  especially preferred selected from halogen and CN;
  also especially preferred selected from the group consisting of F, Cl, CN and $CH_3$;
  more preferred selected from the group consisting of F, Cl and CN;
$R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl) carbonyl or ($C_1$-$C_6$-alkyl)sulfonyl;
  especially preferred H, CN, $CH_3$, $CH_2OCH_3$, $OCH_3$, $COCH_3$ or $SO_2CH_3$;
more preferred hydrogen.
$R^2$ is H, halogen, $C_1$-$C_6$-alkyl or $C_1$-$C_6$-haloalkyl;
  particularly preferred halogen, $C_1$-$C_6$-alkyl or $C_1$-$C_6$-haloalkyl;
  also particularly preferred H, F, $CH_3$ or $CF_3$;
$R^3$ and $R^4$ are independently of one another H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl, $C_3$-$C_6$-cycloalkenyl and three- to six-membered heterocyclyl,
  wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;
independently of one another particularly preferred H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl and $C_3$-$C_6$-cycloalkenyl,
  wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;
independently of one another especially preferred H, halogen, $C_1$-$C_6$-alkyl or $C_1$-$C_6$-haloalkyl;
independently of one another more preferred H, halogen or $C_1$-$C_6$-alkyl;
and
$R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  especially preferred H, CN, $CH_3$, $CH_2OCH_3$, $OCH_3$, $COCH_3$ or $SO_2CH_3$;
  more preferred hydrogen.

Particular preference is given to azines of formula (I.a), which correspond to azines of formula (I) wherein A is (A.1) and $R^1$ and $R^5$ are H:

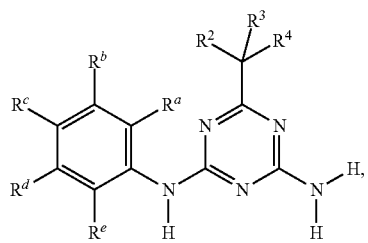

I.a wherein the variables $R^a$, $R^b$, $R^c$, $R^d$, $R^e$, $R^2$, $R^3$ and $R^4$ have the meanings, in particular the preferred meanings, as defined above;
special preference is given to the azines of the formulae (I.a.1) to (I.a.1406) of Table A, where the definitions of the variables $R^a$, $R^b$, $R^c$, $R^d$, $R^e$, $R^2$, $R^3$ and $R^4$ are of particular importance for the compounds according to the invention not only in combination with one another but in each case also on their own:

TABLE A

| No. | $R^a$ | $R^b$ | $R^c$ | $R^d$ | $R^e$ | $R^2$ | $R^3$ | $R^4$ |
|---|---|---|---|---|---|---|---|---|
| I.a.1 | F | H | H | H | F | $CH_3$ | H | H |
| I.a.2 | Cl | H | H | H | F | $CH_3$ | H | H |
| I.a.3 | Br | H | H | H | F | $CH_3$ | H | H |
| I.a.4 | CN | H | H | H | F | $CH_3$ | H | H |
| I.a.5 | $CH_3$ | H | H | H | F | $CH_3$ | H | H |
| I.a.6 | F | H | H | F | F | $CH_3$ | H | H |
| I.a.7 | Cl | H | H | F | F | $CH_3$ | H | H |
| I.a.8 | F | H | H | Cl | F | $CH_3$ | H | H |
| I.a.9 | Cl | H | H | F | F | $CH_3$ | H | H |
| I.a.10 | CN | H | H | F | F | $CH_3$ | H | H |
| I.a.11 | F | H | H | CN | F | $CH_3$ | H | H |
| I.a.12 | CN | H | H | F | F | $CH_3$ | H | H |
| I.a.13 | F | H | F | H | F | $CH_3$ | H | H |
| I.a.14 | Cl | H | F | H | F | $CH_3$ | H | H |
| I.a.15 | CN | H | F | H | F | $CH_3$ | H | H |
| I.a.16 | F | F | F | H | F | $CH_3$ | H | H |
| I.a.17 | Cl | F | F | H | F | $CH_3$ | H | H |
| I.a.18 | F | Cl | F | H | F | $CH_3$ | H | H |
| I.a.19 | Cl | F | F | H | F | $CH_3$ | H | H |
| I.a.20 | CN | F | F | H | F | $CH_3$ | H | H |
| I.a.21 | F | CN | F | H | F | $CH_3$ | H | H |
| I.a.22 | CN | F | F | H | F | $CH_3$ | H | H |
| I.a.23 | F | F | H | F | F | $CH_3$ | H | H |
| I.a.24 | Cl | F | H | F | F | $CH_3$ | H | H |
| I.a.25 | F | Cl | H | F | F | $CH_3$ | H | H |
| I.a.26 | CN | F | H | F | F | $CH_3$ | H | H |
| I.a.27 | F | CN | H | F | F | $CH_3$ | H | H |
| I.a.28 | F | F | F | F | F | $CH_3$ | H | H |
| I.a.29 | Cl | F | F | F | F | $CH_3$ | H | H |
| I.a.30 | F | Cl | F | F | F | $CH_3$ | H | H |
| I.a.31 | CN | F | F | F | F | $CH_3$ | H | H |
| I.a.32 | F | CN | F | F | F | $CH_3$ | H | H |
| I.a.33 | H | F | F | F | F | $CH_3$ | H | H |
| I.a.34 | F | F | Br | F | F | $CH_3$ | H | H |
| I.a.35 | F | F | C≡CH | F | F | $CH_3$ | H | H |
| I.a.36 | $CF_3$ | Cl | H | H | F | $CH_3$ | H | H |
| I.a.37 | F | F | I | F | F | $CH_3$ | H | H |
| I.a.38 | F | H | H | H | F | $CH_3$ | $CH_3$ | H |
| I.a.39 | Cl | H | H | H | F | $CH_3$ | $CH_3$ | H |
| I.a.40 | Br | H | H | H | F | $CH_3$ | $CH_3$ | H |
| I.a.41 | CN | H | H | H | F | $CH_3$ | $CH_3$ | H |
| I.a.42 | $CH_3$ | H | H | H | F | $CH_3$ | $CH_3$ | H |
| I.a.43 | F | H | H | F | F | $CH_3$ | $CH_3$ | H |
| I.a.44 | Cl | H | H | F | F | $CH_3$ | $CH_3$ | H |
| I.a.45 | F | H | H | Cl | F | $CH_3$ | $CH_3$ | H |
| I.a.46 | Cl | H | H | F | F | $CH_3$ | $CH_3$ | H |
| I.a.47 | CN | H | H | F | F | $CH_3$ | $CH_3$ | H |
| I.a.48 | F | H | H | CN | F | $CH_3$ | $CH_3$ | H |
| I.a.49 | CN | H | H | F | F | $CH_3$ | $CH_3$ | H |
| I.a.50 | F | H | F | H | F | $CH_3$ | $CH_3$ | H |
| I.a.51 | Cl | H | F | H | F | $CH_3$ | $CH_3$ | H |
| I.a.52 | CN | H | F | H | F | $CH_3$ | $CH_3$ | H |
| I.a.53 | F | F | F | H | F | $CH_3$ | $CH_3$ | H |
| I.a.54 | Cl | F | F | H | F | $CH_3$ | $CH_3$ | H |
| I.a.55 | F | Cl | F | H | F | $CH_3$ | $CH_3$ | H |
| I.a.56 | Cl | F | F | H | F | $CH_3$ | $CH_3$ | H |
| I.a.57 | CN | F | F | H | F | $CH_3$ | $CH_3$ | H |
| I.a.58 | F | CN | F | H | F | $CH_3$ | $CH_3$ | H |
| I.a.59 | CN | F | F | H | F | $CH_3$ | $CH_3$ | H |
| I.a.60 | F | F | H | F | F | $CH_3$ | $CH_3$ | H |
| I.a.61 | Cl | F | H | F | F | $CH_3$ | $CH_3$ | H |
| I.a.62 | F | Cl | H | F | F | $CH_3$ | $CH_3$ | H |
| I.a.63 | CN | F | H | F | F | $CH_3$ | $CH_3$ | H |
| I.a.64 | F | CN | H | F | F | $CH_3$ | $CH_3$ | H |
| I.a.65 | F | F | F | F | F | $CH_3$ | $CH_3$ | H |
| I.a.66 | Cl | F | F | F | F | $CH_3$ | $CH_3$ | H |
| I.a.67 | F | Cl | F | F | F | $CH_3$ | $CH_3$ | H |
| I.a.68 | CN | F | F | F | F | $CH_3$ | $CH_3$ | H |
| I.a.69 | F | CN | F | F | F | $CH_3$ | $CH_3$ | H |
| I.a.70 | H | F | F | F | F | $CH_3$ | $CH_3$ | H |
| I.a.71 | F | F | Br | F | F | $CH_3$ | $CH_3$ | H |
| I.a.72 | F | F | C≡H | F | F | $CH_3$ | $CH_3$ | H |
| I.a.73 | $CF_3$ | Cl | H | H | F | $CH_3$ | $CH_3$ | H |
| I.a.74 | F | F | I | F | F | $CH_3$ | $CH_3$ | H |
| I.a.75 | F | H | H | H | F | $CH_3$ | $CH_3$ | $CH_3$ |
| I.a.76 | Cl | H | H | H | F | $CH_3$ | $CH_3$ | $CH_3$ |
| I.a.77 | Br | H | H | H | F | $CH_3$ | $CH_3$ | $CH_3$ |
| I.a.78 | CN | H | H | H | F | $CH_3$ | $CH_3$ | $CH_3$ |
| I.a.79 | $CH_3$ | H | H | H | F | $CH_3$ | $CH_3$ | $CH_3$ |
| I.a.80 | F | H | H | F | F | $CH_3$ | $CH_3$ | $CH_3$ |
| I.a.81 | Cl | H | H | F | F | $CH_3$ | $CH_3$ | $CH_3$ |
| I.a.82 | F | H | H | Cl | F | $CH_3$ | $CH_3$ | $CH_3$ |
| I.a.83 | Cl | H | H | F | F | $CH_3$ | $CH_3$ | $CH_3$ |
| I.a.84 | CN | H | H | F | F | $CH_3$ | $CH_3$ | $CH_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.85 | F | H | H | CN | F | $CH_3$ | $CH_3$ | $CH_3$ |
| I.a.86 | CN | H | H | F | F | $CH_3$ | $CH_3$ | $CH_3$ |
| I.a.87 | F | H | F | H | F | $CH_3$ | $CH_3$ | $CH_3$ |
| I.a.88 | Cl | H | F | H | F | $CH_3$ | $CH_3$ | $CH_3$ |
| I.a.89 | CN | H | F | H | F | $CH_3$ | $CH_3$ | $CH_3$ |
| I.a.90 | F | F | F | H | F | $CH_3$ | $CH_3$ | $CH_3$ |
| I.a.91 | Cl | F | F | H | F | $CH_3$ | $CH_3$ | $CH_3$ |
| I.a.92 | F | Cl | F | H | F | $CH_3$ | $CH_3$ | $CH_3$ |
| I.a.93 | Cl | F | F | H | F | $CH_3$ | $CH_3$ | $CH_3$ |
| I.a.94 | CN | F | F | H | F | $CH_3$ | $CH_3$ | $CH_3$ |
| I.a.95 | F | CN | F | H | F | $CH_3$ | $CH_3$ | $CH_3$ |
| I.a.96 | CN | F | F | H | F | $CH_3$ | $CH_3$ | $CH_3$ |
| I.a.97 | F | F | H | F | F | $CH_3$ | $CH_3$ | $CH_3$ |
| I.a.98 | Cl | F | H | F | F | $CH_3$ | $CH_3$ | $CH_3$ |
| I.a.99 | F | Cl | H | F | F | $CH_3$ | $CH_3$ | $CH_3$ |
| I.a.100 | CN | F | H | F | F | $CH_3$ | $CH_3$ | $CH_3$ |
| I.a.101 | F | CN | H | F | F | $CH_3$ | $CH_3$ | $CH_3$ |
| I.a.102 | F | F | F | F | F | $CH_3$ | $CH_3$ | $CH_3$ |
| I.a.103 | Cl | F | F | F | F | $CH_3$ | $CH_3$ | $CH_3$ |
| I.a.104 | F | Cl | F | F | F | $CH_3$ | $CH_3$ | $CH_3$ |
| I.a.105 | CN | F | F | F | F | $CH_3$ | $CH_3$ | $CH_3$ |
| I.a.106 | F | CN | F | F | F | $CH_3$ | $CH_3$ | $CH_3$ |
| I.a.107 | H | F | F | F | F | $CH_3$ | $CH_3$ | $CH_3$ |
| I.a.108 | F | F | Br | F | F | $CH_3$ | $CH_3$ | $CH_3$ |
| I.a.109 | F | F | C≡CH | F | F | $CH_3$ | $CH_3$ | $CH_3$ |
| I.a.110 | $CF_3$ | Cl | H | H | F | $CH_3$ | $CH_3$ | $CH_3$ |
| I.a.111 | F | F | I | F | F | $CH_3$ | $CH_3$ | $CH_3$ |
| I.a.112 | F | H | H | H | F | F | F | F |
| I.a.113 | Cl | H | H | H | F | F | F | F |
| I.a.114 | Br | H | H | H | F | F | F | F |
| I.a.115 | CN | H | H | H | F | F | F | F |
| I.a.116 | $CH_3$ | H | H | H | F | F | F | F |
| I.a.117 | F | H | H | F | F | F | F | F |
| I.a.118 | Cl | H | H | F | F | F | F | F |
| I.a.119 | F | H | H | Cl | F | F | F | F |
| I.a.120 | Cl | H | H | F | F | F | F | F |
| I.a.121 | CN | H | H | F | F | F | F | F |
| I.a.122 | F | H | H | CN | F | F | F | F |
| I.a.123 | CN | H | H | F | F | F | F | F |
| I.a.124 | F | H | F | H | F | F | F | F |
| I.a.125 | Cl | H | F | H | F | F | F | F |
| I.a.126 | CN | H | F | H | F | F | F | F |
| I.a.127 | F | F | F | H | F | F | F | F |
| I.a.128 | Cl | F | F | H | F | F | F | F |
| I.a.129 | F | Cl | F | H | F | F | F | F |
| I.a.130 | Cl | F | F | H | F | F | F | F |
| I.a.131 | CN | F | F | H | F | F | F | F |
| I.a.132 | F | CN | F | H | F | F | F | F |
| I.a.133 | CN | F | F | H | F | F | F | F |
| I.a.134 | F | F | H | F | F | F | F | F |
| I.a.135 | Cl | F | H | F | F | F | F | F |
| I.a.136 | F | Cl | H | F | F | F | F | F |
| I.a.137 | CN | F | H | F | F | F | F | F |
| I.a.138 | F | CN | H | F | F | F | F | F |
| I.a.139 | F | F | F | F | F | F | F | F |
| I.a.140 | Cl | F | F | F | F | F | F | F |
| I.a.141 | F | Cl | F | F | F | F | F | F |
| I.a.142 | CN | F | F | F | F | F | F | F |
| I.a.143 | F | CN | F | F | F | F | F | F |
| I.a.144 | H | F | F | F | F | F | F | F |
| I.a.145 | F | F | Br | F | F | F | F | F |
| I.a.146 | F | F | C≡CH | F | F | F | F | F |
| I.a.147 | $CF_3$ | Cl | H | H | F | F | F | F |
| I.a.148 | F | F | I | F | F | F | F | F |
| I.a.149 | F | H | H | H | F | F | $CF_3$ | F |
| I.a.150 | Cl | H | H | H | F | F | $CF_3$ | F |
| I.a.151 | Br | H | H | H | F | F | $CF_3$ | F |
| I.a.152 | CN | H | H | H | F | F | $CF_3$ | F |
| I.a.153 | $CH_3$ | H | H | H | F | F | $CF_3$ | F |
| I.a.154 | F | H | H | F | F | F | $CF_3$ | F |
| I.a.155 | Cl | H | H | F | F | F | $CF_3$ | F |
| I.a.156 | F | H | H | Cl | F | F | $CF_3$ | F |
| I.a.157 | Cl | H | H | F | F | F | $CF_3$ | F |
| I.a.158 | CN | H | H | F | F | F | $CF_3$ | F |
| I.a.159 | F | H | H | CN | F | F | $CF_3$ | F |
| I.a.160 | CN | H | H | F | F | F | $CF_3$ | F |
| I.a.161 | F | H | F | H | F | F | $CF_3$ | F |
| I.a.162 | Cl | H | F | H | F | F | $CF_3$ | F |
| I.a.163 | CN | H | F | H | F | F | $CF_3$ | F |
| I.a.164 | F | F | F | H | F | F | $CF_3$ | F |
| I.a.165 | Cl | F | F | H | F | F | $CF_3$ | F |
| I.a.166 | F | Cl | F | H | F | F | $CF_3$ | F |
| I.a.167 | Cl | F | F | H | F | F | $CF_3$ | F |
| I.a.168 | CN | F | F | H | F | F | $CF_3$ | F |
| I.a.169 | F | CN | F | H | F | F | $CF_3$ | F |
| I.a.170 | CN | F | F | H | F | F | $CF_3$ | F |
| I.a.171 | F | F | H | F | F | F | $CF_3$ | F |
| I.a.172 | Cl | F | H | F | F | F | $CF_3$ | F |
| I.a.173 | F | Cl | H | F | F | F | $CF_3$ | F |
| I.a.174 | CN | F | H | F | F | F | $CF_3$ | F |
| I.a.175 | F | CN | H | F | F | F | $CF_3$ | F |
| I.a.176 | F | F | F | F | F | F | $CF_3$ | F |
| I.a.177 | Cl | F | F | F | F | F | $CF_3$ | F |
| I.a.178 | F | Cl | F | F | F | F | $CF_3$ | F |
| I.a.179 | CN | F | F | F | F | F | $CF_3$ | F |
| I.a.180 | F | CN | F | F | F | F | $CF_3$ | F |
| I.a.181 | H | F | F | F | F | F | $CF_3$ | F |
| I.a.182 | F | F | Br | F | F | F | $CF_3$ | F |
| I.a.183 | F | F | C≡CH | F | F | F | $CF_3$ | F |
| I.a.184 | $CF_3$ | Cl | H | H | F | F | $CF_3$ | F |
| I.a.185 | F | F | I | F | F | F | $CF_3$ | F |
| I.a.186 | F | H | H | H | F | F | $CH_3$ | F |
| I.a.187 | Cl | H | H | H | F | F | $CH_3$ | F |
| I.a.188 | Br | H | H | H | F | F | $CH_3$ | F |
| I.a.189 | CN | H | H | H | F | F | $CH_3$ | F |
| I.a.190 | $CH_3$ | H | H | H | F | F | $CH_3$ | F |
| I.a.191 | F | H | H | F | F | F | $CH_3$ | F |
| I.a.192 | Cl | H | H | F | F | F | $CH_3$ | F |
| I.a.193 | F | H | H | Cl | F | F | $CH_3$ | F |
| I.a.194 | Cl | H | H | F | F | F | $CH_3$ | F |
| I.a.195 | CN | H | H | F | F | F | $CH_3$ | F |
| I.a.196 | F | H | H | CN | F | F | $CH_3$ | F |
| I.a.197 | CN | H | H | F | F | F | $CH_3$ | F |
| I.a.198 | F | H | F | H | F | F | $CH_3$ | F |
| I.a.199 | Cl | H | F | H | F | F | $CH_3$ | F |
| I.a.200 | CN | H | F | H | F | F | $CH_3$ | F |
| I.a.201 | F | F | F | H | F | F | $CH_3$ | F |
| I.a.202 | Cl | F | F | H | F | F | $CH_3$ | F |
| I.a.203 | F | Cl | F | H | F | F | $CH_3$ | F |
| I.a.204 | Cl | F | F | H | F | F | $CH_3$ | F |
| I.a.205 | CN | F | F | H | F | F | $CH_3$ | F |
| I.a.206 | F | CN | F | H | F | F | $CH_3$ | F |
| I.a.207 | CN | F | F | H | F | F | $CH_3$ | F |
| I.a.208 | F | F | H | F | F | F | $CH_3$ | F |
| I.a.209 | Cl | F | H | F | F | F | $CH_3$ | F |
| I.a.210 | F | Cl | H | F | F | F | $CH_3$ | F |
| I.a.211 | CN | F | H | F | F | F | $CH_3$ | F |
| I.a.212 | F | CN | H | F | F | F | $CH_3$ | F |
| I.a.213 | F | F | F | F | F | F | $CH_3$ | F |
| I.a.214 | Cl | F | F | F | F | F | $CH_3$ | F |
| I.a.215 | F | Cl | F | F | F | F | $CH_3$ | F |
| I.a.216 | CN | F | F | F | F | F | $CH_3$ | F |
| I.a.217 | F | CN | F | F | F | F | $CH_3$ | F |
| I.a.218 | H | F | F | F | F | F | $CH_3$ | F |
| I.a.219 | F | F | Br | F | F | F | $CH_3$ | F |
| I.a.220 | F | F | C≡CH | F | F | F | $CH_3$ | F |
| I.a.221 | $CF_3$ | Cl | H | H | F | F | $CH_3$ | F |
| I.a.222 | F | F | I | F | F | F | $CH_3$ | F |
| I.a.223 | F | H | H | H | F | F | $CH_3$ | H |
| I.a.224 | Cl | H | H | H | F | F | $CH_3$ | H |
| I.a.225 | Br | H | H | H | F | F | $CH_3$ | H |
| I.a.226 | CN | H | H | H | F | F | $CH_3$ | H |
| I.a.227 | $CH_3$ | H | H | H | F | F | $CH_3$ | H |
| I.a.228 | F | H | H | F | F | F | $CH_3$ | H |
| I.a.229 | Cl | H | H | F | F | F | $CH_3$ | H |
| I.a.230 | F | H | H | Cl | F | F | $CH_3$ | H |
| I.a.231 | Cl | H | H | F | F | F | $CH_3$ | H |
| I.a.232 | CN | H | H | F | F | F | $CH_3$ | H |
| I.a.233 | F | H | H | CN | F | F | $CH_3$ | H |
| I.a.234 | CN | H | H | F | F | F | $CH_3$ | H |
| I.a.235 | F | H | F | H | F | F | $CH_3$ | H |
| I.a.236 | Cl | H | F | H | F | F | $CH_3$ | H |
| I.a.237 | CN | H | F | H | F | F | $CH_3$ | H |
| I.a.238 | F | F | F | H | F | F | $CH_3$ | H |
| I.a.239 | Cl | F | F | H | F | F | $CH_3$ | H |
| I.a.240 | F | Cl | F | H | F | F | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.241 | Cl | F | F | H | F | F | $CH_3$ | H |
| I.a.242 | CN | F | F | H | F | F | $CH_3$ | H |
| I.a.243 | F | CN | F | H | F | F | $CH_3$ | H |
| I.a.244 | CN | F | F | H | F | F | $CH_3$ | H |
| I.a.245 | F | F | H | F | F | F | $CH_3$ | H |
| I.a.246 | Cl | F | H | F | F | F | $CH_3$ | H |
| I.a.247 | F | Cl | H | F | F | F | $CH_3$ | H |
| I.a.248 | CN | F | H | F | F | F | $CH_3$ | H |
| I.a.249 | F | CN | H | F | F | F | $CH_3$ | H |
| I.a.250 | F | F | F | F | F | F | $CH_3$ | H |
| I.a.251 | Cl | F | F | F | F | F | $CH_3$ | H |
| I.a.252 | F | Cl | F | F | F | F | $CH_3$ | H |
| I.a.253 | CN | F | F | F | F | F | $CH_3$ | H |
| I.a.254 | F | CN | F | F | F | F | $CH_3$ | H |
| I.a.255 | H | F | F | F | F | F | $CH_3$ | H |
| I.a.256 | F | F | Br | F | F | F | $CH_3$ | H |
| I.a.257 | F | F | C≡CH | F | F | F | $CH_3$ | H |
| I.a.258 | $CF_3$ | Cl | H | H | F | F | $CH_3$ | H |
| I.a.259 | F | F | I | F | F | F | $CH_3$ | H |
| I.a.260 | F | H | H | H | F | F | $CH_3$ | $CH_3$ |
| I.a.261 | Cl | H | H | H | F | F | $CH_3$ | $CH_3$ |
| I.a.262 | Br | H | H | H | F | F | $CH_3$ | $CH_3$ |
| I.a.263 | CN | H | H | H | F | F | $CH_3$ | $CH_3$ |
| I.a.264 | $CH_3$ | H | H | H | F | F | $CH_3$ | $CH_3$ |
| I.a.265 | F | H | H | F | F | F | $CH_3$ | $CH_3$ |
| I.a.266 | Cl | H | H | F | F | F | $CH_3$ | $CH_3$ |
| I.a.267 | F | H | H | Cl | F | F | $CH_3$ | $CH_3$ |
| I.a.268 | Cl | H | H | F | F | F | $CH_3$ | $CH_3$ |
| I.a.269 | CN | H | H | F | F | F | $CH_3$ | $CH_3$ |
| I.a.270 | F | H | H | CN | F | F | $CH_3$ | $CH_3$ |
| I.a.271 | CN | H | H | H | F | F | $CH_3$ | $CH_3$ |
| I.a.272 | F | H | F | H | F | F | $CH_3$ | $CH_3$ |
| I.a.273 | Cl | H | F | H | F | F | $CH_3$ | $CH_3$ |
| I.a.274 | CN | H | F | H | F | F | $CH_3$ | $CH_3$ |
| I.a.275 | F | F | F | H | F | F | $CH_3$ | $CH_3$ |
| I.a.276 | Cl | F | F | H | F | F | $CH_3$ | $CH_3$ |
| I.a.277 | F | Cl | F | H | F | F | $CH_3$ | $CH_3$ |
| I.a.278 | Cl | F | F | H | F | F | $CH_3$ | $CH_3$ |
| I.a.279 | CN | F | F | H | F | F | $CH_3$ | $CH_3$ |
| I.a.280 | F | CN | F | H | F | F | $CH_3$ | $CH_3$ |
| I.a.281 | CN | F | F | H | F | F | $CH_3$ | $CH_3$ |
| I.a.282 | F | F | H | F | F | F | $CH_3$ | $CH_3$ |
| I.a.283 | Cl | F | H | F | F | F | $CH_3$ | $CH_3$ |
| I.a.284 | F | Cl | H | F | F | F | $CH_3$ | $CH_3$ |
| I.a.285 | CN | F | H | F | F | F | $CH_3$ | $CH_3$ |
| I.a.286 | F | CN | H | F | F | F | $CH_3$ | $CH_3$ |
| I.a.287 | F | F | F | F | F | F | $CH_3$ | $CH_3$ |
| I.a.288 | Cl | F | F | F | F | F | $CH_3$ | $CH_3$ |
| I.a.289 | F | Cl | F | F | F | F | $CH_3$ | $CH_3$ |
| I.a.290 | CN | F | F | F | F | F | $CH_3$ | $CH_3$ |
| I.a.291 | F | CN | F | F | F | F | $CH_3$ | $CH_3$ |
| I.a.292 | H | F | F | F | F | F | $CH_3$ | $CH_3$ |
| I.a.293 | F | F | Br | F | F | F | $CH_3$ | $CH_3$ |
| I.a.294 | F | F | C≡CH | F | F | F | $CH_3$ | $CH_3$ |
| I.a.295 | $CF_3$ | Cl | H | H | F | F | $CH_3$ | $CH_3$ |
| I.a.296 | F | F | I | F | F | F | $CH_3$ | $CH_3$ |
| I.a.297 | F | H | H | H | F | Cl | $CH_3$ | $CH_3$ |
| I.a.298 | Cl | H | H | H | F | Cl | $CH_3$ | $CH_3$ |
| I.a.299 | Br | H | H | H | F | Cl | $CH_3$ | $CH_3$ |
| I.a.300 | CN | H | H | H | F | Cl | $CH_3$ | $CH_3$ |
| I.a.301 | $CH_3$ | H | H | H | F | Cl | $CH_3$ | $CH_3$ |
| I.a.302 | F | H | H | F | F | Cl | $CH_3$ | $CH_3$ |
| I.a.303 | Cl | H | H | F | F | Cl | $CH_3$ | $CH_3$ |
| I.a.304 | F | H | H | Cl | F | Cl | $CH_3$ | $CH_3$ |
| I.a.305 | Cl | H | H | F | F | Cl | $CH_3$ | $CH_3$ |
| I.a.306 | CN | H | H | F | F | Cl | $CH_3$ | $CH_3$ |
| I.a.307 | F | H | H | CN | F | Cl | $CH_3$ | $CH_3$ |
| I.a.308 | CN | H | H | F | F | Cl | $CH_3$ | $CH_3$ |
| I.a.309 | F | H | F | H | F | Cl | $CH_3$ | $CH_3$ |
| I.a.310 | Cl | H | F | H | F | Cl | $CH_3$ | $CH_3$ |
| I.a.311 | CN | H | F | H | F | Cl | $CH_3$ | $CH_3$ |
| I.a.312 | F | F | F | H | F | Cl | $CH_3$ | $CH_3$ |
| I.a.313 | Cl | F | F | H | F | Cl | $CH_3$ | $CH_3$ |
| I.a.314 | F | Cl | F | H | F | Cl | $CH_3$ | $CH_3$ |
| I.a.315 | Cl | F | F | H | F | Cl | $CH_3$ | $CH_3$ |
| I.a.316 | CN | F | F | H | F | Cl | $CH_3$ | $CH_3$ |
| I.a.317 | F | CN | F | H | F | Cl | $CH_3$ | $CH_3$ |
| I.a.318 | CN | F | F | H | F | Cl | $CH_3$ | $CH_3$ |
| I.a.319 | F | F | H | F | F | Cl | $CH_3$ | $CH_3$ |
| I.a.320 | Cl | F | H | F | F | Cl | $CH_3$ | $CH_3$ |
| I.a.321 | F | Cl | H | F | F | Cl | $CH_3$ | $CH_3$ |
| I.a.322 | CN | F | H | F | F | Cl | $CH_3$ | $CH_3$ |
| I.a.323 | F | CN | H | F | F | Cl | $CH_3$ | $CH_3$ |
| I.a.324 | F | F | F | F | F | Cl | $CH_3$ | $CH_3$ |
| I.a.325 | Cl | F | F | F | F | Cl | $CH_3$ | $CH_3$ |
| I.a.326 | F | Cl | F | F | F | Cl | $CH_3$ | $CH_3$ |
| I.a.327 | CN | F | F | F | F | Cl | $CH_3$ | $CH_3$ |
| I.a.328 | F | CN | F | F | F | Cl | $CH_3$ | $CH_3$ |
| I.a.329 | H | F | F | F | F | Cl | $CH_3$ | $CH_3$ |
| I.a.330 | F | F | Br | F | F | Cl | $CH_3$ | $CH_3$ |
| I.a.331 | F | F | C≡CH | F | F | Cl | $CH_3$ | $CH_3$ |
| I.a.332 | $CF_3$ | Cl | H | H | F | Cl | $CH_3$ | $CH_3$ |
| I.a.333 | F | F | I | F | F | Cl | $CH_3$ | $CH_3$ |
| I.a.334 | F | H | H | H | F | F | $C_2H_5$ | $CH_3$ |
| I.a.335 | Cl | H | H | H | F | F | $C_2H_5$ | $CH_3$ |
| I.a.336 | Br | H | H | H | F | F | $C_2H_5$ | $CH_3$ |
| I.a.337 | CN | H | H | H | F | F | $C_2H_5$ | $CH_3$ |
| I.a.338 | $CH_3$ | H | H | H | F | F | $C_2H_5$ | $CH_3$ |
| I.a.339 | F | H | H | F | F | F | $C_2H_5$ | $CH_3$ |
| I.a.340 | Cl | H | H | F | F | F | $C_2H_5$ | $CH_3$ |
| I.a.341 | F | H | H | Cl | F | F | $C_2H_5$ | $CH_3$ |
| I.a.342 | Cl | H | H | F | F | F | $C_2H_5$ | $CH_3$ |
| I.a.343 | CN | H | H | F | F | F | $C_2H_5$ | $CH_3$ |
| I.a.344 | F | H | H | CN | F | F | $C_2H_5$ | $CH_3$ |
| I.a.345 | CN | H | H | F | F | F | $C_2H_5$ | $CH_3$ |
| I.a.346 | F | H | F | H | F | F | $C_2H_5$ | $CH_3$ |
| I.a.347 | Cl | H | F | H | F | F | $C_2H_5$ | $CH_3$ |
| I.a.348 | CN | H | F | H | F | F | $C_2H_5$ | $CH_3$ |
| I.a.349 | F | F | F | H | F | F | $C_2H_5$ | $CH_3$ |
| I.a.350 | Cl | F | F | H | F | F | $C_2H_5$ | $CH_3$ |
| I.a.351 | F | Cl | F | H | F | F | $C_2H_5$ | $CH_3$ |
| I.a.352 | Cl | F | F | H | F | F | $C_2H_5$ | $CH_3$ |
| I.a.353 | CN | F | F | H | F | F | $C_2H_5$ | $CH_3$ |
| I.a.354 | F | CN | F | H | F | F | $C_2H_5$ | $CH_3$ |
| I.a.355 | CN | F | F | H | F | F | $C_2H_5$ | $CH_3$ |
| I.a.356 | F | F | H | F | F | F | $C_2H_5$ | $CH_3$ |
| I.a.357 | Cl | F | H | F | F | F | $C_2H_5$ | $CH_3$ |
| I.a.358 | F | Cl | H | F | F | F | $C_2H_5$ | $CH_3$ |
| I.a.359 | CN | F | H | F | F | F | $C_2H_5$ | $CH_3$ |
| I.a.360 | F | CN | H | F | F | F | $C_2H_5$ | $CH_3$ |
| I.a.361 | F | F | F | F | F | F | $C_2H_5$ | $CH_3$ |
| I.a.362 | Cl | F | F | F | F | F | $C_2H_5$ | $CH_3$ |
| I.a.363 | F | Cl | F | F | F | F | $C_2H_5$ | $CH_3$ |
| I.a.364 | CN | F | F | F | F | F | $C_2H_5$ | $CH_3$ |
| I.a.365 | F | CN | F | F | F | F | $C_2H_5$ | $CH_3$ |
| I.a.366 | H | F | F | F | F | F | $C_2H_5$ | $CH_3$ |
| I.a.367 | F | F | Br | F | F | F | $C_2H_5$ | $CH_3$ |
| I.a.368 | F | F | C≡CH | F | F | F | $C_2H_5$ | $CH_3$ |
| I.a.369 | $CF_3$ | Cl | H | H | F | F | $C_2H_5$ | $CH_3$ |
| I.a.370 | F | F | I | F | F | F | $C_2H_5$ | $CH_3$ |
| I.a.371 | F | H | H | H | F | F | $C_2H_5$ | $C_2H_5$ |
| I.a.372 | Cl | H | H | H | F | F | $C_2H_5$ | $C_2H_5$ |
| I.a.373 | Br | H | H | H | F | F | $C_2H_5$ | $C_2H_5$ |
| I.a.374 | CN | H | H | H | F | F | $C_2H_5$ | $C_2H_5$ |
| I.a.375 | $CH_3$ | H | H | H | F | F | $C_2H_5$ | $C_2H_5$ |
| I.a.376 | F | H | H | F | F | F | $C_2H_5$ | $C_2H_5$ |
| I.a.377 | Cl | H | H | F | F | F | $C_2H_5$ | $C_2H_5$ |
| I.a.378 | F | H | H | Cl | F | F | $C_2H_5$ | $C_2H_5$ |
| I.a.379 | Cl | H | H | F | F | F | $C_2H_5$ | $C_2H_5$ |
| I.a.380 | CN | H | H | F | F | F | $C_2H_5$ | $C_2H_5$ |
| I.a.381 | F | H | H | CN | F | F | $C_2H_5$ | $C_2H_5$ |
| I.a.382 | CN | H | H | F | F | F | $C_2H_5$ | $C_2H_5$ |
| I.a.383 | F | H | F | H | F | F | $C_2H_5$ | $C_2H_5$ |
| I.a.384 | Cl | H | F | H | F | F | $C_2H_5$ | $C_2H_5$ |
| I.a.385 | CN | H | F | H | F | F | $C_2H_5$ | $C_2H_5$ |
| I.a.386 | F | F | F | H | F | F | $C_2H_5$ | $C_2H_5$ |
| I.a.387 | Cl | F | F | H | F | F | $C_2H_5$ | $C_2H_5$ |
| I.a.388 | F | Cl | F | H | F | F | $C_2H_5$ | $C_2H_5$ |
| I.a.389 | Cl | F | F | H | F | F | $C_2H_5$ | $C_2H_5$ |
| I.a.390 | CN | F | F | H | F | F | $C_2H_5$ | $C_2H_5$ |
| I.a.391 | F | CN | F | H | F | F | $C_2H_5$ | $C_2H_5$ |
| I.a.392 | CN | F | F | H | F | F | $C_2H_5$ | $C_2H_5$ |
| I.a.393 | F | F | H | F | F | F | $C_2H_5$ | $C_2H_5$ |
| I.a.394 | Cl | F | H | F | F | F | $C_2H_5$ | $C_2H_5$ |
| I.a.395 | F | Cl | H | F | F | F | $C_2H_5$ | $C_2H_5$ |
| I.a.396 | CN | F | H | F | F | F | $C_2H_5$ | $C_2H_5$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.397 | F | CN | H | F | F | F | $C_2H_5$ | $C_2H_5$ |
| I.a.398 | F | F | F | F | F | F | $C_2H_5$ | $C_2H_5$ |
| I.a.399 | Cl | F | F | F | F | F | $C_2H_5$ | $C_2H_5$ |
| I.a.400 | F | Cl | F | F | F | F | $C_2H_5$ | $C_2H_5$ |
| I.a.401 | CN | F | F | F | F | F | $C_2H_5$ | $C_2H_5$ |
| I.a.402 | F | CN | F | F | F | F | $C_2H_5$ | $C_2H_5$ |
| I.a.403 | H | F | F | F | F | F | $C_2H_5$ | $C_2H_5$ |
| I.a.404 | F | F | Br | F | F | F | $C_2H_5$ | $C_2H_5$ |
| I.a.405 | F | F | C≡CH | F | F | F | $C_2H_5$ | $C_2H_5$ |
| I.a.406 | $CF_3$ | Cl | H | H | F | F | $C_2H_5$ | $C_2H_5$ |
| I.a.407 | F | F | I | F | F | F | $C_2H_5$ | $C_2H_5$ |
| I.a.408 | F | H | H | H | F | H | —$(CH_2)_2$— | |
| I.a.409 | Cl | H | H | H | F | H | —$(CH_2)_2$— | |
| I.a.410 | Br | H | H | H | F | H | —$(CH_2)_2$— | |
| I.a.411 | CN | H | H | H | F | H | —$(CH_2)_2$— | |
| I.a.412 | $CH_3$ | H | H | H | F | H | —$(CH_2)_2$— | |
| I.a.413 | F | H | H | F | F | H | —$(CH_2)_2$— | |
| I.a.414 | Cl | H | H | F | F | H | —$(CH_2)_2$— | |
| I.a.415 | F | H | H | Cl | F | H | —$(CH_2)_2$— | |
| I.a.416 | Cl | H | H | F | F | H | —$(CH_2)_2$— | |
| I.a.417 | CN | H | H | F | F | H | —$(CH_2)_2$— | |
| I.a.418 | F | H | H | CN | F | H | —$(CH_2)_2$— | |
| I.a.419 | CN | H | H | F | F | H | —$(CH_2)_2$— | |
| I.a.420 | F | H | F | H | F | H | —$(CH_2)_2$— | |
| I.a.421 | Cl | H | F | H | F | H | —$(CH_2)_2$— | |
| I.a.422 | CN | H | F | H | F | H | —$(CH_2)_2$— | |
| I.a.423 | F | F | F | H | F | H | —$(CH_2)_2$— | |
| I.a.424 | Cl | F | F | H | F | H | —$(CH_2)_2$— | |
| I.a.425 | F | Cl | F | H | F | H | —$(CH_2)_2$— | |
| I.a.426 | Cl | F | F | H | F | H | —$(CH_2)_2$— | |
| I.a.427 | CN | F | F | H | F | H | —$(CH_2)_2$— | |
| I.a.428 | F | CN | F | H | F | H | —$(CH_2)_2$— | |
| I.a.429 | CN | F | F | H | F | H | —$(CH_2)_2$— | |
| I.a.430 | F | F | H | F | F | H | —$(CH_2)_2$— | |
| I.a.431 | Cl | F | H | F | F | H | —$(CH_2)_2$— | |
| I.a.432 | F | Cl | H | F | F | H | —$(CH_2)_2$— | |
| I.a.433 | CN | F | H | F | F | H | —$(CH_2)_2$— | |
| I.a.434 | F | CN | H | F | F | H | —$(CH_2)_2$— | |
| I.a.435 | F | F | F | F | F | H | —$(CH_2)_2$— | |
| I.a.436 | Cl | F | F | F | F | H | —$(CH_2)_2$— | |
| I.a.437 | F | Cl | F | F | F | H | —$(CH_2)_2$— | |
| I.a.438 | CN | F | F | F | F | H | —$(CH_2)_2$— | |
| I.a.439 | F | CN | F | F | F | H | —$(CH_2)_2$— | |
| I.a.440 | H | F | F | F | F | H | —$(CH_2)_2$— | |
| I.a.441 | F | F | Br | F | F | H | —$(CH_2)_2$— | |
| I.a.442 | F | F | C≡CH | F | F | H | —$(CH_2)_2$— | |
| I.a.443 | $CF_3$ | Cl | H | H | F | H | —$(CH_2)_2$— | |
| I.a.444 | F | F | I | F | F | H | —$(CH_2)_2$— | |
| I.a.445 | F | H | H | H | F | H | —$(CH_2)_3$— | |
| I.a.446 | Cl | H | H | H | F | H | —$(CH_2)_3$— | |
| I.a.447 | Br | H | H | H | F | H | —$(CH_2)_3$— | |
| I.a.448 | CN | H | H | H | F | H | —$(CH_2)_3$— | |
| I.a.449 | $CH_3$ | H | H | H | F | H | —$(CH_2)_3$— | |
| I.a.450 | F | H | H | F | F | H | —$(CH_2)_3$— | |
| I.a.451 | Cl | H | H | F | F | H | —$(CH_2)_3$— | |
| I.a.452 | F | H | H | Cl | F | H | —$(CH_2)_3$— | |
| I.a.453 | Cl | H | H | F | F | H | —$(CH_2)_3$— | |
| I.a.454 | CN | H | H | F | F | H | —$(CH_2)_3$— | |
| I.a.455 | F | H | H | CN | F | H | —$(CH_2)_3$— | |
| I.a.456 | CN | H | H | F | F | H | —$(CH_2)_3$— | |
| I.a.457 | F | H | F | H | F | H | —$(CH_2)_3$— | |
| I.a.458 | Cl | H | F | H | F | H | —$(CH_2)_3$— | |
| I.a.459 | CN | H | F | H | F | H | —$(CH_2)_3$— | |
| I.a.460 | F | F | F | H | F | H | —$(CH_2)_3$— | |
| I.a.461 | Cl | F | F | H | F | H | —$(CH_2)_3$— | |
| I.a.462 | F | Cl | F | H | F | H | —$(CH_2)_3$— | |
| I.a.463 | Cl | F | F | H | F | H | —$(CH_2)_3$— | |
| I.a.464 | CN | F | F | H | F | H | —$(CH_2)_3$— | |
| I.a.465 | F | CN | F | H | F | H | —$(CH_2)_3$— | |
| I.a.466 | CN | F | F | H | F | H | —$(CH_2)_3$— | |
| I.a.467 | F | F | H | F | F | H | —$(CH_2)_3$— | |
| I.a.468 | Cl | F | H | F | F | H | —$(CH_2)_3$— | |
| I.a.469 | F | Cl | H | F | F | H | —$(CH_2)_3$— | |
| I.a.470 | CN | F | H | F | F | H | —$(CH_2)_3$— | |
| I.a.471 | F | CN | H | F | F | H | —$(CH_2)_3$— | |
| I.a.472 | F | F | F | F | F | H | —$(CH_2)_3$— | |
| I.a.473 | Cl | F | F | F | F | H | —$(CH_2)_3$— | |
| I.a.474 | F | Cl | F | F | F | H | —$(CH_2)_3$— | |
| I.a.475 | CN | F | F | F | F | H | —$(CH_2)_3$— | |
| I.a.476 | F | CN | F | F | F | H | —$(CH_2)_3$— | |
| I.a.477 | H | F | F | F | F | H | —$(CH_2)_3$— | |
| I.a.478 | F | F | Br | F | F | H | —$(CH_2)_3$— | |
| I.a.479 | F | F | C≡CH | F | F | H | —$(CH_2)_3$— | |
| I.a.480 | $CF_3$ | Cl | H | H | F | H | —$(CH_2)_3$— | |
| I.a.481 | F | F | I | F | F | H | —$(CH_2)_3$— | |
| I.a.482 | F | H | H | H | F | H | —$(CH_2)_4$— | |
| I.a.483 | Cl | H | H | H | F | H | —$(CH_2)_4$— | |
| I.a.484 | Br | H | H | H | F | H | —$(CH_2)_4$— | |
| I.a.485 | CN | H | H | H | F | H | —$(CH_2)_4$— | |
| I.a.486 | $CH_3$ | H | H | H | F | H | —$(CH_2)_4$— | |
| I.a.487 | F | H | H | F | F | H | —$(CH_2)_4$— | |
| I.a.488 | Cl | H | H | F | F | H | —$(CH_2)_4$— | |
| I.a.489 | F | H | H | Cl | F | H | —$(CH_2)_4$— | |
| I.a.490 | Cl | H | H | F | F | H | —$(CH_2)_4$— | |
| I.a.491 | CN | H | H | F | F | H | —$(CH_2)_4$— | |
| I.a.492 | F | H | H | CN | F | H | —$(CH_2)_4$— | |
| I.a.493 | CN | H | H | F | F | H | —$(CH_2)_4$— | |
| I.a.494 | F | H | F | H | F | H | —$(CH_2)_4$— | |
| I.a.495 | Cl | H | F | H | F | H | —$(CH_2)_4$— | |
| I.a.496 | CN | H | F | H | F | H | —$(CH_2)_4$— | |
| I.a.497 | F | F | F | H | F | H | —$(CH_2)_4$— | |
| I.a.498 | Cl | F | F | H | F | H | —$(CH_2)_4$— | |
| I.a.499 | F | Cl | F | H | F | H | —$(CH_2)_4$— | |
| I.a.500 | Cl | F | F | H | F | H | —$(CH_2)_4$— | |
| I.a.501 | CN | F | F | H | F | H | —$(CH_2)_4$— | |
| I.a.502 | F | CN | F | H | F | H | —$(CH_2)_4$— | |
| I.a.503 | CN | F | F | H | F | H | —$(CH_2)_4$— | |
| I.a.504 | F | F | H | F | F | H | —$(CH_2)_4$— | |
| I.a.505 | Cl | F | H | F | F | H | —$(CH_2)_4$— | |
| I.a.506 | F | Cl | H | F | F | H | —$(CH_2)_4$— | |
| I.a.507 | CN | F | H | F | F | H | —$(CH_2)_4$— | |
| I.a.508 | F | CN | H | F | F | H | —$(CH_2)_4$— | |
| I.a.509 | F | F | F | F | F | H | —$(CH_2)_4$— | |
| I.a.510 | Cl | F | F | F | F | H | —$(CH_2)_4$— | |
| I.a.511 | F | Cl | F | F | F | H | —$(CH_2)_4$— | |
| I.a.512 | CN | F | F | F | F | H | —$(CH_2)_4$— | |
| I.a.513 | F | CN | F | F | F | H | —$(CH_2)_4$— | |
| I.a.514 | H | F | F | F | F | H | —$(CH_2)_4$— | |
| I.a.515 | F | F | Br | F | F | H | —$(CH_2)_4$— | |
| I.a.516 | F | F | C≡CH | F | F | H | —$(CH_2)_4$— | |
| I.a.517 | $CF_3$ | Cl | H | H | F | H | —$(CH_2)_4$— | |
| I.a.518 | F | F | I | F | F | H | —$(CH_2)_4$— | |
| I.a.519 | F | H | H | H | F | H | —$(CH_2)_5$— | |
| I.a.520 | Cl | H | H | H | F | H | —$(CH_2)_5$— | |
| I.a.521 | Br | H | H | H | F | H | —$(CH_2)_5$— | |
| I.a.522 | CN | H | H | H | F | H | —$(CH_2)_5$— | |
| I.a.523 | $CH_3$ | H | H | H | F | H | —$(CH_2)_5$— | |
| I.a.524 | F | H | H | F | F | H | —$(CH_2)_5$— | |
| I.a.525 | Cl | H | H | F | F | H | —$(CH_2)_5$— | |
| I.a.526 | F | H | H | Cl | F | H | —$(CH_2)_5$— | |
| I.a.527 | Cl | H | H | F | F | H | —$(CH_2)_5$— | |
| I.a.528 | CN | H | H | F | F | H | —$(CH_2)_5$— | |
| I.a.529 | F | H | H | CN | F | H | —$(CH_2)_5$— | |
| I.a.530 | CN | H | H | F | F | H | —$(CH_2)_5$— | |
| I.a.531 | F | H | F | H | F | H | —$(CH_2)_5$— | |
| I.a.532 | Cl | H | F | H | F | H | —$(CH_2)_5$— | |
| I.a.533 | CN | H | F | H | F | H | —$(CH_2)_5$— | |
| I.a.534 | F | F | F | H | F | H | —$(CH_2)_5$— | |
| I.a.535 | Cl | F | F | H | F | H | —$(CH_2)_5$— | |
| I.a.536 | F | Cl | F | H | F | H | —$(CH_2)_5$— | |
| I.a.537 | Cl | F | F | H | F | H | —$(CH_2)_5$— | |
| I.a.538 | CN | F | F | H | F | H | —$(CH_2)_5$— | |
| I.a.539 | F | CN | F | H | F | H | —$(CH_2)_5$— | |
| I.a.540 | CN | F | F | H | F | H | —$(CH_2)_5$— | |
| I.a.541 | F | F | H | F | F | H | —$(CH_2)_5$— | |
| I.a.542 | Cl | F | H | F | F | H | —$(CH_2)_5$— | |
| I.a.543 | F | Cl | H | F | F | H | —$(CH_2)_5$— | |
| I.a.544 | CN | F | H | F | F | H | —$(CH_2)_5$— | |
| I.a.545 | F | CN | H | F | F | H | —$(CH_2)_5$— | |
| I.a.546 | F | F | F | F | F | H | —$(CH_2)_5$— | |
| I.a.547 | Cl | F | F | F | F | H | —$(CH_2)_5$— | |
| I.a.548 | F | Cl | F | F | F | H | —$(CH_2)_5$— | |
| I.a.549 | CN | F | F | F | F | H | —$(CH_2)_5$— | |
| I.a.550 | F | CN | F | F | F | H | —$(CH_2)_5$— | |
| I.a.551 | H | F | F | F | F | H | —$(CH_2)_5$— | |
| I.a.552 | F | F | Br | F | F | H | —$(CH_2)_5$— | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.553 | F | F | C≡CH | F | F | H | | —(CH$_2$)$_5$— |
| I.a.554 | CF$_3$ | Cl | H | H | F | H | | —(CH$_2$)$_5$— |
| I.a.555 | F | F | I | F | F | H | | —(CH$_2$)$_5$— |
| I.a.556 | F | H | H | H | F | CH$_3$ | | —(CH$_2$)$_2$— |
| I.a.557 | Cl | H | H | H | F | CH$_3$ | | —(CH$_2$)$_2$— |
| I.a.558 | Br | H | H | H | F | CH$_3$ | | —(CH$_2$)$_2$— |
| I.a.559 | CN | H | H | H | F | CH$_3$ | | —(CH$_2$)$_2$— |
| I.a.560 | CH$_3$ | H | H | H | F | CH$_3$ | | —(CH$_2$)$_2$— |
| I.a.561 | F | H | H | F | F | CH$_3$ | | —(CH$_2$)$_2$— |
| I.a.562 | Cl | H | H | F | F | CH$_3$ | | —(CH$_2$)$_2$— |
| I.a.563 | F | H | H | Cl | F | CH$_3$ | | —(CH$_2$)$_2$— |
| I.a.564 | Cl | H | H | F | F | CH$_3$ | | —(CH$_2$)$_2$— |
| I.a.565 | CN | H | H | F | F | CH$_3$ | | —(CH$_2$)$_2$— |
| I.a.566 | F | H | H | CN | F | CH$_3$ | | —(CH$_2$)$_2$— |
| I.a.567 | CN | H | H | F | F | CH$_3$ | | —(CH$_2$)$_2$— |
| I.a.568 | F | H | F | H | F | CH$_3$ | | —(CH$_2$)$_2$— |
| I.a.569 | Cl | H | F | H | F | CH$_3$ | | —(CH$_2$)$_2$— |
| I.a.570 | CN | H | F | H | F | CH$_3$ | | —(CH$_2$)$_2$— |
| I.a.571 | F | F | F | H | F | CH$_3$ | | —(CH$_2$)$_2$— |
| I.a.572 | Cl | F | F | H | F | CH$_3$ | | —(CH$_2$)$_2$— |
| I.a.573 | F | Cl | F | H | F | CH$_3$ | | —(CH$_2$)$_2$— |
| I.a.574 | Cl | F | F | H | F | CH$_3$ | | —(CH$_2$)$_2$— |
| I.a.575 | CN | F | F | H | F | CH$_3$ | | —(CH$_2$)$_2$— |
| I.a.576 | F | CN | F | H | F | CH$_3$ | | —(CH$_2$)$_2$— |
| I.a.577 | CN | F | F | H | F | CH$_3$ | | —(CH$_2$)$_2$— |
| I.a.578 | F | F | H | F | F | CH$_3$ | | —(CH$_2$)$_2$— |
| I.a.579 | Cl | F | H | F | F | CH$_3$ | | —(CH$_2$)$_2$— |
| I.a.580 | F | Cl | H | F | F | CH$_3$ | | —(CH$_2$)$_2$— |
| I.a.581 | CN | F | H | F | F | CH$_3$ | | —(CH$_2$)$_2$— |
| I.a.582 | F | CN | H | F | F | CH$_3$ | | —(CH$_2$)$_2$— |
| I.a.583 | F | F | F | F | F | CH$_3$ | | —(CH$_2$)$_2$— |
| I.a.584 | Cl | F | F | F | F | CH$_3$ | | —(CH$_2$)$_2$— |
| I.a.585 | F | Cl | F | F | F | CH$_3$ | | —(CH$_2$)$_2$— |
| I.a.586 | CN | F | F | F | F | CH$_3$ | | —(CH$_2$)$_2$— |
| I.a.587 | F | CN | F | F | F | CH$_3$ | | —(CH$_2$)$_2$— |
| I.a.588 | H | F | F | F | F | CH$_3$ | | —(CH$_2$)$_2$— |
| I.a.589 | F | F | Br | F | F | CH$_3$ | | —(CH$_2$)$_2$— |
| I.a.590 | F | F | C≡CH | F | F | CH$_3$ | | —(CH$_2$)$_2$— |
| I.a.591 | CF$_3$ | Cl | H | H | F | CH$_3$ | | —(CH$_2$)$_2$— |
| I.a.592 | F | F | I | F | F | CH$_3$ | | —(CH$_2$)$_2$— |
| I.a.593 | F | H | H | H | F | CH$_3$ | | —(CH$_2$)$_3$— |
| I.a.594 | Cl | H | H | H | F | CH$_3$ | | —(CH$_2$)$_3$— |
| I.a.595 | Br | H | H | H | F | CH$_3$ | | —(CH$_2$)$_3$— |
| I.a.596 | CN | H | H | H | F | CH$_3$ | | —(CH$_2$)$_3$— |
| I.a.597 | CH$_3$ | H | H | H | F | CH$_3$ | | —(CH$_2$)$_3$— |
| I.a.598 | F | H | H | F | F | CH$_3$ | | —(CH$_2$)$_3$— |
| I.a.599 | Cl | H | H | F | F | CH$_3$ | | —(CH$_2$)$_3$— |
| I.a.600 | F | H | H | Cl | F | CH$_3$ | | —(CH$_2$)$_3$— |
| I.a.601 | Cl | H | H | F | F | CH$_3$ | | —(CH$_2$)$_3$— |
| I.a.602 | CN | H | H | F | F | CH$_3$ | | —(CH$_2$)$_3$— |
| I.a.603 | F | H | H | CN | F | CH$_3$ | | —(CH$_2$)$_3$— |
| I.a.604 | CN | H | H | F | F | CH$_3$ | | —(CH$_2$)$_3$— |
| I.a.605 | F | H | F | H | F | CH$_3$ | | —(CH$_2$)$_3$— |
| I.a.606 | Cl | H | F | H | F | CH$_3$ | | —(CH$_2$)$_3$— |
| I.a.607 | CN | H | F | H | F | CH$_3$ | | —(CH$_2$)$_3$— |
| I.a.608 | F | F | F | H | F | CH$_3$ | | —(CH$_2$)$_3$— |
| I.a.609 | Cl | F | F | H | F | CH$_3$ | | —(CH$_2$)$_3$— |
| I.a.610 | F | Cl | F | H | F | CH$_3$ | | —(CH$_2$)$_3$— |
| I.a.611 | Cl | F | F | H | F | CH$_3$ | | —(CH$_2$)$_3$— |
| I.a.612 | CN | F | F | H | F | CH$_3$ | | —(CH$_2$)$_3$— |
| I.a.613 | F | CN | F | H | F | CH$_3$ | | —(CH$_2$)$_3$— |
| I.a.614 | CN | F | F | H | F | CH$_3$ | | —(CH$_2$)$_3$— |
| I.a.615 | F | F | H | F | F | CH$_3$ | | —(CH$_2$)$_3$— |
| I.a.616 | Cl | F | H | F | F | CH$_3$ | | —(CH$_2$)$_3$— |
| I.a.617 | F | Cl | H | F | F | CH$_3$ | | —(CH$_2$)$_3$— |
| I.a.618 | CN | F | H | F | F | CH$_3$ | | —(CH$_2$)$_3$— |
| I.a.619 | F | CN | H | F | F | CH$_3$ | | —(CH$_2$)$_3$— |
| I.a.620 | F | F | F | F | F | CH$_3$ | | —(CH$_2$)$_3$— |
| I.a.621 | Cl | F | F | F | F | CH$_3$ | | —(CH$_2$)$_3$— |
| I.a.622 | F | Cl | F | F | F | CH$_3$ | | —(CH$_2$)$_3$— |
| I.a.623 | CN | F | F | F | F | CH$_3$ | | —(CH$_2$)$_3$— |
| I.a.624 | F | CN | F | F | F | CH$_3$ | | —(CH$_2$)$_3$— |
| I.a.625 | H | F | F | F | F | CH$_3$ | | —(CH$_2$)$_3$— |
| I.a.626 | F | F | Br | F | F | CH$_3$ | | —(CH$_2$)$_3$— |
| I.a.627 | F | F | C≡CH | F | F | CH$_3$ | | —(CH$_2$)$_3$— |
| I.a.628 | CF$_3$ | Cl | H | H | F | CH$_3$ | | —(CH$_2$)$_3$— |
| I.a.629 | F | F | I | F | F | CH$_3$ | | —(CH$_2$)$_3$— |
| I.a.630 | F | H | H | H | F | CH$_3$ | | —(CH$_2$)$_4$— |
| I.a.631 | Cl | H | H | H | F | CH$_3$ | | —(CH$_2$)$_4$— |
| I.a.632 | Br | H | H | H | F | CH$_3$ | | —(CH$_2$)$_4$— |
| I.a.633 | CN | H | H | H | F | CH$_3$ | | —(CH$_2$)$_4$— |
| I.a.634 | CH$_3$ | H | H | H | F | CH$_3$ | | —(CH$_2$)$_4$— |
| I.a.635 | F | H | H | F | F | CH$_3$ | | —(CH$_2$)$_4$— |
| I.a.636 | Cl | H | H | F | F | CH$_3$ | | —(CH$_2$)$_4$— |
| I.a.637 | F | H | H | Cl | F | CH$_3$ | | —(CH$_2$)$_4$— |
| I.a.638 | Cl | H | H | F | F | CH$_3$ | | —(CH$_2$)$_4$— |
| I.a.639 | CN | H | H | F | F | CH$_3$ | | —(CH$_2$)$_4$— |
| I.a.640 | F | H | H | CN | F | CH$_3$ | | —(CH$_2$)$_4$— |
| I.a.641 | CN | H | H | F | F | CH$_3$ | | —(CH$_2$)$_4$— |
| I.a.642 | F | H | F | H | F | CH$_3$ | | —(CH$_2$)$_4$— |
| I.a.643 | Cl | H | F | H | F | CH$_3$ | | —(CH$_2$)$_4$— |
| I.a.644 | CN | H | F | H | F | CH$_3$ | | —(CH$_2$)$_4$— |
| I.a.645 | F | F | F | H | F | CH$_3$ | | —(CH$_2$)$_4$— |
| I.a.646 | Cl | F | F | H | F | CH$_3$ | | —(CH$_2$)$_4$— |
| I.a.647 | F | Cl | F | H | F | CH$_3$ | | —(CH$_2$)$_4$— |
| I.a.648 | Cl | F | F | H | F | CH$_3$ | | —(CH$_2$)$_4$— |
| I.a.649 | CN | F | F | H | F | CH$_3$ | | —(CH$_2$)$_4$— |
| I.a.650 | F | CN | F | H | F | CH$_3$ | | —(CH$_2$)$_4$— |
| I.a.651 | CN | F | F | H | F | CH$_3$ | | —(CH$_2$)$_4$— |
| I.a.652 | F | F | H | F | F | CH$_3$ | | —(CH$_2$)$_4$— |
| I.a.653 | Cl | F | H | F | F | CH$_3$ | | —(CH$_2$)$_4$— |
| I.a.654 | F | Cl | H | F | F | CH$_3$ | | —(CH$_2$)$_4$— |
| I.a.655 | CN | F | H | F | F | CH$_3$ | | —(CH$_2$)$_4$— |
| I.a.656 | F | CN | H | F | F | CH$_3$ | | —(CH$_2$)$_4$— |
| I.a.657 | F | F | F | F | F | CH$_3$ | | —(CH$_2$)$_4$— |
| I.a.658 | Cl | F | F | F | F | CH$_3$ | | —(CH$_2$)$_4$— |
| I.a.659 | F | Cl | F | F | F | CH$_3$ | | —(CH$_2$)$_4$— |
| I.a.660 | CN | F | F | F | F | CH$_3$ | | —(CH$_2$)$_4$— |
| I.a.661 | F | CN | F | F | F | CH$_3$ | | —(CH$_2$)$_4$— |
| I.a.662 | H | F | F | F | F | CH$_3$ | | —(CH$_2$)$_4$— |
| I.a.663 | F | F | Br | F | F | CH$_3$ | | —(CH$_2$)$_4$— |
| I.a.664 | F | F | C≡CH | F | F | CH$_3$ | | —(CH$_2$)$_4$— |
| I.a.665 | CF$_3$ | Cl | H | H | F | CH$_3$ | | —(CH$_2$)$_4$— |
| I.a.666 | F | F | I | F | F | CH$_3$ | | —(CH$_2$)$_4$— |
| I.a.667 | F | H | H | H | F | CH$_3$ | | —(CH$_2$)$_5$— |
| I.a.668 | Cl | H | H | H | F | CH$_3$ | | —(CH$_2$)$_5$— |
| I.a.669 | Br | H | H | H | F | CH$_3$ | | —(CH$_2$)$_5$— |
| I.a.670 | CN | H | H | H | F | CH$_3$ | | —(CH$_2$)$_5$— |
| I.a.671 | CH$_3$ | H | H | H | F | CH$_3$ | | —(CH$_2$)$_5$— |
| I.a.672 | F | H | H | F | F | CH$_3$ | | —(CH$_2$)$_5$— |
| I.a.673 | Cl | H | H | F | F | CH$_3$ | | —(CH$_2$)$_5$— |
| I.a.674 | F | H | H | Cl | F | CH$_3$ | | —(CH$_2$)$_5$— |
| I.a.675 | Cl | H | H | F | F | CH$_3$ | | —(CH$_2$)$_5$— |
| I.a.676 | CN | H | H | F | F | CH$_3$ | | —(CH$_2$)$_5$— |
| I.a.677 | F | H | H | CN | F | CH$_3$ | | —(CH$_2$)$_5$— |
| I.a.678 | CN | H | H | F | F | CH$_3$ | | —(CH$_2$)$_5$— |
| I.a.679 | F | H | F | H | F | CH$_3$ | | —(CH$_2$)$_5$— |
| I.a.680 | Cl | H | F | H | F | CH$_3$ | | —(CH$_2$)$_5$— |
| I.a.681 | CN | H | F | H | F | CH$_3$ | | —(CH$_2$)$_5$— |
| I.a.682 | F | F | F | H | F | CH$_3$ | | —(CH$_2$)$_5$— |
| I.a.683 | Cl | F | F | H | F | CH$_3$ | | —(CH$_2$)$_5$— |
| I.a.684 | F | Cl | F | H | F | CH$_3$ | | —(CH$_2$)$_5$— |
| I.a.685 | Cl | F | F | H | F | CH$_3$ | | —(CH$_2$)$_5$— |
| I.a.686 | CN | F | F | H | F | CH$_3$ | | —(CH$_2$)$_5$— |
| I.a.687 | F | CN | F | H | F | CH$_3$ | | —(CH$_2$)$_5$— |
| I.a.688 | CN | F | F | H | F | CH$_3$ | | —(CH$_2$)$_5$— |
| I.a.689 | F | F | H | F | F | CH$_3$ | | —(CH$_2$)$_5$— |
| I.a.690 | Cl | F | H | F | F | CH$_3$ | | —(CH$_2$)$_5$— |
| I.a.691 | F | Cl | H | F | F | CH$_3$ | | —(CH$_2$)$_5$— |
| I.a.692 | CN | F | H | F | F | CH$_3$ | | —(CH$_2$)$_5$— |
| I.a.693 | F | CN | H | F | F | CH$_3$ | | —(CH$_2$)$_5$— |
| I.a.694 | F | F | F | F | F | CH$_3$ | | —(CH$_2$)$_5$— |
| I.a.695 | Cl | F | F | F | F | CH$_3$ | | —(CH$_2$)$_5$— |
| I.a.696 | F | Cl | F | F | F | CH$_3$ | | —(CH$_2$)$_5$— |
| I.a.697 | CN | F | F | F | F | CH$_3$ | | —(CH$_2$)$_5$— |
| I.a.698 | F | CN | F | F | F | CH$_3$ | | —(CH$_2$)$_5$— |
| I.a.699 | H | F | F | F | F | CH$_3$ | | —(CH$_2$)$_5$— |
| I.a.700 | F | F | Br | F | F | CH$_3$ | | —(CH$_2$)$_5$— |
| I.a.701 | F | F | C≡CH | F | F | CH$_3$ | | —(CH$_2$)$_5$— |
| I.a.702 | CF$_3$ | Cl | H | H | F | CH$_3$ | | —(CH$_2$)$_5$— |
| I.a.703 | F | F | I | F | F | CH$_3$ | | —(CH$_2$)$_5$— |
| I.a.704 | F | H | H | H | F | F | | —(CH$_2$)$_2$— |
| I.a.705 | Cl | H | H | H | F | F | | —(CH$_2$)$_2$— |
| I.a.706 | Br | H | H | H | F | F | | —(CH$_2$)$_2$— |
| I.a.707 | CN | H | H | H | F | F | | —(CH$_2$)$_2$— |
| I.a.708 | CH$_3$ | H | H | H | F | F | | —(CH$_2$)$_2$— |

TABLE A-continued

| No. | R$^a$ | R$^b$ | R$^c$ | R$^d$ | R$^e$ | R$^2$ | R$^3$ | R$^4$ |
|---|---|---|---|---|---|---|---|---|
| I.a.709 | F | H | H | F | F | F | | —(CH$_2$)$_2$— |
| I.a.710 | Cl | H | H | F | F | F | | —(CH$_2$)$_2$— |
| I.a.711 | F | H | H | Cl | F | F | | —(CH$_2$)$_2$— |
| I.a.712 | Cl | H | H | F | F | F | | —(CH$_2$)$_2$— |
| I.a.713 | CN | H | H | F | F | F | | —(CH$_2$)$_2$— |
| I.a.714 | F | H | H | CN | F | F | | —(CH$_2$)$_2$— |
| I.a.715 | CN | H | H | F | F | F | | —(CH$_2$)$_2$— |
| I.a.716 | F | H | F | H | F | F | | —(CH$_2$)$_2$— |
| I.a.717 | Cl | H | F | H | F | F | | —(CH$_2$)$_2$— |
| I.a.718 | CN | H | F | H | F | F | | —(CH$_2$)$_2$— |
| I.a.719 | F | F | F | H | F | F | | —(CH$_2$)$_2$— |
| I.a.720 | Cl | F | F | H | F | F | | —(CH$_2$)$_2$— |
| I.a.721 | F | Cl | F | H | F | F | | —(CH$_2$)$_2$— |
| I.a.722 | Cl | F | F | H | F | F | | —(CH$_2$)$_2$— |
| I.a.723 | CN | F | F | H | F | F | | —(CH$_2$)$_2$— |
| I.a.724 | F | CN | F | H | F | F | | —(CH$_2$)$_2$— |
| I.a.725 | CN | F | F | H | F | F | | —(CH$_2$)$_2$— |
| I.a.726 | F | F | H | F | F | F | | —(CH$_2$)$_2$— |
| I.a.727 | Cl | F | H | F | F | F | | —(CH$_2$)$_2$— |
| I.a.728 | F | Cl | H | F | F | F | | —(CH$_2$)$_2$— |
| I.a.729 | CN | F | H | F | F | F | | —(CH$_2$)$_2$— |
| I.a.730 | F | CN | H | F | F | F | | —(CH$_2$)$_2$— |
| I.a.731 | F | F | F | F | F | F | | —(CH$_2$)$_2$— |
| I.a.732 | Cl | F | F | F | F | F | | —(CH$_2$)$_2$— |
| I.a.733 | F | Cl | F | F | F | F | | —(CH$_2$)$_2$— |
| I.a.734 | CN | F | F | F | F | F | | —(CH$_2$)$_2$— |
| I.a.735 | F | CN | F | F | F | F | | —(CH$_2$)$_2$— |
| I.a.736 | H | F | F | F | F | F | | —(CH$_2$)$_2$— |
| I.a.737 | F | F | Br | F | F | F | | —(CH$_2$)$_2$— |
| I.a.738 | F | F | C≡CH | F | F | F | | —(CH$_2$)$_2$— |
| I.a.739 | CF$_3$ | Cl | H | H | F | F | | —(CH$_2$)$_2$— |
| I.a.740 | F | F | I | F | F | F | | —(CH$_2$)$_2$— |
| I.a.741 | F | H | H | H | F | F | | —(CH$_2$)$_3$— |
| I.a.742 | Cl | H | H | H | F | F | | —(CH$_2$)$_3$— |
| I.a.743 | Br | H | H | H | F | F | | —(CH$_2$)$_3$— |
| I.a.744 | CN | H | H | H | F | F | | —(CH$_2$)$_3$— |
| I.a.745 | CH$_3$ | H | H | H | F | F | | —(CH$_2$)$_3$— |
| I.a.746 | F | H | H | F | F | F | | —(CH$_2$)$_3$— |
| I.a.747 | Cl | H | H | F | F | F | | —(CH$_2$)$_3$— |
| I.a.748 | F | H | H | Cl | F | F | | —(CH$_2$)$_3$— |
| I.a.749 | Cl | H | H | F | F | F | | —(CH$_2$)$_3$— |
| I.a.750 | CN | H | H | F | F | F | | —(CH$_2$)$_3$— |
| I.a.751 | F | H | H | CN | F | F | | —(CH$_2$)$_3$— |
| I.a.752 | CN | H | H | F | F | F | | —(CH$_2$)$_3$— |
| I.a.753 | F | H | F | H | F | F | | —(CH$_2$)$_3$— |
| I.a.754 | Cl | H | F | H | F | F | | —(CH$_2$)$_3$— |
| I.a.755 | CN | H | F | H | F | F | | —(CH$_2$)$_3$— |
| I.a.756 | F | F | F | H | F | F | | —(CH$_2$)$_3$— |
| I.a.757 | Cl | F | F | H | F | F | | —(CH$_2$)$_3$— |
| I.a.758 | F | Cl | F | H | F | F | | —(CH$_2$)$_3$— |
| I.a.759 | Cl | F | F | H | F | F | | —(CH$_2$)$_3$— |
| I.a.760 | CN | F | F | H | F | F | | —(CH$_2$)$_3$— |
| I.a.761 | F | CN | F | H | F | F | | —(CH$_2$)$_3$— |
| I.a.762 | CN | F | F | H | F | F | | —(CH$_2$)$_3$— |
| I.a.763 | F | F | H | F | F | F | | —(CH$_2$)$_3$— |
| I.a.764 | Cl | F | H | F | F | F | | —(CH$_2$)$_3$— |
| I.a.765 | F | Cl | H | F | F | F | | —(CH$_2$)$_3$— |
| I.a.766 | CN | F | H | F | F | F | | —(CH$_2$)$_3$— |
| I.a.767 | F | CN | H | F | F | F | | —(CH$_2$)$_3$— |
| I.a.768 | F | F | F | F | F | F | | —(CH$_2$)$_3$— |
| I.a.769 | Cl | F | F | F | F | F | | —(CH$_2$)$_3$— |
| I.a.770 | F | Cl | F | F | F | F | | —(CH$_2$)$_3$— |
| I.a.771 | CN | F | F | F | F | F | | —(CH$_2$)$_3$— |
| I.a.772 | F | CN | F | F | F | F | | —(CH$_2$)$_3$— |
| I.a.773 | H | F | F | F | F | F | | —(CH$_2$)$_3$— |
| I.a.774 | F | F | Br | F | F | F | | —(CH$_2$)$_3$— |
| I.a.775 | F | F | C≡CH | F | F | F | | —(CH$_2$)$_3$— |
| I.a.776 | CF$_3$ | Cl | H | H | F | F | | —(CH$_2$)$_3$— |
| I.a.777 | F | F | I | F | F | F | | —(CH$_2$)$_3$— |
| I.a.778 | F | H | H | H | F | F | | —(CH$_2$)$_4$— |
| I.a.779 | Cl | H | H | H | F | F | | —(CH$_2$)$_4$— |
| I.a.780 | Br | H | H | H | F | F | | —(CH$_2$)$_4$— |
| I.a.781 | CN | H | H | H | F | F | | —(CH$_2$)$_4$— |
| I.a.782 | CH$_3$ | H | H | H | F | F | | —(CH$_2$)$_4$— |
| I.a.783 | F | H | H | F | F | F | | —(CH$_2$)$_4$— |
| I.a.784 | Cl | H | H | F | F | F | | —(CH$_2$)$_4$— |
| I.a.785 | F | H | H | Cl | F | F | | —(CH$_2$)$_4$— |
| I.a.786 | Cl | H | H | F | F | F | | —(CH$_2$)$_4$— |
| I.a.787 | CN | H | H | F | F | F | | —(CH$_2$)$_4$— |
| I.a.788 | F | H | H | CN | F | F | | —(CH$_2$)$_4$— |
| I.a.789 | CN | H | H | F | F | F | | —(CH$_2$)$_4$— |
| I.a.790 | F | H | F | H | F | F | | —(CH$_2$)$_4$— |
| I.a.791 | Cl | H | F | H | F | F | | —(CH$_2$)$_4$— |
| I.a.792 | CN | H | F | H | F | F | | —(CH$_2$)$_4$— |
| I.a.793 | F | F | F | H | F | F | | —(CH$_2$)$_4$— |
| I.a.794 | Cl | F | F | H | F | F | | —(CH$_2$)$_4$— |
| I.a.795 | F | Cl | F | H | F | F | | —(CH$_2$)$_4$— |
| I.a.796 | Cl | F | F | H | F | F | | —(CH$_2$)$_4$— |
| I.a.797 | CN | F | F | H | F | F | | —(CH$_2$)$_4$— |
| I.a.798 | F | CN | F | H | F | F | | —(CH$_2$)$_4$— |
| I.a.799 | CN | F | F | H | F | F | | —(CH$_2$)$_4$— |
| I.a.800 | F | F | H | F | F | F | | —(CH$_2$)$_4$— |
| I.a.801 | Cl | F | H | F | F | F | | —(CH$_2$)$_4$— |
| I.a.802 | F | Cl | H | F | F | F | | —(CH$_2$)$_4$— |
| I.a.803 | CN | F | H | F | F | F | | —(CH$_2$)$_4$— |
| I.a.804 | F | CN | H | F | F | F | | —(CH$_2$)$_4$— |
| I.a.805 | F | F | F | F | F | F | | —(CH$_2$)$_4$— |
| I.a.806 | Cl | F | F | F | F | F | | —(CH$_2$)$_4$— |
| I.a.807 | F | Cl | F | F | F | F | | —(CH$_2$)$_4$— |
| I.a.808 | CN | F | F | F | F | F | | —(CH$_2$)$_4$— |
| I.a.809 | F | CN | F | F | F | F | | —(CH$_2$)$_4$— |
| I.a.810 | H | F | F | F | F | F | | —(CH$_2$)$_4$— |
| I.a.811 | F | F | Br | F | F | F | | —(CH$_2$)$_4$— |
| I.a.812 | F | F | C≡CH | F | F | F | | —(CH$_2$)$_4$— |
| I.a.813 | CF$_3$ | Cl | H | H | F | F | | —(CH$_2$)$_4$— |
| I.a.814 | F | F | I | F | F | F | | —(CH$_2$)$_4$— |
| I.a.815 | F | H | H | H | F | F | | —(CH$_2$)$_5$— |
| I.a.816 | Cl | H | H | H | F | F | | —(CH$_2$)$_5$— |
| I.a.817 | Br | H | H | H | F | F | | —(CH$_2$)$_5$— |
| I.a.818 | CN | H | H | H | F | F | | —(CH$_2$)$_5$— |
| I.a.819 | CH$_3$ | H | H | H | F | F | | —(CH$_2$)$_5$— |
| I.a.820 | F | H | H | F | F | F | | —(CH$_2$)$_5$— |
| I.a.821 | Cl | H | H | F | F | F | | —(CH$_2$)$_5$— |
| I.a.822 | F | H | H | Cl | F | F | | —(CH$_2$)$_5$— |
| I.a.823 | Cl | H | H | F | F | F | | —(CH$_2$)$_5$— |
| I.a.824 | CN | H | H | F | F | F | | —(CH$_2$)$_5$— |
| I.a.825 | F | H | H | CN | F | F | | —(CH$_2$)$_5$— |
| I.a.826 | CN | H | H | F | F | F | | —(CH$_2$)$_5$— |
| I.a.827 | F | H | F | H | F | F | | —(CH$_2$)$_5$— |
| I.a.828 | Cl | H | F | H | F | F | | —(CH$_2$)$_5$— |
| I.a.829 | CN | H | F | H | F | F | | —(CH$_2$)$_5$— |
| I.a.830 | F | F | F | H | F | F | | —(CH$_2$)$_5$— |
| I.a.831 | Cl | F | F | H | F | F | | —(CH$_2$)$_5$— |
| I.a.832 | F | Cl | F | H | F | F | | —(CH$_2$)$_5$— |
| I.a.833 | Cl | F | F | H | F | F | | —(CH$_2$)$_5$— |
| I.a.834 | CN | F | F | H | F | F | | —(CH$_2$)$_5$— |
| I.a.835 | F | CN | F | H | F | F | | —(CH$_2$)$_5$— |
| I.a.836 | CN | F | F | H | F | F | | —(CH$_2$)$_5$— |
| I.a.837 | F | F | H | F | F | F | | —(CH$_2$)$_5$— |
| I.a.838 | Cl | F | H | F | F | F | | —(CH$_2$)$_5$— |
| I.a.839 | F | Cl | H | F | F | F | | —(CH$_2$)$_5$— |
| I.a.840 | CN | F | H | F | F | F | | —(CH$_2$)$_5$— |
| I.a.841 | F | CN | H | F | F | F | | —(CH$_2$)$_5$— |
| I.a.842 | F | F | F | F | F | F | | —(CH$_2$)$_5$— |
| I.a.843 | Cl | F | F | F | F | F | | —(CH$_2$)$_5$— |
| I.a.844 | F | Cl | F | F | F | F | | —(CH$_2$)$_5$— |
| I.a.845 | CN | F | F | F | F | F | | —(CH$_2$)$_5$— |
| I.a.846 | F | CN | F | F | F | F | | —(CH$_2$)$_5$— |
| I.a.847 | H | F | F | F | F | F | | —(CH$_2$)$_5$— |
| I.a.848 | F | F | Br | F | F | F | | —(CH$_2$)$_5$— |
| I.a.849 | F | F | C≡CH | F | F | F | | —(CH$_2$)$_5$— |
| I.a.850 | CF$_3$ | Cl | H | H | F | F | | —(CH$_2$)$_5$— |
| I.a.851 | F | F | I | F | F | F | | —(CH$_2$)$_5$— |
| I.a.852 | F | H | H | H | F | Cl | | —(CH$_2$)$_2$— |
| I.a.853 | Cl | H | H | H | F | Cl | | —(CH$_2$)$_2$— |
| I.a.854 | Br | H | H | H | F | Cl | | —(CH$_2$)$_2$— |
| I.a.855 | CN | H | H | H | F | Cl | | —(CH$_2$)$_2$— |
| I.a.856 | CH$_3$ | H | H | H | F | Cl | | —(CH$_2$)$_2$— |
| I.a.857 | F | H | H | F | F | Cl | | —(CH$_2$)$_2$— |
| I.a.858 | Cl | H | H | F | F | Cl | | —(CH$_2$)$_2$— |
| I.a.859 | F | H | H | Cl | F | Cl | | —(CH$_2$)$_2$— |
| I.a.860 | Cl | H | H | F | F | Cl | | —(CH$_2$)$_2$— |
| I.a.861 | CN | H | H | F | F | Cl | | —(CH$_2$)$_2$— |
| I.a.862 | F | H | H | CN | F | Cl | | —(CH$_2$)$_2$— |
| I.a.863 | CN | H | H | F | F | Cl | | —(CH$_2$)$_2$— |
| I.a.864 | F | H | F | H | F | Cl | | —(CH$_2$)$_2$— |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.865 | Cl | H | F | H | F | Cl | —(CH$_2$)$_2$— | |
| I.a.866 | CN | H | F | H | F | Cl | —(CH$_2$)$_2$— | |
| I.a.867 | F | F | F | H | F | Cl | —(CH$_2$)$_2$— | |
| I.a.868 | Cl | F | F | H | F | Cl | —(CH$_2$)$_2$— | |
| I.a.869 | F | Cl | F | H | F | Cl | —(CH$_2$)$_2$— | |
| I.a.870 | Cl | F | F | H | F | Cl | —(CH$_2$)$_2$— | |
| I.a.871 | CN | F | F | H | F | Cl | —(CH$_2$)$_2$— | |
| I.a.872 | F | CN | F | H | F | Cl | —(CH$_2$)$_2$— | |
| I.a.873 | CN | F | F | H | F | Cl | —(CH$_2$)$_2$— | |
| I.a.874 | F | F | H | F | F | Cl | —(CH$_2$)$_2$— | |
| I.a.875 | Cl | F | H | F | F | Cl | —(CH$_2$)$_2$— | |
| I.a.876 | F | Cl | H | F | F | Cl | —(CH$_2$)$_2$— | |
| I.a.877 | CN | F | H | F | F | Cl | —(CH$_2$)$_2$— | |
| I.a.878 | F | CN | H | F | F | Cl | —(CH$_2$)$_2$— | |
| I.a.879 | F | F | F | F | F | Cl | —(CH$_2$)$_2$— | |
| I.a.880 | Cl | F | F | F | F | Cl | —(CH$_2$)$_2$— | |
| I.a.881 | F | Cl | F | F | F | Cl | —(CH$_2$)$_2$— | |
| I.a.882 | CN | F | F | F | F | Cl | —(CH$_2$)$_2$— | |
| I.a.883 | F | CN | F | F | F | Cl | —(CH$_2$)$_2$— | |
| I.a.884 | H | F | F | F | F | Cl | —(CH$_2$)$_2$— | |
| I.a.885 | F | F | Br | F | F | Cl | —(CH$_2$)$_2$— | |
| I.a.886 | F | F | C≡CH | F | F | Cl | —(CH$_2$)$_2$— | |
| I.a.887 | CF$_3$ | Cl | H | H | F | Cl | —(CH$_2$)$_2$— | |
| I.a.888 | F | F | I | F | F | Cl | —(CH$_2$)$_2$— | |
| I.a.889 | F | H | H | H | F | Cl | —(CH$_2$)$_3$— | |
| I.a.890 | Cl | H | H | H | F | Cl | —(CH$_2$)$_3$— | |
| I.a.891 | Br | H | H | H | F | Cl | —(CH$_2$)$_3$— | |
| I.a.892 | CN | H | H | H | F | Cl | —(CH$_2$)$_3$— | |
| I.a.893 | CH$_3$ | H | H | H | F | Cl | —(CH$_2$)$_3$— | |
| I.a.894 | F | H | H | F | F | Cl | —(CH$_2$)$_3$— | |
| I.a.895 | Cl | H | H | F | F | Cl | —(CH$_2$)$_3$— | |
| I.a.896 | F | H | H | Cl | F | Cl | —(CH$_2$)$_3$— | |
| I.a.897 | Cl | H | H | F | F | Cl | —(CH$_2$)$_3$— | |
| I.a.898 | CN | H | H | F | F | Cl | —(CH$_2$)$_3$— | |
| I.a.899 | F | H | H | CN | F | Cl | —(CH$_2$)$_3$— | |
| I.a.900 | CN | H | H | F | F | Cl | —(CH$_2$)$_3$— | |
| I.a.901 | F | H | F | H | F | Cl | —(CH$_2$)$_3$— | |
| I.a.902 | Cl | H | F | H | F | Cl | —(CH$_2$)$_3$— | |
| I.a.903 | CN | H | F | H | F | Cl | —(CH$_2$)$_3$— | |
| I.a.904 | F | F | F | H | F | Cl | —(CH$_2$)$_3$— | |
| I.a.905 | Cl | F | F | H | F | Cl | —(CH$_2$)$_3$— | |
| I.a.906 | F | Cl | F | H | F | Cl | —(CH$_2$)$_3$— | |
| I.a.907 | Cl | F | F | H | F | Cl | —(CH$_2$)$_3$— | |
| I.a.908 | CN | F | F | H | F | Cl | —(CH$_2$)$_3$— | |
| I.a.909 | F | CN | F | H | F | Cl | —(CH$_2$)$_3$— | |
| I.a.910 | CN | F | F | H | F | Cl | —(CH$_2$)$_3$— | |
| I.a.911 | F | F | H | F | F | Cl | —(CH$_2$)$_3$— | |
| I.a.912 | Cl | F | H | F | F | Cl | —(CH$_2$)$_3$— | |
| I.a.913 | F | Cl | H | F | F | Cl | —(CH$_2$)$_3$— | |
| I.a.914 | CN | F | H | F | F | Cl | —(CH$_2$)$_3$— | |
| I.a.915 | F | CN | H | F | F | Cl | —(CH$_2$)$_3$— | |
| I.a.916 | F | F | F | F | F | Cl | —(CH$_2$)$_3$— | |
| I.a.917 | Cl | F | F | F | F | Cl | —(CH$_2$)$_3$— | |
| I.a.918 | F | Cl | F | F | F | Cl | —(CH$_2$)$_3$— | |
| I.a.919 | CN | F | F | F | F | Cl | —(CH$_2$)$_3$— | |
| I.a.920 | F | CN | F | F | F | Cl | —(CH$_2$)$_3$— | |
| I.a.921 | H | F | F | F | F | Cl | —(CH$_2$)$_3$— | |
| I.a.922 | F | F | Br | F | F | Cl | —(CH$_2$)$_3$— | |
| I.a.923 | F | F | C≡CH | F | F | Cl | —(CH$_2$)$_3$— | |
| I.a.924 | CF$_3$ | Cl | H | H | F | Cl | —(CH$_2$)$_3$— | |
| I.a.925 | F | F | I | F | F | Cl | —(CH$_2$)$_3$— | |
| I.a.926 | F | H | H | H | F | Cl | —(CH$_2$)$_4$— | |
| I.a.927 | Cl | H | H | H | F | Cl | —(CH$_2$)$_4$— | |
| I.a.928 | Br | H | H | H | F | Cl | —(CH$_2$)$_4$— | |
| I.a.929 | CN | H | H | H | F | Cl | —(CH$_2$)$_4$— | |
| I.a.930 | CH$_3$ | H | H | H | F | Cl | —(CH$_2$)$_4$— | |
| I.a.931 | F | H | H | F | F | Cl | —(CH$_2$)$_4$— | |
| I.a.932 | Cl | H | H | F | F | Cl | —(CH$_2$)$_4$— | |
| I.a.933 | F | H | H | Cl | F | Cl | —(CH$_2$)$_4$— | |
| I.a.934 | Cl | H | H | F | F | Cl | —(CH$_2$)$_4$— | |
| I.a.935 | CN | H | H | F | F | Cl | —(CH$_2$)$_4$— | |
| I.a.936 | F | H | H | CN | F | Cl | —(CH$_2$)$_4$— | |
| I.a.937 | CN | H | H | F | F | Cl | —(CH$_2$)$_4$— | |
| I.a.938 | F | H | F | H | F | Cl | —(CH$_2$)$_4$— | |
| I.a.939 | Cl | H | F | H | F | Cl | —(CH$_2$)$_4$— | |
| I.a.940 | CN | H | F | H | F | Cl | —(CH$_2$)$_4$— | |
| I.a.941 | F | F | F | H | F | Cl | —(CH$_2$)$_4$— | |
| I.a.942 | Cl | F | F | H | F | Cl | —(CH$_2$)$_4$— | |
| I.a.943 | F | Cl | F | H | F | Cl | —(CH$_2$)$_4$— | |
| I.a.944 | Cl | F | F | H | F | Cl | —(CH$_2$)$_4$— | |
| I.a.945 | CN | F | F | H | F | Cl | —(CH$_2$)$_4$— | |
| I.a.946 | F | CN | F | H | F | Cl | —(CH$_2$)$_4$— | |
| I.a.947 | CN | F | F | H | F | Cl | —(CH$_2$)$_4$— | |
| I.a.948 | F | F | H | F | F | Cl | —(CH$_2$)$_4$— | |
| I.a.949 | Cl | F | H | F | F | Cl | —(CH$_2$)$_4$— | |
| I.a.950 | F | Cl | H | F | F | Cl | —(CH$_2$)$_4$— | |
| I.a.951 | CN | F | H | F | F | Cl | —(CH$_2$)$_4$— | |
| I.a.952 | F | CN | H | F | F | Cl | —(CH$_2$)$_4$— | |
| I.a.953 | F | F | F | F | F | Cl | —(CH$_2$)$_4$— | |
| I.a.954 | Cl | F | F | F | F | Cl | —(CH$_2$)$_4$— | |
| I.a.955 | F | Cl | F | F | F | Cl | —(CH$_2$)$_4$— | |
| I.a.956 | CN | F | F | F | F | Cl | —(CH$_2$)$_4$— | |
| I.a.957 | F | CN | F | F | F | Cl | —(CH$_2$)$_4$— | |
| I.a.958 | H | F | F | F | F | Cl | —(CH$_2$)$_4$— | |
| I.a.959 | F | F | Br | F | F | Cl | —(CH$_2$)$_4$— | |
| I.a.960 | F | F | C≡CH | F | F | Cl | —(CH$_2$)$_4$— | |
| I.a.961 | CF$_3$ | Cl | H | H | F | Cl | —(CH$_2$)$_4$— | |
| I.a.962 | F | F | I | F | F | Cl | —(CH$_2$)$_4$— | |
| I.a.963 | F | H | H | H | F | Cl | —(CH$_2$)$_5$— | |
| I.a.964 | Cl | H | H | H | F | Cl | —(CH$_2$)$_5$— | |
| I.a.965 | Br | H | H | H | F | Cl | —(CH$_2$)$_5$— | |
| I.a.966 | CN | H | H | H | F | Cl | —(CH$_2$)$_5$— | |
| I.a.967 | CH$_3$ | H | H | H | F | Cl | —(CH$_2$)$_5$— | |
| I.a.968 | F | H | H | F | F | Cl | —(CH$_2$)$_5$— | |
| I.a.969 | Cl | H | H | F | F | Cl | —(CH$_2$)$_5$— | |
| I.a.970 | F | H | H | Cl | F | Cl | —(CH$_2$)$_5$— | |
| I.a.971 | Cl | H | H | F | F | Cl | —(CH$_2$)$_5$— | |
| I.a.972 | CN | H | H | F | F | Cl | —(CH$_2$)$_5$— | |
| I.a.973 | F | H | H | CN | F | Cl | —(CH$_2$)$_5$— | |
| I.a.974 | CN | H | H | F | F | Cl | —(CH$_2$)$_5$— | |
| I.a.975 | F | H | F | H | F | Cl | —(CH$_2$)$_5$— | |
| I.a.976 | Cl | H | F | H | F | Cl | —(CH$_2$)$_5$— | |
| I.a.977 | CN | H | F | H | F | Cl | —(CH$_2$)$_5$— | |
| I.a.978 | F | F | F | H | F | Cl | —(CH$_2$)$_5$— | |
| I.a.979 | Cl | F | F | H | F | Cl | —(CH$_2$)$_5$— | |
| I.a.980 | F | Cl | F | H | F | Cl | —(CH$_2$)$_5$— | |
| I.a.981 | Cl | F | F | H | F | Cl | —(CH$_2$)$_5$— | |
| I.a.982 | CN | F | F | H | F | Cl | —(CH$_2$)$_5$— | |
| I.a.983 | F | CN | F | H | F | Cl | —(CH$_2$)$_5$— | |
| I.a.984 | CN | F | F | H | F | Cl | —(CH$_2$)$_5$— | |
| I.a.985 | F | F | H | F | F | Cl | —(CH$_2$)$_5$— | |
| I.a.986 | Cl | F | H | F | F | Cl | —(CH$_2$)$_5$— | |
| I.a.987 | F | Cl | H | F | F | Cl | —(CH$_2$)$_5$— | |
| I.a.988 | CN | F | H | F | F | Cl | —(CH$_2$)$_5$— | |
| I.a.989 | F | CN | H | F | F | Cl | —(CH$_2$)$_5$— | |
| I.a.990 | F | F | F | F | F | Cl | —(CH$_2$)$_5$— | |
| I.a.991 | Cl | F | F | F | F | Cl | —(CH$_2$)$_5$— | |
| I.a.992 | F | Cl | F | F | F | Cl | —(CH$_2$)$_5$— | |
| I.a.993 | CN | F | F | F | F | Cl | —(CH$_2$)$_5$— | |
| I.a.994 | F | CN | F | F | F | Cl | —(CH$_2$)$_5$— | |
| I.a.995 | H | F | F | F | F | Cl | —(CH$_2$)$_5$— | |
| I.a.996 | F | F | Br | F | F | Cl | —(CH$_2$)$_5$— | |
| I.a.997 | F | F | C≡CH | F | F | Cl | —(CH$_2$)$_5$— | |
| I.a.998 | CF$_3$ | Cl | H | H | F | Cl | —(CH$_2$)$_5$— | |
| I.a.999 | F | F | I | F | F | Cl | —(CH$_2$)$_5$— | |
| I.a.1000 | F | H | H | H | F | C$_2$H$_5$ | CH$_3$ | H |
| I.a.1001 | Cl | H | H | H | F | C$_2$H$_5$ | CH$_3$ | H |
| I.a.1002 | Br | H | H | H | F | C$_2$H$_5$ | CH$_3$ | H |
| I.a.1003 | CN | H | H | H | F | C$_2$H$_5$ | CH$_3$ | H |
| I.a.1004 | CH$_3$ | H | H | H | F | C$_2$H$_5$ | CH$_3$ | H |
| I.a.1005 | F | H | H | F | F | C$_2$H$_5$ | CH$_3$ | H |
| I.a.1006 | Cl | H | H | F | F | C$_2$H$_5$ | CH$_3$ | H |
| I.a.1007 | F | H | H | Cl | F | C$_2$H$_5$ | CH$_3$ | H |
| I.a.1008 | Cl | H | H | F | F | C$_2$H$_5$ | CH$_3$ | H |
| I.a.1009 | CN | H | H | F | F | C$_2$H$_5$ | CH$_3$ | H |
| I.a.1010 | F | H | H | CN | F | C$_2$H$_5$ | CH$_3$ | H |
| I.a.1011 | CN | H | H | F | F | C$_2$H$_5$ | CH$_3$ | H |
| I.a.1012 | F | H | F | H | F | C$_2$H$_5$ | CH$_3$ | H |
| I.a.1013 | Cl | H | F | H | F | C$_2$H$_5$ | CH$_3$ | H |
| I.a.1014 | CN | H | F | H | F | C$_2$H$_5$ | CH$_3$ | H |
| I.a.1015 | F | F | F | H | F | C$_2$H$_5$ | CH$_3$ | H |
| I.a.1016 | Cl | F | F | H | F | C$_2$H$_5$ | CH$_3$ | H |
| I.a.1017 | F | Cl | F | H | F | C$_2$H$_5$ | CH$_3$ | H |
| I.a.1018 | Cl | F | F | H | F | C$_2$H$_5$ | CH$_3$ | H |
| I.a.1019 | CN | F | F | H | F | C$_2$H$_5$ | CH$_3$ | H |
| I.a.1020 | F | CN | F | H | F | C$_2$H$_5$ | CH$_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1021 | CN | F | F | H | F | $C_2H_5$ | $CH_3$ | H |
| I.a.1022 | F | F | H | F | F | $C_2H_5$ | $CH_3$ | H |
| I.a.1023 | Cl | F | H | F | F | $C_2H_5$ | $CH_3$ | H |
| I.a.1024 | F | Cl | H | F | F | $C_2H_5$ | $CH_3$ | H |
| I.a.1025 | CN | F | H | F | F | $C_2H_5$ | $CH_3$ | H |
| I.a.1026 | F | CN | H | F | F | $C_2H_5$ | $CH_3$ | H |
| I.a.1027 | F | F | F | F | F | $C_2H_5$ | $CH_3$ | H |
| I.a.1028 | Cl | F | F | F | F | $C_2H_5$ | $CH_3$ | H |
| I.a.1029 | F | Cl | F | F | F | $C_2H_5$ | $CH_3$ | H |
| I.a.1030 | CN | F | F | F | F | $C_2H_5$ | $CH_3$ | H |
| I.a.1031 | F | CN | F | F | F | $C_2H_5$ | $CH_3$ | H |
| I.a.1032 | H | F | F | F | F | $C_2H_5$ | $CH_3$ | H |
| I.a.1033 | F | F | Br | F | F | $C_2H_5$ | $CH_3$ | H |
| I.a.1034 | F | F | C≡CH | F | F | $C_2H_5$ | $CH_3$ | H |
| I.a.1035 | $CF_3$ | Cl | H | H | F | $C_2H_5$ | $CH_3$ | H |
| I.a.1036 | F | F | I | F | F | $C_2H_5$ | $CH_3$ | H |
| I.a.1037 | F | H | H | H | F | $C_2H_5$ | $C_2H_5$ | H |
| I.a.1038 | Cl | H | H | H | F | $C_2H_5$ | $C_2H_5$ | H |
| I.a.1039 | Br | H | H | H | F | $C_2H_5$ | $C_2H_5$ | H |
| I.a.1040 | CN | H | H | H | F | $C_2H_5$ | $C_2H_5$ | H |
| I.a.1041 | $CH_3$ | H | H | H | F | $C_2H_5$ | $C_2H_5$ | H |
| I.a.1042 | F | H | H | F | F | $C_2H_5$ | $C_2H_5$ | H |
| I.a.1043 | Cl | H | H | F | F | $C_2H_5$ | $C_2H_5$ | H |
| I.a.1044 | F | H | H | Cl | F | $C_2H_5$ | $C_2H_5$ | H |
| I.a.1045 | Cl | H | H | F | F | $C_2H_5$ | $C_2H_5$ | H |
| I.a.1046 | CN | H | H | F | F | $C_2H_5$ | $C_2H_5$ | H |
| I.a.1047 | F | H | H | CN | F | $C_2H_5$ | $C_2H_5$ | H |
| I.a.1048 | CN | H | H | F | F | $C_2H_5$ | $C_2H_5$ | H |
| I.a.1049 | F | H | F | H | F | $C_2H_5$ | $C_2H_5$ | H |
| I.a.1050 | Cl | H | F | H | F | $C_2H_5$ | $C_2H_5$ | H |
| I.a.1051 | CN | H | F | H | F | $C_2H_5$ | $C_2H_5$ | H |
| I.a.1052 | F | F | F | H | F | $C_2H_5$ | $C_2H_5$ | H |
| I.a.1053 | Cl | F | F | H | F | $C_2H_5$ | $C_2H_5$ | H |
| I.a.1054 | F | Cl | F | H | F | $C_2H_5$ | $C_2H_5$ | H |
| I.a.1055 | Cl | F | F | H | F | $C_2H_5$ | $C_2H_5$ | H |
| I.a.1056 | CN | F | F | H | F | $C_2H_5$ | $C_2H_5$ | H |
| I.a.1057 | F | CN | F | H | F | $C_2H_5$ | $C_2H_5$ | H |
| I.a.1058 | CN | F | F | H | F | $C_2H_5$ | $C_2H_5$ | H |
| I.a.1059 | F | F | H | F | F | $C_2H_5$ | $C_2H_5$ | H |
| I.a.1060 | Cl | F | H | F | F | $C_2H_5$ | $C_2H_5$ | H |
| I.a.1061 | F | Cl | H | F | F | $C_2H_5$ | $C_2H_5$ | H |
| I.a.1062 | CN | F | H | F | F | $C_2H_5$ | $C_2H_5$ | H |
| I.a.1063 | F | CN | H | F | F | $C_2H_5$ | $C_2H_5$ | H |
| I.a.1064 | F | F | F | F | F | $C_2H_5$ | $C_2H_5$ | H |
| I.a.1065 | Cl | F | F | F | F | $C_2H_5$ | $C_2H_5$ | H |
| I.a.1066 | F | Cl | F | F | F | $C_2H_5$ | $C_2H_5$ | H |
| I.a.1067 | CN | F | F | F | F | $C_2H_5$ | $C_2H_5$ | H |
| I.a.1068 | F | CN | F | F | F | $C_2H_5$ | $C_2H_5$ | H |
| I.a.1069 | H | F | F | F | F | $C_2H_5$ | $C_2H_5$ | H |
| I.a.1070 | F | F | Br | F | F | $C_2H_5$ | $C_2H_5$ | H |
| I.a.1071 | F | F | C≡CH | F | F | $C_2H_5$ | $C_2H_5$ | H |
| I.a.1072 | $CF_3$ | Cl | H | H | F | $C_2H_5$ | $C_2H_5$ | H |
| I.a.1073 | F | F | I | F | F | $C_2H_5$ | $C_2H_5$ | H |
| I.a.1074 | F | H | H | H | F | $C_2H_5$ | $C_2H_5$ | $CH_3$ |
| I.a.1075 | Cl | H | H | H | F | $C_2H_5$ | $C_2H_5$ | $CH_3$ |
| I.a.1076 | Br | H | H | H | F | $C_2H_5$ | $C_2H_5$ | $CH_3$ |
| I.a.1077 | CN | H | H | H | F | $C_2H_5$ | $C_2H_5$ | $CH_3$ |
| I.a.1078 | $CH_3$ | H | H | H | F | $C_2H_5$ | $C_2H_5$ | $CH_3$ |
| I.a.1079 | F | H | H | F | F | $C_2H_5$ | $C_2H_5$ | $CH_3$ |
| I.a.1080 | Cl | H | H | F | F | $C_2H_5$ | $C_2H_5$ | $CH_3$ |
| I.a.1081 | F | H | H | Cl | F | $C_2H_5$ | $C_2H_5$ | $CH_3$ |
| I.a.1082 | Cl | H | H | F | F | $C_2H_5$ | $C_2H_5$ | $CH_3$ |
| I.a.1083 | CN | H | H | F | F | $C_2H_5$ | $C_2H_5$ | $CH_3$ |
| I.a.1084 | F | H | H | CN | F | $C_2H_5$ | $C_2H_5$ | $CH_3$ |
| I.a.1085 | CN | H | H | F | F | $C_2H_5$ | $C_2H_5$ | $CH_3$ |
| I.a.1086 | F | H | F | H | F | $C_2H_5$ | $C_2H_5$ | $CH_3$ |
| I.a.1087 | Cl | H | F | H | F | $C_2H_5$ | $C_2H_5$ | $CH_3$ |
| I.a.1088 | CN | H | F | H | F | $C_2H_5$ | $C_2H_5$ | $CH_3$ |
| I.a.1089 | F | F | F | H | F | $C_2H_5$ | $C_2H_5$ | $CH_3$ |
| I.a.1090 | Cl | F | F | H | F | $C_2H_5$ | $C_2H_5$ | $CH_3$ |
| I.a.1091 | F | Cl | F | H | F | $C_2H_5$ | $C_2H_5$ | $CH_3$ |
| I.a.1092 | Cl | F | F | H | F | $C_2H_5$ | $C_2H_5$ | $CH_3$ |
| I.a.1093 | CN | F | F | H | F | $C_2H_5$ | $C_2H_5$ | $CH_3$ |
| I.a.1094 | F | CN | F | H | F | $C_2H_5$ | $C_2H_5$ | $CH_3$ |
| I.a.1095 | CN | F | F | H | F | $C_2H_5$ | $C_2H_5$ | $CH_3$ |
| I.a.1096 | F | F | H | F | F | $C_2H_5$ | $C_2H_5$ | $CH_3$ |
| I.a.1097 | Cl | F | H | F | F | $C_2H_5$ | $C_2H_5$ | $CH_3$ |
| I.a.1098 | F | Cl | H | F | F | $C_2H_5$ | $C_2H_5$ | $CH_3$ |
| I.a.1099 | CN | F | H | F | F | $C_2H_5$ | $C_2H_5$ | $CH_3$ |
| I.a.1100 | F | CN | H | F | F | $C_2H_5$ | $C_2H_5$ | $CH_3$ |
| I.a.1101 | F | F | F | F | F | $C_2H_5$ | $C_2H_5$ | $CH_3$ |
| I.a.1102 | Cl | F | F | F | F | $C_2H_5$ | $C_2H_5$ | $CH_3$ |
| I.a.1103 | F | Cl | F | F | F | $C_2H_5$ | $C_2H_5$ | $CH_3$ |
| I.a.1104 | CN | F | F | F | F | $C_2H_5$ | $C_2H_5$ | $CH_3$ |
| I.a.1105 | F | CN | F | F | F | $C_2H_5$ | $C_2H_5$ | $CH_3$ |
| I.a.1106 | H | F | F | F | F | $C_2H_5$ | $C_2H_5$ | $CH_3$ |
| I.a.1107 | F | F | Br | F | F | $C_2H_5$ | $C_2H_5$ | $CH_3$ |
| I.a.1108 | F | F | C≡CH | F | F | $C_2H_5$ | $C_2H_5$ | $CH_3$ |
| I.a.1109 | $CF_3$ | Cl | H | H | F | $C_2H_5$ | $C_2H_5$ | $CH_3$ |
| I.a.1110 | F | F | I | F | F | $C_2H_5$ | $C_2H_5$ | $CH_3$ |
| I.a.1111 | F | H | H | H | F | $C_2H_5$ | $CH_3$ | $CH_3$ |
| I.a.1112 | Cl | H | H | H | F | $C_2H_5$ | $CH_3$ | $CH_3$ |
| I.a.1113 | Br | H | H | H | F | $C_2H_5$ | $CH_3$ | $CH_3$ |
| I.a.1114 | CN | H | H | H | F | $C_2H_5$ | $CH_3$ | $CH_3$ |
| I.a.1115 | $CH_3$ | H | H | H | F | $C_2H_5$ | $CH_3$ | $CH_3$ |
| I.a.1116 | F | H | H | F | F | $C_2H_5$ | $CH_3$ | $CH_3$ |
| I.a.1117 | Cl | H | H | F | F | $C_2H_5$ | $CH_3$ | $CH_3$ |
| I.a.1118 | F | H | H | Cl | F | $C_2H_5$ | $CH_3$ | $CH_3$ |
| I.a.1119 | Cl | H | H | F | F | $C_2H_5$ | $CH_3$ | $CH_3$ |
| I.a.1120 | CN | H | H | F | F | $C_2H_5$ | $CH_3$ | $CH_3$ |
| I.a.1121 | F | H | H | CN | F | $C_2H_5$ | $CH_3$ | $CH_3$ |
| I.a.1122 | CN | H | H | F | F | $C_2H_5$ | $CH_3$ | $CH_3$ |
| I.a.1123 | F | H | F | H | F | $C_2H_5$ | $CH_3$ | $CH_3$ |
| I.a.1124 | Cl | H | F | H | F | $C_2H_5$ | $CH_3$ | $CH_3$ |
| I.a.1125 | CN | H | F | H | F | $C_2H_5$ | $CH_3$ | $CH_3$ |
| I.a.1126 | F | F | F | H | F | $C_2H_5$ | $CH_3$ | $CH_3$ |
| I.a.1127 | Cl | F | F | H | F | $C_2H_5$ | $CH_3$ | $CH_3$ |
| I.a.1128 | F | Cl | F | H | F | $C_2H_5$ | $CH_3$ | $CH_3$ |
| I.a.1129 | Cl | F | F | H | F | $C_2H_5$ | $CH_3$ | $CH_3$ |
| I.a.1130 | CN | F | F | H | F | $C_2H_5$ | $CH_3$ | $CH_3$ |
| I.a.1131 | F | CN | F | H | F | $C_2H_5$ | $CH_3$ | $CH_3$ |
| I.a.1132 | CN | F | F | H | F | $C_2H_5$ | $CH_3$ | $CH_3$ |
| I.a.1133 | F | F | H | F | F | $C_2H_5$ | $CH_3$ | $CH_3$ |
| I.a.1134 | Cl | F | H | F | F | $C_2H_5$ | $CH_3$ | $CH_3$ |
| I.a.1135 | F | Cl | H | F | F | $C_2H_5$ | $CH_3$ | $CH_3$ |
| I.a.1136 | CN | F | H | F | F | $C_2H_5$ | $CH_3$ | $CH_3$ |
| I.a.1137 | F | CN | H | F | F | $C_2H_5$ | $CH_3$ | $CH_3$ |
| I.a.1138 | F | F | F | F | F | $C_2H_5$ | $CH_3$ | $CH_3$ |
| I.a.1139 | Cl | F | F | F | F | $C_2H_5$ | $CH_3$ | $CH_3$ |
| I.a.1140 | F | Cl | F | F | F | $C_2H_5$ | $CH_3$ | $CH_3$ |
| I.a.1141 | CN | F | F | F | F | $C_2H_5$ | $CH_3$ | $CH_3$ |
| I.a.1142 | F | CN | F | F | F | $C_2H_5$ | $CH_3$ | $CH_3$ |
| I.a.1143 | H | F | F | F | F | $C_2H_5$ | $CH_3$ | $CH_3$ |
| I.a.1144 | F | F | Br | F | F | $C_2H_5$ | $CH_3$ | $CH_3$ |
| I.a.1145 | F | F | C≡CH | F | F | $C_2H_5$ | $CH_3$ | $CH_3$ |
| I.a.1146 | $CF_3$ | Cl | H | H | F | $C_2H_5$ | $CH_3$ | $CH_3$ |
| I.a.1147 | F | F | I | F | F | $C_2H_5$ | $CH_3$ | $CH_3$ |
| I.a.1148 | F | H | H | H | F | Cl | $CH_3$ | H |
| I.a.1149 | Cl | H | H | H | F | Cl | $CH_3$ | H |
| I.a.1150 | Br | H | H | H | F | Cl | $CH_3$ | H |
| I.a.1151 | CN | H | H | H | F | Cl | $CH_3$ | H |
| I.a.1152 | $CH_3$ | H | H | H | F | Cl | $CH_3$ | H |
| I.a.1153 | F | H | H | F | F | Cl | $CH_3$ | H |
| I.a.1154 | Cl | H | H | F | F | Cl | $CH_3$ | H |
| I.a.1155 | F | H | H | Cl | F | Cl | $CH_3$ | H |
| I.a.1156 | Cl | H | H | F | F | Cl | $CH_3$ | H |
| I.a.1157 | CN | H | H | F | F | Cl | $CH_3$ | H |
| I.a.1158 | F | H | H | CN | F | Cl | $CH_3$ | H |
| I.a.1159 | CN | H | H | F | F | Cl | $CH_3$ | H |
| I.a.1160 | F | H | F | H | F | Cl | $CH_3$ | H |
| I.a.1161 | Cl | H | F | H | F | Cl | $CH_3$ | H |
| I.a.1162 | CN | H | F | H | F | Cl | $CH_3$ | H |
| I.a.1163 | F | F | F | H | F | Cl | $CH_3$ | H |
| I.a.1164 | Cl | F | F | H | F | Cl | $CH_3$ | H |
| I.a.1165 | F | Cl | F | H | F | Cl | $CH_3$ | H |
| I.a.1166 | Cl | F | F | H | F | Cl | $CH_3$ | H |
| I.a.1167 | CN | F | F | H | F | Cl | $CH_3$ | H |
| I.a.1168 | F | CN | F | H | F | Cl | $CH_3$ | H |
| I.a.1169 | CN | F | F | H | F | Cl | $CH_3$ | H |
| I.a.1170 | F | F | H | F | F | Cl | $CH_3$ | H |
| I.a.1171 | Cl | F | H | F | F | Cl | $CH_3$ | H |
| I.a.1172 | F | Cl | H | F | F | Cl | $CH_3$ | H |
| I.a.1173 | CN | F | H | F | F | Cl | $CH_3$ | H |
| I.a.1174 | F | CN | H | F | F | Cl | $CH_3$ | H |
| I.a.1175 | F | F | F | F | F | Cl | $CH_3$ | H |
| I.a.1176 | Cl | F | F | F | F | Cl | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1177 | F | Cl | F | F | F | Cl | $CH_3$ | H |
| I.a.1178 | CN | F | F | F | F | Cl | $CH_3$ | H |
| I.a.1179 | F | CN | F | F | F | Cl | $CH_3$ | H |
| I.a.1180 | H | F | F | F | F | Cl | $CH_3$ | H |
| I.a.1181 | F | F | Br | F | F | Cl | $CH_3$ | H |
| I.a.1182 | F | F | C≡CH | F | F | Cl | $CH_3$ | H |
| I.a.1183 | $CF_3$ | Cl | H | H | F | Cl | $CH_3$ | H |
| I.a.1184 | F | F | I | F | F | Cl | $CH_3$ | H |
| I.a.1185 | F | H | H | H | F | $CH_2Cl$ | Cl | $CH_3$ |
| I.a.1186 | Cl | H | H | H | F | $CH_2Cl$ | Cl | $CH_3$ |
| I.a.1187 | Br | H | H | H | F | $CH_2Cl$ | Cl | $CH_3$ |
| I.a.1188 | CN | H | H | H | F | $CH_2Cl$ | Cl | $CH_3$ |
| I.a.1189 | $CH_3$ | H | H | H | F | $CH_2Cl$ | Cl | $CH_3$ |
| I.a.1190 | F | H | H | F | F | $CH_2Cl$ | Cl | $CH_3$ |
| I.a.1191 | Cl | H | H | F | F | $CH_2Cl$ | Cl | $CH_3$ |
| I.a.1192 | F | H | H | Cl | F | $CH_2Cl$ | Cl | $CH_3$ |
| I.a.1193 | Cl | H | H | F | F | $CH_2Cl$ | Cl | $CH_3$ |
| I.a.1194 | CN | H | H | F | F | $CH_2Cl$ | Cl | $CH_3$ |
| I.a.1195 | F | H | H | CN | F | $CH_2Cl$ | Cl | $CH_3$ |
| I.a.1196 | CN | H | H | F | F | $CH_2Cl$ | Cl | $CH_3$ |
| I.a.1197 | F | H | F | H | F | $CH_2Cl$ | Cl | $CH_3$ |
| I.a.1198 | Cl | H | F | H | F | $CH_2Cl$ | Cl | $CH_3$ |
| I.a.1199 | CN | H | F | H | F | $CH_2Cl$ | Cl | $CH_3$ |
| I.a.1200 | F | F | F | H | F | $CH_2Cl$ | Cl | $CH_3$ |
| I.a.1201 | Cl | F | F | H | F | $CH_2Cl$ | Cl | $CH_3$ |
| I.a.1202 | F | Cl | F | H | F | $CH_2Cl$ | Cl | $CH_3$ |
| I.a.1203 | Cl | F | F | H | F | $CH_2Cl$ | Cl | $CH_3$ |
| I.a.1204 | CN | F | F | H | F | $CH_2Cl$ | Cl | $CH_3$ |
| I.a.1205 | F | CN | F | H | F | $CH_2Cl$ | Cl | $CH_3$ |
| I.a.1206 | CN | F | F | H | F | $CH_2Cl$ | Cl | $CH_3$ |
| I.a.1207 | F | F | H | F | F | $CH_2Cl$ | Cl | $CH_3$ |
| I.a.1208 | Cl | F | H | F | F | $CH_2Cl$ | Cl | $CH_3$ |
| I.a.1209 | F | Cl | H | F | F | $CH_2Cl$ | Cl | $CH_3$ |
| I.a.1210 | CN | F | H | F | F | $CH_2Cl$ | Cl | $CH_3$ |
| I.a.1211 | F | CN | H | F | F | $CH_2Cl$ | Cl | $CH_3$ |
| I.a.1212 | F | F | F | F | F | $CH_2Cl$ | Cl | $CH_3$ |
| I.a.1213 | Cl | F | F | F | F | $CH_2Cl$ | Cl | $CH_3$ |
| I.a.1214 | F | Cl | F | F | F | $CH_2Cl$ | Cl | $CH_3$ |
| I.a.1215 | CN | F | F | F | F | $CH_2Cl$ | Cl | $CH_3$ |
| I.a.1216 | F | CN | F | F | F | $CH_2Cl$ | Cl | $CH_3$ |
| I.a.1217 | H | F | F | F | F | $CH_2Cl$ | Cl | $CH_3$ |
| I.a.1218 | F | F | Br | F | F | $CH_2Cl$ | Cl | $CH_3$ |
| I.a.1219 | F | F | C≡CH | F | F | $CH_2Cl$ | Cl | $CH_3$ |
| I.a.1220 | $CF_3$ | Cl | H | H | F | $CH_2Cl$ | Cl | $CH_3$ |
| I.a.1221 | F | F | I | F | F | $CH_2Cl$ | Cl | $CH_3$ |
| I.a.1222 | F | H | H | H | F | CN | $CH_3$ | $CH_3$ |
| I.a.1223 | Cl | H | H | H | F | CN | $CH_3$ | $CH_3$ |
| I.a.1224 | Br | H | H | H | F | CN | $CH_3$ | $CH_3$ |
| I.a.1225 | CN | H | H | H | F | CN | $CH_3$ | $CH_3$ |
| I.a.1226 | $CH_3$ | H | H | H | F | CN | $CH_3$ | $CH_3$ |
| I.a.1227 | F | H | H | F | F | CN | $CH_3$ | $CH_3$ |
| I.a.1228 | Cl | H | H | F | F | CN | $CH_3$ | $CH_3$ |
| I.a.1229 | F | H | H | Cl | F | CN | $CH_3$ | $CH_3$ |
| I.a.1230 | Cl | H | H | F | F | CN | $CH_3$ | $CH_3$ |
| I.a.1231 | CN | H | H | F | F | CN | $CH_3$ | $CH_3$ |
| I.a.1232 | F | H | H | CN | F | CN | $CH_3$ | $CH_3$ |
| I.a.1233 | CN | H | H | F | F | CN | $CH_3$ | $CH_3$ |
| I.a.1234 | F | H | F | H | F | CN | $CH_3$ | $CH_3$ |
| I.a.1235 | Cl | H | F | H | F | CN | $CH_3$ | $CH_3$ |
| I.a.1236 | CN | H | F | H | F | CN | $CH_3$ | $CH_3$ |
| I.a.1237 | F | F | F | H | F | CN | $CH_3$ | $CH_3$ |
| I.a.1238 | Cl | F | F | H | F | CN | $CH_3$ | $CH_3$ |
| I.a.1239 | F | Cl | F | H | F | CN | $CH_3$ | $CH_3$ |
| I.a.1240 | Cl | F | F | H | F | CN | $CH_3$ | $CH_3$ |
| I.a.1241 | CN | F | F | H | F | CN | $CH_3$ | $CH_3$ |
| I.a.1242 | F | CN | F | H | F | CN | $CH_3$ | $CH_3$ |
| I.a.1243 | CN | F | F | H | F | CN | $CH_3$ | $CH_3$ |
| I.a.1244 | F | F | H | F | F | CN | $CH_3$ | $CH_3$ |
| I.a.1245 | Cl | F | H | F | F | CN | $CH_3$ | $CH_3$ |
| I.a.1246 | F | Cl | H | F | F | CN | $CH_3$ | $CH_3$ |
| I.a.1247 | CN | F | H | F | F | CN | $CH_3$ | $CH_3$ |
| I.a.1248 | F | CN | H | F | F | CN | $CH_3$ | $CH_3$ |
| I.a.1249 | F | F | F | F | F | CN | $CH_3$ | $CH_3$ |
| I.a.1250 | Cl | F | F | F | F | CN | $CH_3$ | $CH_3$ |
| I.a.1251 | F | Cl | F | F | F | CN | $CH_3$ | $CH_3$ |
| I.a.1252 | CN | F | F | F | F | CN | $CH_3$ | $CH_3$ |
| I.a.1253 | F | CN | F | F | F | CN | $CH_3$ | $CH_3$ |
| I.a.1254 | H | F | F | F | F | CN | $CH_3$ | $CH_3$ |
| I.a.1255 | F | F | Br | F | F | CN | $CH_3$ | $CH_3$ |
| I.a.1256 | F | F | C≡CH | F | F | CN | $CH_3$ | $CH_3$ |
| I.a.1257 | $CF_3$ | Cl | H | H | F | CN | $CH_3$ | $CH_3$ |
| I.a.1258 | F | F | I | F | F | CN | $CH_3$ | $CH_3$ |
| I.a.1259 | F | H | H | H | F | $OCH_3$ | H | H |
| I.a.1260 | Cl | H | H | H | F | $OCH_3$ | H | H |
| I.a.1261 | Br | H | H | H | F | $OCH_3$ | H | H |
| I.a.1262 | CN | H | H | H | F | $OCH_3$ | H | H |
| I.a.1263 | $CH_3$ | H | H | H | F | $OCH_3$ | H | H |
| I.a.1264 | F | H | H | F | F | $OCH_3$ | H | H |
| I.a.1265 | Cl | H | H | F | F | $OCH_3$ | H | H |
| I.a.1266 | F | H | H | Cl | F | $OCH_3$ | H | H |
| I.a.1267 | Cl | H | H | F | F | $OCH_3$ | H | H |
| I.a.1268 | CN | H | H | F | F | $OCH_3$ | H | H |
| I.a.1269 | F | H | H | CN | F | $OCH_3$ | H | H |
| I.a.1270 | CN | H | H | F | F | $OCH_3$ | H | H |
| I.a.1271 | F | H | F | H | F | $OCH_3$ | H | H |
| I.a.1272 | Cl | H | F | H | F | $OCH_3$ | H | H |
| I.a.1273 | CN | H | F | H | F | $OCH_3$ | H | H |
| I.a.1274 | F | F | F | H | F | $OCH_3$ | H | H |
| I.a.1275 | Cl | F | F | H | F | $OCH_3$ | H | H |
| I.a.1276 | F | Cl | F | H | F | $OCH_3$ | H | H |
| I.a.1277 | Cl | F | F | H | F | $OCH_3$ | H | H |
| I.a.1278 | CN | F | F | H | F | $OCH_3$ | H | H |
| I.a.1279 | F | CN | F | H | F | $OCH_3$ | H | H |
| I.a.1280 | CN | F | F | H | F | $OCH_3$ | H | H |
| I.a.1281 | F | F | H | F | F | $OCH_3$ | H | H |
| I.a.1282 | Cl | F | H | F | F | $OCH_3$ | H | H |
| I.a.1283 | F | Cl | H | F | F | $OCH_3$ | H | H |
| I.a.1284 | CN | F | H | F | F | $OCH_3$ | H | H |
| I.a.1285 | F | CN | H | F | F | $OCH_3$ | H | H |
| I.a.1286 | F | F | F | F | F | $OCH_3$ | H | H |
| I.a.1287 | Cl | F | F | F | F | $OCH_3$ | H | H |
| I.a.1288 | F | Cl | F | F | F | $OCH_3$ | H | H |
| I.a.1289 | CN | F | F | F | F | $OCH_3$ | H | H |
| I.a.1290 | F | CN | F | F | F | $OCH_3$ | H | H |
| I.a.1291 | H | F | F | F | F | $OCH_3$ | H | H |
| I.a.1292 | F | F | Br | F | F | $OCH_3$ | H | H |
| I.a.1293 | F | F | C≡CH | F | F | $OCH_3$ | H | H |
| I.a.1294 | $CF_3$ | Cl | H | H | F | $OCH_3$ | H | H |
| I.a.1295 | F | F | I | F | F | $OCH_3$ | H | H |
| I.a.1296 | F | H | H | H | F | $OCH_3$ | $CH_3$ | H |
| I.a.1297 | Cl | H | H | H | F | $OCH_3$ | $CH_3$ | H |
| I.a.1298 | Br | H | H | H | F | $OCH_3$ | $CH_3$ | H |
| I.a.1299 | CN | H | H | H | F | $OCH_3$ | $CH_3$ | H |
| I.a.1300 | $CH_3$ | H | H | H | F | $OCH_3$ | $CH_3$ | H |
| I.a.1301 | F | H | H | F | F | $OCH_3$ | $CH_3$ | H |
| I.a.1302 | Cl | H | H | F | F | $OCH_3$ | $CH_3$ | H |
| I.a.1303 | F | H | H | Cl | F | $OCH_3$ | $CH_3$ | H |
| I.a.1304 | Cl | H | H | F | F | $OCH_3$ | $CH_3$ | H |
| I.a.1305 | CN | H | H | F | F | $OCH_3$ | $CH_3$ | H |
| I.a.1306 | F | H | H | CN | F | $OCH_3$ | $CH_3$ | H |
| I.a.1307 | CN | H | H | F | F | $OCH_3$ | $CH_3$ | H |
| I.a.1308 | F | H | F | H | F | $OCH_3$ | $CH_3$ | H |
| I.a.1309 | Cl | H | F | H | F | $OCH_3$ | $CH_3$ | H |
| I.a.1310 | CN | H | F | H | F | $OCH_3$ | $CH_3$ | H |
| I.a.1311 | F | F | F | H | F | $OCH_3$ | $CH_3$ | H |
| I.a.1312 | Cl | F | F | H | F | $OCH_3$ | $CH_3$ | H |
| I.a.1313 | F | Cl | F | H | F | $OCH_3$ | $CH_3$ | H |
| I.a.1314 | Cl | F | F | H | F | $OCH_3$ | $CH_3$ | H |
| I.a.1315 | CN | F | F | H | F | $OCH_3$ | $CH_3$ | H |
| I.a.1316 | F | CN | F | H | F | $OCH_3$ | $CH_3$ | H |
| I.a.1317 | CN | F | F | H | F | $OCH_3$ | $CH_3$ | H |
| I.a.1318 | F | F | H | F | F | $OCH_3$ | $CH_3$ | H |
| I.a.1319 | Cl | F | H | F | F | $OCH_3$ | $CH_3$ | H |
| I.a.1320 | F | Cl | H | F | F | $OCH_3$ | $CH_3$ | H |
| I.a.1321 | CN | F | H | F | F | $OCH_3$ | $CH_3$ | H |
| I.a.1322 | F | CN | H | F | F | $OCH_3$ | $CH_3$ | H |
| I.a.1323 | F | F | F | F | F | $OCH_3$ | $CH_3$ | H |
| I.a.1324 | Cl | F | F | F | F | $OCH_3$ | $CH_3$ | H |
| I.a.1325 | F | Cl | F | F | F | $OCH_3$ | $CH_3$ | H |
| I.a.1326 | CN | F | F | F | F | $OCH_3$ | $CH_3$ | H |
| I.a.1327 | F | CN | F | F | F | $OCH_3$ | $CH_3$ | H |
| I.a.1328 | H | F | F | F | F | $OCH_3$ | $CH_3$ | H |
| I.a.1329 | F | F | Br | F | F | $OCH_3$ | $CH_3$ | H |
| I.a.1330 | F | F | C≡CH | F | F | $OCH_3$ | $CH_3$ | H |
| I.a.1331 | $CF_3$ | Cl | H | H | F | $OCH_3$ | $CH_3$ | H |
| I.a.1332 | F | F | I | F | F | $OCH_3$ | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1333 | F | H | H | H | F | OCH$_3$ | CH$_3$ | CH$_3$ |
| I.a.1334 | Cl | H | H | H | F | OCH$_3$ | CH$_3$ | CH$_3$ |
| I.a.1335 | Br | H | H | H | F | OCH$_3$ | CH$_3$ | CH$_3$ |
| I.a.1336 | CN | H | H | H | F | OCH$_3$ | CH$_3$ | CH$_3$ |
| I.a.1337 | CH$_3$ | H | H | H | F | OCH$_3$ | CH$_3$ | CH$_3$ |
| I.a.1338 | F | H | H | F | F | OCH$_3$ | CH$_3$ | CH$_3$ |
| I.a.1339 | Cl | H | H | F | F | OCH$_3$ | CH$_3$ | CH$_3$ |
| I.a.1340 | F | H | H | Cl | F | OCH$_3$ | CH$_3$ | CH$_3$ |
| I.a.1341 | Cl | H | H | F | F | OCH$_3$ | CH$_3$ | CH$_3$ |
| I.a.1342 | CN | H | H | F | F | OCH$_3$ | CH$_3$ | CH$_3$ |
| I.a.1343 | F | H | H | CN | F | OCH$_3$ | CH$_3$ | CH$_3$ |
| I.a.1344 | CN | H | H | F | F | OCH$_3$ | CH$_3$ | CH$_3$ |
| I.a.1345 | F | H | F | H | F | OCH$_3$ | CH$_3$ | CH$_3$ |
| I.a.1346 | Cl | H | F | H | F | OCH$_3$ | CH$_3$ | CH$_3$ |
| I.a.1347 | CN | H | F | H | F | OCH$_3$ | CH$_3$ | CH$_3$ |
| I.a.1348 | F | F | F | H | F | OCH$_3$ | CH$_3$ | CH$_3$ |
| I.a.1349 | Cl | F | F | H | F | OCH$_3$ | CH$_3$ | CH$_3$ |
| I.a.1350 | F | Cl | F | H | F | OCH$_3$ | CH$_3$ | CH$_3$ |
| I.a.1351 | Cl | F | F | H | F | OCH$_3$ | CH$_3$ | CH$_3$ |
| I.a.1352 | CN | F | F | H | F | OCH$_3$ | CH$_3$ | CH$_3$ |
| I.a.1353 | F | CN | F | H | F | OCH$_3$ | CH$_3$ | CH$_3$ |
| I.a.1354 | CN | F | F | H | F | OCH$_3$ | CH$_3$ | CH$_3$ |
| I.a.1355 | F | F | H | F | F | OCH$_3$ | CH$_3$ | CH$_3$ |
| I.a.1356 | Cl | F | H | F | F | OCH$_3$ | CH$_3$ | CH$_3$ |
| I.a.1357 | F | Cl | H | F | F | OCH$_3$ | CH$_3$ | CH$_3$ |
| I.a.1358 | CN | F | H | F | F | OCH$_3$ | CH$_3$ | CH$_3$ |
| I.a.1359 | F | CN | H | F | F | OCH$_3$ | CH$_3$ | CH$_3$ |
| I.a.1360 | F | F | F | F | F | OCH$_3$ | CH$_3$ | CH$_3$ |
| I.a.1361 | Cl | F | F | F | F | OCH$_3$ | CH$_3$ | CH$_3$ |
| I.a.1362 | F | Cl | F | F | F | OCH$_3$ | CH$_3$ | CH$_3$ |
| I.a.1363 | CN | F | F | F | F | OCH$_3$ | CH$_3$ | CH$_3$ |
| I.a.1364 | F | CN | F | F | F | OCH$_3$ | CH$_3$ | CH$_3$ |
| I.a.1365 | H | F | F | F | F | OCH$_3$ | CH$_3$ | CH$_3$ |
| I.a.1366 | F | F | Br | F | F | OCH$_3$ | CH$_3$ | CH$_3$ |
| I.a.1367 | F | F | C≡CH | F | F | OCH$_3$ | CH$_3$ | CH$_3$ |
| I.a.1368 | CF$_3$ | Cl | H | H | F | OCH$_3$ | CH$_3$ | CH$_3$ |
| I.a.1369 | F | F | I | F | F | OCH$_3$ | CH$_3$ | CH$_3$ |
| I.a.1370 | F | H | H | H | F | H | —O(CH$_2$)$_3$— | |
| I.a.1371 | Cl | H | H | H | F | H | —O(CH$_2$)$_3$— | |
| I.a.1372 | Br | H | H | H | F | H | —O(CH$_2$)$_3$— | |
| I.a.1373 | CN | H | H | H | F | H | —O(CH$_2$)$_3$— | |
| I.a.1374 | CH$_3$ | H | H | H | F | H | —O(CH$_2$)$_3$— | |
| I.a.1375 | F | H | H | F | F | H | —O(CH$_2$)$_3$— | |
| I.a.1376 | Cl | H | H | F | F | H | —O(CH$_2$)$_3$— | |
| I.a.1377 | F | H | H | Cl | F | H | —O(CH$_2$)$_3$— | |
| I.a.1378 | Cl | H | H | F | F | H | —O(CH$_2$)$_3$— | |
| I.a.1379 | CN | H | H | F | F | H | —O(CH$_2$)$_3$— | |
| I.a.1380 | F | H | H | CN | F | H | —O(CH$_2$)$_3$— | |
| I.a.1381 | CN | H | H | F | F | H | —O(CH$_2$)$_3$— | |
| I.a.1382 | F | H | F | H | F | H | —O(CH$_2$)$_3$— | |
| I.a.1383 | Cl | H | F | H | F | H | —O(CH$_2$)$_3$— | |
| I.a.1384 | CN | H | F | H | F | H | —O(CH$_2$)$_3$— | |
| I.a.1385 | F | F | F | H | F | H | —O(CH$_2$)$_3$— | |
| I.a.1386 | Cl | F | F | H | F | H | —O(CH$_2$)$_3$— | |
| I.a.1387 | F | Cl | F | H | F | H | —O(CH$_2$)$_3$— | |
| I.a.1388 | Cl | F | F | H | F | H | —O(CH$_2$)$_3$— | |
| I.a.1389 | CN | F | F | H | F | H | —O(CH$_2$)$_3$— | |
| I.a.1390 | F | CN | F | H | F | H | —O(CH$_2$)$_3$— | |
| I.a.1391 | CN | F | F | H | F | H | —O(CH$_2$)$_3$— | |
| I.a.1392 | F | F | H | F | F | H | —O(CH$_2$)$_3$— | |
| I.a.1393 | Cl | F | H | F | F | H | —O(CH$_2$)$_3$— | |
| I.a.1394 | F | Cl | H | F | F | H | —O(CH$_2$)$_3$— | |
| I.a.1395 | CN | F | H | F | F | H | —O(CH$_2$)$_3$— | |
| I.a.1396 | F | CN | H | F | F | H | —O(CH$_2$)$_3$— | |
| I.a.1397 | F | F | F | F | F | H | —O(CH$_2$)$_3$— | |
| I.a.1398 | Cl | F | F | F | F | H | —O(CH$_2$)$_3$— | |
| I.a.1399 | F | Cl | F | F | F | H | —O(CH$_2$)$_3$— | |
| I.a.1400 | CN | F | F | F | F | H | —O(CH$_2$)$_3$— | |
| I.a.1401 | F | CN | F | F | F | H | —O(CH$_2$)$_3$— | |
| I.a.1402 | H | F | F | F | F | H | —O(CH$_2$)$_3$— | |
| I.a.1403 | F | F | Br | F | F | H | —O(CH$_2$)$_3$— | |
| I.a.1404 | F | F | C≡CH | F | F | H | —O(CH$_2$)$_3$— | |
| I.a.1405 | CF$_3$ | Cl | H | H | F | H | —O(CH$_2$)$_3$— | |
| I.a.1406 | F | F | I | F | F | H | —O(CH$_2$)$_3$— | |

In another preferred embodiment, the azines useful for the present invention are azines of formula (I)

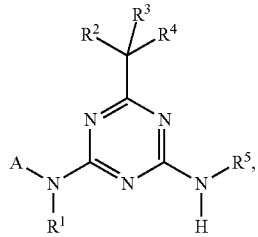

(I)

wherein

A is heteroaryl, which is substituted by 1, 2, 3, 4, 5 or 6 substituents $R^A$ selected from the group consisting of halogen, OH, CN, amino, NO$_2$, C$_1$-C$_6$-alkyl, C$_2$-C$_6$-alkenyl, C$_2$-C$_6$-alkynyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$-alkyl, (C$_1$-C$_6$-alkoxy)-C$_1$-C$_6$-alkoxy, (C$_1$-C$_6$-alkoxy)-C$_2$-C$_6$-alkenyl, (C$_1$-C$_6$-alkoxy)-C$_2$-C$_6$-alkynyl, C$_1$-C$_6$-alkylthio, (C$_1$-C$_6$-alkyl)sulfinyl, (C$_1$-C$_6$-alkyl)sulfonyl, (C$_1$-C$_6$-alkyl)amino, di(C$_1$-C$_6$-alkyl)amino, (C$_1$-C$_6$-alkyl)-carbonyl, (C$_1$-C$_6$-alkoxy)-carbonyl, (C$_1$-C$_6$-alkyl)-carbonyloxy, C$_3$-C$_6$-cycloalkyl, C$_3$-C$_6$-cycloalkoxy, (C$_3$-C$_6$-cycloalkyl)-C$_1$-C$_4$-alkyl, (C$_3$-C$_6$-cycloalkyl)-C$_1$-C$_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, S(O)$_2$NH$_2$, CN, C$_1$-C$_6$-alkyl, C$_2$-C$_6$-alkenyl, C$_2$-C$_6$-alkynyl, (C$_3$-C$_6$-cycloalkyl)-C$_1$-C$_4$-alkyl, C$_1$-C$_6$-alkoxy, (C$_1$-C$_6$-alkoxy)-C$_1$-C$_6$-alkyl, (C$_1$-C$_6$-alkyl)-carbonyl, (C$_1$-C$_6$-alkoxy)carbonyl, (C$_1$-C$_6$-alkyl)sulfonyl, (C$_1$-C$_6$-alkylamino)carbonyl, di(C$_1$-C$_6$-alkyl)aminocarbonyl, (C$_1$-C$_6$-alkylamino)sulfonyl, di(C$_1$-C$_6$-alkyl)aminosulfonyl and (C$_1$-C$_6$-alkoxy)sulfonyl, where the aliphatic and cycloaliphatic parts of the 14 aforementioned radicals are unsubstituted, partly or completely halogenated, phenyl, phenyl-C$_1$-C$_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy;

$R^2$ is H, halogen, OH, CN, C$_1$-C$_6$-alkyl, C$_2$-C$_6$-alkenyl, C$_3$-C$_6$-alkynyl, (C$_1$-C$_6$-alkoxy)-C$_1$-C$_6$-alkyl, C$_3$-C$_6$-cycloalkyl, C$_3$-C$_6$-cycloalkenyl, (C$_3$-C$_6$-cycloalkyl)-C$_1$-C$_4$-alkyl, C$_1$-C$_6$-alkoxy, C$_2$-C$_6$-alkenyloxy, C$_2$-C$_6$-alkynyloxy, C$_3$-C$_6$-cycloalkoxy or (C$_3$-C$_6$-cycloalkyl)-C$_1$-C$_4$-alkoxy, where the aliphatic and cycloaliphatic parts of the 9 aforementioned radicals are unsubstituted, partly or completely halogenated, phenyl, phenyl-C$_1$-C$_6$-alkyl, wherein phenyl in the last 2 mentioned radicals are unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy;

$R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^4$ is selected from the group consisting of H, halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
  wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
  phenyl, phenyl-$C_1$-$C_6$-alkyl, phenylsulfonyl, phenylaminosulfonyl, phenylcarbonyl and phenoxycarbonyl,
    wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

and wherein the variables A, $R^1$, $R^2$, $R^3$, $R^4$ and $R^5$ are in particular:

A is heteroaryl, which is substituted by 1, 2, 3, 4, 5 or 6 substituents $R^A$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
  phenyl, phenyl-$C_1$-$C_6$-alkyl, phenylsulfonyl, phenylaminosulfonyl, phenylcarbonyl and phenoxycarbonyl,
    wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated or phenyl, wherein phenyl is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^4$ is selected from the group consisting of H, halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
  wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
  phenyl, phenyl-$C_1$-$C_6$-alkyl, phenylsulfonyl, phenylaminosulfonyl, phenylcarbonyl and phenoxycarbonyl,
    wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

and wherein the variables A, $R^1$, $R^2$, $R^3$, $R^4$ and $R^5$ are in more particular:

A is heteroaryl, which is substituted by 1, 2, 3, 4, 5 or 6 substituents $R^4$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)carbonyl, ($C_1$-$C_6$-alkoxy)-carbonyl, ($C_1$-$C_6$-alkyl)carbonyloxy, $C_3$-$C_6$-cycloalkyl, $C_3$-$C_6$-cycloalkoxy, ($C_3$-$C_6$-cycloalkyl)-$C_1$-$C_6$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated, $R^3$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^4$ is selected from the group consisting of H, halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkoxy)-carbonyl, ($C_1$-$C_6$-alkoxy)carbonyl, ($C_1$-$C_6$-alkyl) sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

and wherein the variables A, $R^1$, $R^2$, $R^3$, $R^4$ and $R^5$ are preferred:

A is heteroaryl, which is substituted by one to six substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy) carbonyl;

$R^1$ is H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy) carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ is H, halogen, OH, CN, $C_1$-$C_6$-alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated $R^3$ is H, halogen, CN, $C_1$-$C_6$-alkyl, $C_1$-$C_6$-haloalkyl or $C_1$-$C_6$-alkoxy;

$R^4$ is H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy) carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

In another preferred embodiment, the azines useful for the present invention comprise a diaminotriazine compound of formula (I)

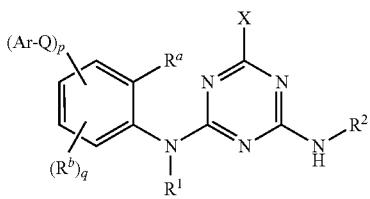

wherein
p is 1 or 2;
q is 0, 1, 2 or 3 provided that p+q is 1, 2, 3 or 4;
Q is a chemical bond, O, S(O)$_m$, CR$^{q1}$R$^{q2}$, NR$^{q3}$, C(O), C(O)O, CR$^{q1}$R$^{q2}$—O, S(O)$_m$NR$^{q3}$ or C(O)NR$^{q3}$,
wherein
m is 0, 1 or 2;
R$^{q1}$, R$^{q2}$ are hydrogen, halogen or C$_1$-C$_4$-alkyl;
R$^{q3}$ is H, CN, C$_1$-C$_6$-alkyl, (C$_1$-C$_6$-alkoxy)-C$_1$-C$_6$-alkyl, (C$_1$-C$_6$-alkyl)-carbonyl, (C$_1$-C$_6$-alkoxy)carbonyl, (C$_1$-C$_6$-alkyl)sulfonyl, where the aliphatic parts of the 6 aforementioned radicals are unsubstituted, partly or completely halogenated;
Ar is phenyl, which is unsubstituted or carries 1, 2, 3, 4 or 5 radicals R$^A$ which are selected from the group consisting of halogen, OH, CN, amino, NO$_2$, C$_1$-C$_6$-alkyl, C$_2$-C$_6$-alkenyl, C$_2$-C$_6$-alkynyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$-alkyl, (C$_1$-C$_6$-alkoxy)-C$_1$-C$_6$-alkoxy, (C$_1$-C$_6$-alkoxy)-C$_2$-C$_6$-alkenyl, (C$_1$-C$_6$-alkoxy)-C$_2$-C$_6$-alkynyl, C$_1$-C$_6$-alkylthio, (C$_1$-C$_6$-alkyl)sulfinyl, (C$_1$-C$_6$-alkyl)sulfonyl, (C$_1$-C$_6$-alkyl)amino, di(C$_1$-C$_6$-alkyl)amino, (C$_1$-C$_6$-alkyl)-carbonyl, (C$_1$-C$_6$-alkoxy)-carbonyl, (C$_1$-C$_6$-alkyl)-carbonyloxy, C$_3$-C$_6$-cycloalkyl, C$_3$-C$_6$-cycloalkoxy, (C$_3$-C$_6$-cycloalkyl)-C$_1$-C$_4$-alkyl, (C$_3$-C$_6$-cycloalkyl)-C$_1$-C$_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups,
phenyl, phenyl-C$_1$-C$_6$-alkyl, phenylsulfonyl, phenylaminosulfonyl, phenylaminocarbonyl, phenyl (C$_1$-C$_6$-alkyl)aminocarbonyl, phenylcarbonyl and phenoxycarbonyl,
wherein phenyl in the last 8 mentioned radicals are unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy,
it being possible that R$^A$ are identical or different;
R$^a$ is selected from the group consisting of hydrogen, halogen, OH, CN, amino, NO$_2$, C$_1$-C$_6$-alkyl, C$_2$-C$_6$-alkenyl, C$_2$-C$_6$-alkynyl, C$_1$-C$_6$-alkoxy, C$_2$-C$_6$-alkenyloxy, C$_2$-C$_6$-alkynyloxy, C$_1$-C$_6$-alkylthio, (C$_1$-C$_6$-alkyl)sulfinyl, (C$_1$-C$_6$-alkyl)sulfonyl, (C$_1$-C$_6$-alkyl)amino, di(C$_1$-C$_6$-alkyl)amino, (C$_1$-C$_6$-alkyl)-carbonyl, (C$_1$-C$_6$-alkoxy)-carbonyl, (C$_1$-C$_6$-alkyl)-carbonyloxy, where the aliphatic and cycloaliphatic parts of the 14 aforementioned radicals are unsubstituted, partly or completely halogenated;
R$^b$ is selected from the group consisting of halogen, OH, CN, amino, NO$_2$, C$_1$-C$_6$-alkyl, C$_2$-C$_6$-alkenyl, C$_2$-C$_6$-alkynyl, C$_1$-C$_6$-alkoxy, C$_2$-C$_6$-alkenyloxy, C$_2$-C$_6$-alkynyloxy, (C$_1$-C$_6$-alkoxy)-C$_1$-C$_6$-alkyl, (C$_1$-C$_6$-alkoxy)-C$_1$-C$_6$-alkoxy, (C$_1$-C$_6$-alkoxy)-C$_2$-C$_6$-alkenyl, (C$_1$-C$_6$-alkoxy)-C$_2$-C$_6$-alkynyl, C$_1$-C$_6$-alkylthio, (C$_1$-C$_6$-alkyl)sulfinyl, (C$_1$-C$_6$-alkyl)sulfonyl, (C$_1$-C$_6$-alkyl)amino, di(C$_1$-C$_6$-alkyl)amino, (C$_1$-C$_6$-alkyl)-carbonyl, (C$_1$-C$_6$-alkoxy)-carbonyl, (C$_1$-C$_6$-alkyl)-carbonyloxy, C$_3$-C$_6$-cycloalkyl, C$_3$-C$_6$-cycloalkoxy, (C$_3$-C$_6$-cycloalkyl)-C$_1$-C$_4$-alkyl, (C$_3$-C$_6$-cycloalkyl)-C$_1$-C$_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups,
for q=2 or 3 it being possible that R$^b$ are identical or different;
R$^1$ is selected from the group consisting of H, OH, S(O)$_2$NH$_2$, CN, C$_1$-C$_6$-alkyl, C$_2$-C$_6$-alkenyl, C$_2$-C$_6$-alkynyl, (C$_3$-C$_6$-cycloalkyl)-C$_1$-C$_4$-alkyl, C$_1$-C$_6$-alkoxy, (C$_1$-C$_6$-alkoxy)-C$_1$-C$_6$-alkyl, (C$_3$-C$_6$-cycloalkyl)-carbonyl, (C$_1$-C$_6$-alkyl)-carbonyl, (C$_1$-C$_6$-alkoxy)carbonyl, (C$_1$-C$_6$-alkyl)sulfonyl, (C$_1$-C$_6$-alkylamino)carbonyl, di(C$_1$-C$_6$-alkyl)aminocarbonyl, (C$_1$-C$_6$-alkylamino)sulfonyl, di(C$_1$-C$_6$-alkyl)aminosulfonyl and (C$_1$-C$_6$-alkoxy)sulfonyl, where the aliphatic and cycloaliphatic parts of the 15 aforementioned radicals are unsubstituted, partly or completely halogenated,
phenyl, phenyl-C$_1$-C$_6$-alkyl, phenylsulfonyl, phenylaminosulfonyl, phenylaminocarbonyl, phenyl (C$_1$-C$_6$-alkyl)aminocarbonyl, phenylcarbonyl and phenoxycarbonyl,
wherein phenyl in the last 8 mentioned radicals are unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy;
R$^2$ is selected from the group consisting of H, OH, S(O)$_2$NH$_2$, CN, C$_1$-C$_6$-alkyl, C$_2$-C$_6$-alkenyl, C$_2$-C$_6$-alkynyl, (C$_3$-C$_6$-cycloalkyl)-C$_1$-C$_4$-alkyl, C$_3$-C$_6$-cycloalkyly carbonyl C$_1$-C$_6$-alkoxy, (C$_1$-C$_6$-alkoxy)-C$_1$-C$_6$-alkyl, (C$_1$-C$_6$-alkyl)carbonyl, (C$_1$-C$_6$-alkoxy)carbonyl, (C$_1$-C$_6$-alkyl)sulfonyl, (C$_1$-C$_6$-alkylamino)carbonyl, di(C$_1$-C$_6$-alkyl)aminocarbonyl, (C$_1$-C$_6$-alkylamino)sulfonyl, di(C$_1$-C$_6$-alkyl)aminosulfonyl and (C$_1$-C$_6$-alkoxy)sulfonyl, where the aliphatic and cycloaliphatic parts of the 15 aforementioned radicals are unsubstituted, partly or completely halogenated,
phenyl, phenylsulfonyl, phenylaminosulfonyl, phenylaminocarbonyl, phenyl(C$_1$-C$_6$-alkyl)aminocarbonyl, phenyl-C$_1$-C$_6$ alkyl, phenoxy, phenylcarbonyl and phenoxycarbonyl,
wherein phenyl in the last 9 mentioned radicals is unsubstituted or substituted by 1, 2, 3, 4 or 5 identical or different substituents selected from the group consisting of halogen, CN, NO$_2$, C$_1$-C$_6$-alkyl, C$_1$-C$_6$-haloalkyl, C$_1$-C$_6$-alkoxy and C$_1$-C$_6$-haloalkoxy;
X is a radical selected from the group consisting of CR$^3$R$^4$R$^5$,
phenyl, which is unsubstituted or carries 1, 2, 3, 4 or 5 radicals R$^{Ar}$ which are identical or different;
NR$^{3a}$R$^{3b}$,
OR$^{3c}$ and
S(O)$_k$R$^{3d}$ with k being 0, 1 or 2
wherein
R$^3$ is selected from the group consisting of H, halogen, OH, CN, C$_1$-C$_6$-alkyl, (C$_1$-C$_6$-alkoxy)-C$_1$-C$_6$-alkyl, C$_3$-C$_6$-cycloalkyl, (C$_3$-C$_6$-cycloalkyl)-C$_1$-C$_4$-alkyl, C$_1$-C$_6$-alkoxy, C$_2$-C$_6$-alkenyloxy, C$_2$-C$_6$-alkynyloxy, $C_3$-$C_6$-cycloalkoxy, ($C_3$-$C_6$-cycloalkyl)-$C_1$-$C_4$-alkoxy, where the aliphatic and cycloaliphatic parts of the 9 aforementioned radicals are unsubstituted, partly or completely halogenated;

$R^4$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;

$R^5$ is selected from the group consisting of halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated;

$R^4$ and $R^5$ together with the carbon atom to which they are attached form a moiety selected from the group consisting of carbonyl, $C_3$-$C_6$-cycloalkyl, $C_3$-$C_6$-cycloalkenyl, three- to six-membered saturated or partially unsaturated heterocyclyl, and the moiety >C=$CR^xR^y$, where $R^x$ and $R^y$ are hydrogen, $C_1$-$C_4$-alkyl or $C_1$-$C_4$-haloalkyl;

$R^{Ar}$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, $R^{3a}$, $R^{3b}$, $R^{3c}$ or $R^{3d}$ are independently of one another are selected from the group consisting of H, CN, S(O)$_2NH_2$, $C_1$-$C_6$-alkyl, $C_2$-$C_6$-alkenyl, $C_2$-$C_6$-alkynyl, $C_3$-$C_6$-cycloalkyl, ($C_3$-$C_6$-cycloalkyl)-$C_1$-$C_6$-alkyl, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_3$-$C_6$-cycloalkyl)-carbonyl, ($C_1$-$C_6$-alkylamino) sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated, phenyl, phenylsulfonyl, phenyl-$C_1$-$C_6$ alkyl, phenylaminosulfonyl, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, or $R^{3a}$, $R^{3b}$ together with the nitrogen atom, to which they are bound, form an N-bound, mono—or bicyclic heterocyclic radical, which may have 1, 2, 3 or 4 further heteroatoms which are selected from N, O and S, which is unsubstituted or substituted by one or more identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, one of $R^{3a}$, $R^{3b}$ may also be OH, $C_1$-$C_6$-alkoxy, $C_3$-$C_6$-cycloalkoxy, ($C_3$-$C_6$-cycloalkyl)-$C_1$-$C_4$-alkoxy $C_2$-$C_6$-alkenyloxy, $C_2$-$C_6$-alkynyloxy, ($C_1$-$C_6$-alkoxy)-$C_1$-$C_6$-alkoxy, where the aliphatic and cycloaliphatic parts of the 7 aforementioned radicals are unsubstituted, partly or completely halogenated, or phenoxy, which is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

including their agriculturally acceptable salts

In another preferred embodiment, the azines useful for the present invention comprises a diaminotriazine compound of the formula:

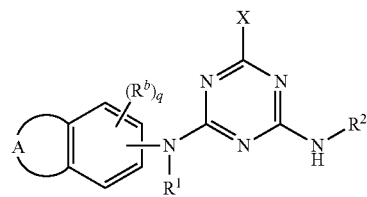

wherein

A is a fused saturated or unsaturated, 5- or 6-membered carbocycle or a fused saturated or unsaturated, 5- or 6-membered heterocycle having 1, 2 or 3 heteroatoms or heteroatom moieties, selected from O, S, S(O)$_p$, N or $NR^c$ as ring members, where the carbocycle and the heterocycle are unsubstituted or carry 1, 2, 3 or 4 radicals $R^A$;

p is 0, 1 or 2 q is 0, 1, 2 or 3;

$R^A$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, it being possible that $R^A$ are identical or different, it being possible that two radicals $R^A$ which are bound at the same carbon atom may together be =O or =$NR^d$;

$R^b$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups,
for q=2 or 3 it being possible that $R^b$ are identical or different;

$R^c$ is selected from the group consisting of H, OH, $S(O)_2NH_2$, CN, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkoxy, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 16 aforementioned radicals are unsubstituted, partly or completely halogenated, $R^d$ is selected from the group consisting of H, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

$R^1$ is selected from the group consisting of H, OH, $S(O)_2NH_2$, CN, $C_3$-$C_6$-cycloalkyl, $C_3$-$C_6$-cycloalkoxy, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 17 aforementioned radicals are unsubstituted, partly or completely halogenated, phenyl, phenyl-$C_1$-$C_6$-alkyl, phenylsulfonyl, phenylaminosulfonyl, phenylaminocarbonyl, phenyl($C_1$-$C_6$-alkyl)aminocarbonyl, phenylcarbonyl and phenoxycarbonyl,
wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is selected from the group consisting of H, OH, $S(O)_2NH_2$, CN, $C_3$-$C_6$-cycloalkyl, $C_3$-$C_6$-cycloalkoxy, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 17 aforementioned radicals are unsubstituted, partly or completely halogenated, phenyl, phenylsulfonyl, phenylaminosulfonyl, phenyl-$C_1$-$C_6$ alkyl, phenoxy, phenylaminocarbonyl, phenyl($C_1$-$C_6$-alkyl)aminocarbonyl, phenylcarbonyl and phenoxycarbonyl,
wherein phenyl in the last 8 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

X is a radical selected from the group consisting of
$CR^3R^4R^5$
phenyl, which is unsubstituted or carries 1, 2, 3, 4 or 5 radicals $R^{Ar}$ which are identical or different;
$NR^{3a}R^{3b}$,
$OR^{3c}$ and
$S(O)_kR^{3d}$ with k being 0, 1 or 2,
wherein
$R^3$ is selected from the group consisting of H, halogen, OH, CN, $C_1$-$C_6$-alkyl, ($C_1$-$C_6$-alkoxy)-$C_1$-$C_6$-alkyl, $C_3$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, ($C_3$-$C_6$-cycloalkyl)-$C_1$-$C_4$-alkoxy, where the aliphatic and cycloaliphatic parts of the 9 aforementioned radicals are unsubstituted, partly or completely halogenated;
$R^4$ is selected from the group consisting of H, halogen, CN, $C_1$-$C_6$-alkyl, $C_1$-$C_6$-haloalkyl, $C_1$-$C_6$-alkoxy and $C_1$-$C_6$-haloalkoxy;
$R^5$ is selected from the group consisting of halogen, CN, $C_1$-$C_6$-alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated;
$R^4$ and $R^5$ together with the carbon atom to which they are attached form a moiety selected from the group consisting of carbonyl, thiocarbonyl, $C_3$-$C_6$-cycloalkyl, $C_3$-$C_6$-cycloalkenyl, three- to six-membered saturated or partially unsaturated heterocyclyl, and the moiety >C=$CR^xR^y$, where $R^x$ and $R^y$ are hydrogen, $C_1$-$C_4$-alkyl or $C_1$-$C_4$-haloalkyl;
$R^{Ar}$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups,
$R^{3a}$, $R^{3b}$, $R^{3c}$ or $R^{3d}$ are independently of one another are selected from the group consisting of H, CN, $S(O)_2NH_2$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, ($C_3$-$C_6$-cycloalkyl)-$C_1$-$C_6$-alkyl, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 16 aforementioned radicals are unsubstituted, partly or completely halogenated,
phenyl, phenylsulfonyl, phenyl-$C_1$-$C_6$ alkyl, phenylaminosulfonyl, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, or $R^{3a}$, $R^{3b}$ together with the nitrogen atom, to which they are bound, form an N-bound, mono—or bicyclic heterocyclic radical, which may have 1, 2, 3 or 4 further heteroatoms which are selected from N, O and S, which is unsubstituted or substituted by one or more identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy, one of $R^{3a}$, $R^{3b}$ may also be OH, $C_1$-$C_6$-alkoxy, $C_3$-$C_6$-cycloalkoxy, ($C_3$-$C_6$-cycloalkyl)-$C_1$-$C_4$-alkoxy, $C_2$-$C_6$-alkenyloxy, $C_2$-$C_6$-alkynyloxy, ($C_1$-$C_6$-alkoxy)-$C_1$-$C_6$-alkoxy, where the aliphatic and cycloaliphatic parts of the 6 aforementioned radicals are unsubstituted, partly or completely halogenated, or phenoxy, which is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

including their agriculturally acceptable salts.

In another preferred embodiment, the azines useful for the present invention comprise a diaminotriazine compound of formula (I)

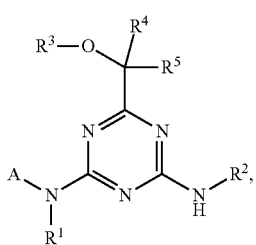

(I)

wherein

A is phenyl, which is substituted by fluorine in the ortho-position and which may additionally carry 1, 2, 3 or 4 identical or different substituents $R^A$ selected from the group consisting of halogen, OH, CN, amino, $NO_2$, $C_1$-$C_6$-alkyl, $C_2$-$C_6$-alkenyl, $C_2$-$C_6$-alkynyl, ($C_1$-$C_6$-alkoxy)-$C_2$-$C_6$-alkyl, ($C_1$-$C_6$-alkoxy)-$C_2$-$C_6$-alkenyl, ($C_1$-$C_6$-alkoxy)-$C_2$-$C_6$-alkynyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, $C_3$-$C_6$-cycloalkyl, ($C_3$-$C_6$-cycloalkyl)-$C_1$-$C_4$-alkyl, where the aliphatic and cycloaliphatic parts of the 11 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenylsulfonyl, phenylaminosulfonyl, phenyl-$C_1$-$C_6$ alkyl, phenoxy, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^3$ is selected from the group consisting of $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, ($C_1$-$C_6$-alkoxy)-$C_1$-$C_6$-alkyl, ($C_1$-$C_6$-alkyl)carbonyl, ($C_1$-$C_6$-alkoxy)carbonyl, ($C_1$-$C_6$-alkylamino)carbonyl and di($C_1$-$C_6$-alkyl)aminocarbonyl, where the aliphatic and cycloaliphatic parts of the 9 aforementioned radicals are unsubstituted, partly or completely halogenated, $R^4$ and $R^5$, together with the carbon atom, to which they are bound form a saturated 3-, 4-, 5- or 6-membered carbocyclic radical or a saturated 3-, 4-, 5- or 6-membered heterocyclic radical, where the carbocyclic radical and the heterocyclic radical are unsubstituted, partly or completely halogenated or carry from 1 to 6 $C_1$-$C_6$-alkyl groups;

including their agriculturally acceptable salts.

The herbicidal compounds (component A) useful for the present invention as disclosed SUPRA may further be used in conjunction with additional herbicides to which the crop plant is naturally tolerant or to which has been made tolerant by mutagenesis as described SUPRA, or to which it is resistant via expression of one or more additional transgenes as mentioned supra. The CESA-inhibiting herbicides useful for the present invention are often best applied in conjunction with one or more other herbicides to obtain control of a wider variety of undesirable vegetation. When used in conjunction with other herbicides (hereinafter referred to a compound B), the presently claimed compounds can be formulated with the other herbicide or herbicides, tank mixed with the other herbicide or herbicides, or applied sequentially with the other herbicide or herbicides.

The further herbicidal compound B (component B) is in particular selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;

b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives such as ethers, esters or amides.

Preference is given to those compositions according to the present invention comprising at least one herbicide B selected from herbicides of class b1, b6, b9, b10 and b11.

Examples of herbicides B which can be used in combination with the compounds of formula (I) according to the present invention are:
b1) from the Group of the Lipid Biosynthesis Inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim,
4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2",4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-ylcarbonic acid methyl ester (CAS 1312337-51-1); 4-(2",4'-Dichloro-4-cyclopropyl-[1,1'-biphenyl]-3-yl)-5,6-dihydro-2,2,6,6-tetramethyl-5-oxo-2H-pyran-3-yl-carbonic acid methyl ester; 4-(4'-Chloro-4-ethyl-2'-fluoro[1,1-biphenyl]-3-yl)-5,6-dihydro-2,2,6,6-tetramethyl-5-oxo-2H-pyran-3-ylcarbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;
b2) from the Group of the ALS Inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam,
pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;
among these, a preferred embodiment of the invention relates to those compositions comprising at least one imidazolinone herbicide;
b3) from the Group of the Photosynthesis Inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the Group of the Protoporphyrinogen-IX Oxidase Inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-$C_5$-7), N-tetrahydrofurfuryl-3-(2-chloro-6-fluoro-4-trifluoromethylphenoxy)-5-methyl-1H-pyrazole-1-carboxamide (CAS 452100-$C_3$-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-$C_0$-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the Group of the Bleacher Herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, clomazone, fenquintrione, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the Group of the EPSP Synthase Inhibitors:

glyphosate, glyphosate-isopropylammonium, glyposate-potassium and glyphosate-trimesium (sulfosate);

b7) from the Group of the Glutamine Synthase Inhibitors:

bilanaphos (bialaphos), bilanaphos-sodium, glufosinate, glufosinate-P and glufosinate-ammonium;

b8) from the Group of the DHP Synthase Inhibitors:

asulam;

b9) from the Group of the Mitosis Inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the Group of the VLCFA Inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

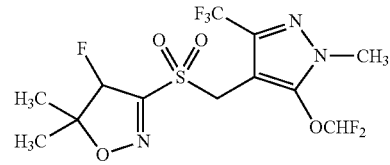

II.1

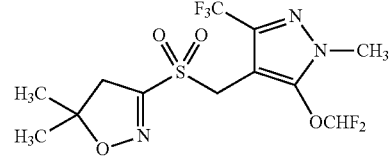

II.2

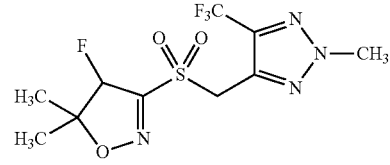

II.3

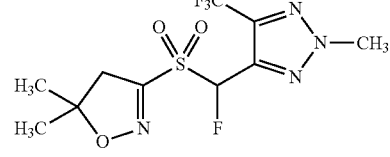

II.4

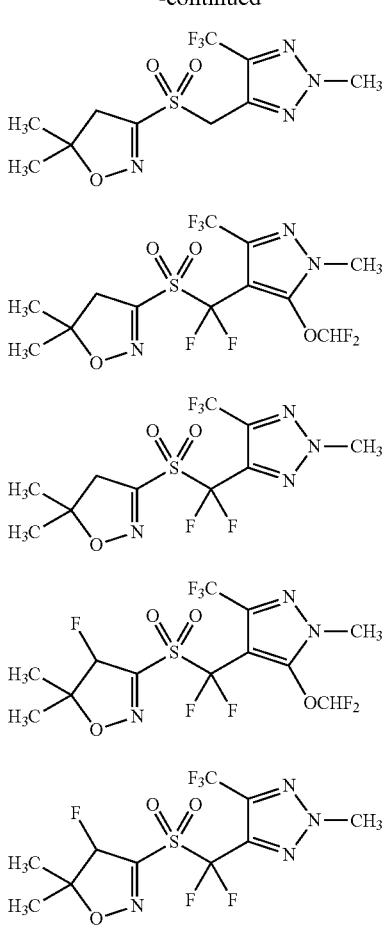

the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the Group of the Cellulose Biosynthesis Inhibitors:

chlorthiamid, dichlobenil, flupoxam, isoxaben and 1-Cyclohexyl-5-pentafluorphenyloxy-1⁴-[1,2,4,6]thiatriazin-3-ylamine;

b12) from the Group of the Decoupler Herbicides:
dinoseb, dinoterb and DNOC and its salts;

b13) from the Group of the Auxinic Herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium.

Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicidal compounds B are the herbicides B as defined above; in particular the herbicides B.1-B.189 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |

TABLE B-continued

| | Herbicide B |
|---|---|
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | saflufenacil |
| B.93 | sulfentrazone |
| B.94 | ethyl [3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate (CAS 353292-31-6) |
| B.95 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.96 | benzobicyclon |
| B.97 | clomazone |
| B.98 | diflufenican |
| B.99 | flurochloridone |
| B.100 | isoxaflutole |
| B.101 | mesotrione |
| B.102 | norflurazon |
| B.103 | picolinafen |
| B.104 | sulcotrione |
| B.105 | tefuryltrione |
| B.106 | tembotrione |
| B.107 | topramezone |
| B.108 | topramezone-sodium |
| B.109 | bicyclopyrone |
| B.110 | amitrole |
| B.111 | fluometuron |
| B.112 | fenquintrione |
| B.113 | glyphosate |
| B.114 | glyphosate-ammonium |
| B.115 | glyphosate-dimethylammonium |
| B.116 | glyphosate-isopropylammonium |
| B.117 | glyphosate-trimesium (sulfosate) |
| B.118 | glyphosate-potassium |
| B.119 | glufosinate |
| B.120 | glufosinate-ammonium |
| B.121 | glufosinate-P |
| B.122 | glufosinate-P-ammonium |
| B.123 | pendimethalin |
| B.124 | trifluralin |
| B.125 | acetochlor |
| B.126 | butachlor |
| B.127 | cafenstrole |
| B.128 | dimethenamid-P |
| B.129 | fentrazamide |
| B.130 | flufenacet |
| B.131 | mefenacet |
| B.132 | metazachlor |
| B.133 | metolachlor |
| B.134 | S-metolachlor |
| B.135 | pretilachlor |
| B.136 | fenoxasulfone |
| B.137 | isoxaben |
| B.138 | ipfencarbazone |
| B.139 | pyroxasulfone |
| B.140 | 2,4-D |
| B.141 | 2,4-D-isobutyl |
| B.142 | 2,4-D-dimethylammonium |
| B.143 | 2,4-D-N,N,N-trimethylethanolammonium |
| B.144 | aminopyralid |
| B.145 | aminopyralid-methyl |
| B.146 | aminopyralid-dimethyl-ammonium |
| B.147 | aminopyralid-tris(2-hydroxypropyl)ammonium |
| B.148 | clopyralid |
| B.149 | clopyralid-methyl |
| B.150 | clopyralid-olamine |
| B.151 | dicamba |
| B.152 | dicamba-butotyl |
| B.153 | dicamba-diglycolamine |
| B.154 | dicamba-dimethylammonium |
| B.155 | dicamba-diolamine |
| B.156 | dicamba-isopropylammonium |
| B.157 | dicamba-potassium |
| B.158 | dicamba-sodium |
| B.159 | dicamba-trolamine |
| B.160 | dicamba-N,N-bis-(3-aminopropyl)methylamine |
| B.161 | dicamba-diethylenetriamine |
| B.162 | fluroxypyr |
| B.163 | fluroxypyr-meptyl |
| B.164 | MCPA |
| B.165 | MCPA-2-ethylhexyl |
| B.166 | MCPA-dimethylammonium |
| B.167 | quinclorac |
| B.168 | quinclorac-dimethylammonium |
| B.169 | quinmerac |
| B.170 | quinmerac-dimethylammonium |
| B.171 | aminocyclopyrachlor |
| B.172 | aminocyclopyrachlor-potassium |
| B.173 | aminocyclopyrachlor-methyl |
| B.174 | diflufenzopyr |
| B.175 | diflufenzopyr-sodium |
| B.176 | dymron |
| B.177 | indanofan |
| B.178 | indaziflam |
| B.179 | oxaziclomefone |
| B.180 | triaziflam |
| B.181 | II.1 |
| B.182 | II.2 |
| B.183 | II.3 |
| B.184 | II.4 |
| B.185 | II.5 |
| B.186 | II.6 |
| B.187 | II.7 |
| B.188 | II.8 |
| B.189 | II.9 |

Moreover, it may be useful to apply the compounds of formula (I) in combination with safeners and optionally with one or more further herbicides. Safeners are chemical compounds which prevent or reduce damage on useful plants without having a major impact on the herbicidal action of the compounds of the formula (I) towards unwanted plants. They can be applied either before sowings (e.g. on seed treatments, shoots or seedlings) or in the pre-emergence application or post-emergence application of the useful plant. The safeners and the compounds of formula (I) and optionally the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diary)-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-C$_7$-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C are the following compounds C.1 to C.17

| C.1 | benoxacor | C.2 | cloquintocet |
| --- | --- | --- | --- |
| C.3 | cloquintocet-mexyl | C.4 | cyprosulfamide |
| C.5 | dichlormid | C.6 | fenchlorazole |
| C.7 | fenchlorazole-ethyl | C.8 | fenclorim |
| C.9 | furilazole | C.10 | isoxadifen |
| C.11 | isoxadifen-ethyl | C.12 | mefenpyr |
| C.13 | mefenpyr-diethyl | C.14 | naphtalic acid anhydride |
| C.15 | 4-(dichloroacetyl)-1-oxa-4-azaspiro[4.5]decane | C.16 | 2,2,5-trimethyl-3-(dichloro-acetyl)-1,3-oxazolidine |
| C.17 | N-(2-Methoxybenzoyl)-4-[(methylaminocarbonyl)amino]benzenesulfonamide | | |

The active compounds B of groups b1) to b15) and the safener compounds C are known herbicides and safeners, see, for example, The Compendium of Pesticide Common Names (www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

In another embodiment, the present invention refers to a method for identifying a CESA-inhibiting herbicide by using a mutated CESA encoded by a nucleic acid which comprises the nucleotide sequence of SEQ ID NO: 36, 37, 38, or 39, or a variant or derivative thereof.

Said method comprises the steps of:

a) generating a transgenic cell or plant comprising a nucleic acid encoding a mutated CESA, wherein the mutated CESA is expressed;

b) applying a CESA-inhibiting herbicide to the transgenic cell or plant of a) and to a control cell or plant of the same variety;

c) determining the growth or the viability of the transgenic cell or plant and the control cell or plant after application of said CESA-inhibiting herbicide, and d) selecting "CESA-inhibiting herbicides" which confer reduced growth to the control cell or plant as compared to the growth of the transgenic cell or plant.

As described above, the present invention teaches compositions and methods for increasing the CESA-inhibiting tolerance of a crop plant or seed as compared to a wild-type variety of the plant or seed. In a preferred embodiment, the CESA-inhibiting tolerance of a crop plant or seed is increased such that the plant or seed can withstand a CESA-inhibiting herbicide application of preferably approximately 1-1000 g ai ha$^{-1}$, more preferably 1-200 g ai ha$^{-1}$, even more preferably 5-150 g ai ha$^{-1}$, and most preferably 10-100 g ai ha$^{-1}$. As used herein, to "withstand" a CESA-inhibiting herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Pre- and/or Post-emergent weed control methods useful in various embodiments hereof utilize about >0.3× application rates of CESA-inhibiting herbicides; in some embodiments, this can be about, for example, >0.3×, >0.4×, >0.5×, >0.6×, >0.7×, >0.8×, >0.9×, or >1× of CESA-inhibiting herbicides. In one embodiment, CESA-inhibiting herbicides-tolerant plants of the present invention have tolerance to a pre- and/or post-emergant application of a CESA-inhibiting herbicides at an amount of about 25 to about 500 g ai/ha. In some embodiments, wherein the CESA-inhibiting herbicides-tolerant plant is a dicot (e.g., soy, cotton), the pre- and/or post-emergant application of the CESA-inhibiting herbicides is at an amount of about 25-250 g ai/ha. In another embodiment, wherein the CESA-inhibiting herbicides-tolerant plant is a monocot (e.g., maize, rice, sorghum), the pre- and/or post-emergant application of the CESA-inhibiting herbicides is at an amount of about 50-500 g ai/ha. In other embodiments, wherein the CESA-inhibiting herbicides-tolerant plant is a Brassica (e.g., canola), the pre- and/or post-emergant application of the CESA-inhibiting herbicides is at an amount of about 25-200 g ai/ha. In pre- and/or post-emergent weed control methods hereof, in some embodiments, the method can utilize CESA-inhibiting herbicides application rates at pre-emergent and/or about 7 to 10 days post-emergent. In another embodiment, the application rate can exceed 8×CESA-inhibiting herbicides; in some embodiments, the rate can be up to 4×CESA-inhibiting herbicides, though more typically it will be about 2.5× or less, or about 2× or less, or about 1× or less.

Furthermore, the present invention provides methods that involve the use of at least one CESA-inhibiting herbicide, optionally in combination with one or more herbicidal compounds B, and, optionally, a safener C, as described in detail supra.

In these methods, the CESA-inhibiting herbicide can be applied by any method known in the art including, but not limited to, seed treatment, soil treatment, and foliar treatment. Prior to application, the CESA-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to CESA-inhibiting herbicide, a wide variety of formulations can be employed for protecting plants from weeds, so as to enhance plant growth and reduce competition for nutrients. A CESA-inhibiting herbicide can be used by itself for pre-emergence, post-emergence, pre-planting, and at-planting control of weeds in areas surrounding the crop plants described herein, or a CESA-inhibiting herbicide formulation can be used that contains other additives. The CESA-inhibiting herbicide can also be used as a seed treatment. Additives found in a CESA-inhibiting herbicide formulation include other herbicides, detergents, adjuvants, spreading agents, sticking agents, stabilizing agents, or the like. The CESA-inhibiting herbicide formulation can be a wet or dry preparation and can include, but is not limited to, flowable powders, emulsifiable concentrates, and liquid concentrates. The CESA-inhibiting herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

As disclosed herein, the CESA nucleic acids of the invention find use in enhancing the CBI herbicide tolerance of plants that comprise in their genomes a gene encoding a herbicide-tolerant mutated CESA protein. Such a gene may be an endogenous gene or a transgene, as described above. Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109), 5-enolpyruvylshikimate-3-phosphate synthase (EPSPS), Glyphosate acetyl transferase (GAT), cytochrome P450 monooxygenase, phosphinothricin acetyltransferase (PAT), Acetohydroxyacid synthase (AHAS; EC 4.1.3.18, also known as acetolactate synthase or ALS), hydroxyphenyl pyruvate dioxygenase (HPPD), Phytoene desaturase (PD), Protoporphyrinogen oxidase (PPO) and dicamba degrading enzymes as disclosed in WO 02/068607, or phenoxyacetic acid- and phenoxypropionic acid-derivative degrading enzymes as disclosed in WO 2008141154 or WO 2005107437. The combinations generated can also include multiple copies of any one of the polynucleotides of interest.

Consequently, Herbicide-tolerant plants of the invention can be used in conjunction with an herbicide to which they are tolerant. Herbicides can be applied to the plants of the invention using any techniques known to those skilled in the art. Herbicides can be applied at any point in the plant cultivation process. For example, herbicides can be applied pre-planting, at planting, pre-emergence, post-emergence or combinations thereof. Herbicides may be applied to seeds and dried to form a layer on the seeds.

In some embodiments, seeds are treated with a safener, followed by a post-emergent application of a CESA-inhibiting herbicides. In one embodiment, the post-emergent application of the CESA-inhibiting herbicides is about 7 to 10 days following planting of safener-treated seeds. In some embodiments, the safener is cloquintocet, dichlormid, fluxofenim, or combinations thereof.

Methods of Controlling Weeds or Undesired Vegetation

In other aspects, the present invention provides a method for controlling weeds at a locus for growth of a plant or plant part thereof, the method comprising: applying a composition comprising a CESA-inhibiting herbicides to the locus.

In some aspects, the present invention provides a method for controlling weeds at a locus for growth of a plant, the method comprising: applying an herbicide composition comprising CESA-inhibiting herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides can be used to control the growth of weeds that may be found growing in the vicinity of the herbicide-tolerant plants invention. In embodiments of this type, an herbicide can be applied to a plot in which herbicide-tolerant plants of the invention are growing in vicinity to weeds. An herbicide to which the herbicide-tolerant plant of the invention is tolerant can then be applied to the plot at a concentration sufficient to kill or inhibit the growth of the weed. Concentrations of herbicide sufficient to kill or inhibit the growth of weeds are known in the art and are disclosed above.

In other embodiments, the present invention provides a method for controlling weeds in the vicinity of a CESA-inhibiting herbicides-tolerant plant of the invention. The method comprises applying an effective amount of a CESA-inhibiting herbicides to the weeds and to the herbicide-tolerant plant, wherein the plant has increased tolerance to CESA-inhibiting herbicide when compared to a wild-type plant. In some embodiments, the CESA-inhibiting herbicides-tolerant plants of the invention are preferably crop plants, including, but not limited to, sunflower, alfalfa, *Brassica* sp., soybean, cotton, safflower, peanut, tobacco, tomato, potato, wheat, rice, maize, sorghum, barley, rye, millet, and sorghum.

In other aspects, herbicide(s) (e.g., CESA-inhibiting herbicides) can also be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed Treatment formulations may additionally comprise binders and optionally colorants.

Binders can be added to improve the adhesion of the active materials on the seeds after treatment. In one embodiments, suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers. Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15: 1, pigment blue 80, pigment yellow 1, pigment yellow 13, pigment red 112, pigment red 48:2, pigment red 48: 1, pigment red 57: 1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The term seed treatment comprises all suitable seed treatment techniques known in the art, such as seed dressing, seed coating, seed dusting, seed soaking, and seed pelleting. In one embodiment, the present invention provides a method of treating soil by the application, in particular into the seed drill: either of a granular formulation containing the CESA-inhibiting herbicides as a composition/formulation (e.g., a granular formulation), with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising CESA-inhibiting herbicides and at least one other herbicide such as, e.g., an AHAS-inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In some embodiments, the seed treatment application with CESA-inhibiting herbicides or with a formulation comprising the CESA-inhibiting herbicides is carried out by spraying or dusting the seeds before sowing of the plants and before emergence of the plants.

In other embodiments, in the treatment of seeds, the corresponding formulations are applied by treating the seeds with an effective amount of CESA-inhibiting herbicides or a formulation comprising the CESA-inhibiting herbicides.

In other aspects, the present invention provides a method for combating undesired vegetation or controlling weeds comprising contacting the seeds of the CESA-inhibiting herbicides-tolerant plants of the present invention before sowing and/or after pregermination with CESA-inhibiting herbicides. The method can further comprise sowing the seeds, for example, in soil in a field or in a potting medium in greenhouse. The method finds particular use in combating undesired vegetation or controlling weeds in the immediate vicinity of the seed. The control of undesired vegetation is understood as the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepiclium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solarium, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

In other embodiments, in the treatment of seeds, the corresponding formulations are applied by treating the seeds with an effective amount of CESA-inhibiting herbicides or a formulation comprising the CESA-inhibiting herbicides.

In still further aspects, treatment of loci, plants, plant parts, or seeds of the present invention comprises application of an agronomically acceptable composition that does not contain an A.I. In one embodiment, the treatment comprises application of an agronomically acceptable composition that does not contain a CESA-inhibiting herbicides A.I. In some embodiments, the treatment comprises application of an agronomically acceptable composition that does not contain a CESA-inhibiting herbicides A.L, wherein the composition comprises one or more of agronomically-acceptable carriers, diluents, excipients, plant growth regulators, and the like. In other embodiments, the treatment comprises application of an agronomically acceptable composition that does not contain a CESA-inhibiting herbicides A.I., wherein the composition comprises an adjuvant. In one embodiment, the adjuvant is a surfactant, a spreader, a sticker, a penetrant, a drift-control agent, a crop oil, an emulsifier, a compatibility agent, or combinations thereof.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1: Identification of Homologue Cellulose Synthase Isoforms in *Brassica napus*

To identify homologue cellulose synthase genes from *Brassica napus* (Chalhoub B. et al. (2014) Science 345:950-953), BLAST searches using the protein sequences of *Arabidopsis thaliana* cellulose synthase isoforms were performed (Altschul et al. (1990) J Mol Biol 215:403-10). Cellulose synthase protein encoding genes from *Brassica napus* were analyzed regarding their phylogenetic relationship by the R software library phangorn (Schliep K P. (2011) Bioinformatics 27:592-593). Bootstrap analyses, to statistically confirm monophyletic groups, were calculated. In addition, relative expression level of cellulose synthase genes were used to select candidate genes for transformation. For this purpose, a cDNA library of *Brassica napus* seedlings were sequenced with one lane Illumina HiSeq2000 with a 2×100 bp paired end run using TruSeq SBS Kit v3 (FC-401-3001 Illumina Inc. San Diego, CA USA). The sequencing raw data were analyzed with FASTQC quality checker (Babraham Bioinformatics 2014), trimmed using EA-Utils fastq-mcf (code.google.com/p/ea-utils/) and further analyzed to remove any Illumina adaptor sequences using CutAdapt coding (code.google.com/p/cutadapt/). For relative expression analysis of the cellulose synthase genes in our *Brassica napus*, reads were mapped using TopHat2 (Kim et al. 2013) and counted using HTseq count (Anders et al. 2015).

Example 2: Engineering Azine-Tolerant *Brassica napus* Having Mutated Cellulose Synthase Sequences For transformation of *Brassica napus*, mutated cellulose synthase sequences based on one of the following sequences SEQ ID NO: 12, 15, 20, and 21, are cloned with standard cloning techniques as described in Sambrook et al. (Molecular cloning (2001) Cold Spring Harbor Laboratory Press) in a binary vector containing resistance marker gene cassette (AHAS) and mutated cellulose synthase sequence (marked as GOD in between ubiquitin promoter (PcUbi) and nopaline synthase terminator (NOS) sequence. Binary plasmids are introduced to *Agrobacterium tumefaciens* for plant transformation.

In general, the transgenic rape seed plants (cv. Kumily) were generated by a modified protocol according to Moloney et al. 1992, (Plant Cell Reports, 8:238-242). To this end, dilutions of overnight cultures of two positive transformed agrobacteria colonies harbouring the plasmid of interest was grown in Murashige-Skoog Medium (Murashige and Skoog 1962 Physiol. Plant. 15, 473) supplemented by 3% saccharose (3MS-Medium). Petiols or Hypocotyls of sterile rapeseed plants were incubated in a petri dish with the agrobacterial suspension for 5-10 minutes. This was followed by a three day co-incubation in darkness at 25° C. on 3MS-Medium with 0.8% bacto-Agar. After three days the culture was put on 16 hours light/8 hours darkness weekly on MS-medium containing 500 mg/l Claforan (Cefotaxime-Natrium), 100 nM Imazetapyr, 20 micromolar Benzylaminopurin (BAP) and 1.6 g/l Glucose. Growing sprouts—indicative for the presence of T-DNA the AHAS selectable marker were transferred to MS-Medium containing 2% saccharose, 250 mg/l Claforan and 0.8% Bacto-Agar. In case that even after three weeks no root formation was observed, a growth hormone 2-Indolbutyl acid was added to the medium for enhancing root formation. Regenerated sprouts obtained on 2MS-Medium with Imazetapyr and Claforan were transferred to the greenhouse for sprouting.

Transgenic *Brassica napus* plants are assayed for improved tolerance to azine herbicides like e. g. 6-cyclopentyl-N4-(2,3,4,5,6-pentafluorophenyl)-1,3,5-triazine-2,4-diamine in 6-well plates. Therefore, 5-6 T1 seeds are sown on vermiculite and watered with half-strength murashige skoog nutrient solution, pH 5.8 (Murashige and Skoog (1962) *Physiologia Plantarum* 15: 473-497). Compounds are dissolved in dimethylsulfoxid (DMSO) and added to the medium (final DMSO concentration 0.1%). Multi well plates are incubated in a growth chamber at 22° C., 75% relative humidity and 110 µmol Phot*$m^{-2}$*$s^{-1}$ with 14: 10 h light: dark photoperiod. Growth inhibition is evaluated seven to ten days after seeding in comparison to wild type plants. Plant injury is rated on a scale of 0% to 100%, 0% being no injury and 100% being complete death.

TABLE X-1

T1 seeds expressing indicated variant of *Brassica napus* CESA variant. 5 individuals per event were treated with the indicated amount of [6-cyclopentyl-N4-(2,3,4,5,6-pentafluorophenyl)-1,3,5-triazine-2,4-diamine] and evaluated for injury 7 days after treatment. Shown are the average phytotox value of 5 individual plants.

| Gene | Seq ID | Variation | Event | Concentration | | | | | |
|---|---|---|---|---|---|---|---|---|---|
| | | | | UTC | 10-9M | 10-8M | 5*10-8M | 10-7M | 10-6M |
| BnaA01g04600D | 21 | G1012R | event 1 | 0 | 0 | 10 | 30 | 50 | 80 |
| BnaA01g04600D | 21 | G1012R | event 2 | 0 | 0 | 10 | 40 | 70 | 85 |
| BnaA01g04600D | 21 | G1012R | event 3 | 0 | 0 | 10 | 50 | 75 | 85 |
| BnaA03g52020D | 15 | G1015R | event 1 | 0 | 0 | 0 | 50 | 75 | 85 |
| BnaA03g52020D | 15 | G1015R | event 2 | 0 | 0 | 0 | 60 | 75 | 80 |
| BnaA03g52020D | 15 | G1015R | event 3 | 0 | 0 | 0 | 65 | 70 | 80 |
| BnaA03g55200D | 12 | S1038F | event 1 | 0 | 0 | 15 | 40 | 75 | 80 |
| BnaA03g55200D | 12 | S1038F | event 2 | 0 | 0 | 0 | 65 | 75 | 90 |
| BnaA03g55200D | 12 | S1038F | event 3 | 0 | 0 | 0 | 65 | 80 | 90 |
| BnaA03g55200D | 12 | S1041L | event 1 | 0 | 0 | 0 | 35 | 75 | 95 |
| BnaA03g55200D | 12 | S1041L | event 2 | 0 | 0 | 10 | 50 | 80 | 90 |
| BnaA03g55200D | 12 | S1041L | event 3 | 0 | 0 | 0 | 60 | 70 | 85 |
| BnaA03g55200D | 12 | S1041L | event 4 | 0 | 0 | 10 | 50 | 60 | 85 |
| BnaAnng01240D | 20 | S1038F | event 1 | 0 | 0 | 0 | 50 | 60 | 80 |

TABLE X-1-continued

T1 seeds expressing indicated variant of *Brassica napus* CESA variant. 5 individuals per event were treated with the indicated amount of [6-cyclopentyl-N4-(2,3,4,5,6-pentafluorophenyl)-1,3,5-triazine-2,4-diamine] and evaluated for injury 7 days after treatment. Shown are the average phytotox value of 5 individual plants.

| Gene | Seq ID | Variation | Event | UTC | 10-9M | 10-8M | 5*10-8M | 10-7M | 10-6M |
|---|---|---|---|---|---|---|---|---|---|
| BnaAnng01240D | 20 | S1038F | event 2 | 0 | 0 | 0 | 65 | 65 | 80 |
| BnaAnng01240D | 20 | S1041L | event 1 | 0 | 0 | 0 | 55 | 70 | 80 |
| BnaAnng01240D | 20 | S1041L | event 2 | 0 | 0 | 0 | 65 | 80 | 80 |
| wildtype | | | | 0 | 4 | 46 | 75 | 80 | 91 |

TABLE X-2

T1 seeds expressing indicated variant of *Brassica napus* CESA variant. 5 individuals per event were treated with the indicated amount of [1[4-chloro-3-(2,2,3,3,3-pentafluoropropoxymethyl)phenyl]-5-phenyl-1,2,4-triazole-3-carboxamide] and evaluated for injury 7 days after treatment. Shown are the average phytotox value of 5 individual plants.

| Gene | Seq ID | Mutation | Event | DMSO | 10-8M | 10-7M | 10-6M | 10-5M | 10-4M |
|---|---|---|---|---|---|---|---|---|---|
| BnaAnng01240D | 20 | S1041L | event 1 | 0 | 0 | 10 | 80 | 85 | 95 |
| BnaAnng01240D | 20 | S1041L | event 2 | 0 | 0 | 0 | 90 | 90 | 90 |
| wildtype | | | | 0 | 4 | 41 | 84 | 93 | 96 |

TABLE X-3

T1 seeds expressing indicated variant of *Brassica napus* CESA variant. 5 individuals per event were treated with the indicated amount of [N2-(4-chloro-3,5,6-trifluoro-2-pyridyl)-6-(1-fluorocyclopentyl)-1,3,5-triazine-2,4-diamine] and evaluated for injury 7 days after treatment. Shown are the average phytotox value of 5 individual plants.

| Gene | Seq ID | Mutation | Event | DMSO | 10-8M | 5*10-8M | 10-7M | 5*10-7 | 10-6M |
|---|---|---|---|---|---|---|---|---|---|
| BnaAnng01240D | 20 | S1038F | event 1 | 0 | 0 | 5 | 30 | 30 | 85 |
| BnaA01g04600D | 21 | G1012R | event 1 | 0 | 0 | 10 | 10 | 75 | 80 |
| BnaAnng01240D | 20 | S1041L | event 1 | 0 | 0 | 0 | 10 | 90 | 90 |
| wildtype | | | | 0 | 8 | 18 | 56 | 78 | 85 |

Example 3: Sequence Analysis

Leaf tissue is collected from clonal plants separated for transplanting and analyzed as individuals. Genomic DNA is extracted using a Wizard® 96 Magnetic DNA Plant System kit (Promega, U.S. Pat. Nos. 6,027,945 & 6,368,800) as directed by the manufacturer. Isolated DNA is PCR amplified using the appropriate forward and reverse primer.

PCR amplification is performed using Hotstar Taq DNA Polymerase (Qiagen) using touchdown thermocycling program as follows: 96° C. for 15 min, followed by 35 cycles (96° C., 30 sec; 58° C.-0.2° C. per cycle, 30 sec; 72° C., 3 min and 30 sec), 10 min at 72° C. PCR products were verified for concentration and fragment size via agarose gel electrophoresis. Dephosphorylated PCR products are analyzed by direct sequence using the PCR primers (DNA Landmarks). Chromatogram trace files (.scf) are analyzed for mutation relative to the wild-type gene using Vector NTI Advance 10™ (Invitrogen). Based on sequence information, mutations are identified in several individuals. Sequence analysis is performed on the representative chromatograms and corresponding AlignX alignment with default settings and edited to call secondary peaks.

Example 4: Demonstration of Herbicide Tolerance

T1/T2 transgenic plants of *Brassica napus* containing cellulose synthase sequences or mutated gene variants thereof are tested for improved tolerance to herbicides in greenhouse studies with azine herbicides. For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly, and grown in the same containers or they are first grown separately and transplanted into the test containers a few days prior to treatment.

Herbicide injury evaluations are taken at 1, 2 and 3 weeks after treatment. Plant biomass reduction is rated on a scale of 0% to 100%, 0% being no reduction of biomass compared to untreated control, and 100% being complete absence of biomass.

Example pictures are shown in FIG. 3.

The tolerance phenotype evaluation of transgenic T1 *Arabidopsis thaliana* plants germinating on sand with an azine-herbicide are done 14-21 days after germination.

Transgenic *Arabidopsis thaliana* plants (T2) are assayed for improved tolerance to azine herbicides like e. g. 6-cyclopentyl-N4-(2,3,4,5,6-pentafluorophenyl)-1,3,5-triazine-

TABLE Y-1

T1 seeds expressing indicated variant of *Brassica napus* CESA variant. 5 individuals per event were treated post emergent with the indicated amount of mentioned compound and evaluated for injury 7 days after treatment. Shown are the average phytotox value of 6 pots with 9 individual plants.

| | | | Application rate [g/ha] | | | | | | | |
|---|---|---|---|---|---|---|---|---|---|---|
| | | | 6-cyclopentyl-N4-(2,3,4,5,6-pentafluorophenyl)-1,3,5-triazine-2,4-diamine | | | | N2-(4-chloro-3,5,6-trifluoro-2-pyridyl)-6-(1-fluorocyclopentyl)-1,3,5-triazine-2,4-diamine | | | |
| Seq ID | Gene | Variant | 3.9 | 7.8 | 15.6 | 31.25 | 7.8 | 15.6 | 31.25 | 62.5 |
| 21 | BnaA01g04600D | G1012R | 17% | 35% | 35% | 60% | 34% | 61% | 65% | 72% |
| 15 | BnaA03g52020D | G1015R | 18% | 43% | 41% | 53% | 34% | 43% | 50% | 73% |
| 15 | BnaA03g52020D | G1015R | 37% | 61% | 45% | 67% | 16% | 41% | 62% | 72% |
| 12 | BnaA03g55200D | S1038F | 23% | 25% | 29% | 34% | 8% | 6% | 47% | 54% |
| 12 | BnaA03g55200D | S1038F | 7% | 19% | 20% | 44% | 21% | 51% | 47% | 68% |
| 12 | BnaA03g55200D | S1041L | 15% | 27% | 42% | 51% | 24% | 53% | 62% | 76% |
| 20 | BnaAnng01240D | S1038F | 1% | 5% | 8% | 27% | 7% | 17% | 47% | 54% |
| 20 | BnaAnng01240D | S1038F | 1% | 10% | 41% | 50% | 10% | 33% | 68% | 71% |
| 20 | BnaAnng01240D | S1041L | 7% | 6% | 15% | 29% | 6% | 9% | 54% | 64% |
| | wildtype | | 23% | 34% | 59% | 73% | 42% | 56% | 70% | 83% |

TABLE Y-2

T1 seeds expressing indicated variant of *Brassica napus* CESA variant. 5 individuals per event were treated pre emergent with the indicated amount of mentioned compound and evaluated for injury 7 days after treatment. Shown are the average phytotox value of 6 pots with 9 individual plants.

| | | | Application rate [g/ha] 6-cyclopentyl-N4-(2,3,4,5,6-pentafluorophenyl)-1,3,5-triazine-2,4-diamine | | | |
|---|---|---|---|---|---|---|
| Seq ID | Gene | Variant | 1.95 | 3.9 | 7.8 | 15.6 |
| 21 | BnaA01g04600D | G1012R | 26% | 18% | 0% | 16% |
| 15 | BnaA03g52020D | G1015R | 27% | 0% | 0% | 21% |
| 20 | BnaAnng01240D | S1038F | 1% | 14% | 8% | 26% |
| | wildtype | | 18% | 26% | 21% | 52% |

Example 5: Engineering Azine-Tolerant *Arabidopsis* Plants Expressing Double-Mutated Cellulose Synthase Sequences For transformation of *Arabidopsis thaliana*, double-mutated cellulose synthase sequences encoding for one of the following protein sequences SEQ ID NO: 1 or 3, are cloned with standard cloning techniques as described in Sambrook et al. (Molecular cloning (2001) Cold Spring Harbor Laboratory Press) in a binary vector containing resistance marker gene cassette (AHAS) and mutated cellulose synthase sequence (marked as GOD in between ubiquitin promoter (PcUbi) and nopaline synthase terminator (NOS) sequence. Binary plasmids are introduced to *Agrobacterium tumefaciens* for plant transformation. *Arabidopsis thaliana* are transformed with wildtype or mutated cellulose synthase sequences by floral dip method as described by McElver and Singh (WO 2008/124495). Transgenic *Arabidopsis* plants are subjected to TaqMan analysis for analysis of the number of integration loci.

2,4-diamine in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia *Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 μmol Phot*m$^{-2}$*s$^{-1}$ with 14:10 h light:dark photoperiod. Growth inhibition is evaluated seven to ten days after seeding in comparison to wild type plants. Tolerance factors are calculated based on IC50 values of growth inhibition of transformed versus non-transformed *Arabidopsis* plants.

TABLE E2-1

Relative tolerance rates of transgenic *Arabidopsis* plants as compared to non-transgenic *Arabidopsis* plants (non-transgenic = 1.0), treated with various cellulose biosynthesis inhibitors. Growth inhibition is evaluated seven to ten days after seeding in comparison to wild type plants.

| Construct | SEQ ID | Variant | N2-(4-chloro-3,5,6-trifluoro-2-pyridyl)-6-(1-fluorocyclopentyl)-1,3,5-triazine-2,4-diamine | 6-cyclopentyl-N4-(2,3,4,5,6-pentafluorophenyl)-1,3,5-triazine-2,4- | 1-(m-tolyl)-5-phenyl-1,2,4-triazole-3-carboxamide | 1-[4-chloro-3-(2,2,3,3,3-penta-fluoropropoxy-methyl)phenyl]-5- |
|---|---|---|---|---|---|---|
| AtCesA1_wt | 1 | — | 2 | 1 | 3 | |
| AtCesA3_wt | 3 | — | 1 | 1 | 4 | |
| AtCesA1_G1009D_G1013R | 1 | G1009D_G1013R | 1 | 1 | 25 | |
| AtCesA3_S983F_S1037F | 3 | S983F_S1037F | 5 | 10 | 80 | |
| AtCesA3_S983F_S1040L | 3 | S983F_S1040L | 4 | 10 | 100 | |
| AtCesA1_P1010L_G1013R | 1 | P1010L_G1013R | 1 | 30 | | 400 |

The invention claimed is:

1. A plant or plant part comprising a polynucleotide encoding a cellulose synthase (CESA) polypeptide having, over the full-length of CESA polypeptide, at least 95% sequence identity to SEQ ID NO: 15, wherein the expression of said polynucleotide confers to the plant or plant part tolerance to CESA-inhibiting herbicides, wherein the CESA polypeptide comprises the following amino acid sequence:

(SEQ ID NO: 30)
[V/I][A/V/S]G[V/I/F]S[Y/D/T]A[V/I/L][N/S][S/N/K]
GY[Q/D/G/E][S/A]WGPL[F/M]G[K/R][L/V][F/L]F wherein the amino acid at position 5, 16, 17, and/or 20 of SEQ ID NO: 30 is substituted by any other amino acid.

2. The plant or plant part of claim 1, wherein the CESA polypeptide has, over the full-length of CESA polypeptide, at least 97% sequence identity to SEQ ID NO: 15.

3. The plant or plant part of claim 1, wherein the CESA polypeptide has, over the full-length of CESA polypeptide, at least 98% sequence identity to SEQ ID NO: 15.

4. The plant or plant part of claim 1, wherein the CESA polypeptide has, over the full-length of CESA polypeptide, at least 99% sequence identity to SEQ ID NO: 15.

5. A plant or plant part comprising a polynucleotide encoding a variant CESA polypeptide having, over the full-length of CESA polypeptide, at least 95% sequence identity to SEQ ID NO: 15, wherein the expression of said polynucleotide confers to the plant or plant part tolerance to CESA-inhibiting herbicides, wherein the CESA polypeptide comprises the following amino acid sequence:

(SEQ ID NO: 30)
[V/l][A/V/S]G[V/I/F]S[Y/D/T]A[V/I/L][N/S][S/N/K]
GY[Q/D/G/E][S/A]WGPL[F/M]G[K/R][L/V][F/L]F wherein the amino acid at position 5, 16, 17, and/or 20 of SEQ ID NO: 30 is substituted by any other amino acid and wherein the amino acid at position 20 of SEQ ID NO: 30 is substituted by any other amino acid.

* * * * *

SEQUENCE LISTING

<160> NUMBER OF SEQ ID NOS: 39

<210> SEQ ID NO 1
<211> LENGTH: 1081
<212> TYPE: PRT
<213> ORGANISM: Arabidopsis thaliana

<400> SEQUENCE: 1

```
Met Glu Ala Ser Ala Gly Leu Val Ala Gly Ser Tyr Arg Arg Asn Glu
1               5                   10                  15

Leu Val Arg Ile Arg His Glu Ser Asp Gly Thr Lys Pro Leu Lys
            20                  25                  30

Asn Met Asn Gly Gln Ile Cys Gln Ile Cys Gly Asp Asp Val Gly Leu
        35                  40                  45

Ala Glu Thr Gly Asp Val Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65                  70                  75                  80

Cys Pro Gln Cys Lys Thr Arg Phe Arg Arg His Arg Gly Ser Pro Arg
                85                  90                  95

Val Glu Gly Asp Glu Asp Glu Asp Val Asp Asp Ile Glu Asn Glu
            100                 105                 110

Phe Asn Tyr Ala Gln Gly Ala Asn Lys Ala Arg His Gln Arg His Gly
        115                 120                 125

Glu Glu Phe Ser Ser Ser Arg His Glu Ser Gln Pro Ile Pro Leu
    130                 135                 140

Leu Thr His Gly His Thr Val Ser Gly Glu Ile Arg Thr Pro Asp Thr
145                 150                 155                 160

Gln Ser Val Arg Thr Thr Ser Gly Pro Leu Gly Pro Ser Asp Arg Asn
                165                 170                 175

Ala Ile Ser Ser Pro Tyr Ile Asp Pro Arg Gln Pro Val Pro Val Arg
            180                 185                 190

Ile Val Asp Pro Ser Lys Asp Leu Asn Ser Tyr Gly Leu Gly Asn Val
        195                 200                 205

Asp Trp Lys Glu Arg Val Glu Gly Trp Lys Leu Lys Gln Glu Lys Asn
    210                 215                 220

Met Leu Gln Met Thr Gly Lys Tyr His Glu Gly Lys Gly Gly Glu Ile
225                 230                 235                 240

Glu Gly Thr Gly Ser Asn Gly Glu Glu Leu Gln Met Ala Asp Asp Thr
                245                 250                 255

Arg Leu Pro Met Ser Arg Val Val Pro Ile Pro Ser Ser Arg Leu Thr
```

-continued

```
              260                 265                 270
Pro Tyr Arg Val Val Ile Ile Leu Arg Leu Ile Ile Leu Cys Phe Phe
            275                 280                 285

Leu Gln Tyr Arg Thr Thr His Pro Val Lys Asn Ala Tyr Pro Leu Trp
            290                 295                 300

Leu Thr Ser Val Ile Cys Glu Ile Trp Phe Ala Phe Ser Trp Leu Leu
305                 310                 315                 320

Asp Gln Phe Pro Lys Trp Tyr Pro Ile Asn Arg Glu Thr Tyr Leu Asp
            325                 330                 335

Arg Leu Ala Ile Arg Tyr Asp Arg Asp Gly Glu Pro Ser Gln Leu Val
            340                 345                 350

Pro Val Asp Val Phe Val Ser Thr Val Asp Pro Leu Lys Glu Pro Pro
            355                 360                 365

Leu Val Thr Ala Asn Thr Val Leu Ser Ile Leu Ser Val Asp Tyr Pro
            370                 375                 380

Val Asp Lys Val Ala Cys Tyr Val Ser Asp Asp Gly Ser Ala Met Leu
385                 390                 395                 400

Thr Phe Glu Ser Leu Ser Glu Thr Ala Glu Phe Ala Lys Lys Trp Val
                405                 410                 415

Pro Phe Cys Lys Lys Phe Asn Ile Glu Pro Arg Ala Pro Glu Phe Tyr
            420                 425                 430

Phe Ala Gln Lys Ile Asp Tyr Leu Lys Asp Lys Ile Gln Pro Ser Phe
            435                 440                 445

Val Lys Glu Arg Arg Ala Met Lys Arg Glu Tyr Glu Glu Phe Lys Val
        450                 455                 460

Arg Ile Asn Ala Leu Val Ala Lys Ala Gln Lys Ile Pro Glu Glu Gly
465                 470                 475                 480

Trp Thr Met Gln Asp Gly Thr Pro Trp Pro Gly Asn Asn Thr Arg Asp
                485                 490                 495

His Pro Gly Met Ile Gln Val Phe Leu Gly His Ser Gly Gly Leu Asp
                500                 505                 510

Thr Asp Gly Asn Glu Leu Pro Arg Leu Ile Tyr Val Ser Arg Glu Lys
            515                 520                 525

Arg Pro Gly Phe Gln His His Lys Lys Ala Gly Ala Met Asn Ala Leu
            530                 535                 540

Ile Arg Val Ser Ala Val Leu Thr Asn Gly Ala Tyr Leu Leu Asn Val
545                 550                 555                 560

Asp Cys Asp His Tyr Phe Asn Asn Ser Lys Ala Ile Lys Glu Ala Met
                565                 570                 575

Cys Phe Met Met Asp Pro Ala Ile Gly Lys Lys Cys Cys Tyr Val Gln
                580                 585                 590

Phe Pro Gln Arg Phe Asp Gly Ile Asp Leu His Asp Arg Tyr Ala Asn
            595                 600                 605

Arg Asn Ile Val Phe Phe Asp Ile Asn Met Lys Gly Leu Asp Gly Ile
            610                 615                 620

Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Glu Asp Leu Glu Pro Asn
                645                 650                 655

Ile Ile Val Lys Ser Cys Cys Gly Ser Arg Lys Lys Gly Lys Ser Ser
            660                 665                 670

Lys Lys Tyr Asn Tyr Glu Lys Arg Arg Gly Ile Asn Arg Ser Asp Ser
            675                 680                 685
```

```
Asn Ala Pro Leu Phe Asn Met Glu Asp Ile Asp Glu Gly Phe Glu Gly
    690                 695                 700
Tyr Asp Asp Glu Arg Ser Ile Leu Met Ser Gln Arg Ser Val Glu Lys
705                 710                 715                 720
Arg Phe Gly Gln Ser Pro Val Phe Ile Ala Ala Thr Phe Met Glu Gln
                725                 730                 735
Gly Gly Ile Pro Pro Thr Thr Asn Pro Ala Thr Leu Leu Lys Glu Ala
            740                 745                 750
Ile His Val Ile Ser Cys Gly Tyr Glu Asp Lys Thr Glu Trp Gly Lys
            755                 760                 765
Glu Ile Gly Trp Ile Tyr Gly Ser Val Thr Glu Asp Ile Leu Thr Gly
    770                 775                 780
Phe Lys Met His Ala Arg Gly Trp Ile Ser Ile Tyr Cys Asn Pro Pro
785                 790                 795                 800
Arg Pro Ala Phe Lys Gly Ser Ala Pro Ile Asn Leu Ser Asp Arg Leu
                805                 810                 815
Asn Gln Val Leu Arg Trp Ala Leu Gly Ser Ile Glu Ile Leu Leu Ser
            820                 825                 830
Arg His Cys Pro Ile Trp Tyr Gly Tyr His Gly Arg Leu Arg Leu Leu
            835                 840                 845
Glu Arg Ile Ala Tyr Ile Asn Thr Ile Val Tyr Pro Ile Thr Ser Ile
    850                 855                 860
Pro Leu Ile Ala Tyr Cys Ile Leu Pro Ala Phe Cys Leu Ile Thr Asp
865                 870                 875                 880
Arg Phe Ile Ile Pro Glu Ile Ser Asn Tyr Ala Ser Ile Trp Phe Ile
                885                 890                 895
Leu Leu Phe Ile Ser Ile Ala Val Thr Gly Ile Leu Glu Leu Arg Trp
            900                 905                 910
Ser Gly Val Ser Ile Glu Asp Trp Trp Arg Asn Glu Gln Phe Trp Val
            915                 920                 925
Ile Gly Gly Thr Ser Ala His Leu Phe Ala Val Phe Gln Gly Leu Leu
    930                 935                 940
Lys Val Leu Ala Gly Ile Asp Thr Asn Phe Thr Val Thr Ser Lys Ala
945                 950                 955                 960
Thr Asp Glu Asp Gly Asp Phe Ala Glu Leu Tyr Ile Phe Lys Trp Thr
                965                 970                 975
Ala Leu Leu Ile Pro Pro Thr Thr Val Leu Leu Val Asn Leu Ile Gly
            980                 985                 990
Ile Val Ala Gly Val Ser Tyr Ala Val Asn Ser Gly Tyr Gln Ser Trp
            995                 1000                1005
Gly Pro Leu Phe Gly Lys Leu Phe Phe Ala Leu Trp Val Ile Ala
    1010                1015                1020
His Leu Tyr Pro Phe Leu Lys Gly Leu Leu Gly Arg Gln Asn Arg
    1025                1030                1035
Thr Pro Thr Ile Val Ile Val Trp Ser Val Leu Leu Ala Ser Ile
    1040                1045                1050
Phe Ser Leu Leu Trp Val Arg Ile Asn Pro Phe Val Asp Ala Asn
    1055                1060                1065
Pro Asn Ala Asn Asn Phe Asn Gly Lys Gly Gly Val Phe
    1070                1075                1080

<210> SEQ ID NO 2
<211> LENGTH: 1084
```

```
<212> TYPE: PRT
<213> ORGANISM: Arabidopsis thaliana

<400> SEQUENCE: 2

Met Asn Thr Gly Gly Arg Leu Ile Ala Gly Ser His Asn Arg Asn Glu
1               5                   10                  15

Phe Val Leu Ile Asn Ala Asp Glu Ser Ala Arg Ile Arg Ser Val Gln
            20                  25                  30

Glu Leu Ser Gly Gln Thr Cys Gln Ile Cys Gly Asp Glu Ile Glu Leu
        35                  40                  45

Thr Val Ser Ser Glu Leu Phe Val Ala Cys Asn Glu Cys Ala Phe Pro
50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
                85                  90                  95

Val Asp Gly Asp Asp Glu Glu Glu Asp Ile Asp Asp Leu Glu Tyr
            100                 105                 110

Glu Phe Asp His Gly Met Asp Pro Glu His Ala Ala Glu Ala Ala Leu
            115                 120                 125

Ser Ser Arg Leu Asn Thr Gly Arg Gly Leu Asp Ser Ala Pro Pro
130                 135                 140

Gly Ser Gln Ile Pro Leu Leu Thr Tyr Cys Asp Glu Asp Ala Asp Met
145                 150                 155                 160

Tyr Ser Asp Arg His Ala Leu Ile Val Pro Pro Ser Thr Gly Tyr Gly
                165                 170                 175

Asn Arg Val Tyr Pro Ala Pro Phe Thr Asp Ser Ser Ala Pro Pro Gln
            180                 185                 190

Ala Arg Ser Met Val Pro Gln Lys Asp Ile Ala Glu Tyr Gly Tyr Gly
        195                 200                 205

Ser Val Ala Trp Lys Asp Arg Met Glu Val Trp Lys Arg Arg Gln Gly
210                 215                 220

Glu Lys Leu Gln Val Ile Lys His Glu Gly Gly Asn Asn Gly Arg Gly
225                 230                 235                 240

Ser Asn Asp Asp Asp Glu Leu Asp Asp Pro Asp Met Pro Met Met Asp
                245                 250                 255

Glu Gly Arg Gln Pro Leu Ser Arg Lys Leu Pro Ile Arg Ser Ser Arg
            260                 265                 270

Ile Asn Pro Tyr Arg Met Leu Ile Leu Cys Arg Leu Ala Ile Leu Gly
        275                 280                 285

Leu Phe Phe His Tyr Arg Ile Leu His Pro Val Asn Asp Ala Tyr Gly
290                 295                 300

Leu Trp Leu Thr Ser Val Ile Cys Glu Ile Trp Phe Ala Val Ser Trp
305                 310                 315                 320

Ile Leu Asp Gln Phe Pro Lys Trp Tyr Pro Ile Glu Arg Glu Thr Tyr
                325                 330                 335

Leu Asp Arg Leu Ser Leu Arg Tyr Glu Lys Glu Gly Lys Pro Ser Gly
            340                 345                 350

Leu Ala Pro Val Asp Val Phe Val Ser Thr Val Asp Pro Leu Lys Glu
        355                 360                 365

Pro Pro Leu Ile Thr Ala Asn Thr Val Leu Ser Ile Leu Ala Val Asp
370                 375                 380

Tyr Pro Val Asp Lys Val Ala Cys Tyr Val Ser Asp Asp Gly Ala Ala
385                 390                 395                 400
```

-continued

```
Met Leu Thr Phe Glu Ala Leu Ser Asp Thr Ala Glu Phe Ala Arg Lys
                405                 410                 415

Trp Val Pro Phe Cys Lys Lys Phe Asn Ile Glu Pro Arg Ala Pro Glu
            420                 425                 430

Trp Tyr Phe Ser Gln Lys Met Asp Tyr Leu Lys Asn Lys Val His Pro
        435                 440                 445

Ala Phe Val Arg Glu Arg Ala Met Lys Arg Asp Tyr Glu Glu Phe
    450                 455                 460

Lys Val Lys Ile Asn Ala Leu Val Ala Thr Ala Gln Lys Val Pro Glu
465                 470                 475                 480

Glu Gly Trp Thr Met Gln Asp Gly Thr Pro Trp Pro Gly Asn Asn Val
                485                 490                 495

Arg Asp His Pro Gly Met Ile Gln Val Phe Leu Gly His Ser Gly Val
            500                 505                 510

Arg Asp Thr Asp Gly Asn Glu Leu Pro Arg Leu Val Tyr Val Ser Arg
        515                 520                 525

Glu Lys Arg Pro Gly Phe Asp His His Lys Lys Ala Gly Ala Met Asn
    530                 535                 540

Ser Leu Ile Arg Val Ser Ala Val Leu Ser Asn Ala Pro Tyr Leu Leu
545                 550                 555                 560

Asn Val Asp Cys Asp His Tyr Ile Asn Asn Ser Lys Ala Ile Arg Glu
                565                 570                 575

Ser Met Cys Phe Met Met Asp Pro Gln Ser Gly Lys Lys Val Cys Tyr
            580                 585                 590

Val Gln Phe Pro Gln Arg Phe Asp Gly Ile Asp Arg His Asp Arg Tyr
        595                 600                 605

Ser Asn Arg Asn Val Val Phe Phe Asp Ile Asn Met Lys Gly Leu Asp
    610                 615                 620

Gly Ile Gln Gly Pro Ile Tyr Val Gly Thr Gly Cys Val Phe Arg Arg
625                 630                 635                 640

Gln Ala Leu Tyr Gly Phe Asp Ala Pro Lys Lys Lys Pro Pro Gly
                645                 650                 655

Lys Thr Cys Asn Cys Trp Pro Lys Trp Cys Cys Leu Cys Cys Gly Leu
            660                 665                 670

Arg Lys Lys Ser Lys Thr Lys Ala Lys Asp Lys Lys Thr Asn Thr Lys
        675                 680                 685

Glu Thr Ser Lys Gln Ile His Ala Leu Glu Asn Val Asp Glu Gly Val
    690                 695                 700

Ile Val Pro Val Ser Asn Val Glu Lys Arg Ser Glu Ala Thr Gln Leu
705                 710                 715                 720

Lys Leu Glu Lys Lys Phe Gly Gln Ser Pro Val Phe Val Ala Ser Ala
                725                 730                 735

Val Leu Gln Asn Gly Gly Val Pro Arg Asn Ala Ser Pro Ala Cys Leu
            740                 745                 750

Leu Arg Glu Ala Ile Gln Val Ile Ser Cys Gly Tyr Glu Asp Lys Thr
        755                 760                 765

Glu Trp Gly Lys Glu Ile Gly Trp Ile Tyr Gly Ser Val Thr Glu Asp
    770                 775                 780

Ile Leu Thr Gly Phe Lys Met His Cys His Gly Trp Arg Ser Val Tyr
785                 790                 795                 800

Cys Met Pro Lys Arg Ala Ala Phe Lys Gly Ser Ala Pro Ile Asn Leu
                805                 810                 815
```

Ser Asp Arg Leu His Gln Val Leu Arg Trp Ala Leu Gly Ser Val Glu
            820                 825                 830

Ile Phe Leu Ser Arg His Cys Pro Ile Trp Tyr Gly Tyr Gly Gly Gly
            835                 840                 845

Leu Lys Trp Leu Glu Arg Phe Ser Tyr Ile Asn Ser Val Val Tyr Pro
            850                 855                 860

Trp Thr Ser Leu Pro Leu Ile Val Tyr Cys Ser Leu Pro Ala Val Cys
865                 870                 875                 880

Leu Leu Thr Gly Lys Phe Ile Val Pro Glu Ile Ser Asn Tyr Ala Gly
                885                 890                 895

Ile Leu Phe Met Leu Met Phe Ile Ser Ile Ala Val Thr Gly Ile Leu
            900                 905                 910

Glu Met Gln Trp Gly Gly Val Gly Ile Asp Asp Trp Trp Arg Asn Glu
            915                 920                 925

Gln Phe Trp Val Ile Gly Gly Ala Ser Ser His Leu Phe Ala Leu Phe
            930                 935                 940

Gln Gly Leu Leu Lys Val Leu Ala Gly Val Asn Thr Asn Phe Thr Val
945                 950                 955                 960

Thr Ser Lys Ala Ala Asp Asp Gly Ala Phe Ser Glu Leu Tyr Ile Phe
                965                 970                 975

Lys Trp Thr Thr Leu Leu Ile Pro Pro Thr Thr Leu Leu Ile Ile Asn
            980                 985                 990

Ile Ile Gly Val Ile Val Gly Val Ser Asp Ala Ile Ser Asn Gly Tyr
            995                 1000                1005

Asp Ser Trp Gly Pro Leu Phe Gly Arg Leu Phe Phe Ala Leu Trp
    1010                1015                1020

Val Ile Val His Leu Tyr Pro Phe Leu Lys Gly Met Leu Gly Lys
    1025                1030                1035

Gln Asp Lys Met Pro Thr Ile Ile Val Val Trp Ser Ile Leu Leu
    1040                1045                1050

Ala Ser Ile Leu Thr Leu Leu Trp Val Arg Val Asn Pro Phe Val
    1055                1060                1065

Ala Lys Gly Gly Pro Val Leu Glu Ile Cys Gly Leu Asn Cys Gly
    1070                1075                1080

Asn

<210> SEQ ID NO 3
<211> LENGTH: 1065
<212> TYPE: PRT
<213> ORGANISM: Arabidopsis thaliana

<400> SEQUENCE: 3

Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

```
Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
            115                 120                 125

Val Ser His Asn His Leu Pro Arg Leu Thr Ser Arg Gln Asp Thr Ser
        130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
            195                 200                 205

Pro Val Ser Thr Gln Ala Ala Ser Glu Arg Gly Gly Val Asp Ile Asp
            210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
            275                 280                 285

Leu Val Ser Val Ile Cys Glu Ile Trp Phe Ala Leu Ser Trp Ile Leu
            290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
            355                 360                 365

Val Asp Lys Val Ser Cys Tyr Val Ser Asp Asp Gly Ala Ala Met Leu
            370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
            435                 440                 445

Arg Ile Asn Ala Leu Val Ser Lys Ala Leu Lys Cys Pro Glu Glu Gly
            450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
            500                 505                 510

Arg Pro Gly Phe Gln His His Lys Lys Ala Gly Ala Met Asn Ala Leu
```

-continued

```
            515                 520                 525
Val Arg Val Ser Ala Val Leu Thr Asn Gly Pro Phe Ile Leu Asn Leu
530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                    565                 570                 575

Phe Pro Gln Arg Phe Asp Gly Ile Asp Lys Asn Asp Arg Tyr Ala Asn
                580                 585                 590

Arg Asn Thr Val Phe Phe Asp Ile Asn Leu Arg Gly Leu Asp Gly Ile
            595                 600                 605

Gln Gly Pro Val Tyr Val Gly Thr Gly Cys Val Phe Asn Arg Thr Ala
        610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                    645                 650                 655

Lys Lys Glu Ser Asp Lys Lys Ser Gly Arg His Thr Asp Ser Thr
                660                 665                 670

Val Pro Val Phe Asn Leu Asp Asp Ile Glu Glu Val Glu Gly Ala
            675                 680                 685

Gly Phe Asp Asp Glu Lys Ala Leu Leu Met Ser Gln Met Ser Leu Glu
690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                    725                 730                 735

Ala Ile His Val Ile Ser Cys Gly Tyr Glu Asp Lys Ser Asp Trp Gly
                740                 745                 750

Met Glu Ile Gly Trp Ile Tyr Gly Ser Val Thr Glu Asp Ile Leu Thr
            755                 760                 765

Gly Phe Lys Met His Ala Arg Gly Trp Arg Ser Ile Tyr Cys Met Pro
        770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
                    805                 810                 815

Ser Arg His Cys Pro Ile Trp Tyr Gly Tyr Asn Gly Arg Leu Lys Phe
                820                 825                 830

Leu Glu Arg Phe Ala Tyr Val Asn Thr Thr Ile Tyr Pro Ile Thr Ser
            835                 840                 845

Ile Pro Leu Leu Met Tyr Cys Thr Leu Pro Ala Val Cys Leu Phe Thr
        850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
                    885                 890                 895

Trp Ser Gly Val Gly Ile Asp Glu Trp Trp Arg Asn Glu Gln Phe Trp
                900                 905                 910

Val Ile Gly Gly Val Ser Ala His Leu Phe Ala Val Phe Gln Gly Ile
            915                 920                 925

Leu Lys Val Leu Ala Gly Ile Asp Thr Asn Phe Thr Val Thr Ser Lys
        930                 935                 940
```

```
Ala Ser Asp Glu Asp Gly Asp Phe Ala Glu Leu Tyr Leu Phe Lys Trp
945                 950                 955                 960

Thr Thr Leu Leu Ile Pro Pro Thr Leu Leu Ile Val Asn Leu Val
            965                 970                 975

Gly Val Val Ala Gly Val Ser Tyr Ala Ile Asn Ser Gly Tyr Gln Ser
            980                 985                 990

Trp Gly Pro Leu Phe Gly Lys Leu Phe Phe Ala Phe Trp Val Ile Val
        995                 1000                1005

His Leu Tyr Pro Phe Leu Lys Gly Leu Met Gly Arg Gln Asn Arg
    1010                1015                1020

Thr Pro Thr Ile Val Val Val Trp Ser Val Leu Leu Ala Ser Ile
    1025                1030                1035

Phe Ser Leu Leu Trp Val Arg Ile Asp Pro Phe Thr Ser Arg Val
    1040                1045                1050

Thr Gly Pro Asp Ile Leu Glu Cys Gly Ile Asn Cys
    1055                1060                1065

<210> SEQ ID NO 4
<211> LENGTH: 1049
<212> TYPE: PRT
<213> ORGANISM: Arabidopsis thaliana

<400> SEQUENCE: 4

Met Glu Pro Asn Thr Met Ala Ser Phe Asp Asp Glu His Arg His Ser
1               5                   10                  15

Ser Phe Ser Ala Lys Ile Cys Lys Val Cys Gly Asp Glu Val Lys Asp
            20                  25                  30

Asp Asp Asn Gly Gln Thr Phe Val Ala Cys His Val Cys Val Tyr Pro
        35                  40                  45

Val Cys Lys Pro Cys Tyr Glu Tyr Glu Arg Ser Asn Gly Asn Lys Cys
    50                  55                  60

Cys Pro Gln Cys Asn Thr Leu Tyr Lys Arg His Lys Gly Ser Pro Lys
65                  70                  75                  80

Ile Ala Gly Asp Glu Glu Asn Asn Gly Pro Asp Asp Ser Asp Asp Glu
                85                  90                  95

Leu Asn Ile Lys Tyr Arg Gln Asp Gly Ser Ser Ile His Gln Asn Phe
            100                 105                 110

Ala Tyr Gly Ser Glu Asn Gly Asp Tyr Asn Ser Lys Gln Gln Trp Arg
        115                 120                 125

Pro Asn Gly Arg Ala Phe Ser Ser Thr Gly Ser Val Leu Gly Lys Asp
    130                 135                 140

Phe Glu Ala Glu Arg Asp Gly Tyr Thr Asp Ala Glu Trp Lys Glu Arg
145                 150                 155                 160

Val Asp Lys Trp Lys Ala Arg Gln Glu Lys Arg Gly Leu Val Thr Lys
                165                 170                 175

Gly Glu Gln Thr Asn Glu Asp Lys Glu Asp Glu Glu Tyr Leu
            180                 185                 190

Asp Ala Glu Ala Arg Gln Pro Leu Trp Arg Lys Val Pro Ile Ser Ser
        195                 200                 205

Ser Lys Ile Ser Pro Tyr Arg Ile Val Ile Leu Arg Leu Val Ile
    210                 215                 220

Leu Val Phe Phe Phe Arg Phe Arg Ile Leu Thr Pro Ala Lys Asp Ala
225                 230                 235                 240

Tyr Pro Leu Trp Leu Ile Ser Val Ile Cys Glu Ile Trp Phe Ala Leu
```

```
                    245                 250                 255
Ser Trp Ile Leu Asp Gln Phe Pro Lys Trp Pro Ile Asn Arg Glu
                260                 265                 270

Thr Tyr Leu Asp Arg Leu Ser Met Arg Phe Glu Arg Asp Gly Glu Lys
                275                 280                 285

Asn Lys Leu Ala Pro Val Asp Val Phe Val Ser Thr Val Asp Pro Leu
                290                 295                 300

Lys Glu Pro Pro Ile Ile Thr Ala Asn Thr Ile Leu Ser Ile Leu Ala
305                             310                 315                 320

Val Asp Tyr Pro Val Asn Lys Val Ser Cys Tyr Val Ser Asp Asp Gly
                    325                 330                 335

Ala Ser Met Leu Leu Phe Asp Thr Leu Ser Glu Thr Ser Glu Phe Ala
                340                 345                 350

Arg Arg Trp Val Pro Phe Cys Lys Lys Tyr Asn Val Glu Pro Arg Ala
                355                 360                 365

Pro Glu Phe Tyr Phe Ser Glu Lys Ile Asp Tyr Leu Lys Asp Lys Val
                370                 375                 380

Gln Thr Thr Phe Val Lys Asp Arg Arg Ala Met Lys Arg Glu Tyr Glu
385                             390                 395                 400

Glu Phe Lys Val Arg Ile Asn Ala Leu Val Ala Lys Ala Gln Lys Lys
                    405                 410                 415

Pro Glu Glu Gly Trp Val Met Gln Asp Gly Thr Pro Trp Pro Gly Asn
                420                 425                 430

Asn Thr Arg Asp His Pro Gly Met Ile Gln Val Tyr Leu Gly Lys Glu
                435                 440                 445

Gly Ala Phe Asp Ile Asp Gly Asn Glu Leu Pro Arg Leu Val Tyr Val
                450                 455                 460

Ser Arg Glu Lys Arg Pro Gly Tyr Ala His His Lys Lys Ala Gly Ala
465                             470                 475                 480

Met Asn Ala Met Val Arg Val Ser Ala Val Leu Thr Asn Ala Pro Phe
                    485                 490                 495

Met Leu Asn Leu Asp Cys Asp His Tyr Ile Asn Asn Ser Lys Ala Ile
                500                 505                 510

Arg Glu Ser Met Cys Phe Leu Met Asp Pro Gln Leu Gly Lys Lys Leu
                515                 520                 525

Cys Tyr Val Gln Phe Pro Gln Arg Phe Asp Gly Ile Asp Leu Asn Asp
                530                 535                 540

Arg Tyr Ala Asn Arg Asn Ile Val Phe Phe Asp Ile Asn Met Arg Gly
545                             550                 555                 560

Leu Asp Gly Ile Gln Gly Pro Val Tyr Val Gly Thr Gly Cys Val Phe
                    565                 570                 575

Asn Arg Pro Ala Leu Tyr Gly Tyr Glu Pro Pro Val Ser Glu Lys Arg
                580                 585                 590

Lys Lys Met Thr Cys Asp Cys Trp Pro Ser Trp Ile Cys Cys Cys Cys
                595                 600                 605

Gly Gly Gly Asn Arg Asn His Lys Ser Asp Ser Ser Lys Lys Lys Ser
                610                 615                 620

Gly Ile Lys Ser Leu Phe Ser Lys Leu Lys Lys Thr Lys Lys Lys
625                             630                 635                 640

Ser Asp Asp Lys Thr Met Ser Ser Tyr Ser Arg Lys Arg Ser Ser Thr
                    645                 650                 655

Glu Ala Ile Phe Asp Leu Glu Asp Ile Glu Glu Gly Leu Glu Gly Tyr
                660                 665                 670
```

Asp Glu Leu Glu Lys Ser Ser Leu Met Ser Gln Lys Asn Phe Glu Lys
            675                 680                 685

Arg Phe Gly Met Ser Pro Val Phe Ile Ala Ser Thr Leu Met Glu Asn
        690                 695                 700

Gly Gly Leu Pro Glu Ala Thr Asn Thr Ser Ser Leu Ile Lys Glu Ala
705                 710                 715                 720

Ile His Val Ile Ser Cys Gly Tyr Glu Glu Lys Thr Glu Trp Gly Lys
                725                 730                 735

Glu Ile Gly Trp Ile Tyr Gly Ser Val Thr Glu Asp Ile Leu Thr Gly
            740                 745                 750

Phe Arg Met His Cys Arg Gly Trp Lys Ser Val Tyr Cys Met Pro Lys
                755                 760                 765

Arg Pro Ala Phe Lys Gly Ser Ala Pro Ile Asn Leu Ser Asp Arg Leu
        770                 775                 780

His Gln Val Leu Arg Trp Ala Leu Gly Ser Val Glu Ile Phe Phe Ser
785                 790                 795                 800

Arg His Cys Pro Leu Trp Tyr Ala Trp Gly Gly Lys Leu Lys Ile Leu
                805                 810                 815

Glu Arg Leu Ala Tyr Ile Asn Thr Ile Val Tyr Pro Phe Thr Ser Ile
            820                 825                 830

Pro Leu Leu Ala Tyr Cys Thr Ile Pro Ala Val Cys Leu Leu Thr Gly
                835                 840                 845

Lys Phe Ile Ile Pro Thr Ile Asn Asn Phe Ala Ser Ile Trp Phe Leu
        850                 855                 860

Ala Leu Phe Leu Ser Ile Ile Ala Thr Ala Ile Leu Glu Leu Arg Trp
865                 870                 875                 880

Ser Gly Val Ser Ile Asn Asp Leu Trp Arg Asn Glu Gln Phe Trp Val
                885                 890                 895

Ile Gly Gly Val Ser Ala His Leu Phe Ala Val Phe Gln Gly Leu Leu
            900                 905                 910

Lys Val Leu Phe Gly Val Asp Thr Asn Phe Thr Val Thr Ser Lys Gly
        915                 920                 925

Ala Ser Asp Glu Ala Asp Glu Phe Gly Asp Leu Tyr Leu Phe Lys Trp
930                 935                 940

Thr Thr Leu Leu Ile Pro Pro Thr Thr Leu Ile Ile Leu Asn Met Val
945                 950                 955                 960

Gly Val Val Ala Gly Val Ser Asp Ala Ile Asn Asn Gly Tyr Gly Ser
                965                 970                 975

Trp Gly Pro Leu Phe Gly Lys Leu Phe Phe Ala Phe Trp Val Ile Val
            980                 985                 990

His Leu Tyr Pro Phe Leu Lys Gly Leu Met Gly Arg Gln Asn Arg Thr
        995                 1000                1005

Pro Thr Ile Val Val Leu Trp Ser Ile Leu Leu Ala Ser Ile Phe
        1010                1015                1020

Ser Leu Val Trp Val Arg Ile Asp Pro Phe Leu Pro Lys Gln Thr
        1025                1030                1035

Gly Pro Leu Leu Lys Gln Cys Gly Val Asp Cys
        1040                1045

<210> SEQ ID NO 5
<211> LENGTH: 1069
<212> TYPE: PRT
<213> ORGANISM: Arabidopsis thaliana

```
<400> SEQUENCE: 5

Met Asn Thr Gly Gly Arg Leu Ile Ala Gly Ser His Asn Arg Asn Glu
1               5                   10                  15

Phe Val Leu Ile Asn Ala Asp Glu Ser Ala Arg Ile Arg Ser Val Glu
                20                  25                  30

Glu Leu Ser Gly Gln Thr Cys Gln Ile Cys Gly Asp Glu Ile Glu Leu
            35                  40                  45

Ser Val Asp Gly Glu Ser Phe Val Ala Cys Asn Glu Cys Ala Phe Pro
    50                  55                  60

Val Cys Arg Pro Cys Tyr Glu Tyr Glu Arg Arg Glu Gly Asn Gln Ser
65                  70                  75                  80

Cys Pro Gln Cys Lys Thr Arg Tyr Lys Arg Ile Lys Gly Ser Pro Arg
                85                  90                  95

Val Glu Gly Asp Glu Glu Asp Asp Gly Ile Asp Asp Leu Asp Phe Glu
            100                 105                 110

Phe Asp Tyr Ser Arg Ser Gly Leu Glu Ser Glu Thr Phe Ser Arg Arg
            115                 120                 125

Asn Ser Glu Phe Asp Leu Ala Ser Ala Pro Pro Gly Ser Gln Ile Pro
130                 135                 140

Leu Leu Thr Tyr Gly Glu Glu Asp Val Glu Ile Ser Ser Asp Ser His
145                 150                 155                 160

Ala Leu Ile Val Ser Pro Ser Pro Gly His Ile His Arg Val His Gln
                165                 170                 175

Pro His Phe Pro Asp Pro Ala Ala His Pro Arg Pro Met Val Pro Gln
            180                 185                 190

Lys Asp Leu Ala Val Tyr Gly Tyr Gly Ser Val Ala Trp Lys Asp Arg
            195                 200                 205

Met Glu Glu Trp Lys Arg Lys Gln Asn Glu Lys Tyr Gln Val Val Lys
210                 215                 220

His Asp Gly Asp Ser Ser Leu Gly Asp Gly Asp Asp Ala Asp Ile Pro
225                 230                 235                 240

Met Met Asp Glu Gly Arg Gln Pro Leu Ser Arg Lys Val Pro Ile Lys
                245                 250                 255

Ser Ser Lys Ile Asn Pro Tyr Arg Met Leu Ile Val Leu Arg Leu Val
                260                 265                 270

Ile Leu Gly Leu Phe Phe His Tyr Arg Ile Leu His Pro Val Asn Asp
            275                 280                 285

Ala Tyr Ala Leu Trp Leu Ile Ser Val Ile Cys Glu Ile Trp Phe Ala
            290                 295                 300

Val Ser Trp Val Leu Asp Gln Phe Pro Lys Trp Tyr Pro Ile Glu Arg
305                 310                 315                 320

Glu Thr Tyr Leu Asp Arg Leu Ser Leu Arg Tyr Glu Lys Glu Gly Lys
                325                 330                 335

Pro Ser Glu Leu Ala Gly Val Asp Val Phe Val Ser Thr Val Asp Pro
            340                 345                 350

Met Lys Glu Pro Pro Leu Ile Thr Ala Asn Thr Val Leu Ser Ile Leu
            355                 360                 365

Ala Val Asp Tyr Pro Val Asp Arg Val Ala Cys Tyr Val Ser Asp Asp
370                 375                 380

Gly Ala Ala Met Leu Thr Phe Glu Ala Leu Ser Glu Thr Ala Glu Phe
385                 390                 395                 400

Ala Arg Lys Trp Val Pro Phe Cys Lys Lys Tyr Thr Ile Glu Pro Arg
                405                 410                 415
```

```
Ala Pro Glu Trp Tyr Phe Cys His Lys Met Asp Tyr Leu Lys Asn Lys
            420                 425                 430

Val His Pro Ala Phe Val Arg Glu Arg Arg Ala Met Lys Arg Asp Tyr
        435                 440                 445

Glu Glu Phe Lys Val Lys Ile Asn Ala Leu Val Ala Thr Ala Gln Lys
    450                 455                 460

Val Pro Glu Glu Gly Trp Thr Met Gln Asp Gly Thr Pro Trp Pro Gly
465                 470                 475                 480

Asn Asn Val Arg Asp His Pro Gly Met Ile Gln Val Phe Leu Gly Asn
                485                 490                 495

Asn Gly Val Arg Asp Val Glu Asn Asn Glu Leu Pro Arg Leu Val Tyr
            500                 505                 510

Val Ser Arg Glu Lys Arg Pro Gly Phe Asp His His Lys Lys Ala Gly
        515                 520                 525

Ala Met Asn Ser Leu Ile Arg Val Ser Gly Val Leu Ser Asn Ala Pro
    530                 535                 540

Tyr Leu Leu Asn Val Asp Cys Asp His Tyr Ile Asn Asn Ser Lys Ala
545                 550                 555                 560

Leu Arg Glu Ala Met Cys Phe Met Met Asp Pro Gln Ser Gly Lys Lys
                565                 570                 575

Ile Cys Tyr Val Gln Phe Pro Gln Arg Phe Asp Gly Ile Asp Lys Ser
            580                 585                 590

Asp Arg Tyr Ser Asn Arg Asn Val Val Phe Phe Asp Ile Asn Met Lys
        595                 600                 605

Gly Leu Asp Gly Leu Gln Gly Pro Ile Tyr Val Gly Thr Gly Cys Val
    610                 615                 620

Phe Arg Arg Gln Ala Leu Tyr Gly Phe Asp Ala Pro Lys Lys Lys Lys
625                 630                 635                 640

Thr Lys Arg Met Thr Cys Asn Cys Trp Pro Lys Trp Cys Leu Phe Cys
                645                 650                 655

Cys Gly Leu Arg Lys Asn Arg Lys Ser Lys Thr Thr Asp Lys Lys Lys
            660                 665                 670

Lys Asn Arg Glu Ala Ser Lys Gln Ile His Ala Leu Glu Asn Ile Glu
        675                 680                 685

Glu Gly Thr Lys Gly Thr Asn Asp Ala Ala Lys Ser Pro Glu Ala Ala
    690                 695                 700

Gln Leu Lys Leu Glu Lys Lys Phe Gly Gln Ser Pro Val Phe Val Ala
705                 710                 715                 720

Ser Ala Gly Met Glu Asn Gly Gly Leu Ala Arg Asn Ala Ser Pro Ala
                725                 730                 735

Ser Leu Leu Arg Glu Ala Ile Gln Val Ile Ser Cys Gly Tyr Glu Asp
            740                 745                 750

Lys Thr Glu Trp Gly Lys Glu Ile Gly Trp Ile Tyr Gly Ser Val Thr
        755                 760                 765

Glu Asp Ile Leu Thr Gly Phe Lys Met His Ser His Gly Trp Arg Ser
    770                 775                 780

Val Tyr Cys Thr Pro Lys Ile Pro Ala Phe Lys Gly Ser Ala Pro Ile
785                 790                 795                 800

Asn Leu Ser Asp Arg Leu His Gln Val Leu Arg Trp Ala Leu Gly Ser
                805                 810                 815

Val Glu Ile Phe Leu Ser Arg His Cys Pro Ile Trp Tyr Gly Tyr Gly
            820                 825                 830
```

```
Gly Gly Leu Lys Trp Leu Glu Arg Leu Ser Tyr Ile Asn Ser Val Val
            835                 840                 845

Tyr Pro Trp Thr Ser Ile Pro Leu Leu Val Tyr Cys Ser Leu Pro Ala
850                 855                 860

Ile Cys Leu Leu Thr Gly Lys Phe Ile Val Pro Glu Ile Ser Asn Tyr
865                 870                 875                 880

Ala Ser Ile Leu Phe Met Ala Leu Phe Gly Ser Ile Ala Val Thr Gly
            885                 890                 895

Ile Leu Glu Met Gln Trp Gly Lys Val Gly Ile Asp Asp Trp Trp Arg
            900                 905                 910

Asn Glu Gln Phe Trp Val Ile Gly Val Ser Ala His Leu Phe Ala
            915                 920                 925

Leu Phe Gln Gly Leu Leu Lys Val Leu Ala Gly Val Glu Thr Asn Phe
    930                 935                 940

Thr Val Thr Ser Lys Ala Ala Asp Asp Gly Glu Phe Ser Glu Leu Tyr
945                 950                 955                 960

Ile Phe Lys Trp Thr Ser Leu Leu Ile Pro Pro Thr Thr Leu Leu Ile
            965                 970                 975

Ile Asn Val Ile Gly Val Ile Val Gly Ile Ser Asp Ala Ile Ser Asn
            980                 985                 990

Gly Tyr Asp Ser Trp Gly Pro Leu Phe Gly Arg Leu Phe Phe Ala Phe
            995                 1000                1005

Trp Val Ile Leu His Leu Tyr Pro Phe Leu Lys Gly Leu Leu Gly
    1010                1015                1020

Lys Gln Asp Arg Met Pro Thr Ile Ile Leu Val Trp Ser Ile Leu
    1025                1030                1035

Leu Ala Ser Ile Leu Thr Leu Leu Trp Val Arg Val Asn Pro Phe
    1040                1045                1050

Val Ala Lys Gly Gly Pro Ile Leu Glu Ile Cys Gly Leu Asp Cys
    1055                1060                1065

Leu

<210> SEQ ID NO 6
<211> LENGTH: 1084
<212> TYPE: PRT
<213> ORGANISM: Arabidopsis thaliana

<400> SEQUENCE: 6

Met Asn Thr Gly Gly Arg Leu Ile Ala Gly Ser His Asn Arg Asn Glu
1               5                   10                  15

Phe Val Leu Ile Asn Ala Asp Glu Asn Ala Arg Ile Arg Ser Val Gln
            20                  25                  30

Glu Leu Ser Gly Gln Thr Cys Gln Ile Cys Arg Asp Glu Ile Glu Leu
        35                  40                  45

Thr Val Asp Gly Glu Pro Phe Val Ala Cys Asn Glu Cys Ala Phe Pro
50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Phe Lys Arg Leu Lys Gly Ser Pro Arg
            85                  90                  95

Val Glu Gly Asp Glu Glu Asp Asp Ile Asp Asp Leu Asp Asn Glu
            100                 105                 110

Phe Glu Tyr Gly Asn Asn Gly Ile Gly Phe Asp Gln Val Ser Glu Gly
        115                 120                 125
```

```
Met Ser Ile Ser Arg Arg Asn Ser Gly Phe Pro Gln Ser Asp Leu Asp
    130                 135                 140

Ser Ala Pro Pro Gly Ser Gln Ile Pro Leu Leu Thr Tyr Gly Asp Glu
145                 150                 155                 160

Asp Val Glu Ile Ser Ser Asp Arg His Ala Leu Ile Val Pro Pro Ser
                165                 170                 175

Leu Gly Gly His Gly Asn Arg Val His Pro Val Ser Leu Ser Asp Pro
                    180                 185                 190

Thr Val Ala Ala His Pro Arg Pro Met Val Pro Gln Lys Asp Leu Ala
            195                 200                 205

Val Tyr Gly Tyr Gly Ser Val Ala Trp Lys Asp Arg Met Glu Glu Trp
    210                 215                 220

Lys Arg Lys Gln Asn Glu Lys Leu Gln Val Val Arg His Glu Gly Asp
225                 230                 235                 240

Pro Asp Phe Glu Asp Gly Asp Ala Asp Phe Pro Met Met Asp Glu
                245                 250                 255

Gly Arg Gln Pro Leu Ser Arg Lys Ile Pro Ile Lys Ser Ser Lys Ile
                260                 265                 270

Asn Pro Tyr Arg Met Leu Ile Val Leu Arg Leu Val Ile Leu Gly Leu
    275                 280                 285

Phe Phe His Tyr Arg Ile Leu His Pro Val Lys Asp Ala Tyr Ala Leu
    290                 295                 300

Trp Leu Ile Ser Val Ile Cys Glu Ile Trp Phe Ala Val Ser Trp Val
305                 310                 315                 320

Leu Asp Gln Phe Pro Lys Trp Tyr Pro Ile Glu Arg Glu Thr Tyr Leu
                325                 330                 335

Asp Arg Leu Ser Leu Arg Tyr Glu Lys Glu Gly Lys Pro Ser Gly Leu
                340                 345                 350

Ser Pro Val Asp Val Phe Val Ser Thr Val Asp Pro Leu Lys Glu Pro
            355                 360                 365

Pro Leu Ile Thr Ala Asn Thr Val Leu Ser Ile Leu Ala Val Asp Tyr
    370                 375                 380

Pro Val Asp Lys Val Ala Cys Tyr Val Ser Asp Asp Gly Ala Ala Met
385                 390                 395                 400

Leu Thr Phe Glu Ala Leu Ser Glu Thr Ala Glu Phe Ala Arg Lys Trp
                405                 410                 415

Val Pro Phe Cys Lys Lys Tyr Cys Ile Glu Pro Arg Ala Pro Glu Trp
                420                 425                 430

Tyr Phe Cys His Lys Met Asp Tyr Leu Lys Asn Lys Val His Pro Ala
                435                 440                 445

Phe Val Arg Glu Arg Arg Ala Met Lys Arg Asp Tyr Glu Glu Phe Lys
    450                 455                 460

Val Lys Ile Asn Ala Leu Val Ala Thr Ala Gln Lys Val Pro Glu Asp
465                 470                 475                 480

Gly Trp Thr Met Gln Asp Gly Thr Pro Trp Pro Gly Asn Ser Val Arg
                485                 490                 495

Asp His Pro Gly Met Ile Gln Val Phe Leu Gly Ser Asp Gly Val Arg
                500                 505                 510

Asp Val Glu Asn Asn Glu Leu Pro Arg Leu Val Tyr Val Ser Arg Glu
            515                 520                 525

Lys Arg Pro Gly Phe Asp His His Lys Lys Ala Gly Ala Met Asn Ser
    530                 535                 540

Leu Ile Arg Val Ser Gly Val Leu Ser Asn Ala Pro Tyr Leu Leu Asn
```

```
             545                 550                 555                 560
Val Asp Cys Asp His Tyr Ile Asn Asn Ser Lys Ala Leu Arg Glu Ala
                565                 570                 575
Met Cys Phe Met Met Asp Pro Gln Ser Gly Lys Lys Ile Cys Tyr Val
                580                 585                 590
Gln Phe Pro Gln Arg Phe Asp Gly Ile Asp Arg His Asp Arg Tyr Ser
            595                 600                 605
Asn Arg Asn Val Val Phe Phe Asp Ile Asn Met Lys Gly Leu Asp Gly
        610                 615                 620
Leu Gln Gly Pro Ile Tyr Val Gly Thr Gly Cys Val Phe Arg Arg Gln
625                 630                 635                 640
Ala Leu Tyr Gly Phe Asp Ala Pro Lys Lys Lys Gly Pro Arg Lys
                645                 650                 655
Thr Cys Asn Cys Trp Pro Lys Trp Cys Leu Leu Cys Phe Gly Ser Arg
                660                 665                 670
Lys Asn Arg Lys Ala Lys Thr Val Ala Ala Asp Lys Lys Lys Lys Asn
            675                 680                 685
Arg Glu Ala Ser Lys Gln Ile His Ala Leu Glu Asn Ile Glu Glu Gly
        690                 695                 700
Arg Val Thr Lys Gly Ser Asn Val Glu Gln Ser Thr Glu Ala Met Gln
705                 710                 715                 720
Met Lys Leu Glu Lys Lys Phe Gly Gln Ser Pro Val Phe Val Ala Ser
                725                 730                 735
Ala Arg Met Glu Asn Gly Gly Met Ala Arg Asn Ala Ser Pro Ala Cys
                740                 745                 750
Leu Leu Lys Glu Ala Ile Gln Val Ile Ser Cys Gly Tyr Glu Asp Lys
            755                 760                 765
Thr Glu Trp Gly Lys Glu Ile Gly Trp Ile Tyr Gly Ser Val Thr Glu
        770                 775                 780
Asp Ile Leu Thr Gly Phe Lys Met His Ser His Gly Trp Arg Ser Val
785                 790                 795                 800
Tyr Cys Thr Pro Lys Leu Ala Ala Phe Lys Gly Ser Ala Pro Ile Asn
                805                 810                 815
Leu Ser Asp Arg Leu His Gln Val Leu Arg Trp Ala Leu Gly Ser Val
                820                 825                 830
Glu Ile Phe Leu Ser Arg His Cys Pro Ile Trp Tyr Gly Tyr Gly Gly
            835                 840                 845
Gly Leu Lys Trp Leu Glu Arg Leu Ser Tyr Ile Asn Ser Val Val Tyr
        850                 855                 860
Pro Trp Thr Ser Leu Pro Leu Ile Val Tyr Cys Ser Leu Pro Ala Ile
865                 870                 875                 880
Cys Leu Leu Thr Gly Lys Phe Ile Val Pro Glu Ile Ser Asn Tyr Ala
                885                 890                 895
Ser Ile Leu Phe Met Ala Leu Phe Ser Ser Ile Ala Ile Thr Gly Ile
                900                 905                 910
Leu Glu Met Gln Trp Gly Lys Val Gly Ile Asp Asp Trp Trp Arg Asn
            915                 920                 925
Glu Gln Phe Trp Val Ile Gly Gly Val Ser Ala His Leu Phe Ala Leu
        930                 935                 940
Phe Gln Gly Leu Leu Lys Val Leu Ala Gly Val Asp Thr Asn Phe Thr
945                 950                 955                 960
Val Thr Ser Lys Ala Ala Asp Asp Gly Glu Phe Ser Asp Leu Tyr Leu
                965                 970                 975
```

```
Phe Lys Trp Thr Ser Leu Leu Ile Pro Pro Met Thr Leu Leu Ile Ile
            980                 985                 990

Asn Val Ile Gly Val Ile Val Gly Val Ser Asp Ala Ile Ser Asn Gly
            995                1000                1005

Tyr Asp Ser Trp Gly Pro Leu Phe Gly Arg Leu Phe Phe Ala Leu
           1010                1015                1020

Trp Val Ile Ile His Leu Tyr Pro Phe Leu Lys Gly Leu Leu Gly
           1025                1030                1035

Lys Gln Asp Arg Met Pro Thr Ile Ile Val Val Trp Ser Ile Leu
           1040                1045                1050

Leu Ala Ser Ile Leu Thr Leu Leu Trp Val Arg Val Asn Pro Phe
           1055                1060                1065

Val Ala Lys Gly Gly Pro Ile Leu Glu Ile Cys Gly Leu Asp Cys
           1070                1075                1080

Leu

<210> SEQ ID NO 7
<211> LENGTH: 1026
<212> TYPE: PRT
<213> ORGANISM: Arabidopsis thaliana

<400> SEQUENCE: 7

Met Glu Ala Ser Ala Gly Leu Val Ala Gly Ser His Asn Arg Asn Glu
1               5                  10                  15

Leu Val Val Ile His Asn His Glu Glu Pro Lys Pro Leu Lys Asn Leu
            20                  25                  30

Asp Gly Gln Phe Cys Glu Ile Cys Gly Asp Gln Ile Gly Leu Thr Val
        35                  40                  45

Glu Gly Asp Leu Phe Val Ala Cys Asn Glu Cys Gly Phe Pro Ala Cys
    50                  55                  60

Arg Pro Cys Tyr Glu Tyr Glu Arg Arg Glu Gly Thr Gln Asn Cys Pro
65                  70                  75                  80

Gln Cys Lys Thr Arg Tyr Lys Arg Leu Arg Gly Ser Pro Arg Val Glu
                85                  90                  95

Gly Asp Glu Asp Glu Asp Ile Asp Asp Ile Glu Tyr Glu Phe Asn
            100                 105                 110

Ile Glu His Glu Gln Asp Lys His Lys His Ser Ala Glu Ala Met Leu
        115                 120                 125

Tyr Gly Lys Met Ser Tyr Gly Arg Gly Pro Glu Asp Asp Glu Asn Gly
    130                 135                 140

Arg Phe Pro Pro Val Ile Ala Gly Gly His Ser Gly Glu Phe Pro Val
145                 150                 155                 160

Gly Gly Gly Tyr Gly Asn Gly Glu His Gly Leu His Lys Arg Val His
                165                 170                 175

Pro Tyr Pro Ser Ser Glu Ala Gly Ser Glu Gly Gly Trp Arg Glu Arg
            180                 185                 190

Met Asp Asp Trp Lys Leu Gln His Gly Asn Leu Gly Pro Glu Pro Asp
        195                 200                 205

Asp Asp Pro Glu Met Gly Leu Ile Asp Glu Ala Arg Gln Pro Leu Ser
    210                 215                 220

Arg Lys Val Pro Ile Ala Ser Ser Lys Ile Asn Pro Tyr Arg Met Val
225                 230                 235                 240

Ile Val Ala Arg Leu Val Ile Leu Ala Val Phe Leu Arg Tyr Arg Leu
                245                 250                 255
```

```
Leu Asn Pro Val His Asp Ala Leu Gly Leu Trp Leu Thr Ser Val Ile
        260                 265                 270

Cys Glu Ile Trp Phe Ala Val Ser Trp Ile Leu Asp Gln Phe Pro Lys
            275                 280                 285

Trp Phe Pro Ile Glu Arg Glu Thr Tyr Leu Asp Arg Leu Ser Leu Arg
290                 295                 300

Tyr Glu Arg Glu Gly Glu Pro Asn Met Leu Ala Pro Val Asp Val Phe
305                 310                 315                 320

Val Ser Thr Val Asp Pro Leu Lys Glu Pro Pro Leu Val Thr Ser Asn
                325                 330                 335

Thr Val Leu Ser Ile Leu Ala Met Asp Tyr Pro Val Glu Lys Ile Ser
            340                 345                 350

Cys Tyr Val Ser Asp Asp Gly Ala Ser Met Leu Thr Phe Glu Ser Leu
            355                 360                 365

Ser Glu Thr Ala Glu Phe Ala Arg Lys Trp Val Pro Phe Cys Lys Lys
        370                 375                 380

Phe Ser Ile Glu Pro Arg Ala Pro Glu Met Tyr Phe Thr Leu Lys Val
385                 390                 395                 400

Asp Tyr Leu Gln Asp Lys Val His Pro Thr Phe Val Lys Glu Arg Arg
                405                 410                 415

Ala Met Lys Arg Glu Tyr Glu Glu Phe Lys Val Arg Ile Asn Ala Gln
            420                 425                 430

Val Ala Lys Ala Ser Lys Val Pro Leu Glu Gly Trp Ile Met Gln Asp
        435                 440                 445

Gly Thr Pro Trp Pro Gly Asn Asn Thr Lys Asp His Pro Gly Met Ile
        450                 455                 460

Gln Val Phe Leu Gly His Ser Gly Gly Phe Asp Val Glu Gly His Glu
465                 470                 475                 480

Leu Pro Arg Leu Val Tyr Val Ser Arg Glu Lys Arg Pro Gly Phe Gln
                485                 490                 495

His His Lys Lys Ala Gly Ala Met Asn Ala Leu Val Arg Val Ala Gly
            500                 505                 510

Val Leu Thr Asn Ala Pro Phe Met Leu Asn Leu Asp Cys Asp His Tyr
        515                 520                 525

Val Asn Asn Ser Lys Ala Val Arg Glu Ala Met Cys Phe Leu Met Asp
530                 535                 540

Pro Gln Ile Gly Lys Lys Val Cys Tyr Val Gln Phe Pro Gln Arg Phe
545                 550                 555                 560

Asp Gly Ile Asp Thr Asn Asp Arg Tyr Ala Asn Arg Asn Thr Val Phe
                565                 570                 575

Phe Asp Ile Asn Met Lys Gly Leu Asp Gly Ile Gln Gly Pro Val Tyr
            580                 585                 590

Val Gly Thr Gly Cys Val Phe Lys Arg Gln Ala Leu Tyr Gly Tyr Glu
        595                 600                 605

Pro Pro Lys Gly Pro Lys Arg Pro Lys Met Ile Ser Cys Gly Cys Cys
        610                 615                 620

Pro Cys Phe Gly Arg Arg Arg Lys Asn Lys Phe Ser Lys Asn Asp
625                 630                 635                 640

Met Asn Gly Asp Val Ala Ala Leu Gly Gly Ala Glu Gly Asp Lys Glu
                645                 650                 655

His Leu Met Ser Glu Met Asn Phe Glu Lys Thr Phe Gly Gln Ser Ser
            660                 665                 670
```

```
Ile Phe Val Thr Ser Thr Leu Met Glu Glu Gly Val Pro Pro Ser
            675                 680                 685

Ser Ser Pro Ala Val Leu Leu Lys Glu Ala Ile His Val Ile Ser Cys
    690                 695                 700

Gly Tyr Glu Asp Lys Thr Glu Trp Gly Thr Glu Leu Gly Trp Ile Tyr
705                 710                 715                 720

Gly Ser Ile Thr Glu Asp Ile Leu Thr Gly Phe Lys Met His Cys Arg
                725                 730                 735

Gly Trp Arg Ser Ile Tyr Cys Met Pro Lys Arg Pro Ala Phe Lys Gly
            740                 745                 750

Ser Ala Pro Ile Asn Leu Ser Asp Arg Leu Asn Gln Val Leu Arg Trp
        755                 760                 765

Ala Leu Gly Ser Val Glu Ile Phe Phe Ser Arg His Ser Pro Leu Trp
    770                 775                 780

Tyr Gly Tyr Lys Gly Gly Lys Leu Lys Trp Leu Glu Arg Phe Ala Tyr
785                 790                 795                 800

Ala Asn Thr Thr Ile Tyr Pro Phe Thr Ser Ile Pro Leu Leu Ala Tyr
                805                 810                 815

Cys Ile Leu Pro Ala Ile Cys Leu Leu Thr Asp Lys Phe Ile Met Pro
            820                 825                 830

Pro Ile Ser Thr Phe Ala Ser Leu Phe Phe Ile Ser Leu Phe Met Ser
        835                 840                 845

Ile Ile Val Thr Gly Ile Leu Glu Leu Arg Trp Ser Gly Val Ser Ile
    850                 855                 860

Glu Glu Trp Trp Arg Asn Glu Gln Phe Trp Val Ile Gly Gly Ile Ser
865                 870                 875                 880

Ala His Leu Phe Ala Val Val Gln Gly Leu Leu Lys Ile Leu Ala Gly
                885                 890                 895

Ile Asp Thr Asn Phe Thr Val Thr Ser Lys Ala Thr Asp Asp Asp Asp
            900                 905                 910

Phe Gly Glu Leu Tyr Ala Phe Lys Trp Thr Thr Leu Leu Ile Pro Pro
        915                 920                 925

Thr Thr Val Leu Ile Ile Asn Ile Val Gly Val Val Ala Gly Ile Ser
    930                 935                 940

Asp Ala Ile Asn Asn Gly Tyr Gln Ser Trp Gly Pro Leu Phe Gly Lys
945                 950                 955                 960

Leu Phe Phe Ser Phe Trp Val Ile Val His Leu Tyr Pro Phe Leu Lys
                965                 970                 975

Gly Leu Met Gly Arg Gln Asn Arg Thr Pro Thr Ile Val Ile Trp
            980                 985                 990

Ser Val Leu Leu Ala Ser Ile Phe Ser Leu Leu Trp Val Arg Ile Asp
        995                1000                1005

Pro Phe Val Leu Lys Thr Lys Gly Pro Asp Thr Ser Lys Cys Gly
    1010                1015                1020

Ile Asn Cys
    1025

<210> SEQ ID NO 8
<211> LENGTH: 985
<212> TYPE: PRT
<213> ORGANISM: Arabidopsis thaliana

<400> SEQUENCE: 8

Met Met Glu Ser Arg Ser Pro Ile Cys Asn Thr Cys Gly Glu Glu Ile
1               5                   10                  15
```

-continued

```
Gly Val Lys Ser Asn Gly Glu Phe Phe Val Ala Cys His Glu Cys Ser
             20                  25                  30
Phe Pro Ile Cys Lys Ala Cys Leu Glu Tyr Glu Phe Lys Glu Gly Arg
         35                  40                  45
Arg Ile Cys Leu Arg Cys Gly Asn Pro Tyr Asp Glu Asn Val Phe Asp
     50                  55                  60
Asp Val Glu Thr Lys Thr Ser Lys Thr Gln Ser Ile Val Pro Thr Gln
 65                  70                  75                  80
Thr Asn Asn Thr Ser Gln Asp Ser Gly Ile His Ala Arg His Ile Ser
                 85                  90                  95
Thr Val Ser Thr Ile Asp Ser Glu Leu Asn Asp Glu Tyr Gly Asn Pro
            100                 105                 110
Ile Trp Lys Asn Arg Val Glu Ser Trp Lys Asp Lys Asp Lys Lys
        115                 120                 125
Ser Lys Lys Lys Lys Asp Pro Lys Ala Thr Lys Ala Glu Gln His
    130                 135                 140
Glu Ala Gln Ile Pro Thr Gln Gln His Met Glu Asp Thr Pro Pro Asn
145                 150                 155                 160
Thr Glu Ser Gly Ala Thr Asp Val Leu Ser Val Val Ile Pro Ile Pro
                165                 170                 175
Arg Thr Lys Ile Thr Ser Tyr Arg Ile Val Ile Met Arg Leu Ile
            180                 185                 190
Ile Leu Ala Leu Phe Phe Asn Tyr Arg Ile Thr His Pro Val Asp Ser
        195                 200                 205
Ala Tyr Gly Leu Trp Leu Thr Ser Val Ile Cys Glu Ile Trp Phe Ala
    210                 215                 220
Val Ser Trp Val Leu Asp Gln Phe Pro Lys Trp Ser Pro Ile Asn Arg
225                 230                 235                 240
Glu Thr Tyr Ile Asp Arg Leu Ser Ala Arg Phe Glu Arg Glu Gly Glu
                245                 250                 255
Gln Ser Gln Leu Ala Ala Val Asp Phe Phe Val Ser Thr Val Asp Pro
            260                 265                 270
Leu Lys Glu Pro Pro Leu Ile Thr Ala Asn Thr Val Leu Ser Ile Leu
        275                 280                 285
Ala Leu Asp Tyr Pro Val Asp Lys Val Ser Cys Tyr Val Ser Asp Asp
    290                 295                 300
Gly Ala Ala Met Leu Ser Phe Glu Ser Leu Val Glu Thr Ala Asp Phe
305                 310                 315                 320
Ala Arg Lys Trp Val Pro Phe Cys Lys Lys Tyr Ser Ile Glu Pro Arg
                325                 330                 335
Ala Pro Glu Phe Tyr Phe Ser Leu Lys Ile Asp Tyr Leu Arg Asp Lys
            340                 345                 350
Val Gln Pro Ser Phe Val Lys Glu Arg Arg Ala Met Lys Arg Asp Tyr
        355                 360                 365
Glu Glu Phe Lys Ile Arg Met Asn Ala Leu Val Ala Lys Ala Gln Lys
    370                 375                 380
Thr Pro Glu Glu Gly Trp Thr Met Gln Asp Gly Thr Ser Trp Pro Gly
385                 390                 395                 400
Asn Asn Thr Arg Asp His Pro Gly Met Ile Gln Val Phe Leu Gly Tyr
                405                 410                 415
Ser Gly Ala Arg Asp Ile Glu Gly Asn Glu Leu Pro Arg Leu Val Tyr
            420                 425                 430
```

```
Val Ser Arg Glu Lys Arg Pro Gly Tyr Gln His His Lys Ala Gly
            435                 440                 445

Ala Glu Asn Ala Leu Val Arg Val Ser Ala Val Leu Thr Asn Ala Pro
450                 455                 460

Phe Ile Leu Asn Leu Asp Cys Asp His Tyr Val Asn Asn Ser Lys Ala
465                 470                 475                 480

Val Arg Glu Ala Met Cys Phe Leu Met Asp Pro Val Val Gly Gln Asp
                485                 490                 495

Val Cys Phe Val Gln Phe Pro Gln Arg Phe Asp Gly Ile Asp Lys Ser
            500                 505                 510

Asp Arg Tyr Ala Asn Arg Asn Ile Val Phe Phe Asp Val Asn Met Arg
        515                 520                 525

Gly Leu Asp Gly Ile Gln Gly Pro Val Tyr Val Gly Thr Gly Thr Val
    530                 535                 540

Phe Arg Arg Gln Ala Leu Tyr Gly Tyr Ser Pro Ser Lys Pro Arg
545                 550                 555                 560

Ile Leu Pro Gln Ser Ser Ser Ser Cys Cys Cys Leu Thr Lys Lys
                565                 570                 575

Lys Gln Pro Gln Asp Pro Ser Glu Ile Tyr Lys Asp Ala Lys Arg Glu
                580                 585                 590

Glu Leu Asp Ala Ala Ile Phe Asn Leu Gly Asp Leu Asp Asn Tyr Asp
            595                 600                 605

Glu Tyr Asp Arg Ser Met Leu Ile Ser Gln Thr Ser Phe Glu Lys Thr
        610                 615                 620

Phe Gly Leu Ser Thr Val Phe Ile Glu Ser Thr Leu Met Glu Asn Gly
625                 630                 635                 640

Gly Val Pro Asp Ser Val Asn Pro Ser Thr Leu Ile Lys Glu Ala Ile
                645                 650                 655

His Val Ile Ser Cys Gly Tyr Glu Glu Lys Thr Glu Trp Gly Lys Glu
                660                 665                 670

Ile Gly Trp Ile Tyr Gly Ser Ile Thr Glu Asp Ile Leu Thr Gly Phe
            675                 680                 685

Lys Met His Cys Arg Gly Trp Arg Ser Ile Tyr Cys Met Pro Leu Arg
690                 695                 700

Pro Ala Phe Lys Gly Ser Ala Pro Ile Asn Leu Ser Asp Arg Leu His
705                 710                 715                 720

Gln Val Leu Arg Trp Ala Leu Gly Ser Val Glu Ile Phe Leu Ser Arg
                725                 730                 735

His Cys Pro Leu Trp Tyr Gly Cys Ser Gly Arg Leu Lys Leu Leu
                740                 745                 750

Gln Arg Leu Ala Tyr Ile Asn Thr Ile Val Tyr Pro Phe Thr Ser Leu
            755                 760                 765

Pro Leu Val Ala Tyr Cys Thr Leu Pro Ala Ile Cys Leu Leu Thr Gly
770                 775                 780

Lys Phe Ile Ile Pro Thr Leu Ser Asn Leu Ala Ser Met Leu Phe Leu
785                 790                 795                 800

Gly Leu Phe Ile Ser Ile Ile Leu Thr Ser Val Leu Glu Leu Arg Trp
                805                 810                 815

Ser Gly Val Ser Ile Glu Asp Leu Trp Arg Asn Glu Gln Phe Trp Val
            820                 825                 830

Ile Gly Gly Val Ser Ala His Leu Phe Ala Val Phe Gln Gly Phe Leu
                835                 840                 845

Lys Met Leu Ala Gly Leu Asp Thr Asn Phe Thr Val Thr Ser Lys Thr
```

-continued

```
            850                 855                 860
Ala Asp Asp Leu Glu Phe Gly Glu Leu Tyr Ile Val Lys Trp Thr Thr
865                 870                 875                 880

Leu Leu Ile Pro Pro Thr Ser Leu Leu Ile Ile Asn Leu Val Gly Val
                885                 890                 895

Val Ala Gly Phe Ser Asp Ala Leu Asn Lys Gly Tyr Glu Ala Trp Gly
                900                 905                 910

Pro Leu Phe Gly Lys Val Phe Phe Ala Phe Trp Val Ile Leu His Leu
                915                 920                 925

Tyr Pro Phe Leu Lys Gly Leu Met Gly Arg Gln Asn Arg Thr Pro Thr
        930                 935                 940

Ile Val Ile Leu Trp Ser Ile Leu Leu Ala Ser Val Phe Ser Leu Val
945                 950                 955                 960

Trp Val Arg Ile Asn Pro Phe Val Ser Lys Thr Asp Thr Thr Ser Leu
                965                 970                 975

Ser Leu Asn Cys Leu Leu Ile Asp Cys
                980                 985

<210> SEQ ID NO 9
<211> LENGTH: 1088
<212> TYPE: PRT
<213> ORGANISM: Arabidopsis thaliana

<400> SEQUENCE: 9

Met Asn Thr Gly Gly Arg Leu Ile Ala Gly Ser His Asn Arg Asn Glu
1               5                   10                  15

Phe Val Leu Ile Asn Ala Asp Asp Thr Ala Arg Ile Arg Ser Ala Glu
                20                  25                  30

Glu Leu Ser Gly Gln Thr Cys Lys Ile Cys Arg Asp Glu Ile Glu Leu
            35                  40                  45

Thr Asp Asn Gly Glu Pro Phe Ile Ala Cys Asn Glu Cys Ala Phe Pro
50                  55                  60

Thr Cys Arg Pro Cys Tyr Glu Tyr Glu Arg Arg Glu Gly Asn Gln Ala
65                  70                  75                  80

Cys Pro Gln Cys Gly Thr Arg Tyr Lys Arg Ile Lys Gly Ser Pro Arg
                85                  90                  95

Val Glu Gly Asp Glu Asp Asp Ile Asp Asp Leu Glu His Glu
                100                 105                 110

Phe Tyr Gly Met Asp Pro Glu His Val Thr Glu Ala Ala Leu Tyr Tyr
                115                 120                 125

Met Arg Leu Asn Thr Gly Arg Gly Thr Asp Glu Val Ser His Leu Tyr
        130                 135                 140

Ser Ala Ser Pro Gly Ser Glu Val Pro Leu Leu Thr Tyr Cys Asp Glu
145                 150                 155                 160

Asp Ser Asp Met Tyr Ser Asp Arg His Ala Leu Ile Val Pro Pro Ser
                165                 170                 175

Thr Gly Leu Gly Asn Arg Val His His Val Pro Phe Thr Asp Ser Phe
                180                 185                 190

Ala Ser Ile His Thr Arg Pro Met Val Pro Gln Lys Asp Leu Thr Val
            195                 200                 205

Tyr Gly Tyr Gly Ser Val Ala Trp Lys Asp Arg Met Glu Val Trp Lys
        210                 215                 220

Lys Gln Gln Ile Glu Lys Leu Gln Val Val Lys Asn Glu Arg Val Asn
225                 230                 235                 240
```

```
Asp Gly Asp Gly Asp Gly Phe Ile Val Asp Glu Leu Asp Asp Pro Gly
                245                 250                 255
Leu Pro Met Met Asp Glu Gly Arg Gln Pro Leu Ser Arg Lys Leu Pro
            260                 265                 270
Ile Arg Ser Ser Arg Ile Asn Pro Tyr Arg Met Leu Ile Phe Cys Arg
        275                 280                 285
Leu Ala Ile Leu Gly Leu Phe Phe His Tyr Arg Ile Leu His Pro Val
    290                 295                 300
Asn Asp Ala Phe Gly Leu Trp Leu Thr Ser Val Ile Cys Glu Ile Trp
305                 310                 315                 320
Phe Ala Val Ser Trp Ile Leu Asp Gln Phe Pro Lys Trp Tyr Pro Ile
                325                 330                 335
Glu Arg Glu Thr Tyr Leu Asp Arg Leu Ser Leu Arg Tyr Glu Lys Glu
            340                 345                 350
Gly Lys Pro Ser Glu Leu Ala Pro Val Asp Val Phe Val Ser Thr Val
        355                 360                 365
Asp Pro Leu Lys Glu Pro Pro Leu Ile Thr Ala Asn Thr Val Leu Ser
    370                 375                 380
Ile Leu Ala Val Asp Tyr Pro Val Glu Lys Val Ala Cys Tyr Val Ser
385                 390                 395                 400
Asp Asp Gly Ala Ala Met Leu Thr Phe Glu Ala Leu Ser Tyr Thr Ala
                405                 410                 415
Glu Phe Ala Arg Lys Trp Val Pro Phe Cys Lys Lys Phe Ser Ile Glu
            420                 425                 430
Pro Arg Ala Pro Glu Trp Tyr Phe Ser Gln Lys Met Asp Tyr Leu Lys
        435                 440                 445
His Lys Val Asp Pro Ala Phe Val Met Glu Arg Arg Ala Met Lys Arg
    450                 455                 460
Asp Tyr Glu Glu Phe Lys Val Lys Ile Asn Ala Leu Val Ser Val Ser
465                 470                 475                 480
Gln Lys Val Pro Glu Asp Gly Trp Thr Met Gln Asp Gly Thr Pro Trp
                485                 490                 495
Pro Gly Asn Asn Val Arg Asp His Pro Gly Met Ile Gln Val Phe Leu
            500                 505                 510
Gly His Ser Gly Val Cys Asp Met Asp Gly Asn Glu Leu Pro Arg Leu
        515                 520                 525
Val Tyr Val Ser Arg Glu Lys Arg Pro Gly Phe Asp His His Lys Lys
    530                 535                 540
Ala Gly Ala Met Asn Ser Leu Ile Arg Val Ser Ala Val Leu Ser Asn
545                 550                 555                 560
Ala Pro Tyr Leu Leu Asn Val Asp Cys Asp His Tyr Ile Asn Asn Ser
                565                 570                 575
Lys Ala Ile Arg Glu Ala Met Cys Phe Met Met Asp Pro Gln Ser Gly
            580                 585                 590
Lys Lys Ile Cys Tyr Val Gln Phe Pro Gln Arg Phe Asp Gly Ile Asp
        595                 600                 605
Arg His Asp Arg Tyr Ser Asn Arg Asn Val Val Phe Phe Asp Ile Asn
    610                 615                 620
Met Lys Gly Leu Asp Gly Ile Gln Gly Pro Ile Tyr Val Gly Thr Gly
625                 630                 635                 640
Cys Val Phe Arg Arg Gln Ala Leu Tyr Gly Phe Asp Ala Pro Lys Lys
                645                 650                 655
Lys Gln Pro Pro Gly Arg Thr Cys Asn Cys Trp Pro Lys Trp Cys Cys
```

-continued

```
                660                 665                 670
Leu Cys Cys Gly Met Arg Lys Lys Thr Gly Lys Val Lys Asp Asn
            675                 680                 685
Gln Arg Lys Lys Pro Lys Glu Thr Ser Lys Gln Ile His Ala Leu Glu
            690                 695                 700
His Ile Glu Glu Gly Leu Gln Val Thr Asn Ala Glu Asn Asn Ser Glu
705                 710                 715                 720
Thr Ala Gln Leu Lys Leu Glu Lys Lys Phe Gly Gln Ser Pro Val Leu
            725                 730                 735
Val Ala Ser Thr Leu Leu Leu Asn Gly Gly Val Pro Ser Asn Val Asn
                740                 745                 750
Pro Ala Ser Leu Leu Arg Glu Ser Ile Gln Val Ile Ser Cys Gly Tyr
            755                 760                 765
Glu Glu Lys Thr Glu Trp Gly Lys Glu Ile Gly Trp Ile Tyr Gly Ser
            770                 775                 780
Val Thr Glu Asp Ile Leu Thr Gly Phe Lys Met His Cys His Gly Trp
785                 790                 795                 800
Arg Ser Val Tyr Cys Met Pro Lys Arg Ala Ala Phe Lys Gly Ser Ala
                805                 810                 815
Pro Ile Asn Leu Ser Asp Arg Leu His Gln Val Leu Arg Trp Ala Leu
                820                 825                 830
Gly Ser Val Glu Ile Phe Leu Ser Arg His Cys Pro Ile Trp Tyr Gly
            835                 840                 845
Tyr Gly Gly Gly Leu Lys Trp Leu Glu Arg Phe Ser Tyr Ile Asn Ser
850                 855                 860
Val Val Tyr Pro Trp Thr Ser Leu Pro Leu Leu Val Tyr Cys Ser Leu
865                 870                 875                 880
Pro Ala Ile Cys Leu Leu Thr Gly Lys Phe Ile Val Pro Glu Ile Ser
                885                 890                 895
Asn Tyr Ala Gly Ile Leu Phe Leu Leu Met Phe Met Ser Ile Ala Val
                900                 905                 910
Thr Gly Ile Leu Glu Met Gln Trp Gly Lys Ile Gly Ile Asp Asp Trp
            915                 920                 925
Trp Arg Asn Glu Gln Phe Trp Val Ile Gly Gly Val Ser Ser His Leu
            930                 935                 940
Phe Ala Leu Phe Gln Gly Leu Leu Lys Val Leu Ala Gly Val Ser Thr
945                 950                 955                 960
Asn Phe Thr Val Thr Ser Lys Ala Ala Asp Asp Gly Glu Phe Ser Glu
                965                 970                 975
Leu Tyr Ile Phe Lys Trp Thr Ser Leu Leu Ile Pro Pro Thr Thr Leu
            980                 985                 990
Leu Ile Ile Asn Ile Val Gly Val  Ile Val Gly Val Ser  Asp Ala Ile
            995                 1000                1005
Asn Asn  Gly Tyr Asp Ser Trp  Gly Pro Leu Phe Gly  Arg Leu Phe
      1010                1015                1020
Phe Ala  Leu Trp Val Ile Val  His Leu Tyr Pro Phe  Leu Lys Gly
      1025                1030                1035
Leu Leu  Gly Lys Gln Asp Arg  Val Pro Thr Ile Ile  Leu Val Trp
      1040                1045                1050
Ser Ile  Leu Leu Ala Ser Ile  Leu Thr Leu Leu Trp  Val Arg Val
      1055                1060                1065
Asn Pro  Phe Val Ser Lys Asp  Gly Pro Val Leu Glu  Ile Cys Gly
      1070                1075                1080
```

Leu Asp Cys Leu Lys
      1085

<210> SEQ ID NO 10
<211> LENGTH: 1065
<212> TYPE: PRT
<213> ORGANISM: Arabidopsis thaliana

<400> SEQUENCE: 10

Met Val Ala Gly Ser Tyr Arg Arg Tyr Glu Phe Val Arg Asn Arg Asp
1               5                   10                  15

Asp Ser Asp Asp Gly Leu Lys Pro Leu Lys Asp Leu Asn Gly Gln Ile
            20                  25                  30

Cys Gln Ile Cys Gly Asp Asp Val Gly Leu Thr Lys Thr Gly Asn Val
        35                  40                  45

Phe Val Ala Cys Asn Glu Cys Gly Phe Pro Leu Cys Gln Ser Cys Tyr
    50                  55                  60

Glu Tyr Glu Arg Lys Asp Gly Ser Gln Cys Cys Pro Gln Cys Lys Ala
65                  70                  75                  80

Arg Phe Arg Arg His Asn Gly Ser Pro Arg Val Glu Val Asp Glu Lys
                85                  90                  95

Glu Asp Asp Val Asn Asp Ile Glu Asn Glu Phe Asp Tyr Thr Gln Gly
            100                 105                 110

Asn Asn Lys Ala Arg Leu Pro His Arg Ala Glu Glu Phe Ser Ser Ser
        115                 120                 125

Ser Arg His Glu Glu Ser Leu Pro Val Ser Leu Leu Thr His Gly His
    130                 135                 140

Pro Val Ser Gly Glu Ile Pro Thr Pro Asp Arg Asn Ala Thr Leu Ser
145                 150                 155                 160

Pro Cys Ile Asp Pro Gln Leu Pro Gly Ile Tyr Gln Leu Leu Leu Leu
                165                 170                 175

Pro Val Arg Ile Leu Asp Pro Ser Lys Asp Leu Asn Ser Tyr Gly Leu
            180                 185                 190

Val Asn Val Asp Trp Lys Lys Arg Ile Gln Gly Trp Lys Leu Lys Gln
        195                 200                 205

Asp Lys Asn Met Ile His Met Thr Gly Lys Tyr His Glu Gly Lys Gly
    210                 215                 220

Gly Glu Phe Glu Gly Thr Gly Ser Asn Gly Asp Glu Leu Gln Met Val
225                 230                 235                 240

Asp Asp Ala Arg Leu Pro Met Ser Arg Val Val His Phe Pro Ser Ala
                245                 250                 255

Arg Met Thr Pro Tyr Arg Ile Val Ile Val Leu Arg Leu Ile Ile Leu
            260                 265                 270

Gly Val Phe Leu His Tyr Arg Thr Thr His Pro Val Lys Asp Ala Tyr
        275                 280                 285

Ala Leu Trp Leu Thr Ser Val Ile Cys Glu Ile Trp Phe Ala Phe Ser
    290                 295                 300

Trp Leu Leu Asp Gln Phe Pro Lys Trp Tyr Pro Ile Asn Arg Glu Thr
305                 310                 315                 320

Phe Leu Asp Arg Leu Ala Leu Arg Tyr Asp Arg Asp Gly Glu Pro Ser
                325                 330                 335

Gln Leu Ala Pro Val Asp Val Phe Val Ser Thr Val Asp Pro Met Lys
            340                 345                 350

Glu Pro Pro Leu Val Thr Ala Asn Thr Val Leu Ser Ile Leu Ala Val

-continued

```
            355                 360                 365
Asp Tyr Pro Val Asp Lys Val Ala Cys Tyr Val Ser Asp Asp Gly Ser
            370                 375                 380
Ala Met Leu Thr Phe Glu Ala Leu Ser Glu Thr Ala Glu Phe Ser Lys
385                 390                 395                 400
Lys Trp Val Pro Phe Cys Lys Lys Phe Asn Ile Glu Pro Arg Ala Pro
                    405                 410                 415
Glu Phe Tyr Phe Ser Gln Lys Ile Asp Tyr Leu Lys Asp Lys Ile Gln
                420                 425                 430
Pro Ser Phe Val Lys Glu Arg Ala Met Lys Arg Glu Tyr Glu Glu
            435                 440                 445
Phe Lys Val Arg Ile Asn Ile Leu Val Ala Lys Ala Gln Lys Ile Pro
450                 455                 460
Glu Asp Gly Trp Thr Met Glu Asp Gly Thr Ser Trp Pro Gly Asn Asn
465                 470                 475                 480
Pro Arg Asp His Pro Gly Met Ile Gln Val Phe Leu Gly His Ser Gly
                    485                 490                 495
Gly Leu Asp Thr Asp Gly Asn Glu Leu Pro Arg Leu Ile Tyr Val Ser
                500                 505                 510
Arg Glu Lys Arg Pro Gly Phe Gln His His Lys Lys Ala Gly Ala Met
            515                 520                 525
Asn Ala Leu Ile Arg Val Ser Ala Val Leu Thr Asn Gly Ala Tyr Leu
            530                 535                 540
Leu Asn Val Asp Cys Asp His Tyr Phe Asn Asn Ser Lys Ala Ile Lys
545                 550                 555                 560
Glu Ala Met Cys Phe Met Met Asp Pro Ala Ile Gly Lys Lys Cys Cys
                    565                 570                 575
Tyr Val Gln Phe Pro Gln Arg Phe Asp Gly Ile Asp Leu His Asp Arg
                580                 585                 590
Tyr Ala Asn Arg Asn Thr Val Phe Phe Asp Ile Asn Leu Lys Gly Leu
            595                 600                 605
Asp Gly Ile Gln Gly Pro Val Tyr Val Gly Thr Gly Cys Cys Phe Asn
            610                 615                 620
Arg Gln Ala Leu Tyr Gly Tyr Asp Pro Val Leu Thr Glu Glu Asp Leu
625                 630                 635                 640
Glu Pro Asn Ile Ile Val Lys Ser Cys Phe Gly Ser Arg Lys Lys Gly
                    645                 650                 655
Lys Ser Arg Lys Ile Pro Asn Tyr Glu Asp Asn Arg Ser Ile Lys Arg
                660                 665                 670
Ser Asp Ser Asn Val Pro Leu Phe Asn Met Glu Asp Ile Asp Glu Asp
            675                 680                 685
Val Glu Gly Tyr Glu Asp Glu Met Ser Leu Leu Val Ser Gln Lys Arg
            690                 695                 700
Leu Glu Lys Arg Phe Gly Gln Ser Pro Val Phe Ile Ala Ala Thr Phe
705                 710                 715                 720
Met Glu Gln Gly Gly Leu Pro Ser Thr Thr Asn Pro Leu Thr Leu Leu
                    725                 730                 735
Lys Glu Ala Ile His Val Ile Ser Cys Gly Tyr Glu Ala Lys Thr Asp
                740                 745                 750
Trp Gly Lys Glu Ile Gly Trp Ile Tyr Gly Ser Val Thr Glu Asp Ile
            755                 760                 765
Leu Thr Gly Phe Lys Met His Ala Arg Gly Trp Ile Ser Ile Tyr Cys
770                 775                 780
```

-continued

Val Pro Ser Arg Pro Ala Phe Lys Gly Ser Ala Pro Ile Asn Leu Ser
785                 790                 795                 800

Asp Arg Leu Asn Gln Val Leu Arg Trp Ala Leu Gly Ser Ile Glu Ile
                805                 810                 815

Leu Leu Ser Arg His Cys Pro Ile Trp Tyr Gly Tyr Asn Gly Arg Leu
            820                 825                 830

Lys Leu Leu Glu Arg Ile Ala Tyr Ile Asn Thr Ile Val Tyr Pro Ile
        835                 840                 845

Thr Ser Ile Pro Leu Leu Ala Tyr Cys Met Leu Pro Ala Phe Cys Leu
    850                 855                 860

Ile Thr Asn Thr Phe Ile Ile Pro Glu Ile Ser Asn Leu Ala Ser Leu
865                 870                 875                 880

Cys Phe Met Leu Leu Phe Ala Ser Ile Tyr Ala Ser Ala Ile Leu Glu
                885                 890                 895

Leu Lys Trp Ser Asp Val Ala Leu Glu Asp Trp Trp Arg Asn Glu Gln
            900                 905                 910

Phe Trp Val Ile Gly Gly Thr Ser Ala His Leu Phe Ala Val Phe Gln
        915                 920                 925

Gly Leu Leu Lys Val Phe Ala Gly Ile Asp Thr Asn Phe Thr Val Thr
    930                 935                 940

Ser Lys Ala Ser Asp Glu Asp Gly Asp Phe Ala Glu Leu Tyr Val Phe
945                 950                 955                 960

Lys Trp Thr Ser Leu Leu Ile Pro Pro Thr Thr Ile Leu Leu Val Asn
                965                 970                 975

Leu Val Gly Ile Val Ala Gly Val Ser Tyr Ala Ile Asn Ser Gly Tyr
            980                 985                 990

Gln Ser Trp Gly Pro Leu Met Gly Lys Leu Leu Phe Ala Phe Trp Val
        995                 1000                1005

Val Ala His Leu Tyr Pro Phe Leu Lys Gly Leu Leu Gly Arg Gln
    1010                1015                1020

Asn Arg Thr Pro Thr Ile Val Ile Val Trp Ser Ala Leu Leu Ala
    1025                1030                1035

Ser Ile Phe Ser Leu Leu Trp Val Arg Ile Asn Pro Phe Val Ser
    1040                1045                1050

Thr Thr Gly Val Met Ser Asn Ser Phe Met Gly Glu
    1055                1060                1065

<210> SEQ ID NO 11
<211> LENGTH: 1082
<212> TYPE: PRT
<213> ORGANISM: Brassica napus

<400> SEQUENCE: 11

Met Asn Thr Gly Gly Arg Leu Val Ala Gly Ser His Asn Arg Asn Glu
1               5                   10                  15

Phe Val Leu Ile Asn Ala Asp Glu Ser Ala Arg Ile Arg Ser Val Gln
            20                  25                  30

Glu Leu Ser Gly Gln Thr Cys Lys Ile Cys Arg Asp Glu Ile Glu Leu
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg

```
                    85                  90                  95
Val Glu Asn Asp Glu Glu Asp Asp Ile Asp Asp Leu Asp Asn Glu
                100                 105                 110
Phe Glu Tyr Glu Asn Gly Gly Val Gly Phe Asp Gln Val Ser Glu Gly
                115                 120                 125
Met Ser Val Ser Arg Arg His Ser Gly Phe Pro Gln Ser Asp Leu Asp
130                 135                 140
Ser Ala Pro Pro Gly Ser Gln Ile Pro Leu Leu Thr Tyr Gly Asp Glu
145                 150                 155                 160
Asp Ile Glu Ile Ser Ser Asp Arg His Ala Leu Ile Val Pro Pro Ser
                165                 170                 175
Ile Gly Gly His Ser Asn Lys Ser His Pro Ala Ser Leu Ser Asp Pro
                180                 185                 190
Thr Ile Ala Ala His Pro Arg Pro Met Val Pro Gln Lys Asp Leu Ala
                195                 200                 205
Val Tyr Gly Tyr Gly Ser Val Ala Trp Lys Asp Arg Met Glu Asp Trp
                210                 215                 220
Lys Lys Lys Gln Asn Glu Lys Leu Gln Val Val Arg His Glu Gly Asp
225                 230                 235                 240
Pro Asp Phe Glu Asp Gly Asp Ile Pro Met Met Asp Glu Gly Arg
                245                 250                 255
Gln Pro Leu Ser Arg Lys Ile Pro Ile Lys Ser Ser Lys Ile Asn Pro
                260                 265                 270
Tyr Arg Met Leu Ile Val Leu Arg Leu Val Ile Leu Gly Leu Phe Phe
                275                 280                 285
His Tyr Arg Ile Leu His Pro Val Lys Asp Ala Tyr Ala Leu Trp Leu
                290                 295                 300
Ile Ser Val Ile Cys Glu Ile Trp Phe Ala Val Ser Trp Val Leu Asp
305                 310                 315                 320
Gln Phe Pro Lys Trp Tyr Pro Ile Glu Arg Glu Thr Tyr Leu Asp Arg
                325                 330                 335
Leu Ser Leu Arg Tyr Glu Lys Glu Gly Lys Pro Ser Glu Leu Ser Ala
                340                 345                 350
Val Asp Val Phe Val Ser Thr Val Asp Pro Leu Lys Glu Pro Pro Leu
                355                 360                 365
Ile Thr Ala Asn Thr Val Leu Ser Ile Leu Ala Val Asp Tyr Pro Val
                370                 375                 380
Asp Arg Val Ala Cys Tyr Val Ser Asp Asp Gly Ala Ala Met Leu Thr
385                 390                 395                 400
Phe Glu Ala Leu Ser Glu Thr Ala Glu Phe Ala Arg Lys Trp Val Pro
                405                 410                 415
Phe Cys Lys Lys Tyr Cys Ile Glu Pro Arg Ala Pro Glu Trp Tyr Phe
                420                 425                 430
Cys His Lys Met Asp Tyr Leu Lys Asn Lys Val His Pro Ala Phe Val
                435                 440                 445
Arg Glu Arg Arg Ala Met Lys Arg Asp Tyr Glu Glu Phe Lys Val Lys
                450                 455                 460
Ile Asn Ala Leu Val Ala Thr Ala Gln Lys Val Pro Glu Glu Gly Trp
465                 470                 475                 480
Thr Met Gln Asp Gly Thr Pro Trp Pro Gly Asn Ser Val Arg Asp His
                485                 490                 495
Pro Gly Met Ile Gln Val Phe Leu Gly Ser Asp Gly Val Arg Asp Val
                500                 505                 510
```

-continued

```
Glu Asn Asn Glu Leu Pro Arg Leu Val Tyr Val Ser Arg Glu Lys Arg
            515                 520                 525

Pro Gly Phe Asp His His Lys Lys Ala Gly Ala Met Asn Ser Leu Ile
        530                 535                 540

Arg Val Ser Gly Val Leu Ser Asn Ala Pro Tyr Leu Leu Asn Val Asp
545                 550                 555                 560

Cys Asp His Tyr Ile Asn Asn Ser Lys Ala Leu Arg Glu Ala Met Cys
                565                 570                 575

Phe Met Met Asp Pro Gln Ser Gly Lys Lys Ile Cys Tyr Val Gln Phe
            580                 585                 590

Pro Gln Arg Phe Asp Gly Ile Asp Arg His Asp Arg Tyr Ser Asn Arg
        595                 600                 605

Asn Val Val Phe Phe Asp Ile Asn Met Lys Gly Leu Asp Gly Leu Gln
    610                 615                 620

Gly Pro Ile Tyr Val Gly Thr Gly Cys Val Phe Arg Arg Gln Ala Leu
625                 630                 635                 640

Tyr Gly Phe Asp Ala Pro Lys Lys Lys Ala Pro Arg Lys Thr Cys
                645                 650                 655

Asn Cys Trp Pro Lys Trp Cys Phe Met Cys Cys Gly Ser Arg Lys Asn
            660                 665                 670

Arg Gln Ala Lys Lys Val Ala Ala Asp Lys Lys Lys Asn Arg Glu
        675                 680                 685

Ala Ser Lys Gln Ile His Ala Leu Glu Asn Ile Glu Glu Gly Ser Val
    690                 695                 700

Thr Lys Gly Ser Asn Val Glu Gln Ser Thr Glu Ala Met Gln Leu Lys
705                 710                 715                 720

Leu Glu Lys Lys Phe Gly Gln Ser Pro Val Phe Val Ala Ser Ala Arg
                725                 730                 735

Met Gln Asn Gly Gly Met Ala Arg Asn Ala Ser Pro Ala Cys Leu Leu
            740                 745                 750

Lys Glu Ala Ile Gln Val Ile Ser Cys Gly Tyr Glu Asp Lys Thr Glu
        755                 760                 765

Trp Gly Lys Glu Ile Gly Trp Ile Tyr Gly Ser Val Thr Glu Asp Ile
    770                 775                 780

Leu Thr Gly Phe Lys Met His Ser His Gly Trp Arg Ser Val Tyr Cys
785                 790                 795                 800

Thr Pro Lys Leu Pro Ala Phe Lys Gly Ser Ala Pro Ile Asn Leu Ser
                805                 810                 815

Asp Arg Leu His Gln Val Leu Arg Trp Ala Leu Gly Ser Val Glu Ile
            820                 825                 830

Phe Leu Ser Arg His Cys Pro Ile Trp Tyr Gly Tyr Gly Gly Gly Leu
        835                 840                 845

Lys Trp Leu Glu Arg Leu Ser Tyr Ile Asn Ser Val Val Tyr Pro Trp
    850                 855                 860

Thr Ser Leu Pro Leu Ile Val Tyr Cys Ser Leu Pro Ala Ile Cys Leu
865                 870                 875                 880

Leu Thr Gly Lys Phe Ile Val Pro Glu Ile Ser Asn Tyr Ala Ser Ile
                885                 890                 895

Leu Phe Met Ala Leu Phe Ser Ser Ile Ala Ile Thr Gly Ile Leu Glu
            900                 905                 910

Met Gln Trp Gly Lys Val Gly Ile Asp Asp Trp Trp Arg Asn Glu Gln
        915                 920                 925
```

```
Phe Trp Val Ile Gly Gly Val Ser Ala His Leu Phe Ala Leu Phe Gln
930                 935                 940

Gly Leu Leu Lys Val Leu Ala Gly Val Asp Thr Asn Phe Thr Val Thr
945                 950                 955                 960

Ser Lys Ala Ala Asp Asp Gly Glu Phe Ser Asp Leu Tyr Leu Phe Lys
                965                 970                 975

Trp Thr Ser Leu Leu Ile Pro Pro Thr Thr Leu Leu Ile Ile Asn Met
            980                 985                 990

Ile Gly Ile Val Val Gly Ile Ser Asp Ala Ile Ser Asn Gly Tyr Asp
        995                 1000                1005

Ser Trp Gly Pro Leu Phe Gly Arg Leu Phe Phe Ala Leu Trp Val
    1010                1015                1020

Val Ile His Leu Tyr Pro Phe Leu Lys Gly Leu Leu Gly Lys Gln
    1025                1030                1035

Asp Arg Met Pro Thr Ile Ile Ile Val Trp Ser Ile Leu Ile Ala
    1040                1045                1050

Ser Ile Leu Thr Leu Leu Trp Val Arg Val Asn Pro Phe Val Ala
    1055                1060                1065

Lys Gly Gly Pro Val Leu Glu Ile Cys Gly Leu Asp Cys Leu
    1070                1075                1080

<210> SEQ ID NO 12
<211> LENGTH: 1066
<212> TYPE: PRT
<213> ORGANISM: Brassica napus

<400> SEQUENCE: 12

Met Glu Ser Glu Gly Glu Thr Ala Gly Lys Pro Met Thr Ser Val Gly
1               5                   10                  15

Gly Gln Ile Cys Gln Ile Cys Ser Asp Asn Val Gly Lys Thr Val Asp
            20                  25                  30

Gly Asp Arg Phe Val Ala Cys Asp Val Cys Gly Phe Pro Val Cys Arg
        35                  40                  45

Pro Cys Tyr Glu Phe Glu Arg Lys Asp Gly Asn Gln Ser Cys Pro Gln
    50                  55                  60

Cys Lys Thr Thr Tyr Lys Arg His Lys Gly Ser Pro Ala Ile Pro Gly
65                  70                  75                  80

Asp Lys Asp Glu Asp Val Phe Ala Asp Glu Ala Thr Val Glu Leu Ser
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Gln Pro Glu Tyr Asp Lys Glu
        115                 120                 125

Val Ser His Asn His Leu Pro Arg Leu Thr Ser Arg Gln Glu Thr Ser
    130                 135                 140

Gly Glu Phe Ser Ala Ala Ser Pro Glu Arg Leu Ser Val Ser Ser Thr
145                 150                 155                 160

Ile Gly Gly Gly Lys Arg Leu Pro Tyr Ser Ser Asp Ile Asn Gln Ser
                165                 170                 175

Pro His Arg Arg Ile Ser Asp Pro Val Gly Leu Gly Asn Val Ala Trp
            180                 185                 190

Lys Glu Arg Val Asp Gly Trp Lys Met Lys Gln Glu Lys Asn Asn Gly
        195                 200                 205

Gly Pro Val Ser Thr Gln Ala Ala Ser Glu Arg Gly Gly Gly Asp Ile
    210                 215                 220
```

```
Asp Ala Ser Thr Asp Ile Leu Ala Asp Glu Ala Leu Leu Asn Asp Glu
225                 230                 235                 240

Ala Arg Gln Pro Leu Ser Arg Lys Val Ser Ile Pro Ser Ser Arg Ile
            245                 250                 255

Asn Pro Tyr Arg Met Val Ile Met Leu Arg Leu Val Ile Leu Cys Leu
            260                 265                 270

Phe Leu His Tyr Arg Ile Thr Asn Pro Val Pro Asn Ala Phe Thr Leu
        275                 280                 285

Trp Leu Ile Ser Val Ile Cys Glu Ile Trp Phe Ala Phe Ser Trp Ile
        290                 295                 300

Leu Asp Gln Phe Pro Lys Trp Phe Pro Val Asn Arg Glu Thr Tyr Leu
305                 310                 315                 320

Asp Arg Leu Ala Leu Arg Tyr Asp Arg Glu Gly Glu Pro Ser Gln Leu
                325                 330                 335

Ala Ala Val Asp Ile Phe Val Ser Thr Val Asp Pro Leu Lys Glu Pro
            340                 345                 350

Pro Leu Val Thr Ala Asn Thr Val Leu Ser Ile Leu Ala Val Asp Tyr
        355                 360                 365

Pro Val Asp Lys Val Ser Cys Tyr Val Ser Asp Asp Gly Ala Ala Met
370                 375                 380

Leu Ser Phe Glu Ala Leu Ala Glu Thr Ser Glu Phe Ala Arg Lys Trp
385                 390                 395                 400

Val Pro Phe Cys Lys Lys Tyr Ser Ile Glu Pro Arg Ala Pro Glu Trp
                405                 410                 415

Tyr Phe Ala Ala Lys Ile Asp Tyr Leu Lys Asp Lys Val Gln Thr Ser
            420                 425                 430

Phe Val Lys Asp Arg Arg Ala Met Lys Arg Glu Tyr Glu Glu Phe Lys
        435                 440                 445

Ile Arg Ile Asn Ala Leu Val Ser Lys Ala Leu Lys Cys Pro Glu Glu
        450                 455                 460

Gly Trp Val Met Gln Asp Gly Thr Pro Trp Pro Gly Asn Asn Thr Arg
465                 470                 475                 480

Asp His Pro Gly Met Ile Gln Val Phe Leu Gly Gln Asn Gly Gly Leu
                485                 490                 495

Asp Ala Glu Gly Asn Glu Leu Pro Arg Leu Val Tyr Val Ser Arg Glu
            500                 505                 510

Lys Arg Pro Gly Phe Gln His His Lys Lys Ala Gly Ala Met Asn Ala
        515                 520                 525

Leu Val Arg Val Ser Ala Val Leu Thr Asn Gly Pro Phe Ile Leu Asn
        530                 535                 540

Leu Asp Cys Asp His Tyr Ile Asn Asn Ser Lys Ala Leu Arg Glu Ala
545                 550                 555                 560

Met Cys Phe Leu Met Asp Pro Asn Leu Gly Lys Gln Val Cys Tyr Val
                565                 570                 575

Gln Phe Pro Gln Arg Phe Asp Gly Ile Asp Lys Asn Asp Arg Tyr Ala
            580                 585                 590

Asn Arg Asn Thr Val Phe Phe Asp Ile Asn Leu Arg Gly Leu Asp Gly
        595                 600                 605

Ile Gln Gly Pro Val Tyr Val Gly Thr Gly Cys Val Phe Asn Arg Thr
        610                 615                 620

Ala Leu Tyr Gly Tyr Glu Pro Pro Ile Lys Val Lys His Lys Lys Pro
625                 630                 635                 640
```

```
Ser Leu Leu Ser Lys Ile Cys Gly Gly Ser Arg Lys Asn Ser Lys
            645                 650                 655

Ser Lys Lys Asp Ser Asp Lys Lys Ser Gly Arg His Thr Asp Ser
        660                 665                 670

Thr Val Pro Val Phe Asn Leu Asp Asp Ile Glu Glu Gly Val Glu Gly
            675                 680                 685

Ala Gly Phe Asp Asp Glu Lys Ala Leu Leu Met Ser Gln Met Ser Leu
    690                 695                 700

Glu Lys Arg Phe Gly Gln Ser Ala Val Phe Val Ala Ser Thr Leu Met
705                 710                 715                 720

Glu Asn Gly Gly Val Pro Pro Thr Glu Thr Pro Glu Asn Leu Leu Lys
                725                 730                 735

Glu Ala Ile His Val Ile Ser Cys Gly Tyr Glu Asp Lys Ser Asp Trp
            740                 745                 750

Gly Met Glu Ile Gly Trp Ile Tyr Gly Ser Val Thr Glu Asp Ile Leu
        755                 760                 765

Thr Gly Phe Lys Met His Ala Arg Gly Trp Arg Ser Ile Tyr Cys Met
    770                 775                 780

Pro Lys Leu Pro Ala Phe Lys Gly Ser Ala Pro Ile Asn Leu Ser Asp
785                 790                 795                 800

Arg Leu Asn Gln Val Leu Arg Trp Ala Leu Gly Ser Val Glu Ile Leu
                805                 810                 815

Phe Ser Arg His Cys Pro Ile Trp Tyr Gly Tyr Ser Gly Arg Leu Lys
            820                 825                 830

Phe Leu Glu Arg Phe Ala Tyr Val Asn Thr Thr Ile Tyr Pro Leu Thr
        835                 840                 845

Ser Val Pro Leu Leu Leu Tyr Cys Thr Leu Pro Ala Val Cys Leu Phe
    850                 855                 860

Thr Asn Gln Phe Ile Ile Pro Gln Ile Ser Asn Ile Ala Ser Ile Trp
865                 870                 875                 880

Phe Leu Ser Leu Phe Leu Ser Ile Phe Ala Thr Gly Ile Leu Glu Met
                885                 890                 895

Arg Trp Ser Gly Val Gly Ile Asp Glu Trp Trp Arg Asn Glu Gln Phe
            900                 905                 910

Trp Val Ile Gly Gly Val Ser Ala His Leu Phe Ala Val Phe Gln Gly
        915                 920                 925

Leu Leu Lys Val Leu Ala Gly Ile Asp Thr Asn Phe Thr Val Thr Ser
    930                 935                 940

Lys Ala Ser Asp Glu Asp Gly Asp Phe Ala Glu Leu Tyr Leu Phe Lys
945                 950                 955                 960

Trp Thr Thr Leu Leu Ile Pro Pro Thr Thr Leu Leu Ile Val Asn Leu
                965                 970                 975

Val Gly Val Val Ala Gly Phe Ser Tyr Ala Ile Asn Ser Gly Tyr Gln
            980                 985                 990

Ser Trp Gly Pro Leu Phe Gly Lys Leu Phe Phe Ala Phe Trp Val Ile
        995                 1000                1005

Val His Leu Tyr Pro Phe Leu Lys Gly Leu Met Gly Arg Gln Asn
    1010                1015                1020

Arg Thr Pro Thr Ile Val Val Val Trp Ser Val Leu Leu Ala Ser
    1025                1030                1035

Ile Phe Ser Leu Leu Trp Val Arg Ile Asp Pro Phe Thr Lys Arg
    1040                1045                1050

Val Thr Gly Pro Asp Ile Leu Glu Cys Gly Ile Asn Cys
```

-continued

```
              1055                1060                1065
```

<210> SEQ ID NO 13
<211> LENGTH: 1084
<212> TYPE: PRT
<213> ORGANISM: Brassica napus

<400> SEQUENCE: 13

```
Met Asn Thr Gly Gly Arg Leu Ile Ala Gly Ser His Asn Arg Asn Glu
1               5                   10                  15

Phe Val Leu Ile Asn Ala Asp Glu Ser Ala Arg Ile Arg Ser Val Gln
            20                  25                  30

Glu Leu Arg Gly Gln Thr Cys Glu Ile Cys Arg Asp Glu Val Glu Leu
        35                  40                  45

Thr Val Asp Gly Glu Pro Phe Val Ala Cys Asn Glu Cys Ala Phe Pro
50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Leu Lys Gly Ser Pro Arg
                85                  90                  95

Val Glu Asn Asp Glu Glu Asp Asp Ile Asp Ile Asp Asn Glu
            100                 105                 110

Phe Asp Tyr Met Asn Asn Gly Gly Ile Gly Phe Asp Gln Val Ser Glu
        115                 120                 125

Gly Met Ser Val Ser Arg Arg His Ser Gly Phe Pro Gln Ser Asp Leu
130                 135                 140

Asp Ser Ala Pro Pro Gly Ser Gln Ile Pro Leu Leu Thr Tyr Gly Asp
145                 150                 155                 160

Glu Asp Ile Glu Ile Ser Ser Asp Arg His Ala Leu Ile Val Pro Pro
                165                 170                 175

Ser Leu Ser Gly His Ser His Arg Gly His Pro Ala Ser Leu Ser Asp
            180                 185                 190

Pro Thr Ile Ala Ala His Pro Arg Pro Met Val Pro Gln Lys Asp Leu
        195                 200                 205

Ala Val Tyr Gly Tyr Gly Ser Val Ala Trp Lys Asp Arg Met Glu Glu
210                 215                 220

Trp Lys Arg Lys Gln Asn Glu Lys Leu Gln Val Val Lys His Glu Gly
225                 230                 235                 240

Asp Pro Asp Phe Glu Asp Gly Asp Ile Pro Met Met Asp Glu Gly
                245                 250                 255

Arg Gln Pro Leu Ser Arg Lys Ile Pro Ile Lys Ser Ser Lys Ile Asn
            260                 265                 270

Pro Tyr Arg Met Leu Ile Val Leu Arg Leu Val Ile Leu Gly Leu Phe
        275                 280                 285

Phe His Tyr Arg Ile Leu His Pro Val Lys Asp Ala Tyr Ala Leu Trp
290                 295                 300

Leu Ile Ser Val Ile Cys Glu Ile Trp Phe Ala Val Ser Trp Val Leu
305                 310                 315                 320

Asp Gln Phe Pro Lys Trp Tyr Pro Ile Glu Arg Glu Thr Tyr Leu Asp
                325                 330                 335

Arg Leu Ser Leu Arg Tyr Glu Lys Glu Gly Lys Pro Ser Glu Leu Ser
            340                 345                 350

Ala Val Asp Val Phe Val Ser Thr Val Asp Pro Leu Lys Glu Pro Pro
        355                 360                 365
```

```
Leu Ile Thr Ala Asn Thr Val Leu Ser Ile Leu Ala Val Asp Tyr Pro
370                 375                 380

Val Asp Arg Val Ala Cys Tyr Val Ser Asp Asp Gly Ala Ala Met Leu
385                 390                 395                 400

Thr Phe Glu Ala Leu Ser Glu Thr Ala Glu Phe Ala Arg Lys Trp Val
            405                 410                 415

Pro Phe Cys Lys Lys Tyr Cys Ile Glu Pro Arg Ala Pro Glu Trp Tyr
            420                 425                 430

Phe Cys His Lys Met Asp Tyr Leu Lys Asn Lys Val His Pro Ala Phe
            435                 440                 445

Val Arg Glu Arg Ala Met Lys Arg Asp Tyr Glu Glu Phe Lys Val
450                 455                 460

Lys Ile Asn Ala Leu Val Ala Thr Ala Gln Lys Val Pro Glu Glu Gly
465                 470                 475                 480

Trp Thr Met Gln Asp Gly Thr Pro Trp Pro Gly Asn Ser Thr Arg Asp
                485                 490                 495

His Pro Gly Met Ile Gln Val Phe Leu Gly Ser Asp Gly Val Arg Asp
            500                 505                 510

Val Glu Asn Asn Glu Leu Pro Arg Leu Val Tyr Val Ser Arg Glu Lys
            515                 520                 525

Arg Pro Gly Phe Asp His His Lys Lys Ala Gly Ala Met Asn Ser Leu
530                 535                 540

Ile Arg Val Ser Gly Val Leu Ser Asn Ala Pro Tyr Leu Leu Asn Val
545                 550                 555                 560

Asp Cys Asp His Tyr Ile Asn Asn Ser Lys Ala Leu Arg Glu Ala Met
                565                 570                 575

Cys Phe Met Met Asp Pro Gln Ser Gly Lys Lys Ile Cys Tyr Val Gln
                580                 585                 590

Phe Pro Gln Arg Phe Asp Gly Ile Asp Arg His Asp Arg Tyr Ser Asn
            595                 600                 605

Arg Asn Val Val Phe Phe Asp Ile Asn Met Lys Gly Leu Asp Gly Leu
            610                 615                 620

Gln Gly Pro Ile Tyr Val Gly Thr Gly Cys Val Phe Arg Arg Gln Ala
625                 630                 635                 640

Leu Tyr Gly Phe Asp Ala Pro Lys Lys Lys Ala Pro Arg Lys Thr
                645                 650                 655

Cys Asn Cys Trp Pro Lys Trp Cys Phe Leu Cys Cys Gly Ser Arg Lys
                660                 665                 670

Asn Arg Lys Ala Lys Thr Ala Ala Asp Lys Lys Lys Asn Arg
            675                 680                 685

Glu Ala Ser Lys Gln Ile His Ala Leu Glu Asn Ile Glu Glu Gly Arg
690                 695                 700

Val Thr Thr Lys Gly Ser Asn Val Glu Leu Ser Thr Glu Ala Met Gln
705                 710                 715                 720

Leu Lys Leu Glu Lys Lys Phe Gly Gln Ser Pro Val Phe Val Ala Ser
                725                 730                 735

Ala Arg Met Glu Asn Gly Gly Met Ala Arg Asn Ala Ser Pro Ala Cys
            740                 745                 750

Leu Leu Lys Glu Ala Ile Gln Val Ile Ser Cys Gly Tyr Glu Asp Lys
            755                 760                 765

Thr Glu Trp Gly Lys Glu Ile Gly Trp Ile Tyr Gly Ser Val Thr Glu
            770                 775                 780

Asp Ile Leu Thr Gly Phe Lys Met His Ser His Gly Trp Arg Ser Val
```

```
                785                 790                 795                 800
Tyr Cys Thr Pro Lys Leu Pro Ala Phe Lys Gly Ser Ala Pro Ile Asn
                805                 810                 815

Leu Ser Asp Arg Leu His Gln Val Leu Arg Trp Ala Leu Gly Ser Val
                820                 825                 830

Glu Ile Phe Leu Ser Arg His Cys Pro Ile Trp Tyr Gly Tyr Gly Gly
                835                 840                 845

Gly Leu Lys Trp Leu Glu Arg Leu Ser Tyr Ile Asn Ser Val Val Tyr
    850                 855                 860

Pro Trp Thr Ser Leu Pro Leu Ile Val Tyr Cys Ser Leu Pro Ala Ile
865                 870                 875                 880

Cys Leu Leu Thr Gly Lys Phe Ile Val Pro Glu Ile Ser Asn Tyr Ala
                885                 890                 895

Ser Ile Leu Phe Met Ala Leu Phe Ser Ser Ile Ala Val Thr Gly Ile
                900                 905                 910

Leu Glu Met Gln Trp Gly Lys Val Gly Ile Asp Asp Trp Trp Arg Asn
                915                 920                 925

Glu Gln Phe Trp Val Ile Gly Val Ser Ala His Leu Phe Ala Leu
    930                 935                 940

Phe Gln Gly Leu Leu Lys Val Leu Ala Gly Val Asp Thr Asn Phe Thr
945                 950                 955                 960

Val Thr Ser Lys Ala Ala Asp Asp Gly Glu Phe Ser Asp Leu Tyr Leu
                965                 970                 975

Phe Lys Trp Thr Ser Leu Leu Ile Pro Pro Thr Thr Leu Leu Ile Ile
                980                 985                 990

Asn Val Ile Gly Ile Val Val Gly Ile Ser Asp Ala Ile Ser Asn Gly
                995                 1000                1005

Tyr Asp Ser Trp Gly Pro Leu Phe Gly Arg Leu Phe Phe Ala Leu
    1010                1015                1020

Trp Val Val Ile His Leu Tyr Pro Phe Leu Lys Gly Leu Leu Gly
    1025                1030                1035

Lys Gln Asp Arg Met Pro Thr Ile Ile Val Val Trp Ser Ile Leu
    1040                1045                1050

Leu Ala Ser Ile Leu Thr Leu Leu Trp Val Arg Val Asn Pro Phe
    1055                1060                1065

Val Ala Lys Gly Gly Pro Ile Leu Glu Ile Cys Gly Leu Asp Cys
    1070                1075                1080

Leu

<210> SEQ ID NO 14
<211> LENGTH: 1079
<212> TYPE: PRT
<213> ORGANISM: Brassica napus

<400> SEQUENCE: 14

Met Asn Thr Gly Gly Arg Leu Ile Ala Gly Ser His Asn Arg Asn Glu
1               5                   10                  15

Phe Val Leu Ile Asn Ala Asp Glu Asn Ala Arg Ile Arg Ser Val Gln
                20                  25                  30

Glu Leu Arg Gly Gln Thr Cys Ile Cys Arg Asp Ile Glu Ser
            35                  40                  45

Thr Val Asp Gly Glu Pro Phe Val Ala Cys Asn Glu Cys Ala Phe Pro
        50                  55                  60

Val Cys Arg Pro Cys Tyr Glu Tyr Glu Arg Arg Glu Gly Asn Gln Ala
```

```
              65                  70                  75                  80
Cys Pro Gln Cys Lys Thr Arg Tyr Lys Arg Ile Lys Gly Ser Pro Arg
                85                  90                  95
Val Glu Asn Asp Glu Glu Asp Val Asp Ile Asp Asn Glu
               100                 105                 110
Phe Glu Tyr Gly Gly Asn Gly Ile Gly Phe Asp Gln Val Ser Glu Gly
               115                 120                 125
Val Ser Val Ser Arg Arg His Ser Gly Asp Leu Asp Ser Ala Pro Pro
130                 135                 140
Gly Ser Gln Ile Pro Leu Leu Thr Tyr Gly Asp Glu Asp Ile Glu Ile
145                 150                 155                 160
Ser Ser Asp Arg His Ala Leu Ile Val Pro Ser Leu Ser Gly His
                165                 170                 175
Gly Ser Arg Val His Pro Val Ser Leu Ser Asp Pro Thr Ile Ala Ala
                180                 185                 190
His Pro Arg Pro Met Val Pro Gln Lys Asp Leu Ala Val Tyr Gly Tyr
                195                 200                 205
Gly Ser Val Ala Trp Lys Asp Arg Met Glu Glu Trp Lys Arg Lys Gln
210                 215                 220
Asn Glu Lys Leu Gln Val Val Arg His Glu Gly Asp Pro Asp Phe Glu
225                 230                 235                 240
Asp Gly Asp Asp Ile Pro Met Met Asp Glu Gly Arg Gln Pro Leu Ser
                245                 250                 255
Arg Lys Ile Pro Ile Lys Ser Ser Lys Ile Asn Pro Tyr Arg Met Leu
                260                 265                 270
Ile Val Leu Arg Leu Val Ile Leu Ser Leu Phe Phe His Tyr Arg Ile
                275                 280                 285
Leu His Pro Val Lys Asp Ala Tyr Ala Leu Trp Leu Thr Ser Val Ile
                290                 295                 300
Cys Glu Ile Trp Phe Ala Val Ser Trp Val Leu Asp Gln Phe Pro Lys
305                 310                 315                 320
Trp Tyr Pro Ile Glu Arg Glu Thr Tyr Leu Asp Arg Leu Ser Leu Arg
                325                 330                 335
Tyr Glu Lys Glu Gly Lys Pro Ser Glu Leu Ser Pro Val Asp Val Phe
                340                 345                 350
Val Ser Thr Val Asp Pro Leu Lys Glu Pro Pro Leu Ile Thr Ala Asn
                355                 360                 365
Thr Val Leu Ser Ile Leu Ala Val Asp Tyr Pro Val Asp Lys Val Ala
                370                 375                 380
Cys Tyr Val Ser Asp Asp Gly Ala Ala Met Leu Thr Phe Glu Ala Leu
385                 390                 395                 400
Ser Glu Thr Ala Glu Phe Ala Arg Lys Trp Val Pro Phe Cys Lys Lys
                405                 410                 415
Tyr Cys Ile Glu Pro Arg Ala Pro Glu Trp Tyr Phe Cys His Lys Met
                420                 425                 430
Asp Tyr Leu Lys Asn Lys Val His Pro Ala Phe Val Arg Glu Arg Arg
                435                 440                 445
Ala Met Lys Arg Asp Tyr Glu Glu Phe Lys Val Lys Ile Asn Ala Leu
450                 455                 460
Val Ala Thr Ala Gln Lys Val Pro Glu Glu Gly Trp Thr Met Gln Asp
465                 470                 475                 480
Gly Thr Pro Trp Pro Gly Asn Ser Thr Arg Asp His Pro Gly Met Ile
                485                 490                 495
```

```
Gln Val Phe Leu Gly Thr Asp Gly Val Arg Asp Val Glu Asn Asn Glu
            500                 505                 510

Leu Pro Arg Leu Val Tyr Val Ser Arg Glu Lys Arg Pro Gly Phe Asp
            515                 520                 525

His His Lys Lys Ala Gly Ala Met Asn Ser Leu Ile Arg Val Ser Gly
            530                 535                 540

Val Leu Ser Asn Ala Pro Tyr Leu Leu Asn Val Asp Cys Asp His Tyr
545                 550                 555                 560

Ile Asn Asn Ser Lys Ala Leu Arg Glu Ala Met Cys Phe Met Met Asp
                565                 570                 575

Pro Gln Ser Gly Lys Lys Ile Cys Tyr Val Gln Phe Pro Gln Arg Phe
            580                 585                 590

Asp Gly Ile Asp Arg His Asp Arg Tyr Ser Asn Arg Asn Val Val Phe
            595                 600                 605

Phe Asp Ile Asn Met Lys Gly Leu Asp Gly Leu Gln Gly Pro Ile Tyr
            610                 615                 620

Val Gly Thr Gly Cys Val Phe Arg Arg Gln Ala Leu Tyr Gly Phe Asp
625                 630                 635                 640

Ala Pro Lys Lys Lys Ala Pro Arg Lys Thr Cys Asn Cys Trp Pro
                645                 650                 655

Lys Trp Cys Phe Leu Cys Cys Gly Ser Arg Lys Asn Arg Lys Ala Lys
            660                 665                 670

Thr Leu Ala Ala Ala Asp Lys Lys Lys Asn Arg Glu Ala Ser Lys
            675                 680                 685

Gln Ile His Ala Leu Glu Asn Ile Glu Glu Gly Pro Val Thr Lys Gly
            690                 695                 700

Ser Asn Val Glu Leu Ser Ser Glu Ala Met Gln Leu Lys Leu Glu Lys
705                 710                 715                 720

Lys Phe Gly Gln Ser Pro Val Phe Val Ala Ser Ala Arg Met Gln Asn
            725                 730                 735

Gly Gly Met Ala Arg Asn Ala Ser Pro Ala Cys Leu Leu Lys Glu Ala
            740                 745                 750

Ile Gln Val Ile Ser Cys Gly Tyr Glu Asp Lys Thr Glu Trp Gly Lys
            755                 760                 765

Glu Ile Gly Trp Ile Tyr Gly Ser Val Thr Glu Asp Ile Leu Thr Gly
            770                 775                 780

Phe Lys Met His Ser His Gly Trp Arg Ser Val Tyr Cys Thr Pro Lys
785                 790                 795                 800

Leu Pro Ala Phe Lys Gly Ser Ala Pro Ile Asn Leu Ser Asp Arg Leu
            805                 810                 815

His Gln Val Leu Arg Trp Ala Leu Gly Ser Val Glu Ile Phe Leu Ser
            820                 825                 830

Arg His Cys Pro Ile Trp Tyr Gly Tyr Gly Gly Gly Leu Lys Trp Leu
            835                 840                 845

Glu Arg Leu Ser Tyr Ile Asn Ser Val Val Tyr Pro Trp Thr Ser Leu
            850                 855                 860

Pro Leu Ile Val Tyr Cys Ser Leu Pro Ala Ile Cys Leu Leu Thr Gly
865                 870                 875                 880

Lys Phe Ile Val Pro Glu Ile Ser Asn Tyr Ala Ser Ile Leu Phe Met
            885                 890                 895

Ala Leu Phe Ser Ser Ile Ala Val Thr Gly Ile Leu Glu Met Gln Trp
            900                 905                 910
```

```
Gly Lys Val Gly Ile Asp Asp Trp Trp Arg Asn Glu Gln Phe Trp Val
            915                 920                 925

Ile Gly Gly Val Ser Ala His Leu Phe Ala Leu Phe Gln Gly Leu Leu
    930                 935                 940

Lys Val Leu Ala Gly Val Asp Thr Asn Phe Thr Val Thr Ser Lys Ala
945                 950                 955                 960

Ala Asp Asp Gly Glu Phe Ser Asp Leu Tyr Leu Phe Lys Trp Thr Ser
                965                 970                 975

Leu Leu Ile Pro Pro Thr Leu Leu Ile Ile Asn Val Ile Gly Ile
                980                 985                 990

Val Val Gly Ile Ser Asp Ala Ile Ser Asn Gly Tyr Asp Ser Trp Gly
            995                 1000                1005

Pro Leu Phe Gly Arg Leu Phe  Phe Ala Leu Trp Val  Val Ile His
    1010                1015                1020

Leu Tyr  Pro Phe Leu Lys Gly  Leu Leu Gly Lys Gln  Asp Arg Met
    1025                1030                1035

Pro Thr  Ile Ile Val Val Trp  Ser Ile Leu Leu Ala  Ser Ile Leu
    1040                1045                1050

Thr Leu  Leu Trp Val Arg Val  Asn Pro Phe Val Ala  Lys Gly Gly
    1055                1060                1065

Pro Val  Leu Glu Ile Cys Gly  Leu Asp Cys Leu
    1070                1075

<210> SEQ ID NO 15
<211> LENGTH: 1083
<212> TYPE: PRT
<213> ORGANISM: Brassica napus

<400> SEQUENCE: 15

Met Glu Ala Ser Ala Gly Leu Val Ala Gly Ser Tyr Arg Arg Asn Glu
1               5                   10                  15

Leu Val Arg Ile Arg His Glu Ser Asp Gly Gly Ser Lys Ala Met Lys
                20                  25                  30

Asn Met Asp Pro His Thr Cys Gln Ile Cys Gly Asp Asn Ala Gly Leu
            35                  40                  45

Thr Glu Thr Gly Asp Leu Phe Val Ala Cys Asn Glu Cys Ala Phe Pro
50              55                  60

Val Cys Arg Pro Cys Tyr Glu Tyr Glu Arg Lys Asp Gly Thr Gln Cys
65                  70                  75                  80

Cys Pro Gln Cys Lys Thr Arg Tyr Arg Arg Leu Arg Gly His Pro Arg
                85                  90                  95

Val Glu Gly Asp Glu Asp Glu Asp Val Asp Asp Ile Glu Asn Glu
                100                 105                 110

Phe Asn Tyr Ala Gln Gly Ala Asn Lys Gly Arg Arg Gln Arg His
            115                 120                 125

Gly Glu Glu Phe Ser Ser Ser Arg His Glu Ser Gln Pro Ile Pro
130                 135                 140

Leu Leu Thr His Gly His Thr Val Ser Gly Glu Ile Arg Thr Pro Asp
145                 150                 155                 160

Thr Gln Ser Val Arg Thr Thr Ser Gly Pro Leu Gly Pro Gly Asp Arg
                165                 170                 175

Asn Ala Ile Ser Ser Pro Tyr Ile Asp Pro Arg Gln Pro Val Pro Val
            180                 185                 190

Arg Ile Val Asp Pro Ser Lys Asp Leu Asn Ser Tyr Gly Leu Gly Asn
        195                 200                 205
```

```
Val Asp Trp Lys Glu Arg Val Glu Gly Trp Lys Leu Lys Gln Glu Lys
    210                 215                 220

Asn Met Val Gln Met Thr Gly Lys Tyr His Glu Gly Lys Gly Gly Glu
225                 230                 235                 240

Ile Glu Gly Thr Gly Ser Asn Gly Glu Glu Leu Gln Met Ala Asp Asp
                245                 250                 255

Ser Arg Leu Pro Met Ser Arg Ile Val Pro Ile Pro Pro Ser His Leu
                260                 265                 270

Thr Pro Tyr Arg Val Val Ile Ile Leu Arg Leu Ile Ile Leu Gly Phe
            275                 280                 285

Phe Leu Gln Tyr Arg Thr Thr His Pro Val Lys Asp Ala Tyr Pro Leu
    290                 295                 300

Trp Leu Thr Ser Val Ile Cys Glu Ile Trp Phe Ala Phe Ser Trp Leu
305                 310                 315                 320

Leu Asp Gln Phe Pro Lys Trp Tyr Pro Ile Asn Arg Glu Thr Tyr Leu
                325                 330                 335

Asp Arg Leu Ala Ile Arg Tyr Asp Arg Asp Gly Glu Pro Ser Gln Leu
            340                 345                 350

Thr Pro Val Asp Val Phe Val Ser Thr Val Asp Pro Leu Lys Glu Pro
    355                 360                 365

Pro Leu Val Thr Ala Asn Thr Val Leu Ser Ile Leu Ala Val Asp Tyr
370                 375                 380

Pro Val Asp Lys Val Ala Cys Tyr Val Ser Asp Asp Gly Ala Ala Met
385                 390                 395                 400

Leu Thr Phe Glu Ser Leu Ser Glu Thr Ala Glu Phe Ala Lys Lys Trp
                405                 410                 415

Val Pro Phe Cys Lys Lys Phe Ser Ile Glu Pro Arg Ala Pro Glu Phe
            420                 425                 430

Tyr Phe Ala Gln Lys Ile Asp Tyr Leu Lys Asp Lys Ile Gln Pro Ser
    435                 440                 445

Phe Val Lys Glu Arg Arg Ala Met Lys Arg Glu Tyr Glu Glu Phe Lys
450                 455                 460

Val Arg Ile Asn Ala Leu Val Ala Lys Ala Gln Lys Ile Pro Glu Glu
465                 470                 475                 480

Gly Trp Thr Met Gln Asp Gly Thr Pro Trp Pro Gly Asn Asn Thr Arg
                485                 490                 495

Asp His Pro Gly Met Ile Gln Val Phe Leu Gly His Ser Gly Gly Leu
            500                 505                 510

Asp Thr Asp Gly Asn Glu Leu Pro Arg Leu Ile Tyr Val Ser Arg Glu
    515                 520                 525

Lys Arg Pro Gly Phe Gln His His Lys Lys Ala Gly Ala Met Asn Ala
530                 535                 540

Leu Ile Arg Val Ser Ala Val Leu Thr Asn Gly Ala Tyr Leu Leu Asn
545                 550                 555                 560

Val Asp Cys Asp His Tyr Phe Asn Asn Ser Lys Ala Ile Lys Glu Ala
                565                 570                 575

Met Cys Phe Leu Met Asp Pro Ala Tyr Gly Lys Lys Cys Cys Tyr Val
            580                 585                 590

Gln Phe Pro Gln Arg Phe Asp Gly Ile Asp Leu His Asp Arg Tyr Ala
    595                 600                 605

Asn Arg Asn Ile Val Phe Phe Asp Ile Asn Leu Lys Gly Leu Asp Gly
610                 615                 620
```

```
Ile Gln Gly Pro Val Tyr Val Gly Thr Gly Cys Cys Phe Asn Arg Gln
625                 630                 635                 640

Ala Leu Tyr Gly Tyr Asp Pro Val Leu Thr Glu Glu Asp Leu Glu Pro
                645                 650                 655

Asn Ile Ile Val Lys Ser Cys Cys Gly Ser Arg Lys Gly Lys Lys
            660                 665                 670

Ser Lys Lys Tyr Asn Tyr Asp Gln Gln Arg Arg Gly Ile Asn Arg Ser
        675                 680                 685

Asp Ser Asn Ala Pro Leu Phe Asn Met Asp Asp Ile Glu Glu Gly Phe
690                 695                 700

Glu Gly Tyr Asp Asp Glu Arg Ser Ile Leu Met Ser Gln Lys Ser Val
705                 710                 715                 720

Glu Lys Arg Phe Gly Gln Ser Pro Val Phe Ile Ala Ala Thr Phe Met
                725                 730                 735

Glu Gln Gly Gly Ile Pro Pro Thr Thr Asn Pro Ala Thr Leu Leu Lys
                740                 745                 750

Glu Ala Ile His Val Ile Ser Cys Gly Tyr Glu Asp Lys Thr Glu Trp
            755                 760                 765

Gly Lys Glu Ile Gly Trp Ile Tyr Gly Ser Val Thr Glu Asp Ile Leu
770                 775                 780

Thr Gly Phe Lys Met His Ala Arg Gly Trp Met Ser Ile Tyr Cys Asn
785                 790                 795                 800

Pro Pro Arg Pro Ala Phe Lys Gly Ser Ala Pro Ile Asn Leu Ser Asp
                805                 810                 815

Arg Leu Asn Gln Val Leu Arg Trp Ala Leu Gly Ser Ile Glu Ile Leu
            820                 825                 830

Leu Ser Arg His Cys Pro Ile Trp Tyr Gly Tyr Thr Gly Arg Leu Arg
            835                 840                 845

Leu Leu Glu Arg Leu Ala Tyr Ile Asn Thr Ile Val Tyr Pro Ile Thr
850                 855                 860

Ala Leu Pro Leu Ile Ala Tyr Cys Ile Leu Pro Ala Phe Cys Leu Ile
865                 870                 875                 880

Thr Asp Lys Phe Ile Ile Pro Glu Ile Ser Asn Tyr Ala Ser Ile Trp
                885                 890                 895

Phe Ile Leu Leu Phe Ile Ser Ile Ala Val Thr Gly Val Leu Glu Leu
                900                 905                 910

Arg Trp Ser Gly Val Ser Ile Glu Asp Trp Trp Arg Asn Glu Gln Phe
            915                 920                 925

Trp Val Ile Gly Gly Thr Ser Ala His Leu Phe Ala Val Phe Gln Gly
930                 935                 940

Leu Leu Lys Val Leu Ala Gly Ile Asp Thr Asn Phe Thr Val Thr Ser
945                 950                 955                 960

Lys Ala Ser Asp Glu Asp Gly Asp Phe Ala Glu Leu Tyr Ile Phe Lys
                965                 970                 975

Trp Thr Ala Leu Leu Ile Pro Pro Thr Thr Val Leu Val Val Asn Leu
            980                 985                 990

Ile Gly Ile Val Ala Gly Val Ser Tyr Ala Val Asn Ser Gly Tyr Gln
            995                 1000                1005

Ser Trp Gly Pro Leu Phe Gly Lys Leu Phe Phe Ala Leu Trp Val
        1010                1015                1020

Ile Ala His Leu Tyr Pro Phe Leu Lys Gly Leu Met Gly Arg Gln
        1025                1030                1035

Asn Arg Thr Pro Thr Ile Val Ile Val Trp Ser Val Leu Leu Ala
```

```
              1040                1045                1050

Ser Ile Phe Ser Leu Leu Trp Val Arg Ile Asn Pro Phe Val Ser
              1055                1060                1065

Val Thr Pro Glu Ala Asn Pro Thr Ala Val Pro Gly Gly Val Phe
              1070                1075                1080

<210> SEQ ID NO 16
<211> LENGTH: 1066
<212> TYPE: PRT
<213> ORGANISM: Brassica napus

<400> SEQUENCE: 16

Met Glu Ser Asp Gly Glu Thr Ala Gly Lys Pro Met Thr Ser Val Gly
1               5                   10                  15

Gly Gln Ile Cys Gln Ile Cys Ser Asp Ser Val Gly Lys Thr Val Asp
            20                  25                  30

Gly Asp Arg Phe Val Ala Cys Asp Ile Cys Gly Phe Pro Val Cys Arg
        35                  40                  45

Pro Cys Tyr Glu Tyr Glu Arg Lys His Gly Asn Gln Ser Cys Pro Gln
    50                  55                  60

Cys Lys Thr Thr Tyr Lys Arg His Lys Gly Ser Pro Ala Ile Pro Gly
65                  70                  75                  80

Asp Lys Asp Glu Asp Val Phe Ala Asp Glu Ala Thr Val Glu Leu Asn
                85                  90                  95

Tyr Pro Gln Lys Glu Lys Ile Ser Glu Arg Met Leu Gly Trp His Leu
            100                 105                 110

Thr Arg Gly Lys Ser Glu Glu Met Gly Gln Pro Glu Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Cys Asp Ile Asn Gln Ser
                165                 170                 175

Pro Asn Arg Arg Ile Ser Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Gly Pro Val Ser Thr Gln Ala Ala Ser Glu Arg Gly Gly Asp Ile
    210                 215                 220

Asp Ala Ser Thr Asp Ile Leu Ala Asp Glu Ala Leu Leu Asn Asp Glu
225                 230                 235                 240

Ala Arg Gln Pro Leu Ser Arg Lys Val Ser Ile Pro Ser Ser Arg Ile
                245                 250                 255

Asn Pro Tyr Arg Met Val Ile Met Leu Arg Leu Val Ile Leu Cys Leu
            260                 265                 270

Phe Leu His Tyr Arg Ile Thr Asn Pro Val Pro Asn Ala Phe Thr Leu
        275                 280                 285

Trp Leu Ile Ser Val Ile Cys Glu Ile Trp Phe Ala Phe Ser Trp Ile
    290                 295                 300

Leu Asp Gln Phe Pro Lys Trp Phe Pro Val Asn Arg Glu Thr Tyr Leu
305                 310                 315                 320

Asp Arg Leu Ala Leu Arg Tyr Asp Arg Glu Gly Glu Pro Ser Gln Leu
                325                 330                 335
```

```
Ala Ala Val Asp Ile Phe Val Ser Thr Val Asp Pro Leu Lys Glu Pro
            340                 345                 350

Pro Leu Val Thr Ala Asn Thr Val Leu Ser Ile Leu Ala Val Asp Tyr
            355                 360                 365

Pro Val Asp Lys Val Ser Cys Tyr Val Ser Asp Gly Ala Ala Met
    370                 375                 380

Leu Ser Phe Glu Ala Leu Ala Glu Thr Ser Glu Phe Ala Arg Lys Trp
385                 390                 395                 400

Val Pro Phe Cys Lys Lys Tyr Ser Ile Glu Pro Arg Ala Pro Glu Trp
            405                 410                 415

Tyr Phe Ala Ala Lys Ile Asp Tyr Leu Lys Asp Lys Val Gln Thr Ser
            420                 425                 430

Phe Val Lys Asp Arg Arg Ala Met Lys Arg Glu Tyr Glu Glu Phe Lys
            435                 440                 445

Ile Arg Ile Asn Ala Leu Val Ser Lys Ala Leu Lys Cys Pro Glu Glu
            450                 455                 460

Gly Trp Val Met Gln Asp Gly Thr Pro Trp Pro Gly Asn Asn Thr Arg
465                 470                 475                 480

Asp His Pro Gly Met Ile Gln Val Phe Leu Gly Gln Asn Gly Gly Leu
            485                 490                 495

Asp Ala Glu Gly Asn Glu Leu Pro Arg Leu Val Tyr Val Ser Arg Glu
            500                 505                 510

Lys Arg Pro Gly Phe Gln His His Lys Lys Ala Gly Ala Met Asn Ala
            515                 520                 525

Leu Val Arg Val Ser Ala Val Leu Thr Asn Gly Pro Phe Ile Leu Asn
            530                 535                 540

Leu Asp Cys Asp His Tyr Ile Asn Asn Ser Lys Ala Leu Arg Glu Ala
545                 550                 555                 560

Met Cys Phe Leu Met Asp Pro Asn Leu Gly Lys Gln Val Cys Tyr Val
                565                 570                 575

Gln Phe Pro Gln Arg Phe Asp Gly Ile Asp Lys Asn Asp Arg Tyr Ala
            580                 585                 590

Asn Arg Asn Thr Val Phe Phe Asp Ile Asn Leu Arg Gly Leu Asp Gly
            595                 600                 605

Ile Gln Gly Pro Val Tyr Val Gly Thr Gly Cys Val Phe Asn Arg Thr
            610                 615                 620

Ala Leu Tyr Gly Tyr Glu Pro Pro Ile Lys Val Lys His Lys Lys Pro
625                 630                 635                 640

Ser Leu Leu Ser Lys Leu Cys Gly Gly Ser Arg Lys Lys Asn Ser Lys
                645                 650                 655

Ser Lys Lys Asp Ser Asp Lys Lys Ser Gly Arg His Thr Asp Ser
            660                 665                 670

Thr Val Pro Val Phe Asn Leu Asp Asp Ile Glu Glu Gly Val Glu Gly
            675                 680                 685

Ala Gly Phe Asp Asp Glu Lys Ala Leu Leu Met Ser Gln Met Ser Leu
            690                 695                 700

Glu Lys Arg Phe Gly Gln Ser Ala Val Phe Val Ala Ser Thr Leu Met
705                 710                 715                 720

Glu Asn Gly Gly Val Pro Pro Thr Glu Thr Pro Glu Asn Leu Leu Lys
                725                 730                 735

Glu Ala Ile His Val Ile Ser Cys Gly Tyr Glu Asp Lys Ser Asp Trp
            740                 745                 750

Gly Met Glu Ile Gly Trp Ile Tyr Gly Ser Val Thr Glu Asp Ile Leu
```

```
                755                 760                 765
Thr Gly Phe Lys Met His Ala Arg Gly Trp Arg Ser Ile Tyr Cys Met
770                 775                 780

Pro Lys Leu Pro Ala Phe Lys Gly Ser Ala Pro Ile Asn Leu Ser Asp
785                 790                 795                 800

Arg Leu Asn Gln Val Leu Arg Trp Ala Leu Gly Ser Val Glu Ile Leu
                805                 810                 815

Phe Ser Arg His Cys Pro Ile Trp Tyr Gly Tyr Ser Gly Arg Leu Lys
                820                 825                 830

Phe Leu Glu Arg Phe Ala Tyr Val Asn Thr Thr Ile Tyr Pro Leu Thr
                835                 840                 845

Ser Val Pro Leu Leu Leu Tyr Cys Thr Leu Pro Ala Val Cys Leu Phe
850                 855                 860

Thr Asn Gln Phe Ile Ile Pro Gln Ile Ser Asn Ile Ala Ser Ile Trp
865                 870                 875                 880

Phe Leu Ser Leu Phe Leu Ser Ile Phe Ala Thr Gly Ile Leu Glu Met
                885                 890                 895

Arg Trp Ser Gly Val Gly Ile Asp Glu Trp Trp Arg Asn Glu Gln Phe
                900                 905                 910

Trp Val Ile Gly Gly Val Ser Ala His Leu Phe Ala Val Phe Gln Gly
                915                 920                 925

Leu Leu Lys Val Leu Ala Gly Ile Asp Thr Asn Phe Thr Val Thr Ser
930                 935                 940

Lys Ala Ser Asp Glu Asp Gly Asp Phe Ala Glu Leu Tyr Leu Phe Lys
945                 950                 955                 960

Trp Thr Thr Leu Leu Ile Pro Pro Thr Thr Leu Leu Ile Val Asn Leu
                965                 970                 975

Val Gly Val Val Ala Gly Phe Ser Tyr Ala Ile Asn Ser Gly Tyr Gln
                980                 985                 990

Ser Trp Gly Pro Leu Phe Gly Lys Leu Phe Phe Ala Phe Trp Val Ile
                995                 1000                1005

Val His Leu Tyr Pro Phe Leu Lys Gly Leu Met Gly Arg Gln Asn
1010                1015                1020

Arg Thr Pro Thr Ile Val Val Trp Ser Val Leu Leu Ala Ser
1025                1030                1035

Ile Phe Ser Leu Leu Trp Val Arg Ile Asp Pro Phe Thr Lys Arg
1040                1045                1050

Val Thr Gly Pro Asp Ile Leu Glu Cys Gly Ile Asn Cys
1055                1060                1065

<210> SEQ ID NO 17
<211> LENGTH: 1082
<212> TYPE: PRT
<213> ORGANISM: Brassica napus

<400> SEQUENCE: 17

Met Asn Thr Gly Gly Arg Leu Val Ala Gly Ser His Asn Arg Asn Glu
1               5                   10                  15

Phe Val Leu Ile Asn Ala Asp Glu Ser Ala Arg Ile Arg Ser Val Gln
                20                  25                  30

Glu Leu Ser Gly Gln Thr Cys Lys Ile Cys Arg Asp Glu Ile Glu Leu
        35                  40                  45

Thr Val Asp Gly Glu Pro Phe Val Ala Cys Asn Glu Cys Ala Phe Pro
50                  55                  60
```

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
            85                  90                  95

Val Glu Asn Asp Glu Glu Glu Asp Ile Asp Asp Leu Asp Asn Glu
            100                 105                 110

Phe Glu Tyr Glu Asn Gly Gly Val Gly Phe Asp Gln Val Ser Glu Gly
            115                 120                 125

Met Ser Val Ser Arg Arg His Ser Gly Phe Pro Gln Ser Asp Leu Asp
            130                 135                 140

Ser Ala Pro Pro Gly Ser Gln Ile Pro Leu Leu Thr Tyr Gly Asp Glu
145                 150                 155                 160

Asp Ile Glu Ile Ser Ser Asp Arg His Ala Leu Ile Val Pro Pro Ser
            165                 170                 175

Ile Gly Gly His Ser Asn Lys Ser His Pro Ala Ser Leu Ser Asp Pro
            180                 185                 190

Thr Ile Ala Ala His Pro Arg Pro Met Val Pro Gln Lys Asp Leu Ala
            195                 200                 205

Val Tyr Gly Tyr Gly Ser Val Ala Trp Lys Asp Arg Met Glu Asp Trp
210                 215                 220

Lys Lys Lys Gln Asn Glu Lys Leu Gln Val Val Arg His Glu Gly Asp
225                 230                 235                 240

Pro Asp Phe Glu Asp Gly Asp Asp Ile Pro Met Met Asp Glu Gly Arg
            245                 250                 255

Gln Pro Leu Ser Arg Lys Ile Pro Ile Lys Ser Ser Lys Ile Asn Pro
            260                 265                 270

Tyr Arg Met Leu Ile Val Leu Arg Leu Val Ile Leu Gly Leu Phe Phe
            275                 280                 285

His Tyr Arg Ile Leu His Pro Val Lys Asp Ala Tyr Ala Leu Trp Leu
            290                 295                 300

Ile Ser Val Ile Cys Glu Ile Trp Phe Ala Val Ser Trp Val Leu Asp
305                 310                 315                 320

Gln Phe Pro Lys Trp Tyr Pro Ile Glu Arg Glu Thr Tyr Leu Asp Arg
            325                 330                 335

Leu Ser Leu Arg Tyr Glu Lys Glu Gly Lys Pro Ser Glu Leu Ser Ala
            340                 345                 350

Val Asp Val Phe Val Ser Thr Val Asp Pro Leu Lys Glu Pro Pro Leu
            355                 360                 365

Ile Thr Ala Asn Thr Val Leu Ser Ile Leu Ala Val Asp Tyr Pro Val
            370                 375                 380

Asp Arg Val Ala Cys Tyr Val Ser Asp Asp Gly Ala Ala Met Leu Thr
385                 390                 395                 400

Phe Glu Ala Leu Ser Glu Thr Ala Glu Phe Ala Arg Lys Trp Val Pro
            405                 410                 415

Phe Cys Lys Lys Tyr Cys Ile Glu Pro Arg Ala Pro Glu Trp Tyr Phe
            420                 425                 430

Cys His Lys Met Asp Tyr Leu Lys Asn Lys Val His Pro Ala Phe Val
            435                 440                 445

Arg Glu Arg Arg Ala Met Lys Arg Asp Tyr Glu Glu Phe Lys Val Lys
            450                 455                 460

Ile Asn Ala Leu Val Ala Thr Ala Gln Lys Val Pro Glu Glu Gly Trp
465                 470                 475                 480

Thr Met Gln Asp Gly Thr Pro Trp Pro Gly Asn Ser Val Arg Asp His

-continued

```
                    485                 490                 495
Pro Gly Met Ile Gln Val Phe Leu Gly Ser Asp Gly Val Arg Asp Val
                500                 505                 510
Glu Asn Asn Glu Leu Pro Arg Leu Val Tyr Val Ser Arg Glu Lys Arg
                515                 520                 525
Pro Gly Phe Asp His His Lys Lys Ala Gly Ala Met Asn Ser Leu Ile
                530                 535                 540
Arg Val Ser Gly Val Leu Ser Asn Ala Pro Tyr Leu Leu Asn Val Asp
545                 550                 555                 560
Cys Asp His Tyr Ile Asn Asn Ser Lys Ala Leu Arg Glu Ala Met Cys
                565                 570                 575
Phe Met Met Asp Pro Gln Ser Gly Lys Lys Ile Cys Tyr Val Gln Phe
                580                 585                 590
Pro Gln Arg Phe Asp Gly Ile Asp Arg His Asp Arg Tyr Ser Asn Arg
                595                 600                 605
Asn Val Val Phe Phe Asp Ile Asn Met Lys Gly Leu Asp Gly Leu Gln
                610                 615                 620
Gly Pro Ile Tyr Val Gly Thr Gly Cys Val Phe Arg Arg Gln Ala Leu
625                 630                 635                 640
Tyr Gly Phe Asp Ala Pro Lys Lys Lys Ala Pro Arg Lys Thr Cys
                            645                 650                 655
Asn Cys Trp Pro Lys Trp Cys Phe Met Cys Cys Gly Ser Arg Lys Asn
                660                 665                 670
Arg Gln Ala Lys Lys Val Ala Ala Asp Lys Lys Lys Asn Arg Glu
                675                 680                 685
Ala Ser Lys Gln Ile His Ala Leu Glu Asn Ile Glu Glu Gly Ser Val
                690                 695                 700
Thr Lys Gly Ser Asn Val Glu Gln Ser Thr Glu Ala Met Gln Leu Lys
705                 710                 715                 720
Leu Glu Lys Lys Phe Gly Gln Ser Pro Val Phe Val Ala Ser Ala Arg
                725                 730                 735
Met Gln Asn Gly Gly Met Ala Arg Asn Ala Ser Pro Ala Cys Leu Leu
                740                 745                 750
Lys Glu Ala Ile Gln Val Ile Ser Cys Gly Tyr Glu Asp Lys Thr Glu
                755                 760                 765
Trp Gly Lys Glu Ile Gly Trp Ile Tyr Gly Ser Val Thr Glu Asp Ile
                770                 775                 780
Leu Thr Gly Phe Lys Met His Ser His Gly Trp Arg Ser Val Tyr Cys
785                 790                 795                 800
Thr Pro Lys Leu Pro Ala Phe Lys Gly Ser Ala Pro Ile Asn Leu Ser
                805                 810                 815
Asp Arg Leu His Gln Val Leu Arg Trp Ala Leu Gly Ser Val Glu Ile
                820                 825                 830
Phe Leu Ser Arg His Cys Pro Ile Trp Tyr Gly Tyr Gly Gly Gly Leu
                835                 840                 845
Lys Trp Leu Glu Arg Leu Ser Tyr Ile Asn Ser Val Val Tyr Pro Trp
                850                 855                 860
Thr Ser Leu Pro Leu Ile Val Tyr Cys Ser Leu Pro Ala Ile Cys Leu
865                 870                 875                 880
Leu Thr Gly Lys Phe Ile Val Pro Glu Ile Ser Asn Tyr Ala Ser Ile
                            885                 890                 895
Leu Phe Met Ala Leu Phe Ser Ser Ile Ala Ile Thr Gly Ile Leu Glu
                900                 905                 910
```

```
Met Gln Trp Gly Lys Val Gly Ile Asp Asp Trp Trp Arg Asn Glu Gln
        915                 920                 925

Phe Trp Val Ile Gly Gly Val Ser Ala His Leu Phe Ala Leu Phe Gln
        930                 935                 940

Gly Leu Leu Lys Val Leu Ala Gly Val Asp Thr Asn Phe Thr Val Thr
945                 950                 955                 960

Ser Lys Ala Ala Asp Asp Gly Glu Phe Ser Asp Leu Tyr Leu Phe Lys
                965                 970                 975

Trp Thr Ser Leu Leu Ile Pro Pro Thr Thr Leu Leu Ile Ile Asn Val
            980                 985                 990

Ile Gly Ile Val Val Gly Ile Ser Asp Ala Ile Ser Asn Gly Tyr Asp
        995                 1000                1005

Ser Trp Gly Pro Leu Phe Gly Arg Leu Phe Phe Ala Leu Trp Val
    1010                1015                1020

Val Ile His Leu Tyr Pro Phe Leu Lys Gly Leu Leu Gly Lys Gln
    1025                1030                1035

Asp Arg Met Pro Thr Ile Ile Val Val Trp Ser Ile Leu Leu Ala
    1040                1045                1050

Ser Ile Leu Thr Leu Leu Trp Val Arg Val Asn Pro Phe Val Ala
    1055                1060                1065

Lys Gly Gly Pro Val Leu Glu Ile Cys Gly Leu Asp Cys Leu
    1070                1075                1080

<210> SEQ ID NO 18
<211> LENGTH: 1079
<212> TYPE: PRT
<213> ORGANISM: Brassica napus

<400> SEQUENCE: 18

Met Asn Thr Gly Gly Arg Leu Ile Ala Gly Ser His Asn Arg Asn Glu
1               5                   10                  15

Phe Val Leu Ile Asn Ala Asp Glu Asn Ala Arg Ile Arg Ser Val Gln
            20                  25                  30

Glu Leu Arg Gly Gln Thr Cys Glu Ile Cys Arg Asp Glu Ile Glu Ser
        35                  40                  45

Thr Val Glu Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
                85                  90                  95

Val Glu Asn Asp Glu Glu Asp Asp Val Asp Asp Ile Asp Asn Glu
            100                 105                 110

Phe Glu Tyr Gly Gly Asn Gly Ile Gly Phe Asp Gln Val Ser Glu Gly
        115                 120                 125

Val Ser Val Ser Arg Arg His Ser Gly Asp Leu Asp Ser Ala Pro Pro
    130                 135                 140

Gly Ser Gln Ile Pro Leu Leu Thr Tyr Gly Asp Glu Asp Ile Glu Ile
145                 150                 155                 160

Ser Ser Asp Arg His Ala Leu Ile Val Pro Ser Leu Ser Gly His
                165                 170                 175

Gly Ser Lys Val His Pro Val Ser Leu Ser Asp Pro Thr Ile Ala Ala
            180                 185                 190

His Pro Arg Pro Met Val Pro Gln Lys Asp Leu Ala Val Tyr Gly Tyr
```

```
            195                 200                 205
Gly Ser Val Ala Trp Lys Asp Arg Met Glu Trp Lys Arg Lys Gln
210                 215                 220
Asn Glu Lys Leu Gln Val Val Arg His Glu Gly Asp Pro Asp Phe Glu
225                 230                 235                 240
Asp Gly Asp Asp Ile Pro Met Met Asp Glu Gly Arg Gln Pro Leu Ser
                245                 250                 255
Arg Lys Ile Pro Ile Lys Ser Ser Lys Ile Asn Pro Tyr Arg Met Leu
                260                 265                 270
Ile Val Leu Arg Leu Val Ile Leu Ser Leu Phe Phe His Tyr Arg Ile
                275                 280                 285
Leu His Pro Val Lys Asp Ala Tyr Ala Leu Trp Leu Thr Ser Val Ile
                290                 295                 300
Cys Glu Ile Trp Phe Ala Val Ser Trp Val Leu Asp Gln Phe Pro Lys
305                 310                 315                 320
Trp Tyr Pro Ile Glu Arg Glu Thr Tyr Leu Asp Arg Leu Ser Leu Arg
                325                 330                 335
Tyr Glu Lys Glu Gly Lys Pro Ser Glu Leu Ser Pro Val Asp Val Phe
                340                 345                 350
Val Ser Thr Val Asp Pro Leu Lys Glu Pro Pro Leu Ile Thr Ala Asn
                355                 360                 365
Thr Val Leu Ser Ile Leu Ala Val Asp Tyr Pro Val Asp Lys Val Ala
                370                 375                 380
Cys Tyr Val Ser Asp Asp Gly Ala Ala Met Leu Thr Phe Glu Ala Leu
385                 390                 395                 400
Ser Glu Thr Ala Glu Phe Ala Arg Lys Trp Val Pro Phe Cys Lys Lys
                405                 410                 415
Tyr Cys Ile Glu Pro Arg Ala Pro Glu Trp Tyr Phe Cys His Lys Met
                420                 425                 430
Asp Tyr Leu Lys Asn Lys Val His Pro Ala Phe Val Arg Glu Arg Arg
                435                 440                 445
Ala Met Lys Arg Asp Tyr Glu Glu Phe Lys Val Lys Ile Asn Ala Leu
450                 455                 460
Val Ala Thr Ala Gln Lys Val Pro Glu Glu Gly Trp Thr Met Gln Asp
465                 470                 475                 480
Gly Thr Pro Trp Pro Gly Asn Ser Thr Arg Asp His Pro Gly Met Ile
                485                 490                 495
Gln Val Phe Leu Gly Ser Asp Gly Val Arg Asp Val Glu Asn Asn Glu
                500                 505                 510
Leu Pro Arg Leu Val Tyr Val Ser Arg Glu Lys Arg Pro Gly Phe Asp
                515                 520                 525
His His Lys Lys Ala Gly Ala Met Asn Ser Leu Ile Arg Val Ser Gly
                530                 535                 540
Val Leu Ser Asn Ala Pro Tyr Leu Leu Asn Val Asp Cys Asp His Tyr
545                 550                 555                 560
Ile Asn Asn Ser Lys Ala Leu Arg Glu Ala Met Cys Phe Met Met Asp
                565                 570                 575
Pro Gln Ser Gly Lys Lys Ile Cys Tyr Val Gln Phe Pro Gln Arg Phe
                580                 585                 590
Asp Gly Ile Asp Arg His Asp Arg Tyr Ser Asn Arg Asn Val Val Phe
                595                 600                 605
Phe Asp Ile Asn Met Lys Gly Leu Asp Gly Leu Gln Gly Pro Ile Tyr
                610                 615                 620
```

-continued

Val Gly Thr Gly Cys Val Phe Arg Arg Gln Ala Leu Tyr Gly Phe Asp
625                 630                 635                 640

Ala Pro Lys Lys Lys Ala Pro Arg Lys Thr Cys Asn Cys Trp Pro
            645                 650                 655

Lys Trp Cys Phe Leu Cys Cys Gly Ser Arg Lys Asn Arg Lys Ala Lys
        660                 665                 670

Thr Leu Ala Ala Ala Asp Lys Lys Lys Asn Arg Glu Ala Ser Lys
    675                 680                 685

Gln Ile His Ala Leu Glu Asn Ile Glu Glu Gly Pro Val Ser Lys Gly
    690                 695                 700

Ser Asn Val Glu Leu Ser Ser Glu Val Met Gln Leu Lys Leu Glu Lys
705                 710                 715                 720

Lys Phe Gly Gln Ser Pro Val Phe Val Ala Ser Ala Arg Met Gln Asn
                725                 730                 735

Gly Gly Met Ala Arg Asn Ala Ser Pro Ala Cys Leu Leu Lys Glu Ala
            740                 745                 750

Ile Gln Val Ile Ser Cys Gly Tyr Glu Asp Lys Thr Glu Trp Gly Lys
        755                 760                 765

Glu Ile Gly Trp Ile Tyr Gly Ser Val Thr Glu Asp Ile Leu Thr Gly
    770                 775                 780

Phe Lys Met His Ser His Gly Trp Arg Ser Val Tyr Cys Thr Pro Lys
785                 790                 795                 800

Leu Pro Ala Phe Lys Gly Ser Ala Pro Ile Asn Leu Ser Asp Arg Leu
                805                 810                 815

His Gln Val Leu Arg Trp Ala Leu Gly Ser Val Glu Ile Phe Leu Ser
            820                 825                 830

Arg His Cys Pro Ile Trp Tyr Gly Tyr Gly Gly Gly Leu Lys Trp Leu
        835                 840                 845

Glu Arg Leu Ser Tyr Ile Asn Ser Val Val Tyr Pro Trp Thr Ser Leu
    850                 855                 860

Pro Leu Ile Val Tyr Cys Ser Leu Pro Ala Ile Cys Leu Leu Thr Gly
865                 870                 875                 880

Lys Phe Ile Val Pro Glu Ile Ser Asn Tyr Ala Ser Ile Leu Phe Met
                885                 890                 895

Ala Leu Phe Ser Ser Ile Ala Val Thr Gly Ile Leu Glu Met Gln Trp
            900                 905                 910

Gly Lys Val Gly Ile Asp Asp Trp Trp Arg Asn Glu Gln Phe Trp Val
        915                 920                 925

Ile Gly Gly Val Ser Ala His Leu Phe Ala Leu Phe Gln Gly Leu Leu
    930                 935                 940

Lys Val Leu Ala Gly Val Asp Thr Asn Phe Thr Val Thr Ser Lys Ala
945                 950                 955                 960

Ala Asp Asp Gly Glu Phe Ser Asp Leu Tyr Leu Phe Lys Trp Thr Ser
                965                 970                 975

Leu Leu Ile Pro Pro Thr Thr Leu Leu Ile Ile Asn Val Ile Gly Ile
            980                 985                 990

Val Val Gly Ile Ser Asp Ala Ile Ser Asn Gly Tyr Asp Ser Trp Gly
        995                 1000                1005

Pro Leu Phe Gly Arg Leu Phe Phe Ala Leu Trp Val Val Ile His
    1010                1015                1020

Leu Tyr Pro Phe Leu Lys Gly Leu Leu Gly Lys Gln Asp Arg Met
    1025                1030                1035

-continued

```
Pro Thr Ile Ile Val Val Trp Ser Ile Leu Leu Ala Ser Ile Leu
    1040                1045                1050

Thr Leu Leu Trp Val Arg Val Asn Pro Phe Val Ala Lys Gly Gly
    1055                1060                1065

Pro Val Leu Glu Ile Cys Gly Leu Asp Cys Leu
    1070                1075

<210> SEQ ID NO 19
<211> LENGTH: 1083
<212> TYPE: PRT
<213> ORGANISM: Brassica napus

<400> SEQUENCE: 19

Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Ala Leu Lys
            20                  25                  30

Asn Met Asp Pro His Thr Cys Gln Ile Cys Gly Asp Asn Ala Gly Leu
        35                  40                  45

Thr Glu Thr Gly Asp Leu Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65                  70                  75                  80

Cys Pro Gln Cys Lys Thr Arg Tyr Arg Arg Leu Arg Gly Ser Pro Arg
                85                  90                  95

Val Glu Gly Asp Glu Asp Glu Asp Val Asp Asp Ile Glu Asn Glu
            100                 105                 110

Phe Asn Tyr Thr Gln Gly Ala Asn Lys Gly Arg Arg Gln Gln Arg His
        115                 120                 125

Gly Glu Glu Phe Ser Ser Ser Arg His Glu Ser Gln Pro Ile Pro
    130                 135                 140

Leu Leu Thr His Gly His Thr Val Ser Gly Glu Ile Arg Thr Pro Asp
145                 150                 155                 160

Thr Gln Ser Val Arg Thr Thr Ser Gly Pro Leu Gly Pro Gly Asp Arg
                165                 170                 175

Asn Ala Ile Ser Ser Pro Tyr Ile Asp Pro Arg Gln Pro Val Pro Val
            180                 185                 190

Arg Ile Val Asp Pro Ser Lys Asp Leu Asn Ser Tyr Gly Leu Gly Asn
        195                 200                 205

Val Asp Trp Lys Glu Arg Val Glu Gly Trp Lys Leu Lys Gln Glu Lys
    210                 215                 220

Asn Met Val Gln Met Thr Gly Lys Tyr His Glu Gly Lys Gly Gly Glu
225                 230                 235                 240

Ile Glu Gly Thr Gly Ser Asn Gly Glu Glu Leu Gln Met Ala Asp Asp
                245                 250                 255

Thr Arg Leu Pro Met Ser Arg Ile Val Pro Ile Pro Ser His Leu
            260                 265                 270

Thr Pro Tyr Arg Val Val Ile Ile Leu Arg Leu Ile Ile Leu Gly Phe
        275                 280                 285

Phe Leu Gln Tyr Arg Thr Thr His Pro Val Lys Asp Ala Tyr Pro Leu
    290                 295                 300

Trp Leu Thr Ser Val Ile Cys Glu Ile Trp Phe Ala Phe Ser Trp Leu
305                 310                 315                 320

Leu Asp Gln Phe Pro Lys Trp Tyr Pro Ile Asn Arg Glu Thr Tyr Leu
                325                 330                 335
```

```
Asp Arg Leu Ala Ile Arg Tyr Asp Arg Asp Gly Glu Pro Ser Gln Leu
            340                 345                 350

Thr Pro Val Asp Val Phe Val Ser Thr Val Asp Pro Leu Lys Glu Pro
            355                 360                 365

Pro Leu Val Thr Ala Asn Thr Val Leu Ser Ile Leu Ala Val Asp Tyr
370                 375                 380

Pro Val Asp Lys Val Ala Cys Tyr Val Ser Asp Asp Gly Ala Ala Met
385                 390                 395                 400

Leu Thr Phe Glu Ser Leu Ser Glu Thr Ala Glu Phe Ala Lys Lys Trp
                405                 410                 415

Val Pro Phe Cys Lys Lys Phe Ser Ile Glu Pro Arg Ala Pro Glu Phe
            420                 425                 430

Tyr Phe Ala Gln Lys Ile Asp Tyr Leu Lys Asp Lys Ile Gln Pro Ser
            435                 440                 445

Phe Val Lys Glu Arg Arg Ala Met Lys Arg Glu Tyr Glu Glu Phe Lys
            450                 455                 460

Val Arg Ile Asn Ala Leu Val Ala Lys Ala Gln Lys Ile Pro Glu Glu
465                 470                 475                 480

Gly Trp Thr Met Gln Asp Gly Thr Pro Trp Pro Gly Asn Asn Thr Arg
                485                 490                 495

Asp His Pro Gly Met Ile Gln Val Phe Leu Gly His Ser Gly Gly Leu
            500                 505                 510

Asp Thr Asp Gly Asn Glu Leu Pro Arg Leu Ile Tyr Val Ser Arg Glu
            515                 520                 525

Lys Arg Pro Gly Phe Gln His Lys Lys Ala Gly Ala Met Asn Ala
            530                 535                 540

Leu Ile Arg Val Ser Ala Val Leu Thr Asn Gly Ala Tyr Leu Leu Asn
545                 550                 555                 560

Val Asp Cys Asp His Tyr Phe Asn Asn Ser Lys Ala Ile Lys Glu Ala
                565                 570                 575

Met Cys Phe Leu Met Asp Pro Ala Tyr Gly Lys Lys Cys Cys Tyr Val
            580                 585                 590

Gln Phe Pro Gln Arg Phe Asp Gly Ile Asp Leu His Asp Arg Tyr Ala
            595                 600                 605

Asn Arg Asn Ile Val Phe Phe Asp Ile Asn Leu Lys Gly Leu Asp Gly
            610                 615                 620

Ile Gln Gly Pro Val Tyr Val Gly Thr Gly Cys Cys Phe Asn Arg Gln
625                 630                 635                 640

Ala Leu Tyr Gly Tyr Asp Pro Val Leu Thr Glu Glu Asp Leu Glu Pro
                645                 650                 655

Asn Ile Ile Val Lys Ser Cys Cys Gly Ser Arg Lys Lys Gly Lys Lys
            660                 665                 670

Ser Lys Lys Tyr Asn Tyr Asp Gln Gln Arg Arg Gly Ile Asn Arg Ser
            675                 680                 685

Asp Ser Asn Ala Pro Leu Phe Asn Met Asp Asp Ile Glu Glu Gly Phe
            690                 695                 700

Glu Gly Tyr Asp Asp Glu Arg Ser Ile Leu Met Ser Gln Lys Ser Val
705                 710                 715                 720

Glu Lys Arg Phe Gly Gln Ser Pro Val Phe Ile Ala Ala Thr Phe Met
            725                 730                 735

Glu Gln Gly Gly Ile Pro Pro Thr Thr Asn Pro Ala Thr Leu Leu Lys
            740                 745                 750
```

```
Glu Ala Ile His Val Ile Ser Cys Gly Tyr Glu Asp Lys Thr Glu Trp
            755                 760                 765

Gly Lys Glu Ile Gly Trp Ile Tyr Gly Ser Val Thr Glu Asp Ile Leu
        770                 775                 780

Thr Gly Phe Lys Met His Ala Arg Gly Trp Met Ser Ile Tyr Cys Asn
785                 790                 795                 800

Pro Pro Arg Pro Ala Phe Lys Gly Ser Ala Pro Ile Asn Leu Ser Asp
                805                 810                 815

Arg Leu Asn Gln Val Leu Arg Trp Ala Leu Gly Ser Ile Glu Ile Leu
            820                 825                 830

Leu Ser Arg His Cys Pro Ile Trp Tyr Gly Tyr Thr Gly Arg Leu Arg
        835                 840                 845

Leu Leu Glu Arg Leu Ala Tyr Ile Asn Thr Ile Val Tyr Pro Ile Thr
    850                 855                 860

Ala Leu Pro Leu Ile Ala Tyr Cys Ile Leu Pro Ala Phe Cys Leu Ile
865                 870                 875                 880

Thr Asp Lys Phe Ile Ile Pro Glu Ile Ser Asn Tyr Ala Ser Ile Trp
                885                 890                 895

Phe Ile Leu Leu Phe Ile Ser Ile Ala Val Thr Gly Val Leu Glu Leu
            900                 905                 910

Arg Trp Ser Gly Val Ser Ile Glu Asp Trp Trp Arg Asn Glu Gln Phe
        915                 920                 925

Trp Val Ile Gly Gly Thr Ser Ala His Leu Phe Ala Val Phe Gln Gly
    930                 935                 940

Leu Leu Lys Val Leu Ala Gly Ile Asp Thr Asn Phe Thr Val Thr Ser
945                 950                 955                 960

Lys Ala Ser Asp Glu Asp Gly Asp Phe Ala Glu Leu Tyr Ile Phe Lys
                965                 970                 975

Trp Thr Ala Leu Leu Ile Pro Pro Thr Thr Val Leu Val Asn Leu
            980                 985                 990

Ile Gly Ile Val Ala Gly Val Ser Tyr Ala Val Asn Ser Gly Tyr Gln
        995                 1000                1005

Ser Trp Gly Pro Leu Phe Gly Lys Leu Phe Phe Ala Leu Trp Val
    1010                1015                1020

Ile Ala His Leu Tyr Pro Phe Leu Lys Gly Leu Met Gly Arg Gln
    1025                1030                1035

Asn Arg Thr Pro Thr Ile Val Ile Val Trp Ser Val Leu Leu Ala
    1040                1045                1050

Ser Ile Phe Ser Leu Leu Trp Val Arg Ile Asn Pro Phe Val Ser
    1055                1060                1065

Val Thr Pro Gln Ala Asn Pro Thr Ala Val Pro Gly Gly Val Phe
    1070                1075                1080

<210> SEQ ID NO 20
<211> LENGTH: 1066
<212> TYPE: PRT
<213> ORGANISM: Brassica napus

<400> SEQUENCE: 20

Met Glu Ser Asp Gly Glu Thr Ala Gly Lys Pro Met Thr Ser Val Gly
1               5                   10                  15

Gly Gln Ile Cys Gln Ile Cys Ser Asp Asn Val Gly Lys Thr Val Asp
            20                  25                  30

Gly Asp Arg Phe Val Ala Cys Asp Ile Cys Gly Phe Pro Val Cys Arg
        35                  40                  45
```

-continued

```
Pro Cys Tyr Glu Tyr Glu Arg Lys His Gly Asn Gln Ser Cys Pro Gln
    50                  55                  60
Cys Lys Thr Thr Tyr Lys Arg His Lys Gly Ser Pro Ala Ile Pro Gly
65                  70                  75                  80
Asp Lys Asp Glu Asp Val Phe Ala Asp Glu Ala Thr Val Glu Leu Asn
                85                  90                  95
Tyr Pro Gln Lys Glu Lys Ile Ser Glu Arg Met Leu Gly Trp His Leu
            100                 105                 110
Thr Arg Gly Lys Ser Glu Glu Met Gly Gln Pro Glu Tyr Asp Lys Glu
            115                 120                 125
Val Ser His Asn His Leu Pro Arg Leu Thr Ser Arg Gln Asp Thr Ser
            130                 135                 140
Gly Glu Phe Ser Ala Ala Ser Pro Glu Arg Leu Ser Val Ser Ser Thr
145                 150                 155                 160
Ile Ala Gly Gly Lys Arg Leu Pro Tyr Ser Ser Asp Ile Asn Gln Ser
                165                 170                 175
Pro Asn Arg Arg Ile Ser Asp Pro Val Gly Leu Gly Asn Val Ala Trp
            180                 185                 190
Lys Glu Arg Val Asp Gly Trp Lys Met Lys Gln Glu Lys Asn Asn Gly
            195                 200                 205
Gly Pro Val Ser Thr Gln Ala Ala Ser Glu Arg Gly Gly Gly Asp Ile
    210                 215                 220
Asp Ala Ser Thr Asp Ile Leu Ala Asp Glu Ala Leu Leu Asn Asp Glu
225                 230                 235                 240
Ala Arg Gln Pro Leu Ser Arg Lys Val Ser Ile Pro Ser Ser Arg Ile
                245                 250                 255
Asn Pro Tyr Arg Met Val Ile Met Leu Arg Leu Val Ile Leu Cys Leu
            260                 265                 270
Phe Leu His Tyr Arg Ile Thr Asn Pro Val Pro Asn Ala Phe Thr Leu
            275                 280                 285
Trp Leu Ile Ser Val Ile Cys Glu Ile Trp Phe Ala Phe Ser Trp Ile
            290                 295                 300
Leu Asp Gln Phe Pro Lys Trp Phe Pro Val Asn Arg Glu Thr Tyr Leu
305                 310                 315                 320
Asp Arg Leu Ala Leu Arg Tyr Asp Arg Glu Gly Glu Pro Ser Gln Leu
                325                 330                 335
Ala Ala Val Asp Ile Phe Val Ser Thr Val Asp Pro Leu Lys Glu Pro
            340                 345                 350
Pro Leu Val Thr Ala Asn Thr Val Leu Ser Ile Leu Ala Val Asp Tyr
            355                 360                 365
Pro Val Asp Lys Val Ser Cys Tyr Val Ser Asp Gly Ala Ala Met
            370                 375                 380
Leu Ser Phe Glu Ala Leu Ala Glu Thr Ser Glu Phe Ala Arg Lys Trp
385                 390                 395                 400
Val Pro Phe Cys Lys Lys Tyr Ser Ile Glu Pro Arg Ala Pro Glu Trp
                405                 410                 415
Tyr Phe Ala Ala Lys Ile Asp Tyr Leu Lys Asp Lys Val Gln Thr Ser
            420                 425                 430
Phe Val Lys Asp Arg Arg Ala Met Lys Arg Glu Tyr Glu Glu Phe Lys
            435                 440                 445
Ile Arg Ile Asn Ala Leu Val Ser Lys Ala Leu Lys Cys Pro Glu Glu
    450                 455                 460
```

```
Gly Trp Val Met Gln Asp Gly Thr Pro Trp Pro Gly Asn Asn Thr Arg
465                 470                 475                 480

Asp His Pro Gly Met Ile Gln Val Phe Leu Gly Gln Asn Gly Gly Leu
            485                 490                 495

Asp Ala Glu Gly Asn Glu Leu Pro Arg Leu Val Tyr Val Ser Arg Glu
        500                 505                 510

Lys Arg Pro Gly Phe Gln His His Lys Lys Ala Gly Ala Met Asn Ala
    515                 520                 525

Leu Val Arg Val Ser Ala Val Leu Thr Asn Gly Pro Phe Ile Leu Asn
530                 535                 540

Leu Asp Cys Asp His Tyr Ile Asn Asn Ser Lys Ala Leu Arg Glu Ala
545                 550                 555                 560

Met Cys Phe Leu Met Asp Pro Asn Leu Gly Lys Gln Val Cys Tyr Val
                565                 570                 575

Gln Phe Pro Gln Arg Phe Asp Gly Ile Asp Lys Asn Asp Arg Tyr Ala
            580                 585                 590

Asn Arg Asn Thr Val Phe Phe Asp Ile Asn Leu Arg Gly Leu Asp Gly
        595                 600                 605

Ile Gln Gly Pro Val Tyr Val Gly Thr Gly Cys Val Phe Asn Arg Thr
    610                 615                 620

Ala Leu Tyr Gly Tyr Glu Pro Pro Ile Lys Val Lys His Lys Lys Pro
625                 630                 635                 640

Ser Leu Leu Ser Lys Leu Cys Gly Gly Ser Arg Lys Lys Asn Ser Lys
                645                 650                 655

Ser Lys Lys Asp Ser Asp Lys Lys Ser Gly Arg His Thr Asp Ser
            660                 665                 670

Thr Val Pro Val Phe Asn Leu Asp Asp Ile Glu Glu Gly Val Glu Gly
            675                 680                 685

Ala Gly Phe Asp Asp Glu Lys Ala Leu Leu Met Ser Gln Met Ser Leu
        690                 695                 700

Glu Lys Arg Phe Gly Gln Ser Ala Val Phe Val Ala Ser Thr Leu Met
705                 710                 715                 720

Glu Asn Gly Gly Val Pro Pro Thr Glu Thr Pro Glu Asn Leu Leu Lys
                725                 730                 735

Glu Ala Ile His Val Ile Ser Cys Gly Tyr Glu Asp Lys Ser Asp Trp
            740                 745                 750

Gly Met Glu Ile Gly Trp Ile Tyr Gly Ser Val Thr Glu Asp Ile Leu
        755                 760                 765

Thr Gly Phe Lys Met His Ala Arg Gly Trp Arg Ser Ile Tyr Cys Met
770                 775                 780

Pro Lys Leu Pro Ala Phe Lys Gly Ser Ala Pro Ile Asn Leu Ser Asp
785                 790                 795                 800

Arg Leu Asn Gln Val Leu Arg Trp Ala Leu Gly Ser Val Glu Ile Leu
            805                 810                 815

Phe Ser Arg His Cys Pro Ile Trp Tyr Gly Tyr Ser Gly Arg Leu Lys
        820                 825                 830

Phe Leu Glu Arg Phe Ala Tyr Val Asn Thr Thr Ile Tyr Pro Leu Thr
    835                 840                 845

Ser Val Pro Leu Leu Phe Tyr Cys Thr Leu Pro Ala Val Cys Leu Phe
    850                 855                 860

Thr Asn Gln Phe Ile Ile Pro Gln Ile Ser Asn Ile Ala Ser Ile Trp
865                 870                 875                 880

Phe Leu Ser Leu Phe Leu Ser Ile Phe Ala Thr Gly Ile Leu Glu Met
```

```
                    885                 890                 895
Arg Trp Ser Gly Val Gly Ile Asp Glu Trp Trp Arg Asn Glu Gln Phe
                200                 905                 910

Trp Val Ile Gly Gly Val Ser Ala His Leu Phe Ala Val Phe Gln Gly
                915                 920                 925

Leu Leu Lys Val Leu Ala Gly Ile Asp Thr Asn Phe Thr Val Thr Ser
                930                 935                 940

Lys Ala Ser Asp Glu Asp Gly Asp Phe Ala Glu Leu Tyr Leu Phe Lys
945                 950                 955                 960

Trp Thr Thr Leu Leu Ile Pro Pro Thr Leu Leu Ile Val Asn Leu
                965                 970                 975

Val Gly Val Val Ala Gly Phe Ser Tyr Ala Ile Asn Ser Gly Tyr Gln
                980                 985                 990

Ser Trp Gly Pro Leu Phe Gly Lys Leu Phe Phe Ala Phe Trp Val Ile
                995                1000                1005

Val His Leu Tyr Pro Phe Leu Lys Gly Leu Met Gly Arg Gln Asn
               1010                1015                1020

Arg Thr Pro Thr Ile Val Val Trp Ser Val Leu Leu Ala Ser
               1025                1030                1035

Ile Phe Ser Leu Leu Trp Val Arg Ile Asp Pro Phe Thr Lys Arg
               1040                1045                1050

Val Thr Gly Pro Asp Ile Leu Glu Cys Gly Ile Asn Cys
               1055                1060                1065

<210> SEQ ID NO 21
<211> LENGTH: 1080
<212> TYPE: PRT
<213> ORGANISM: Brassica napus

<400> SEQUENCE: 21

Met Glu Ala Ser Ser Gly Leu Val Ala Gly Ser Tyr Arg Arg Asn Glu
1               5                   10                  15

Leu Val Arg Ile Arg His Glu Ser Asp Gly Ser Lys Pro Leu Lys
                20                  25                  30

Asn Met Asp Arg Glu Ile Cys Gln Ile Cys Gly Asp His Ala Gly Leu
                35                  40                  45

Thr Glu Thr Gly Asp Leu Phe Val Ala Cys Asn Glu Cys Ala Phe Pro
50                  55                  60

Val Cys Arg Pro Cys Tyr Asp Tyr Glu Arg Lys Asp Gly Thr Gln Cys
65                  70                  75                  80

Cys Pro His Cys Lys Thr Arg Tyr Arg Arg Leu Arg Gly His Pro Arg
                85                  90                  95

Val Glu Gly Asp Glu Asp Glu Asp Val Asp Asp Ile Glu Asn Glu
                100                 105                 110

Phe Ser Tyr Ala Gln Gly Gly Ala Asn Lys Pro Arg Arg Arg Glu Glu
                115                 120                 125

Phe Ser Ser Ser Ser Arg His Asp Ser Gln Pro Ile Pro Leu Leu Thr
                130                 135                 140

His Gly His Gly Val Ser Gly Glu Ile Arg Thr Pro Asp Thr Gln Ser
145                 150                 155                 160

Val Arg Thr Thr Ser Gly Pro Leu Gly Pro Gly Glu Arg Asn Ala Ile
                165                 170                 175

Ser Ser Ser Tyr Ile Asp Pro Arg Gln Pro Val Pro Val Arg Ile Val
                180                 185                 190
```

```
Asp Pro Ser Lys Asp Leu Asn Ser Tyr Gly Leu Gly Asn Val Asp Trp
            195                 200                 205

Lys Glu Arg Val Glu Gly Trp Lys Leu Lys Gln Glu Lys Asn Met Leu
    210                 215                 220

Gln Met Thr Gly Lys Tyr His Glu Gly Lys Gly Gly Glu Ile Glu Gly
225                 230                 235                 240

Thr Gly Ser Asn Gly Glu Glu Leu Gln Met Ala Asp Asp Thr Arg Leu
                245                 250                 255

Pro Met Ser Arg Ile Val Pro Ile Pro Ser His Leu Thr Pro Tyr
                260                 265                 270

Arg Val Val Ile Ile Leu Arg Leu Ile Ile Leu Gly Phe Phe Leu Gln
                275                 280                 285

Tyr Arg Thr Thr His Pro Val Lys Asp Ala Tyr Pro Leu Trp Leu Thr
    290                 295                 300

Ser Val Ile Cys Glu Ile Trp Phe Ala Phe Ser Trp Leu Leu Asp Gln
305                 310                 315                 320

Phe Pro Lys Trp Tyr Pro Ile Asn Arg Glu Thr Tyr Leu Asp Arg Leu
                325                 330                 335

Ala Ile Arg Tyr Asp Arg Glu Gly Glu Pro Ser Gln Leu Thr Pro Val
                340                 345                 350

Asp Val Phe Val Ser Thr Val Asp Pro Leu Lys Glu Pro Pro Leu Val
                355                 360                 365

Thr Ala Asn Thr Val Leu Ser Ile Leu Ala Val Asp Tyr Pro Val Asp
                370                 375                 380

Lys Val Ala Cys Tyr Val Ser Asp Asp Gly Ala Ala Met Leu Thr Phe
385                 390                 395                 400

Glu Ser Leu Ser Glu Thr Ala Glu Phe Ala Lys Lys Trp Val Pro Phe
                405                 410                 415

Cys Lys Lys Phe Ser Ile Glu Pro Arg Ala Pro Glu Phe Tyr Phe Gln
                420                 425                 430

Gln Lys Ile Asp Tyr Leu Lys Asp Lys Ile Gln Pro Ser Phe Val Lys
                435                 440                 445

Glu Arg Arg Ala Met Lys Arg Glu Tyr Glu Glu Phe Lys Val Arg Ile
450                 455                 460

Asn Ala Leu Val Ala Lys Ala Gln Lys Ile Pro Glu Glu Gly Trp Thr
465                 470                 475                 480

Met Gln Asp Gly Thr Pro Trp Pro Gly Asn Asn Thr Arg Asp His Pro
                485                 490                 495

Gly Met Ile Gln Val Phe Leu Gly His Ser Gly Gly Leu Asp Thr Asp
                500                 505                 510

Gly Asn Glu Leu Pro Arg Leu Ile Tyr Val Ser Arg Glu Lys Arg Pro
                515                 520                 525

Gly Phe Gln His His Lys Lys Ala Gly Ala Met Asn Ala Leu Ile Arg
                530                 535                 540

Val Ser Ala Val Leu Thr Asn Gly Ala Tyr Leu Leu Asn Val Asp Cys
545                 550                 555                 560

Asp His Tyr Phe Asn Asn Ser Lys Ala Ile Lys Glu Ala Met Cys Phe
                565                 570                 575

Leu Met Asp Pro Ala Tyr Gly Lys Lys Cys Cys Tyr Val Gln Phe Pro
                580                 585                 590

Gln Arg Phe Asp Gly Ile Asp Leu His Asp Arg Tyr Ala Asn Arg Asn
                595                 600                 605

Ile Val Phe Phe Asp Ile Asn Leu Lys Gly Leu Asp Gly Ile Gln Gly
```

```
            610                 615                 620
Pro Val Tyr Val Gly Thr Gly Cys Cys Phe Asn Arg Gln Ala Leu Tyr
625                 630                 635                 640

Gly Tyr Asp Pro Val Leu Thr Glu Glu Asp Leu Lys Pro Asn Ile Ile
                645                 650                 655

Val Lys Ser Cys Cys Gly Ser Arg Lys Gly Lys Asn Ser Lys Lys
            660                 665                 670

Tyr Ser Tyr Asp Gln Lys Arg Arg Gly Ile Ser Arg Ser Asp Ser Asn
            675                 680                 685

Ala Pro Leu Phe Asn Met Asp Asp Ile Asp Glu Gly Phe Glu Gly Tyr
            690                 695                 700

Asp Asp Asp Arg Ser Ile Leu Met Ser Gln Lys Ser Val Glu Lys Arg
705                 710                 715                 720

Phe Gly Gln Ser Pro Val Phe Ile Ala Ala Thr Phe Met Glu Gln Gly
                725                 730                 735

Gly Ile Pro Pro Thr Thr Asn Pro Ala Thr Leu Leu Lys Glu Ala Ile
                740                 745                 750

His Val Ile Ser Cys Gly Tyr Glu Asp Lys Thr Glu Trp Gly Lys Glu
            755                 760                 765

Ile Gly Trp Ile Tyr Gly Ser Val Thr Glu Asp Ile Leu Thr Gly Phe
            770                 775                 780

Lys Met His Ala Arg Gly Trp Met Ser Ile Tyr Cys Asn Pro Pro Arg
785                 790                 795                 800

Pro Ala Phe Lys Gly Ser Ala Pro Ile Asn Leu Ser Asp Arg Leu Asn
                805                 810                 815

Gln Val Leu Arg Trp Ala Leu Gly Ser Ile Glu Ile Leu Leu Ser Arg
                820                 825                 830

His Cys Pro Ile Trp Tyr Gly Tyr Thr Gly Arg Leu Arg Leu Leu Glu
            835                 840                 845

Arg Leu Ala Tyr Ile Asn Thr Ile Val Tyr Pro Ile Thr Ala Leu Pro
850                 855                 860

Leu Ile Ala Tyr Cys Ile Leu Pro Ala Phe Cys Leu Ile Thr Asp Lys
865                 870                 875                 880

Phe Ile Ile Pro Glu Ile Ser Asn Tyr Ala Ser Ile Trp Phe Ile Leu
                885                 890                 895

Leu Phe Ile Ser Ile Ala Val Thr Gly Ile Leu Glu Leu Arg Trp Ser
                900                 905                 910

Gly Val Ser Ile Glu Asp Trp Trp Arg Asn Glu Gln Phe Trp Val Ile
            915                 920                 925

Gly Gly Thr Ser Ala His Leu Phe Ala Val Phe Gln Gly Leu Leu Lys
            930                 935                 940

Val Leu Ala Gly Ile Asp Thr Asn Phe Thr Val Thr Ser Lys Ala Ser
945                 950                 955                 960

Asp Glu Asp Gly Asp Phe Ala Glu Leu Tyr Ile Phe Lys Trp Thr Ala
                965                 970                 975

Leu Leu Ile Pro Pro Thr Thr Val Leu Val Val Asn Met Ile Gly Ile
                980                 985                 990

Val Ala Gly Val Ser Tyr Ala Ile Asn Ser Gly Tyr Gln Ser Trp Gly
            995                 1000                1005

Pro Leu Phe Gly Lys Leu Phe Phe Ala Leu Trp Val Ile Ala His
            1010                1015                1020

Leu Tyr Pro Phe Leu Lys Gly Leu Leu Gly Arg Gln Asn Arg Thr
        1025                1030                1035
```

```
Pro Thr Ile Val Ile Val Trp Ser Val Leu Leu Ala Ser Ile Phe
    1040                1045                1050

Ser Leu Leu Trp Val Arg Ile Asn Pro Phe Val Ser Val Thr Pro
    1055                1060                1065

Ala Ala Asn Pro Asn Ala Val Pro Gly Gly Val Phe
        1070                1075                1080

<210> SEQ ID NO 22
<211> LENGTH: 1080
<212> TYPE: PRT
<213> ORGANISM: Brassica napus

<400> SEQUENCE: 22

Met Glu Ala Ser Ser Gly Leu Val Ala Gly Ser Tyr Arg Arg Asn Glu
1               5                   10                  15

Leu Val Arg Ile Arg His Glu Ser Asp Gly Ser Lys Pro Leu Lys
            20                  25                  30

Asn Met Asp Arg Glu Ile Cys Gln Ile Cys Gly Asp His Ala Gly Leu
        35                  40                  45

Thr Glu Thr Gly Asp Leu Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65              70                  75                  80

Cys Pro His Cys Lys Thr Arg Tyr Arg Arg Leu Arg Gly His Pro Arg
                85                  90                  95

Val Glu Gly Asp Glu Asp Glu Asp Val Asp Ile Glu Asn Glu
            100                 105                 110

Phe Ser Tyr Ala Gln Gly Gly Ala Asn Lys Pro Arg Arg Arg Glu Glu
        115                 120                 125

Phe Ser Ser Ser Arg His Asp Ser Gln Pro Ile Pro Leu Leu Thr
    130                 135                 140

His Gly His Gly Val Ser Gly Glu Ile Arg Thr Pro Asp Thr Gln Ser
145                 150                 155                 160

Val Arg Thr Thr Ser Gly Pro Leu Gly Pro Gly Asp Arg Asn Ala Ile
                165                 170                 175

Ser Ser Pro Tyr Ile Asp Pro Arg Gln Pro Val Pro Val Arg Ile Val
            180                 185                 190

Asp Pro Ser Lys Asp Leu Asn Ser Tyr Gly Leu Gly Asn Val Asp Trp
        195                 200                 205

Lys Glu Arg Val Glu Gly Trp Lys Leu Lys Gln Glu Lys Asn Met Leu
    210                 215                 220

Gln Met Thr Gly Lys Tyr His Glu Gly Lys Gly Gly Glu Ile Glu Gly
225                 230                 235                 240

Thr Gly Ser Asn Gly Glu Glu Leu Gln Met Ala Asp Asp Ser Arg Leu
                245                 250                 255

Pro Met Ser Arg Ile Val Pro Ile Pro Pro Ser His Leu Thr Pro Tyr
            260                 265                 270

Arg Val Val Ile Ile Leu Arg Leu Ile Ile Leu Gly Phe Phe Leu Gln
        275                 280                 285

Tyr Arg Thr Thr His Pro Val Lys Asp Ala Tyr Pro Leu Trp Leu Thr
    290                 295                 300

Ser Val Ile Cys Glu Ile Trp Phe Ala Phe Ser Trp Leu Leu Asp Gln
305                 310                 315                 320

Phe Pro Lys Trp Tyr Pro Ile Asn Arg Glu Thr Tyr Leu Asp Arg Leu
```

-continued

```
                325                 330                 335
Ala Ile Arg Tyr Asp Arg Asp Gly Glu Pro Ser Gln Leu Thr Pro Val
                340                 345                 350
Asp Val Phe Val Ser Thr Val Asp Pro Leu Lys Glu Pro Pro Leu Val
                355                 360                 365
Thr Ala Asn Thr Val Leu Ser Ile Leu Ala Val Asp Tyr Pro Val Asp
                370                 375                 380
Lys Val Ala Cys Tyr Val Ser Asp Asp Gly Ala Ala Met Leu Thr Phe
385                 390                 395                 400
Glu Ser Leu Ser Glu Thr Ala Glu Phe Ala Lys Lys Trp Val Pro Phe
                405                 410                 415
Cys Lys Lys Phe Ser Ile Glu Pro Arg Ala Pro Glu Phe Tyr Phe Ala
                420                 425                 430
Gln Lys Ile Asp Tyr Leu Lys Asp Lys Ile Gln Pro Ser Phe Val Lys
                435                 440                 445
Glu Arg Arg Ala Met Lys Arg Glu Tyr Glu Glu Phe Lys Val Arg Ile
                450                 455                 460
Asn Ala Leu Val Ala Lys Ala Gln Lys Val Pro Glu Glu Gly Trp Thr
465                 470                 475                 480
Met Gln Asp Gly Thr Pro Trp Pro Gly Asn Asn Thr Arg Asp His Pro
                485                 490                 495
Gly Met Ile Gln Val Phe Leu Gly His Ser Gly Gly Leu Asp Thr Asp
                500                 505                 510
Gly Asn Glu Leu Pro Arg Leu Ile Tyr Val Ser Arg Glu Lys Arg Pro
                515                 520                 525
Gly Phe Gln His His Lys Lys Ala Gly Ala Met Asn Ala Leu Ile Arg
                530                 535                 540
Val Ser Ala Val Leu Thr Asn Gly Ala Tyr Leu Leu Asn Val Asp Cys
545                 550                 555                 560
Asp His Tyr Phe Asn Asn Ser Lys Ala Ile Lys Glu Ala Met Cys Phe
                565                 570                 575
Leu Met Asp Pro Ala Tyr Gly Lys Lys Cys Cys Tyr Val Gln Phe Pro
                580                 585                 590
Gln Arg Phe Asp Gly Ile Asp Leu His Asp Arg Tyr Ala Asn Arg Asn
                595                 600                 605
Ile Val Phe Phe Asp Ile Asn Leu Lys Gly Leu Asp Gly Ile Gln Gly
                610                 615                 620
Pro Val Tyr Val Gly Thr Gly Cys Cys Phe Asn Arg Gln Ala Leu Tyr
625                 630                 635                 640
Gly Tyr Asp Pro Val Leu Thr Glu Glu Asp Leu Gln Pro Asn Ile Ile
                645                 650                 655
Val Lys Ser Cys Cys Gly Ser Arg Lys Lys Gly Lys Asn Ser Lys Lys
                660                 665                 670
Tyr Ser Tyr Asp Gln Lys Arg Arg Gly Ile Ser Arg Ser Asp Ser Asn
                675                 680                 685
Ala Pro Leu Phe Asn Met Asp Asp Ile Asp Glu Gly Phe Glu Gly Tyr
                690                 695                 700
Asp Asp Asp Arg Ser Ile Leu Met Ser Gln Lys Arg Val Glu Lys Arg
705                 710                 715                 720
Phe Gly Gln Ser Pro Val Phe Ile Ala Ala Thr Phe Met Glu Gln Gly
                725                 730                 735
Gly Ile Pro Pro Thr Thr Asn Pro Ala Thr Leu Leu Lys Glu Ala Ile
                740                 745                 750
```

```
His Val Ile Ser Cys Gly Tyr Glu Asp Lys Thr Glu Trp Gly Lys Glu
            755                 760                 765

Ile Gly Trp Ile Tyr Gly Ser Val Thr Glu Asp Ile Leu Thr Gly Phe
        770                 775                 780

Lys Met His Ala Arg Gly Trp Met Ser Ile Tyr Cys Asn Pro Pro Arg
785                 790                 795                 800

Pro Ala Phe Lys Gly Ser Ala Pro Ile Asn Leu Ser Asp Arg Leu Asn
                805                 810                 815

Gln Val Leu Arg Trp Ala Leu Gly Ser Ile Glu Ile Leu Leu Ser Arg
            820                 825                 830

His Cys Pro Ile Trp Tyr Gly Tyr Thr Gly Arg Leu Arg Leu Leu Glu
        835                 840                 845

Arg Leu Ala Tyr Ile Asn Thr Ile Val Tyr Pro Ile Thr Ala Leu Pro
850                 855                 860

Leu Ile Ala Tyr Cys Ile Leu Pro Ala Phe Cys Leu Ile Thr Asp Lys
865                 870                 875                 880

Phe Ile Ile Pro Glu Ile Ser Asn Tyr Ala Ser Ile Trp Phe Ile Leu
                885                 890                 895

Leu Phe Ile Ser Ile Ala Val Thr Gly Ile Leu Glu Leu Arg Trp Ser
            900                 905                 910

Gly Val Ser Ile Glu Asp Trp Trp Arg Asn Glu Gln Phe Trp Val Ile
        915                 920                 925

Gly Gly Thr Ser Ala His Leu Phe Ala Val Phe Gln Gly Leu Leu Lys
        930                 935                 940

Val Leu Ala Gly Ile Asp Thr Asn Phe Thr Val Thr Ser Lys Ala Ser
945                 950                 955                 960

Asp Glu Asp Gly Asp Phe Ala Glu Leu Tyr Ile Phe Lys Trp Thr Ala
                965                 970                 975

Leu Leu Ile Pro Pro Thr Thr Val Leu Val Val Asn Leu Ile Gly Ile
            980                 985                 990

Val Ala Gly Val Ser Tyr Ala Ile  Asn Ser Gly Tyr Gln  Ser Trp Gly
        995                 1000                1005

Pro Leu  Phe Gly Lys Leu Phe  Phe Ala Leu Trp Val  Ile Ala His
    1010                1015                1020

Leu Tyr  Pro Phe Leu Lys Gly  Leu Leu Gly Arg Gln  Asn Arg Thr
    1025                1030                1035

Pro Thr  Ile Val Ile Val Trp  Ser Val Leu Leu Ala  Ser Ile Phe
    1040                1045                1050

Ser Leu  Leu Trp Val Arg Ile  Asn Pro Phe Val Ser  Val Ile Pro
    1055                1060                1065

Ala Ala  Asn Pro Asn Ala Val  Pro Gly Gly Val Phe
    1070                1075                1080

<210> SEQ ID NO 23
<211> LENGTH: 1066
<212> TYPE: PRT
<213> ORGANISM: Brassica napus

<400> SEQUENCE: 23

Met Glu Ser Glu Gly Glu Thr Ala Gly Lys Pro Met Thr Ser Val Gly
1               5                   10                  15

Gly Gln Ile Cys Gln Ile Cys Ser Asp Asn Val Gly Lys Thr Val Asp
            20                  25                  30

Gly Asp Trp Phe Val Ala Cys Asp Val Cys Gly Phe Pro Val Cys Arg
```

```
            35                  40                  45
Pro Cys Tyr Asp Phe Glu Arg Lys Asp Gly Asn Gln Ser Cys Pro Gln
 50                  55                  60

Cys Lys Thr Thr Tyr Lys Arg His Lys Gly Ser Pro Ala Ile Pro Gly
 65                  70                  75                  80

Asp Lys Asp Glu Asp Val Phe Ala Asp Ala Thr Val Glu Leu Ser
                 85                  90                  95

Tyr Pro Gln Lys Glu Lys Ile Ser Glu Arg Met Leu Gly Trp His Leu
                100                 105                 110

Thr Arg Gly Lys Gly Glu Glu Met Gly Gln Pro Glu Tyr Asp Lys Glu
                115                 120                 125

Val Ser His Asn His Leu Pro Arg Leu Thr Ser Arg Gln Glu Thr Ser
    130                 135                 140

Gly Glu Phe Ser Ala Ala Ser Pro Glu Arg Leu Ser Val Ser Ser Thr
145                 150                 155                 160

Ile Gly Gly Lys Arg Leu Pro Tyr Ser Ser Asp Ile Asn Gln Ser
                165                 170                 175

Pro His Arg Arg Ile Ser Asp Pro Val Gly Leu Gly Asn Val Ala Trp
                180                 185                 190

Lys Glu Arg Val Asp Gly Trp Lys Met Lys Gln Glu Lys Asn Asn Gly
    195                 200                 205

Gly Pro Val Ser Thr Gln Ala Ala Ser Glu Arg Gly Gly Asp Ile
    210                 215                 220

Asp Ala Ser Thr Asp Ile Leu Ala Asp Glu Ala Leu Leu Asn Asp Glu
225                 230                 235                 240

Ala Arg Gln Pro Leu Ser Arg Lys Val Ser Ile Pro Ser Ser Arg Ile
                245                 250                 255

Asn Pro Tyr Arg Met Val Ile Met Leu Arg Leu Val Ile Leu Cys Leu
                260                 265                 270

Phe Leu His Tyr Arg Ile Thr Asn Pro Val Pro Asn Ala Phe Thr Leu
    275                 280                 285

Trp Leu Ile Ser Val Ile Cys Glu Ile Trp Phe Ala Phe Ser Trp Ile
290                 295                 300

Leu Asp Gln Phe Pro Lys Trp Phe Pro Val Asn Arg Glu Thr Tyr Leu
305                 310                 315                 320

Asp Arg Leu Ala Leu Arg Tyr Asp Arg Glu Gly Glu Pro Ser Gln Leu
                325                 330                 335

Ala Ala Val Asp Ile Phe Val Ser Thr Val Asp Pro Leu Lys Glu Pro
                340                 345                 350

Pro Leu Val Thr Ala Asn Thr Val Leu Ser Ile Leu Ala Val Asp Tyr
                355                 360                 365

Pro Val Asp Lys Val Ser Cys Tyr Val Ser Asp Asp Gly Ala Ala Met
                370                 375                 380

Leu Ser Phe Glu Ala Leu Ala Glu Thr Ser Glu Phe Ala Arg Lys Trp
385                 390                 395                 400

Val Pro Phe Cys Lys Lys Tyr Ser Ile Glu Pro Arg Ala Pro Glu Trp
                405                 410                 415

Tyr Phe Ala Ala Lys Ile Asp Tyr Leu Lys Asp Lys Val Gln Thr Ser
                420                 425                 430

Phe Val Lys Asp Arg Arg Ala Met Lys Arg Glu Tyr Glu Glu Phe Lys
                435                 440                 445

Ile Arg Ile Asn Ala Leu Val Ser Lys Ala Leu Lys Cys Pro Glu Glu
                450                 455                 460
```

```
Gly Trp Val Met Gln Asp Gly Thr Pro Trp Pro Gly Asn Asn Thr Arg
465                 470                 475                 480

Asp His Pro Gly Met Ile Gln Val Phe Leu Gly Gln Asn Gly Gly Leu
                485                 490                 495

Asp Ala Glu Gly Asn Glu Leu Pro Arg Leu Val Tyr Val Ser Arg Glu
            500                 505                 510

Lys Arg Pro Gly Phe Gln His His Lys Lys Ala Gly Ala Met Asn Ala
                515                 520                 525

Leu Val Arg Val Ser Ala Val Leu Thr Asn Gly Pro Phe Ile Leu Asn
530                 535                 540

Leu Asp Cys Asp His Tyr Ile Asn Asn Ser Lys Ala Leu Arg Glu Ala
545                 550                 555                 560

Met Cys Phe Leu Met Asp Pro Asn Leu Gly Lys Gln Val Cys Tyr Val
                565                 570                 575

Gln Phe Pro Gln Arg Phe Asp Gly Ile Asp Lys Asn Asp Arg Tyr Ala
            580                 585                 590

Asn Arg Asn Thr Val Phe Phe Asp Ile Asn Leu Arg Gly Leu Asp Gly
        595                 600                 605

Ile Gln Gly Pro Val Tyr Val Gly Thr Gly Cys Val Phe Asn Arg Thr
610                 615                 620

Ala Leu Tyr Gly Tyr Glu Pro Pro Ile Lys Val Lys His Lys Pro
625                 630                 635                 640

Ser Leu Leu Ser Lys Leu Cys Gly Gly Ser Arg Lys Lys Asn Ser Lys
                645                 650                 655

Ser Lys Lys Asp Ser Asp Lys Lys Ser Gly Arg His Thr Asp Ser
            660                 665                 670

Thr Val Pro Val Phe Asn Leu Asp Asp Ile Glu Glu Gly Val Glu Gly
            675                 680                 685

Ala Gly Phe Asp Asp Glu Lys Ala Leu Leu Met Ser Gln Met Ser Leu
690                 695                 700

Glu Lys Arg Phe Gly Gln Ser Ala Val Phe Val Ala Ser Thr Leu Met
705                 710                 715                 720

Glu Asn Gly Gly Val Pro Pro Thr Glu Thr Pro Glu Asn Leu Leu Lys
                725                 730                 735

Glu Ala Ile His Val Ile Ser Cys Gly Tyr Glu Asp Lys Ser Asp Trp
            740                 745                 750

Gly Met Glu Ile Gly Trp Ile Tyr Gly Ser Val Thr Glu Asp Ile Leu
            755                 760                 765

Thr Gly Phe Lys Met His Ala Arg Gly Trp Arg Ser Ile Tyr Cys Met
            770                 775                 780

Pro Lys Leu Pro Ala Phe Lys Gly Ser Ala Pro Ile Asn Leu Ser Asp
785                 790                 795                 800

Arg Leu Asn Gln Val Leu Arg Trp Ala Leu Gly Ser Val Glu Ile Leu
                805                 810                 815

Phe Ser Arg His Cys Pro Ile Trp Tyr Gly Tyr Ser Gly Arg Leu Lys
            820                 825                 830

Phe Leu Glu Arg Phe Ala Tyr Val Asn Thr Thr Ile Tyr Pro Leu Thr
            835                 840                 845

Ser Val Pro Leu Leu Leu Tyr Cys Thr Leu Pro Ala Val Cys Leu Phe
        850                 855                 860

Thr Asn Gln Phe Ile Ile Pro Gln Ile Ser Asn Ile Ala Ser Ile Trp
865                 870                 875                 880
```

```
Phe Leu Ser Leu Phe Leu Ser Ile Phe Ala Thr Gly Ile Leu Glu Met
                885                 890                 895

Arg Trp Ser Gly Val Gly Ile Asp Glu Trp Trp Arg Asn Glu Gln Phe
            900                 905                 910

Trp Val Ile Gly Gly Val Ser Ala His Leu Phe Ala Val Phe Gln Gly
        915                 920                 925

Leu Leu Lys Val Leu Ala Gly Ile Asp Thr Asn Phe Thr Val Thr Ser
930                 935                 940

Lys Ala Ser Asp Glu Asp Gly Asp Phe Ala Glu Leu Tyr Leu Phe Lys
945                 950                 955                 960

Trp Thr Thr Leu Leu Ile Pro Pro Thr Thr Leu Leu Ile Val Asn Leu
                965                 970                 975

Val Gly Val Val Ala Gly Phe Ser Tyr Ala Ile Asn Ser Gly Tyr Gln
            980                 985                 990

Ser Trp Gly Pro Leu Phe Gly Lys Leu Phe Phe Ala Phe Trp Val Ile
        995                 1000                1005

Val His Leu Tyr Pro Phe Leu Lys Gly Leu Met Gly Arg Gln Asn
    1010                1015                1020

Arg Thr Pro Thr Ile Val Val Trp Ser Val Leu Leu Ala Ser
    1025                1030                1035

Ile Phe Ser Leu Leu Trp Val Arg Ile Asp Pro Phe Thr Lys Arg
    1040                1045                1050

Val Thr Gly Pro Asp Ile Leu Glu Cys Gly Ile Asn Cys
    1055                1060                1065

<210> SEQ ID NO 24
<211> LENGTH: 1084
<212> TYPE: PRT
<213> ORGANISM: Brassica napus

<400> SEQUENCE: 24

Met Asn Thr Gly Gly Arg Leu Ile Ala Gly Ser His Asn Arg Asn Glu
1               5                   10                  15

Phe Val Leu Ile Asn Ala Asp Glu Ser Ala Arg Ile Arg Ser Val Gln
                20                  25                  30

Glu Leu Arg Gly Gln Thr Cys Glu Ile Cys Arg Asp Glu Val Glu Leu
            35                  40                  45

Thr Val Asp Gly Glu Pro Phe Val Ala Cys Asn Glu Cys Ala Phe Pro
        50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Leu Lys Gly Ser Pro Arg
                85                  90                  95

Val Glu Asn Asp Glu Glu Glu Asp Ile Asp Ile Asp Asn Glu
                100                 105                 110

Phe Asp Tyr Met Asn Asn Gly Gly Ile Gly Phe Asp Gln Val Ser Glu
                115                 120                 125

Gly Met Ser Val Ser Arg Arg His Ser Gly Phe Pro Gln Ser Asp Leu
        130                 135                 140

Asp Ser Ala Pro Pro Gly Ser Gln Ile Pro Leu Leu Thr Tyr Gly Asp
145                 150                 155                 160

Glu Asp Ile Glu Ile Ser Ser Asp Arg His Ala Leu Ile Val Pro Pro
                165                 170                 175

Ser Leu Ser Gly His Ser His Arg Gly His Pro Ala Ser Leu Ser Asp
                180                 185                 190
```

```
Pro Thr Ile Ala Ala His Pro Arg Pro Met Val Pro Gln Lys Asp Leu
        195                 200                 205

Ala Val Tyr Gly Tyr Gly Ser Val Ala Trp Lys Asp Arg Met Glu Glu
210                 215                 220

Trp Lys Arg Lys Gln Asn Glu Lys Leu Glu Val Val Lys His Glu Gly
225                 230                 235                 240

Asp Pro Asp Phe Glu Asp Gly Asp Asp Ile Pro Met Met Asp Glu Gly
                245                 250                 255

Arg Gln Pro Leu Ser Arg Lys Ile Pro Ile Lys Ser Ser Lys Ile Asn
            260                 265                 270

Pro Tyr Arg Met Leu Ile Val Leu Arg Leu Val Ile Leu Gly Leu Phe
        275                 280                 285

Phe His Tyr Arg Ile Leu His Pro Val Lys Asp Ala Tyr Ala Leu Trp
    290                 295                 300

Leu Ile Ser Val Ile Cys Glu Ile Trp Phe Ala Val Ser Trp Val Leu
305                 310                 315                 320

Asp Gln Phe Pro Lys Trp Tyr Pro Ile Glu Arg Glu Thr Tyr Leu Asp
                325                 330                 335

Arg Leu Ser Leu Arg Tyr Glu Lys Glu Gly Lys Pro Ser Glu Leu Ser
            340                 345                 350

Ala Val Asp Val Phe Val Ser Thr Val Asp Pro Leu Lys Glu Pro Pro
        355                 360                 365

Leu Ile Thr Ala Asn Thr Val Leu Ser Ile Leu Ala Val Asp Tyr Pro
        370                 375                 380

Val Asp Arg Val Ala Cys Tyr Val Ser Asp Asp Gly Ala Ala Met Leu
385                 390                 395                 400

Thr Phe Glu Ala Leu Ser Glu Thr Ala Glu Phe Ala Arg Lys Trp Val
                405                 410                 415

Pro Phe Cys Lys Lys Tyr Cys Ile Glu Pro Arg Ala Pro Glu Trp Tyr
            420                 425                 430

Phe Cys His Lys Met Asp Tyr Leu Lys Asn Lys Val His Pro Ala Phe
        435                 440                 445

Val Arg Glu Arg Arg Ala Met Lys Arg Asp Tyr Glu Glu Phe Lys Val
    450                 455                 460

Lys Ile Asn Ala Leu Val Ala Thr Ala Gln Lys Val Pro Glu Glu Gly
465                 470                 475                 480

Trp Thr Met Gln Asp Gly Thr Pro Trp Pro Gly Asn Ser Thr Arg Asp
                485                 490                 495

His Pro Gly Met Ile Gln Val Phe Leu Gly Ser Asp Gly Val Arg Asp
            500                 505                 510

Val Glu Asn Asn Glu Leu Pro Arg Leu Val Tyr Val Ser Arg Glu Lys
        515                 520                 525

Arg Pro Gly Phe Asp His His Lys Lys Ala Gly Ala Met Asn Ser Leu
        530                 535                 540

Ile Arg Val Ser Gly Val Leu Ser Asn Ala Pro Tyr Leu Leu Asn Val
545                 550                 555                 560

Asp Cys Asp His Tyr Ile Asn Asn Ser Lys Ala Leu Arg Glu Ala Met
                565                 570                 575

Cys Phe Met Met Asp Pro Gln Ser Gly Lys Lys Ile Cys Tyr Val Gln
            580                 585                 590

Phe Pro Gln Arg Phe Asp Gly Ile Asp Arg His Asp Arg Tyr Ser Asn
        595                 600                 605
```

-continued

```
Arg Asn Val Val Phe Phe Asp Ile Asn Met Lys Gly Leu Asp Gly Leu
610                 615                 620

Gln Gly Pro Ile Tyr Val Gly Thr Gly Cys Val Phe Arg Arg Gln Ala
625                 630                 635                 640

Leu Tyr Gly Phe Asp Ala Pro Lys Lys Lys Ala Pro Arg Lys Thr
                645                 650                 655

Cys Asn Cys Trp Pro Lys Trp Cys Phe Leu Cys Cys Gly Ser Arg Lys
                660                 665                 670

Asn Arg Lys Ala Lys Thr Ala Ala Asp Lys Lys Lys Asn Arg
            675                 680                 685

Glu Ala Ser Lys Gln Ile His Ala Leu Glu Asn Ile Glu Glu Gly Arg
690                 695                 700

Val Thr Thr Lys Gly Ser Asn Val Glu Leu Ser Thr Glu Ala Met Gln
705                 710                 715                 720

Leu Lys Leu Glu Lys Lys Phe Gly Gln Ser Pro Val Phe Val Ala Ser
                725                 730                 735

Ala Arg Met Glu Asn Gly Gly Met Ala Arg Asn Ala Ser Pro Ala Cys
                740                 745                 750

Leu Leu Lys Glu Ala Ile Gln Val Ile Ser Cys Gly Tyr Glu Asp Lys
            755                 760                 765

Thr Glu Trp Gly Lys Glu Ile Gly Trp Ile Tyr Gly Ser Val Thr Glu
770                 775                 780

Asp Ile Leu Thr Gly Phe Lys Met His Ser His Gly Trp Arg Ser Val
785                 790                 795                 800

Tyr Cys Thr Pro Lys Leu Pro Ala Phe Lys Gly Ser Ala Pro Ile Asn
                805                 810                 815

Leu Ser Asp Arg Leu His Gln Val Leu Arg Trp Ala Leu Gly Ser Val
            820                 825                 830

Glu Ile Phe Leu Ser Arg His Cys Pro Ile Trp Tyr Gly Tyr Gly Gly
            835                 840                 845

Gly Leu Lys Trp Leu Glu Arg Leu Ser Tyr Ile Asn Ser Val Val Tyr
850                 855                 860

Pro Trp Thr Ser Leu Pro Leu Ile Val Tyr Cys Ser Leu Pro Ala Ile
865                 870                 875                 880

Cys Leu Leu Thr Gly Lys Phe Ile Val Pro Glu Ile Ser Asn Tyr Ala
                885                 890                 895

Ser Ile Leu Phe Met Ala Leu Phe Ser Ser Ile Ala Val Thr Gly Ile
                900                 905                 910

Leu Glu Met Gln Trp Gly Lys Val Gly Ile Asp Asp Trp Trp Arg Asn
            915                 920                 925

Glu Gln Phe Trp Val Ile Gly Gly Val Ser Ala His Leu Phe Ala Leu
930                 935                 940

Phe Gln Gly Leu Leu Lys Val Leu Ala Gly Val Asp Thr Asn Phe Thr
945                 950                 955                 960

Val Thr Ser Lys Ala Ala Asp Asp Gly Glu Phe Ser Asp Leu Tyr Leu
                965                 970                 975

Phe Lys Trp Thr Ser Leu Leu Ile Pro Pro Thr Thr Leu Leu Ile Ile
            980                 985                 990

Asn Val Ile Gly Ile Val Val Gly Ile Ser Asp Ala Ile Ser Asn Gly
            995                 1000                1005

Tyr Asp Ser Trp Gly Pro Leu Phe Gly Arg Leu Phe Phe Ala Leu
    1010                1015                1020

Trp Val Val Ile His Leu Tyr Pro Phe Leu Lys Gly Leu Leu Gly
```

```
                        1025                1030                1035

Lys Gln Asp Arg Met Pro Thr Ile Ile Val Val Trp Ser Ile Leu
            1040                1045                1050

Leu Ala Ser Ile Leu Thr Leu Leu Trp Val Arg Val Asn Pro Phe
        1055                1060                1065

Val Ala Lys Gly Gly Pro Ile Leu Glu Ile Cys Gly Leu Asp Cys
    1070                1075                1080

Leu

<210> SEQ ID NO 25
<211> LENGTH: 1079
<212> TYPE: PRT
<213> ORGANISM: Helianthus annum

<400> SEQUENCE: 25

Met Gln Ala Asn Gly Gly Leu Val Ala Gly Ser His Lys Arg Asn Glu
1               5                   10                  15

Leu Val Arg Ile Arg His Asp Ser Asp Gly Gly Pro Lys Pro Leu Lys
            20                  25                  30

Asp Leu Asn Gly Gln Thr Cys Gln Ile Cys Gly Asp Thr Val Gly Leu
        35                  40                  45

Thr Glu Thr Gly Asp Ile Phe Val Ala Cys Asn Glu Cys Ala Phe Pro
    50                  55                  60

Val Cys Arg Pro Cys Tyr Glu Tyr Glu Arg Arg Asp Gly Asn Gln Ala
65                  70                  75                  80

Cys Pro Gln Cys Lys Thr Arg Tyr Arg Arg His Lys Gly Ser Pro Arg
                85                  90                  95

Val Asp Gly Asp Glu Glu Glu Asp Val Asp Asp Leu Glu Asn Glu
            100                 105                 110

Phe Ser Tyr Pro Gln Gly Asn Asn Lys Ala Ala Arg Gln Trp Gln Gly
        115                 120                 125

Asp Asp Ala Asn Leu Ser Ser Ser Ala Arg His Asp Pro Leu Pro Leu
    130                 135                 140

Leu Thr Asn Gly Gln Gln Val Ser Gly Glu Ile Pro Ser Val Arg Asp
145                 150                 155                 160

Asn Leu Ser Val Arg Ser Thr Ser Gly Pro Leu Gly Pro Ser Asp Lys
                165                 170                 175

Gln Leu Pro Tyr Ile Asp Pro Arg Gln Pro Val Pro Val Arg Ile Val
            180                 185                 190

Asp Pro Thr Lys Asp Leu Asn Ala Tyr Gly Leu Gly Asn Val Asp Trp
        195                 200                 205

Lys Glu Arg Val Glu Gly Trp Lys Leu Lys Gln Glu Lys Asn Met Gln
    210                 215                 220

Met Thr Asn Arg Tyr Gly Gly Glu Gly Lys Gly Gly Asp Glu Ile Glu
225                 230                 235                 240

Arg Thr Gly Ser Asn Gly Glu Glu Leu Gln Met Ala Asp Asp Ala Arg
                245                 250                 255

Gln Pro Met Ser Arg Val Val Pro Ile Ser Ser Ala His Leu Thr Pro
            260                 265                 270

Tyr Arg Ile Val Ile Ile Leu Arg Leu Ile Ile Leu Gly Phe Phe Leu
        275                 280                 285

Gln Tyr Arg Cys Ser His Pro Val Asn Asp Ala Tyr Pro Leu Trp Leu
    290                 295                 300

Val Ser Val Ile Cys Glu Val Trp Phe Ala Leu Ser Trp Leu Leu Asp
```

```
            305                 310                 315                 320
        Gln Phe Pro Lys Trp Phe Pro Val Glu Arg Glu Thr Tyr Leu Asp Arg
                        325                 330                 335

Leu Ala Leu Arg Tyr Asp Arg Glu Gly Glu Pro Ser Gln Leu Ala Pro
                        340                 345                 350

Ile Asp Val Phe Val Ser Thr Val Asp Pro Leu Lys Glu Pro Pro Leu
                        355                 360                 365

Ile Thr Ala Asn Thr Val Leu Ser Ile Leu Ala Val Asp Tyr Pro Val
                        370                 375                 380

Asp Lys Val Ser Cys Tyr Val Ser Asp Gly Ser Ala Met Leu Thr
        385                 390                 395                 400

Phe Glu Ser Leu Ser Glu Thr Ala Glu Phe Ala Arg Lys Trp Val Pro
                        405                 410                 415

Phe Cys Lys Lys His Ser Ile Glu Pro Arg Ala Pro Glu Phe Tyr Phe
                        420                 425                 430

Ala Gln Lys Ile Asp Tyr Leu Lys Asp Lys Ile Gln Pro Ser Phe Val
                        435                 440                 445

Lys Glu Arg Arg Ala Met Lys Arg Glu Tyr Glu Glu Phe Lys Val Arg
                        450                 455                 460

Ile Asn Ala Leu Val Ala Lys Ala Gln Lys Met Pro Glu Glu Gly Trp
        465                 470                 475                 480

Thr Met Gln Asp Gly Thr Pro Trp Pro Gly Asn Asn Pro Arg Asp His
                        485                 490                 495

Pro Gly Met Ile Gln Val Phe Leu Gly His Ser Gly Gly Leu Asp Thr
                        500                 505                 510

Asp Gly Asn Glu Leu Pro Arg Leu Val Tyr Val Ser Arg Glu Lys Arg
                        515                 520                 525

Pro Gly Phe Gln His His Lys Lys Ala Gly Ala Met Asn Ala Leu Ile
                        530                 535                 540

Arg Val Ser Ala Val Leu Thr Asn Gly Ala Tyr Leu Leu Asn Val Asp
        545                 550                 555                 560

Cys Asp His Tyr Phe Asn Asn Ser Lys Ala Leu Lys Glu Ala Met Cys
                        565                 570                 575

Phe Met Met Asp Pro Ala Tyr Gly Lys Lys Thr Cys Tyr Val Gln Phe
                        580                 585                 590

Pro Gln Arg Phe Asp Gly Ile Asp Leu His Asp Arg Tyr Ala Asn Arg
                        595                 600                 605

Asn Ile Val Phe Phe Asp Ile Asn Leu Lys Gly Leu Asp Gly Ile Gln
        610                 615                 620

Gly Pro Val Tyr Val Gly Thr Gly Cys Cys Phe Asn Arg Gln Ala Leu
        625                 630                 635                 640

Tyr Gly Tyr Asp Pro Val Leu Thr Glu Ala Asp Leu Glu Pro Asn Ile
                        645                 650                 655

Ile Ile Lys Ser Cys Cys Gly Ser Arg Lys Lys Gly Lys Asn Ser Asn
                        660                 665                 670

Lys Tyr Thr Asp Lys Lys Arg Ala Val Lys Arg Ser Glu Ser Asn Ile
                        675                 680                 685

Pro Ile Phe Asn Thr Glu Asp Met Asp Glu Gly Val Glu Gly Tyr Asp
                        690                 695                 700

Glu Glu Lys Ser Leu Leu Met Ser Gln Arg Ser Leu Glu Lys Arg Phe
        705                 710                 715                 720

Gly Gln Ser Ser Val Phe Ile Ser Ala Thr Phe Met Glu Met Gly Gly
                        725                 730                 735
```

```
Ile Pro Pro Thr Thr Asn Ser Ala Thr Leu Lys Glu Ala Ile His
            740                 745                 750

Val Ile Ser Cys Gly Tyr Glu Asp Lys Thr Glu Trp Gly Lys Glu Ile
            755                 760                 765

Gly Trp Ile Tyr Gly Ser Val Thr Glu Asp Ile Leu Thr Gly Phe Lys
            770                 775                 780

Met His Ala Arg Gly Trp Ile Ser Ile Tyr Cys Met Pro Pro Arg Pro
785                 790                 795                 800

Ala Phe Lys Gly Ser Ala Pro Ile Asn Leu Ser Asp Arg Leu Asn Gln
                805                 810                 815

Val Leu Arg Trp Ala Leu Gly Ser Ile Glu Ile Leu Leu Ser Arg His
            820                 825                 830

Cys Pro Ile Trp Tyr Gly Tyr Asn Gly Lys Leu Lys Leu Leu Glu Arg
            835                 840                 845

Leu Ala Tyr Ile Asn Thr Ile Val Tyr Pro Leu Thr Ser Ile Pro Leu
            850                 855                 860

Leu Ala Tyr Cys Val Leu Pro Ala Val Cys Leu Leu Thr Gly Lys Phe
865                 870                 875                 880

Ile Ile Pro Glu Ile Ser Asn Tyr Ala Ser Met Trp Phe Ile Leu Leu
                885                 890                 895

Phe Ile Ser Ile Ala Ala Thr Gly Ile Leu Glu Leu Arg Trp Ser Gly
            900                 905                 910

Val Ser Ile Glu Asp Trp Trp Arg Asn Glu Gln Phe Trp Val Ile Gly
            915                 920                 925

Gly Thr Ser Ala His Leu Phe Ala Val Phe Gln Gly Leu Leu Lys Val
            930                 935                 940

Leu Ala Gly Ile Asp Thr Asn Phe Thr Val Thr Ser Lys Ala Ser Asp
945                 950                 955                 960

Glu Asp Gly Asp Phe Ala Glu Leu Tyr Ile Phe Lys Trp Thr Ala Leu
                965                 970                 975

Leu Ile Pro Pro Thr Thr Val Leu Ile Val Asn Leu Val Gly Ile Val
            980                 985                 990

Ser Gly Val Ser Thr Ala Ile Asn Ser Gly Tyr Gln Ser Trp Gly Pro
            995                 1000                1005

Leu Phe Gly Lys Leu Phe Phe Ala Ile Trp Val Ile Val His Leu
    1010                1015                1020

Tyr Pro Phe Leu Lys Gly Leu Leu Gly Arg Gln Asn Arg Thr Pro
    1025                1030                1035

Thr Ile Val Ile Val Trp Ser Ile Leu Leu Ala Ser Ile Phe Ser
    1040                1045                1050

Leu Leu Trp Val Arg Ile Asp Pro Phe Thr Thr Asp Asp Lys Leu
    1055                1060                1065

Asp Ser Ile Arg Gly Gln Cys Gly Ile Asp Cys
    1070                1075

<210> SEQ ID NO 26
<211> LENGTH: 1081
<212> TYPE: PRT
<213> ORGANISM: Helianthus annum

<400> SEQUENCE: 26

Met Glu Ser Glu Gly Glu Thr Gly Gly Thr Ser Met Lys Asn Val Gly
1               5                   10                  15

Gly Gln Val Cys Gln Ile Cys Gly Asp Thr Val Gly Thr Thr Ala Lys
```

```
               20                  25                  30
        Gly Asp Pro Phe Val Ala Cys Asp Val Cys Ala Phe Pro Val Cys Arg
                     35                  40                  45

Pro Cys Tyr Glu Tyr Glu Arg Lys Asp Gly Asn Gln Ser Cys Pro Gln
         50                  55                  60

Cys Lys Thr Arg Tyr Lys Arg Leu Lys Gly Ser Pro Ala Ile Pro Gly
         65                  70                  75                  80

Asp Arg Glu Glu Ile Asp Gly Asp Glu Thr Thr Asn Phe Pro
                         85                  90                  95

Phe Ser Ser Gln Thr Gln Asn Glu Lys Gln Lys Thr Ala Glu Arg Met
                    100                 105                 110

Leu Asn Trp His Met Thr Tyr Gly Arg Gly Asp Asp Asn Ser Ala Pro
                    115                 120                 125

Asn Tyr Asp Lys Glu Val Ser His Asn His Ile Pro Leu Leu Thr Gly
                    130                 135                 140

Gly His Glu Val Ser Gly Glu Leu Ser Ala Ala Ser Pro Gln Arg Leu
        145                 150                 155                 160

Ser Val Ser Ser Pro Pro Gly Gly Glu Arg Leu Thr His Ser Leu
                         165                 170                 175

Pro Tyr Ser Ala Tyr Ala Asn Gln Ser Pro Asn Ile Arg Val Val Asp
                    180                 185                 190

Pro Val Arg Glu Phe Gly Ser Thr Gly Leu Gly Asn Leu Ala Trp Lys
                    195                 200                 205

Glu Arg Val Asp Gly Trp Lys Met Lys Gln Asp Lys Asn Val Ala Pro
                    210                 215                 220

Met Thr Thr Ser Arg Ala Ala Ser Glu Arg Gly Gln Asp Ile Asp Ala
        225                 230                 235                 240

Ser Thr Asp Val Leu Asp Ala Leu Leu Asn Asp Glu Ala Arg Gln
                         245                 250                 255

Pro Leu Ser Arg Lys Val Ser Ile Pro Ser Ser Arg Ile Asn Pro Tyr
                    260                 265                 270

Arg Met Val Ile Val Leu Arg Leu Val Ile Leu Cys Ile Phe Leu His
                    275                 280                 285

Tyr Arg Ile Thr Asn Pro Val Thr Asn Ala Tyr Pro Leu Trp Leu Leu
                    290                 295                 300

Ser Val Ile Cys Glu Ile Trp Phe Ala Ile Ser Trp Ile Leu Asp Gln
        305                 310                 315                 320

Phe Pro Lys Trp Leu Pro Val Asn Arg Glu Thr Tyr Leu Asp Arg Leu
                    325                 330                 335

Ser Leu Arg Tyr Glu Arg Glu Gly Glu Pro Ser Gln Leu Ala Ala Val
                    340                 345                 350

Asp Ile Phe Val Ser Thr Val Asp Pro Leu Lys Glu Pro Leu Val
                    355                 360                 365

Thr Ala Asn Thr Val Leu Ser Ile Leu Ala Val Asp Tyr Pro Val Asp
                    370                 375                 380

Lys Val Ser Cys Tyr Val Ser Asp Asp Gly Ala Ala Met Leu Ser Phe
        385                 390                 395                 400

Glu Ser Leu Ser Glu Thr Ser Glu Phe Ala Arg Lys Trp Val Pro Phe
                    405                 410                 415

Cys Lys Lys Tyr Asn Ile Glu Pro Arg Ala Pro Glu Trp Tyr Phe Ala
                    420                 425                 430

Gln Lys Ile Asp Tyr Leu Lys Asp Lys Ile Gln Pro Thr Phe Val Lys
                    435                 440                 445
```

```
Asp Arg Arg Ala Met Lys Arg Glu Tyr Glu Phe Lys Ile Arg Ile
    450             455                 460

Asn Gly Leu Val Ala Lys Ala Gln Lys Val Pro Asp Glu Gly Trp Ile
465             470                 475                 480

Met Gln Asp Gly Thr Pro Trp Pro Gly Asn Asn Thr Arg Asp His Pro
                485                 490                 495

Gly Met Ile Gln Val Phe Leu Gly Gln Asn Gly Gly Leu Asp Ser Glu
                500                 505                 510

Gly Asn Glu Leu Pro Arg Leu Val Tyr Val Ser Arg Glu Lys Arg Pro
            515                 520                 525

Gly Phe Gln His His Lys Lys Ala Gly Ala Met Asn Ala Leu Val Arg
    530                 535                 540

Val Ser Ala Val Leu Thr Asn Gly Pro Phe Leu Leu Asn Leu Asp Cys
545             550                 555                 560

Asp His Tyr Ile Asn Asn Ser Lys Ala Leu Arg Glu Ala Met Cys Phe
                565                 570                 575

Met Met Asp Pro Asn Leu Gly Lys Tyr Val Cys Tyr Val Gln Phe Pro
                580                 585                 590

Gln Arg Phe Asp Gly Ile Asp Arg Asn Asp Arg Tyr Ala Asn Arg Asn
    595                 600                 605

Thr Val Phe Phe Asp Ile Asn Leu Arg Gly Leu Asp Gly Ile Gln Gly
    610                 615                 620

Pro Val Tyr Val Gly Thr Gly Cys Val Phe Asn Arg Thr Ala Leu Tyr
625             630                 635                 640

Gly Tyr Glu Pro Pro Leu Lys Pro Lys Lys Arg Glu Lys Gly Phe
                645                 650                 655

Phe Ser Ser Cys Phe Gly Glu Ser Arg Lys Lys Ser Ser Lys Ser Ser
                660                 665                 670

Lys Lys Gly Ser Asp Lys Lys Ser Ser Lys Pro Val Asp Pro Thr
    675                 680                 685

Val Pro Val Phe Ser Leu Glu Asp Ile Glu Glu Val Glu Gly Ala
    690                 695                 700

Gly Phe Asp Asp Glu Lys Ser Leu Leu Met Ser Gln Met Ser Leu Glu
705             710                 715                 720

Lys Arg Phe Gly Gln Ser Ala Val Phe Val Ala Ser Thr Leu Met Glu
                725                 730                 735

Asn Gly Gly Val Pro Gln Ser Ala Ala Pro Glu Thr Leu Leu Lys Glu
            740                 745                 750

Ala Ile His Val Ile Ser Cys Gly Tyr Glu Asp Lys Thr Asp Trp Gly
    755                 760                 765

Asn Glu Ile Gly Trp Ile Tyr Gly Ser Val Thr Glu Asp Ile Leu Thr
    770                 775                 780

Gly Phe Lys Met His Ala Arg Gly Trp Arg Ser Ile Tyr Cys Met Pro
785             790                 795                 800

Pro Arg Pro Ala Phe Lys Gly Ser Ala Pro Ile Asn Leu Ser Asp Arg
                805                 810                 815

Leu Asn Gln Val Leu Arg Trp Ala Leu Gly Ser Val Glu Ile Leu Phe
            820                 825                 830

Ser Arg His Cys Pro Ile Trp Tyr Gly Tyr Ser Gly Arg Leu Lys Trp
        835                 840                 845

Leu Glu Arg Phe Ala Tyr Ile Asn Thr Thr Ile Tyr Pro Ile Thr Ser
850                 855                 860
```

```
Ile Pro Leu Leu Val Tyr Cys Thr Leu Pro Ala Val Cys Leu Leu Thr
865                 870                 875                 880

Gly Lys Phe Ile Ile Pro Gln Ile Ser Asn Leu Ala Ser Leu Trp Phe
                885                 890                 895

Ile Ser Leu Phe Leu Ser Ile Phe Ala Thr Gly Ile Leu Glu Met Arg
            900                 905                 910

Trp Ser Gly Val Gly Ile Asp Glu Trp Trp Arg Asn Glu Gln Phe Trp
            915                 920                 925

Val Ile Gly Gly Val Ser Ala His Leu Phe Ala Val Phe Gln Gly Leu
930                 935                 940

Leu Lys Val Leu Ala Gly Ile Asp Thr Asn Phe Thr Val Thr Ser Lys
945                 950                 955                 960

Ala Ser Asp Glu Asp Gly Asp Phe Ala Glu Leu Tyr Leu Phe Lys Trp
                965                 970                 975

Thr Thr Leu Leu Ile Pro Pro Thr Thr Leu Leu Ile Val Asn Leu Val
            980                 985                 990

Gly Val Val Ala Gly Ile Ser Tyr Ala Ile Asn Ser Gly Tyr Gln Ser
                995                 1000                1005

Trp Gly Pro Leu Phe Gly Lys Leu Phe Phe Ala Phe Trp Val Ile
    1010            1015                1020

Val His Leu Tyr Pro Phe Leu Lys Gly Leu Met Gly Lys Gln Asn
    1025            1030                1035

Arg Thr Pro Thr Ile Val Val Trp Ser Ile Leu Leu Ala Ser
    1040            1045                1050

Ile Phe Ser Leu Leu Trp Val Arg Ile Asp Pro Phe Thr Thr Lys
    1055            1060                1065

Val Thr Gly Pro Asp Val Lys Phe Cys Gly Ile Asn Cys
    1070            1075                1080

<210> SEQ ID NO 27
<211> LENGTH: 1040
<212> TYPE: PRT
<213> ORGANISM: Helianthus annum

<400> SEQUENCE: 27

Met Gln Ala Ser Ala Gly Leu Val Ala Gly Ser His Asn Arg Asn Glu
1               5                   10                  15

Leu Val Val Ile His Gly His Glu Glu Pro Lys Pro Leu Lys Asp Met
                20                  25                  30

Thr Gly Gln Val Cys Glu Ile Cys Gly Asp Glu Ile Gly Leu Thr Val
            35                  40                  45

Asp Gly Asp Leu Phe Val Ala Cys Asn Glu Cys Gly Phe Pro Val Cys
50                  55                  60

Arg Pro Cys Tyr Glu Tyr Glu Arg Arg Glu Gly Ser Gln Asn Cys Pro
65                  70                  75                  80

Gln Cys Lys Thr Arg Tyr Lys Arg Leu Lys Gly Ser Pro Arg Val Glu
                85                  90                  95

Gly Asp Asp Asp Glu Glu Asp Val Asp Ile Glu His Glu Phe Asn
                100                 105                 110

Ile Asp Asp Glu His Asn Lys Asn Asn Asn Ile Ala Glu Ala Met Leu
            115                 120                 125

His Gly Lys Met Ser Tyr Gly Arg Gly Pro Glu Asp Asp Asn Asn
            130                 135                 140

Asn Thr Gln Tyr Pro Pro Val Ile Ala Gly Arg Ser Ala His Val Ser
145                 150                 155                 160
```

-continued

```
Asp Glu Phe Pro Ile Ser Thr Gln Pro His Gly Glu His Leu Ser Ser
                165                 170                 175

Leu His Lys Arg Val His Pro Tyr Gly Ser Pro Glu Tyr Gly Ser Gly
            180                 185                 190

Arg Trp Asp Asp Lys Lys Asp Gly Gly Trp Lys Glu Arg Met Glu Glu
        195                 200                 205

Trp Lys Met His Gln Gln Gly Asn Leu Gly Ala Glu Ile Asp Asp Ser
    210                 215                 220

Val Asp Pro Asp Met Ala Met Leu Asp Glu Ala Arg Gln Pro Leu Ser
225                 230                 235                 240

Arg Lys Val Pro Ile Ala Ser Ser Lys Ile Asn Pro Tyr Arg Met Val
                245                 250                 255

Ile Val Ala Arg Leu Phe Ile Leu Ala Ile Phe Leu Arg Tyr Arg Leu
            260                 265                 270

Met Asn Pro Val Gln Asp Gly Phe Gly Leu Trp Leu Thr Ser Val Ile
        275                 280                 285

Cys Glu Ile Trp Phe Ala Phe Ser Trp Ile Leu Asp Gln Phe Pro Lys
    290                 295                 300

Trp Phe Pro Ile Asp Arg Glu Thr Tyr Leu Asp Arg Leu Ser Leu Arg
305                 310                 315                 320

Tyr Glu Arg Glu Gly Glu Pro Asn Met Leu Cys Pro Val Asp Val Phe
                325                 330                 335

Val Ser Thr Val Asp Pro Leu Lys Glu Pro Pro Leu Val Thr Ala Asn
            340                 345                 350

Thr Val Leu Ser Ile Leu Ala Met Asp Tyr Pro Val Asp Lys Ile Ser
        355                 360                 365

Cys Tyr Ile Ser Asp Asp Gly Ala Ser Met Leu Ser Phe Glu Ser Leu
    370                 375                 380

Ser Glu Thr Ala Glu Phe Ala Arg Lys Trp Val Pro Phe Cys Lys Lys
385                 390                 395                 400

Phe Ala Ile Glu Pro Arg Ala Pro Glu Met Tyr Phe Ser Asp Lys Ile
                405                 410                 415

Asp Tyr Leu Lys Asp Lys Val Gln Pro Thr Phe Val Lys Glu Arg Arg
            420                 425                 430

Ala Met Lys Arg Glu Tyr Glu Glu Phe Lys Val Arg Ile Asn Ala Leu
        435                 440                 445

Val Ala Lys Ala Met Lys Ala Pro Ala Glu Gly Trp Ile Met Gln Asp
    450                 455                 460

Gly Thr Pro Trp Pro Gly Asn Asn Thr Lys Asp His Pro Gly Met Ile
465                 470                 475                 480

Gln Val Phe Leu Gly Gln Ser Gly Gly Thr Asp Val Glu Gly Asn Glu
                485                 490                 495

Leu Pro Arg Leu Val Tyr Val Ser Arg Glu Lys Arg Pro Gly Phe Gln
            500                 505                 510

His His Lys Lys Ala Gly Ala Met Asn Ala Leu Val Arg Val Ser Gly
        515                 520                 525

Val Leu Thr Asn Ala Pro Phe Met Leu Asn Leu Asp Cys Asp His Tyr
    530                 535                 540

Leu Asn Asn Ser Lys Ala Ala Arg Glu Ala Met Cys Phe Leu Met Asp
545                 550                 555                 560

Pro Gln Ile Gly Arg Lys Val Cys Tyr Val Gln Phe Pro Gln Arg Phe
                565                 570                 575
```

-continued

```
Asp Gly Ile Asp Arg His Asp Arg Tyr Ala Asn Arg Asn Thr Val Phe
            580                 585                 590

Phe Asp Ile Asn Met Lys Gly Leu Asp Gly Ile Gln Gly Pro Val Tyr
        595                 600                 605

Val Gly Thr Gly Cys Val Phe Arg Arg Gln Ala Leu Tyr Gly Tyr Asp
    610                 615                 620

Pro Pro Lys Gly Pro Lys Arg Pro Lys Met Val Ser Cys Asp Cys Cys
625                 630                 635                 640

Pro Cys Phe Gly Arg Arg Lys Lys Asn Pro Lys Phe Glu Lys His Gly
                645                 650                 655

Asp Val Glu Asn Val Gln Gly Tyr Asn Asp Asp Lys Glu Leu Leu
            660                 665                 670

Lys Ser Gln Met Asn Phe Glu Lys Lys Phe Gly Gln Ser Ala Ile Phe
        675                 680                 685

Val Thr Ser Thr Leu Met Val Asp Gly Gly Val Pro Pro Ser Ser Ser
    690                 695                 700

Pro Ala Ser Leu Leu Lys Glu Ala Ile His Val Ile Ser Cys Gly Tyr
705                 710                 715                 720

Glu Asp Lys Thr Glu Trp Gly Leu Glu Leu Gly Trp Ile Tyr Gly Ser
                725                 730                 735

Ile Thr Glu Asp Ile Leu Thr Gly Phe Lys Met His Cys Arg Gly Trp
            740                 745                 750

Arg Ser Ile Tyr Cys Met Pro Lys Arg Pro Ala Phe Lys Gly Ser Ala
        755                 760                 765

Pro Ile Asn Leu Ser Asp Arg Leu Asn Gln Val Leu Arg Trp Ala Leu
    770                 775                 780

Gly Ser Val Glu Ile Phe Phe Ser Arg His Ser Pro Leu Leu Tyr Gly
785                 790                 795                 800

Tyr Lys Gly Gly Asn Leu Lys Trp Leu Glu Arg Phe Ala Tyr Val Asn
                805                 810                 815

Thr Thr Ile Tyr Pro Phe Thr Ala Leu Pro Leu Leu Ala Tyr Cys Ile
            820                 825                 830

Leu Pro Ala Ile Cys Leu Leu Thr Gly Lys Phe Ile Met Pro Glu Ile
        835                 840                 845

Ser Thr Leu Ala Ser Leu Phe Phe Ile Ser Leu Phe Leu Ser Ile Phe
    850                 855                 860

Ala Thr Gly Ile Leu Glu Leu Arg Trp Ser Gly Val Ser Ile Glu Glu
865                 870                 875                 880

Trp Trp Arg Asn Glu Gln Phe Trp Val Ile Gly Gly Val Ser Ala His
                885                 890                 895

Leu Phe Ala Val Ile Gln Gly Leu Leu Lys Val Leu Ala Gly Ile Asp
            900                 905                 910

Thr Asn Phe Thr Val Thr Ser Lys Ala Thr Asp Asp Glu Glu Phe Gly
        915                 920                 925

Glu Leu Tyr Ala Phe Lys Trp Thr Thr Leu Leu Ile Pro Pro Thr Thr
    930                 935                 940

Ile Leu Ile Ile Asn Met Val Gly Val Ala Gly Ile Ser Asp Ala
945                 950                 955                 960

Ile Asn Asn Gly Tyr Gln Ser Trp Gly Pro Leu Phe Gly Lys Leu Phe
                965                 970                 975

Phe Ala Phe Trp Val Ile Leu His Leu Tyr Pro Phe Leu Lys Gly Leu
            980                 985                 990

Met Gly Lys Gln Asn Arg Thr Pro  Thr Ile Val Val Ile  Trp Ser Ile
```

```
                              995                 1000                1005

Leu Leu Ala Ser Ile Phe Ser Leu Leu Trp Val Arg Ile Asp Pro
            1010                1015                1020

Phe Val Leu Lys Thr Lys Gly Pro Asp Val Lys Gln Cys Gly Leu
            1025                1030                1035

Asn Cys
            1040

<210> SEQ ID NO 28
<211> LENGTH: 736
<212> TYPE: PRT
<213> ORGANISM: Helianthus annum

<400> SEQUENCE: 28

His Ala Leu Ile Ile Pro Pro Phe Met Asn Arg Ala Lys Arg Val His
  1               5                  10                  15

Pro Met Pro Phe Ser Asp Thr Ala Ser Ser Val Ser Leu Pro Pro Arg
             20                  25                  30

Pro Met Asp Pro Lys Lys Asp Leu Ala Val Tyr Gly Tyr Gly Thr Val
         35                  40                  45

Ala Trp Lys Asp Arg Met Glu Glu Trp Arg Arg Gln Asn Asp Lys
 50                  55                  60

Leu Gln Met Val Lys His Gln Gly Asp Gly Gly Gly Gln Asn Asp
 65                  70                  75                  80

Gly Asp Val Asp Asp Pro Asp Met Pro Lys Met Asp Glu Gly Arg Gln
             85                  90                  95

Pro Leu Ser Arg Lys Leu Pro Ile Ser Ser Ser Lys Ile Asn Pro Tyr
            100                 105                 110

Arg Met Val Ile Leu Ile Arg Met Ala Ile Leu Gly Leu Phe Phe His
            115                 120                 125

Tyr Arg Ile Leu His Pro Val Asn Asp Ala Tyr Ala Leu Trp Leu Ile
        130                 135                 140

Ser Val Ile Cys Glu Ile Trp Phe Ala Val Ser Trp Ile Phe Asp Gln
145                 150                 155                 160

Phe Pro Lys Trp Phe Pro Ile Glu Arg Glu Thr Tyr Leu Asp Arg Leu
                165                 170                 175

Ser Leu Arg Tyr Glu Lys Glu Gly Lys Pro Ser Glu Leu Ala Pro Val
            180                 185                 190

Asp Val Phe Val Ser Thr Val Asp Pro Met Lys Glu Pro Pro Leu Ile
            195                 200                 205

Thr Ala Asn Thr Val Leu Ser Ile Leu Ala Val Asp Tyr Pro Val Asp
        210                 215                 220

Lys Val Ala Cys Tyr Val Ser Asp Asp Gly Ala Ala Met Leu Thr Phe
225                 230                 235                 240

Glu Ala Leu Ser Glu Thr Ser Glu Phe Ala Arg Lys Trp Val Pro Phe
                245                 250                 255

Cys Lys Lys Phe Asn Ile Glu Pro Arg Ala Pro Glu Trp Tyr Phe Ala
            260                 265                 270

Glu Lys Val Asp Tyr Leu Lys Asp Lys Val His Pro Ser Phe Val Arg
            275                 280                 285

Glu Arg Arg Ala Met Lys Arg Glu Tyr Glu Glu Phe Lys Ile Arg Ile
        290                 295                 300

Asn Gly Leu Val Thr Met Ala Gln Lys Val Pro Glu Glu Gly Trp Thr
305                 310                 315                 320
```

-continued

```
Met Gln Asp Gly Thr Pro Trp Pro Gly Asn Asp Val Arg Asp His Pro
                325                 330                 335
Gly Met Ile Gln Val Phe Leu Gly Gln Ser Gly Gly Leu Asp Ser Glu
        340                 345                 350
Gly Asn Glu Leu Pro Arg Leu Val Tyr Val Ser Arg Glu Lys Arg Pro
    355                 360                 365
Gly Phe Gln His His Lys Lys Ala Gly Ala Met Asn Ala Leu Val Arg
370                 375                 380
Val Ser Ala Val Leu Asn Asn Gly Pro Phe Ile Leu Asn Leu Asp Cys
385                 390                 395                 400
Asp His Tyr Ile Asn Asn Ser Lys Ala Leu Arg Glu Ala Met Cys Phe
                405                 410                 415
Met Met Asp Pro Asn Leu Gly Lys Tyr Val Cys Tyr Val Gln Phe Pro
        420                 425                 430
Gln Arg Phe Asp Gly Ile Asp Arg Asn Asp Arg Tyr Ala Asn Arg Asn
    435                 440                 445
Thr Val Phe Phe Asp Ile Asn Leu Arg Gly Leu Asp Gly Ile Gln Gly
450                 455                 460
Pro Val Tyr Val Gly Thr Gly Cys Val Phe Asn Arg Thr Ala Leu Tyr
465                 470                 475                 480
Gly Tyr Glu Pro Pro Ile Lys Pro Lys Lys Arg Glu Lys Gly Val
                485                 490                 495
Leu Ser Ser Cys Phe Gly Ala Ser Arg Asn Lys Ser Ser Asn Ser Asn
                500                 505                 510
Lys Lys Gly Ser Asp Lys Lys Ser Ser Arg His Asp Asp Pro Thr
    515                 520                 525
Val Pro Val Phe Ser Leu Glu Asp Ile Glu Glu Gly Val Glu Gly Val
530                 535                 540
Gly Ile Asp Asp Glu Lys Ser Leu Leu Met Ser Gln Met Thr Leu Glu
545                 550                 555                 560
Lys Arg Phe Gly Gln Ser Ala Val Phe Val Ala Ser Thr Leu Met Glu
                565                 570                 575
Asn Gly Gly Val Pro Gln Ser Ala Ala Pro Glu Thr Leu Leu Lys Glu
        580                 585                 590
Ala Ile His Val Ile Ser Cys Gly Tyr Glu Asp Lys Thr Asp Trp Gly
    595                 600                 605
Ser Glu Ile Gly Trp Ile Tyr Gly Ser Val Thr Glu Asp Ile Leu Thr
    610                 615                 620
Gly Phe Lys Met His Ala Arg Gly Trp Arg Ser Ile Tyr Cys Met Pro
625                 630                 635                 640
Pro Arg Ala Ala Phe Lys Gly Ser Ala Pro Ile Asn Leu Ser Asp Arg
                645                 650                 655
Leu Asn Gln Val Leu Arg Trp Ala Leu Gly Ser Ile Glu Ile Leu Phe
        660                 665                 670
Ser Arg His Cys Pro Ile Trp Tyr Gly Tyr Ser Gly Arg Leu Lys Trp
    675                 680                 685
Leu Glu Arg Leu Ala Cys Ile Asn Thr Thr Ile Tyr Pro Val Thr Ala
    690                 695                 700
Ile Pro Leu Leu Val Tyr Cys Thr Leu Pro Ala Val Cys Leu Leu Thr
705                 710                 715                 720
Gly Lys Phe Ile Ile Pro Gln Ile Ser Asn Leu Ala Ser Leu Trp Phe
                725                 730                 735
```

```
<210> SEQ ID NO 29
<211> LENGTH: 509
<212> TYPE: PRT
<213> ORGANISM: Helianthus annum

<400> SEQUENCE: 29

Met Leu Gln Gly Ile Ile Ser Ile Leu Ile Ile Arg Val His Lys Ile
1               5                   10                  15

Ile Glu Ile Cys Ile Cys Ser Thr Cys Phe Leu Gly Asn Asn Gly Val
            20                  25                  30

Gln Asp Val Glu Gly Asn Lys Leu Gln Arg Leu Val Tyr Val Ser Arg
        35                  40                  45

Glu Lys Arg Pro Gly Phe Asp His His Lys Lys Ala Gly Ala Met Asn
    50                  55                  60

Ala Leu Ile Arg Val Ser Ala Val Ile Ser Asn Ala Pro Tyr Met Leu
65                  70                  75                  80

Asn Val Asp Cys Asp His Tyr Ile Asn Asn Ser Lys Ala Leu Arg Glu
                85                  90                  95

Ala Met Cys Phe Met Met Asp Pro Thr Ser Gly Lys Lys Ile Cys Tyr
            100                 105                 110

Val Gln Phe Pro Gln Arg Phe Asp Gly Ile Asp Arg His Asp Arg Tyr
        115                 120                 125

Ser Asn Arg Asn Val Val Phe Phe Asp Ile Asn Met Lys Gly Leu Asp
130                 135                 140

Gly Ile Gln Gly Pro Ile Tyr Val Gly Thr Gly Cys Val Phe Arg Arg
145                 150                 155                 160

Gln Ala Leu Tyr Gly Tyr Asp Ala Pro Thr Lys Lys Lys Pro Pro Gly
                165                 170                 175

Lys Thr Cys Asn Cys Leu Pro Lys Trp Leu Cys Cys Cys Ser Ser
            180                 185                 190

Arg Lys Lys Lys Ala Lys Gly Lys Ser Lys Lys Ser Lys Glu Lys Ser
        195                 200                 205

Thr Lys Gly Lys Lys Ser Lys Asp Pro Pro Thr Gln Ile His Ala Leu
    210                 215                 220

Glu Asn Ile Glu Glu Gly Ile Glu Gly Ile Asp Ser Glu Lys Ser Ser
225                 230                 235                 240

Leu Met Pro Gln Ile Lys Phe Glu Lys Lys Phe Gly Gln Ser Pro Val
                245                 250                 255

Phe Ile Ala Ser Thr Leu Leu Glu Asp Gly Gly Val Pro Pro Gly Ala
            260                 265                 270

Ser Ser Ala Ser Leu Leu Lys Glu Ala Ile His Val Ile Ser Cys Gly
        275                 280                 285

Tyr Glu Asp Lys Thr Glu Trp Gly Lys Glu Val Gly Trp Ile Tyr Gly
    290                 295                 300

Ser Val Thr Glu Asp Ile Leu Thr Gly Phe Lys Met His Cys His Gly
305                 310                 315                 320

Trp Arg Ser Val Tyr Cys Ile Pro Lys Arg Ala Ala Phe Lys Gly Ser
                325                 330                 335

Ala Pro Ile Asn Leu Ser Asp Arg Leu His Gln Val Leu Arg Trp Ala
            340                 345                 350

Leu Gly Ser Val Glu Ile Leu Leu Ser Arg His Cys Pro Ile Trp Tyr
        355                 360                 365

Gly Tyr Gly Cys Gly Leu Lys Pro Leu Glu Arg Phe Ser Tyr Ile Asn
    370                 375                 380
```

```
Ser Val Val Tyr Pro Leu Thr Ser Val Pro Leu Ala Tyr Cys Thr
385                 390                 395                 400

Leu Pro Ala Val Cys Leu Leu Thr Gly Lys Phe Ile Val Pro Glu Ile
            405                 410                 415

Ser Asn Tyr Ala Ser Ile Leu Phe Met Leu Met Phe Leu Ser Ile Ala
            420                 425                 430

Val Thr Ser Ile Leu Glu Ile Gln Trp Gly Val Gly Ile Asp Asp
        435                 440                 445

Leu Trp Arg Asn Glu Gln Phe Trp Val Ile Gly Val Ser Ala His
    450                 455                 460

Leu Phe Ala Leu Val Gln Gly Leu Leu Lys Val Leu Ala Gly Val Asn
465                 470                 475                 480

Thr Asn Phe Thr Val Thr Ser Lys Gly Gly Asp Asp Gly Glu Phe Ser
            485                 490                 495

Glu Leu Tyr Leu Phe Lys Trp Thr Thr Leu Leu Ile Pro
        500                 505
```

```
<210> SEQ ID NO 30
<211> LENGTH: 24
<212> TYPE: PRT
<213> ORGANISM: Artificial
<220> FEATURE:
<223> OTHER INFORMATION: Synthetic Polypeptide
<220> FEATURE:
<221> NAME/KEY: MISC_FEATURE
<223> OTHER INFORMATION: Motif 1a
<220> FEATURE:
<221> NAME/KEY: VARIANT
<222> LOCATION: (1)..(1)
<223> OTHER INFORMATION: / replace = "Ile"
<220> FEATURE:
<221> NAME/KEY: VARIANT
<222> LOCATION: (2)..(2)
<223> OTHER INFORMATION: / replace = "Val" or "Ser"
<220> FEATURE:
<221> NAME/KEY: VARIANT
<222> LOCATION: (4)..(4)
<223> OTHER INFORMATION: / replace = "Ile" or "Phe"
<220> FEATURE:
<221> NAME/KEY: VARIANT
<222> LOCATION: (6)..(6)
<223> OTHER INFORMATION: / replace = "Asp", or "Thr"
<220> FEATURE:
<221> NAME/KEY: VARIANT
<222> LOCATION: (8)..(8)
<223> OTHER INFORMATION: / replace = "Ile", or "Leu"
<220> FEATURE:
<221> NAME/KEY: VARIANT
<222> LOCATION: (9)..(9)
<223> OTHER INFORMATION: / replace = "Ser"
<220> FEATURE:
<221> NAME/KEY: VARIANT
<222> LOCATION: (10)..(10)
<223> OTHER INFORMATION: / replace = "Asn" or "Lys"
<220> FEATURE:
<221> NAME/KEY: VARIANT
<222> LOCATION: (13)..(13)
<223> OTHER INFORMATION: / replace = "Asp", "Gly", or "Glu",
<220> FEATURE:
<221> NAME/KEY: VARIANT
<222> LOCATION: (14)..(14)
<223> OTHER INFORMATION: / replace = "Ala"
<220> FEATURE:
<221> NAME/KEY: VARIANT
<222> LOCATION: (19)..(19)
<223> OTHER INFORMATION: / replace = "Met",
<220> FEATURE:
<221> NAME/KEY: VARIANT
<222> LOCATION: (21)..(21)
<223> OTHER INFORMATION: / replace = "Arg"
<220> FEATURE:
```

```
<221> NAME/KEY: VARIANT
<222> LOCATION: (22)..(22)
<223> OTHER INFORMATION: / replace = "Val"
<220> FEATURE:
<221> NAME/KEY: VARIANT
<222> LOCATION: (23)..(23)
<223> OTHER INFORMATION: / replace = "Leu"

<400> SEQUENCE: 30

Val Ala Gly Val Ser Tyr Ala Val Asn Ser Gly Tyr Gln Ser Trp Gly
1               5                   10                  15

Pro Leu Phe Gly Lys Leu Phe Phe
            20

<210> SEQ ID NO 31
<211> LENGTH: 24
<212> TYPE: PRT
<213> ORGANISM: Artificial
<220> FEATURE:
<223> OTHER INFORMATION: Synthetic Polypeptide
<220> FEATURE:
<221> NAME/KEY: MISC_FEATURE
<223> OTHER INFORMATION: Motif 1b
<220> FEATURE:
<221> NAME/KEY: VARIANT
<222> LOCATION: (1)..(1)
<223> OTHER INFORMATION: / replace = "Ile"
<220> FEATURE:
<221> NAME/KEY: VARIANT
<222> LOCATION: (2)..(2)
<223> OTHER INFORMATION: / replace = "Val" or "Ser"
<220> FEATURE:
<221> NAME/KEY: VARIANT
<222> LOCATION: (4)..(4)
<223> OTHER INFORMATION: / replace = "Ile" or "Phe"
<220> FEATURE:
<221> NAME/KEY: VARIANT
<222> LOCATION: (6)..(6)
<223> OTHER INFORMATION: / replace = "Asp" or "Thr"
<220> FEATURE:
<221> NAME/KEY: VARIANT
<222> LOCATION: (8)..(8)
<223> OTHER INFORMATION: / replace = "Ile"
<220> FEATURE:
<221> NAME/KEY: VARIANT
<222> LOCATION: (9)..(9)
<223> OTHER INFORMATION: / replace = "Ser"
<220> FEATURE:
<221> NAME/KEY: VARIANT
<222> LOCATION: (10)..(10)
<223> OTHER INFORMATION: / replace = "Asn"
<220> FEATURE:
<221> NAME/KEY: VARIANT
<222> LOCATION: (13)..(13)
<223> OTHER INFORMATION: / replace = "Asp"
<220> FEATURE:
<221> NAME/KEY: VARIANT
<222> LOCATION: (19)..(19)
<223> OTHER INFORMATION: / replace = "Met"
<220> FEATURE:
<221> NAME/KEY: VARIANT
<222> LOCATION: (21)..(21)
<223> OTHER INFORMATION: / replace = "Arg"
<220> FEATURE:
<221> NAME/KEY: VARIANT
<222> LOCATION: (23)..(23)
<223> OTHER INFORMATION: / replace = "Leu"

<400> SEQUENCE: 31

Val Ala Gly Val Ser Tyr Ala Val Asn Ser Gly Tyr Gln Ser Trp Gly
1               5                   10                  15

Pro Leu Phe Gly Lys Leu Phe Phe
            20
```

```
<210> SEQ ID NO 32
<211> LENGTH: 24
<212> TYPE: PRT
<213> ORGANISM: Artificial
<220> FEATURE:
<223> OTHER INFORMATION: Synthetic Polypeptide
<220> FEATURE:
<221> NAME/KEY: MISC_FEATURE
<223> OTHER INFORMATION: Motif 1c
<220> FEATURE:
<221> NAME/KEY: VARIANT
<222> LOCATION: (2)..(2)
<223> OTHER INFORMATION: / replace = "Ser"
<220> FEATURE:
<221> NAME/KEY: VARIANT
<222> LOCATION: (4)..(4)
<223> OTHER INFORMATION: / replace = "Ile"
<220> FEATURE:
<221> NAME/KEY: VARIANT
<222> LOCATION: (6)..(6)
<223> OTHER INFORMATION: / replace = "Thr"
<220> FEATURE:
<221> NAME/KEY: VARIANT
<222> LOCATION: (8)..(8)
<223> OTHER INFORMATION: / replace = "Ile"
<220> FEATURE:
<221> NAME/KEY: VARIANT
<222> LOCATION: (19)..(19)
<223> OTHER INFORMATION: / replace = "Met"
<220> FEATURE:
<221> NAME/KEY: VARIANT
<222> LOCATION: (23)..(23)
<223> OTHER INFORMATION: / replace = "Leu"

<400> SEQUENCE: 32

Val Ala Gly Val Ser Tyr Ala Val Asn Ser Gly Tyr Gln Ser Trp Gly
1               5                   10                  15

Pro Leu Phe Gly Lys Leu Phe Phe
            20

<210> SEQ ID NO 33
<211> LENGTH: 20
<212> TYPE: PRT
<213> ORGANISM: Artificial
<220> FEATURE:
<223> OTHER INFORMATION: Motif 2a
<220> FEATURE:
<221> NAME/KEY: MISC_FEATURE
<223> OTHER INFORMATION: Motif 2a
<220> FEATURE:
<221> NAME/KEY: VARIANT
<222> LOCATION: (1)..(1)
<223> OTHER INFORMATION: / replace = "Leu" or "Ile"
<220> FEATURE:
<221> NAME/KEY: VARIANT
<222> LOCATION: (4)..(4)
<223> OTHER INFORMATION: / replace = "Ala" or "Ile"
<220> FEATURE:
<221> NAME/KEY: VARIANT
<222> LOCATION: (6)..(6)
<223> OTHER INFORMATION: / replace = "Ile"
<220> FEATURE:
<221> NAME/KEY: VARIANT
<222> LOCATION: (9)..(9)
<223> OTHER INFORMATION: / replace = "Val"
<220> FEATURE:
<221> NAME/KEY: VARIANT
<222> LOCATION: (10)..(10)
<223> OTHER INFORMATION: / replace = "Leu"
<220> FEATURE:
<221> NAME/KEY: VARIANT
<222> LOCATION: (11)..(11)
<223> OTHER INFORMATION: / replace = "Thr"
<220> FEATURE:
<221> NAME/KEY: VARIANT
```

```
<222> LOCATION: (13)..(13)
<223> OTHER INFORMATION: / replace = "Val"
<220> FEATURE:
<221> NAME/KEY: VARIANT
<222> LOCATION: (17)..(17)
<223> OTHER INFORMATION: / replace = "Val"
<220> FEATURE:
<221> NAME/KEY: VARIANT
<222> LOCATION: (18)..(18)
<223> OTHER INFORMATION: / replace = "Asp"

<400> SEQUENCE: 33

Val Trp Ser Val Leu Leu Ala Ser Ile Phe Ser Leu Leu Trp Val Arg
1               5                   10                  15

Ile Asn Pro Phe
            20

<210> SEQ ID NO 34
<211> LENGTH: 20
<212> TYPE: PRT
<213> ORGANISM: Artificial
<220> FEATURE:
<223> OTHER INFORMATION: Synthetic Polypeptide
<220> FEATURE:
<221> NAME/KEY: MISC_FEATURE
<223> OTHER INFORMATION: Motif 2b
<220> FEATURE:
<221> NAME/KEY: VARIANT
<222> LOCATION: (4)..(4)
<223> OTHER INFORMATION: / replace = "Ala" or "Ile"
<220> FEATURE:
<221> NAME/KEY: VARIANT
<222> LOCATION: (6)..(6)
<223> OTHER INFORMATION: / replace = "Ile"
<220> FEATURE:
<221> NAME/KEY: VARIANT
<222> LOCATION: (10)..(10)
<223> OTHER INFORMATION: / replace = "Leu"
<220> FEATURE:
<221> NAME/KEY: VARIANT
<222> LOCATION: (11)..(11)
<223> OTHER INFORMATION: / replace = "Thr"
<220> FEATURE:
<221> NAME/KEY: VARIANT
<222> LOCATION: (17)..(17)
<223> OTHER INFORMATION: / replace = "Val"
<220> FEATURE:
<221> NAME/KEY: VARIANT
<222> LOCATION: (18)..(18)
<223> OTHER INFORMATION: / replace = "Asp"

<400> SEQUENCE: 34

Val Trp Ser Val Leu Leu Ala Ser Ile Phe Ser Leu Leu Trp Val Arg
1               5                   10                  15

Ile Asn Pro Phe
            20

<210> SEQ ID NO 35
<211> LENGTH: 20
<212> TYPE: PRT
<213> ORGANISM: Artificial
<220> FEATURE:
<223> OTHER INFORMATION: Synthetic Polypeptide
<220> FEATURE:
<221> NAME/KEY: MISC_FEATURE
<223> OTHER INFORMATION: Motif 2c
<220> FEATURE:
<221> NAME/KEY: VARIANT
<222> LOCATION: (4)..(4)
<223> OTHER INFORMATION: / replace = "Ala" or "Ile"
<220> FEATURE:
<221> NAME/KEY: VARIANT
<222> LOCATION: (18)..(18)
```

<223> OTHER INFORMATION: / replace = "Asp"

<400> SEQUENCE: 35

Val Trp Ser Val Leu Leu Ala Ser Ile Phe Ser Leu Leu Trp Val Arg
1               5                   10                  15
Ile Asn Pro Phe
            20

<210> SEQ ID NO 36
<211> LENGTH: 3452
<212> TYPE: DNA
<213> ORGANISM: Brassica napus

<400> SEQUENCE: 36

```
gatctaatcg catttcgctt atccccagca gatttgaact ctccctacga ttcgttgatc    60
gtatatggaa tccgaaggag aaaccgcggg taagccgatg acgagcgtcg gcggccagat   120
atgccagatc tgtagtgaca atgtaggcaa gactgttgat ggagaccggt tcgtggcgtg   180
tgatgtttgt ggattcccgg tttgcaggcc ttgctatgag tttgagagga aggatgggaa   240
tcaatcttgt cctcagtgca aaaccactta caagaggcac aagggagtc ctgctattcc    300
tggtgataaa gatgaggatg tcttcgctga tgaagcaact gttgagttaa gctacccgca   360
gaaggagaag atttcggaga ggatgcttgg gtggcatctt acacgtggca aggagagga   420
gatggggcag cctgagtatg acaaagaggt ttctcataat catctccctc gtctcaccag   480
tagacaagag acttcaggag agttttctgc tgcctcgcct gaacgcctct ctgtttcttc   540
taccattggt ggtggaaagc gccttcccta ttcatctgat atcaatcaat caccacatag   600
aaggatttcg gatcctgttg gactagggaa tgtagcttgg aaggagagag ttgatggctg   660
gaaaatgaag caggagaaga ataatggtgg tcctgtgagc acccaggctg cttctgaaag   720
aggtggagga gatattgatg ccagcactga tatcctcgca gatgaggctt gctgaatga    780
cgaagcgaga cagcctctgt cgaggaaagt ttcgattcct tcatcaagga tcaatcctta   840
ccgaatggtt attatgttgc gtcttgtcat tctatgtctc ttcttgcact accgtataac   900
aaatccagtg ccaaatgcct tcactctgtg gctgatctca gtgatatgtg agatctggtt   960
tgccttttcc tggattttgg atcagttccc caaatggttt cctgtcaacc gtgaaaccta  1020
cctagatagg cttgctttaa gatatgatcg tgaaggtgag ccttcacagc tagcggctgt  1080
ggacatcttc gtgagtactg ttgaccccctt gaaggagcca cccccttgtga ctgctaacac  1140
agtgctctct atttttggctg ttgactaccc ggttgacaag gtgtcctgtt atgtttctga  1200
tgatggtgct gctatgttat catttgaagc acttgcagaa acatcagagt ttgctcgtaa  1260
atgggtacca ttctgcaaga aatatagcat tgagcctcgc gcaccagaat ggtatttgc   1320
tgcgaaaata gattatctga aggataaagt tcagacatca tttgtcaaag atcgtagagc  1380
tatgaagagg gaatatgagg aatttaagat ccgaatcaat gcacttgttt ctaaggccct  1440
taaatgtcct gaagaagggt gggttatgca agatggcaca ccatggcctg gaaataatac  1500
aagagaccat ccaggaatga tccaggtttt cttagggcaa aacggtgggc ttgatgcaga  1560
gggcaatgag cttccgcgtt tggtgtatgt ttctcgagaa aagcgaccag gattccagca  1620
ccacaaaaag gctggtgcta tgaatgcact tgttagagtt tcagcagtcc ttaccaatgg  1680
accttttcatc ttgaatcttg attgtgatca ttacatcaat aacagcaagg ccttgagaga  1740
agcaatgtgc ttcctgatgg atccaaacct agggaagcaa gtgtgttatg ttcagttccc  1800
tcaaagattc gatggtatcg ataagaacga tagatatgct aatcgtaata ccgttttctt  1860
```

```
tgatatcaac ttgagaggtt tagatgggat tcaaggacct gtatatgtgg gaactgggtg    1920
tgttttcaac agaacagcat tatatggtta tgaacctcca attaaagtaa aacacaagaa    1980
gccaagtctt ttatctaaga tctgtggtgg gtcaagaaag aagaattcca aatctaagaa    2040
agattcggac aaaaagaaat caggcaggca tactgactca actgttcctg tattcaacct    2100
tgatgacata aagagggag ttgaaggtgc tggttttgac gatgaaaagg cgctcttgat     2160
gtcacaaatg agcctggaga agcgatttgg acagtctgct gttttgttg cgtctaccct     2220 aatggaaaat ggaggcgttc ctcctacaga aactcctgaa aaccttctca agaggcgat    2280 ccatgtcatt agttgtggat acgaggataa gtcagactgg ggaatggaga ttggatggat    2340
ctatggttcg gtgacagaag atattctgac tgggttcaag atgcatgccc gtggatggag    2400
atccatttac tgtatgccaa agcttccggc gttcaagggg tctgctccta tcaatctttc    2460
agatcgtctg aaccaagtgc tgaggtgggc tctaggttcc gttgagattc tcttcagtcg    2520
gcattgtcct atatggtatg gttacagtgg gaggcttaaa tttcttgaga ggtttgcata    2580
tgtgaacacc accatctacc cactcacctc cgtccctctt ctcttgtatt gtacattgcc    2640
cgccgtttgt ctcttcacca accagttcat catccctcag attagtaaca ttgcaagtat    2700
atggtttctg tctctctttc tgtctatttt cgccacgggt atactcgaaa tgaggtggag    2760
tggcgtaggc atagacgaat ggtggagaaa cgagcagttc tgggtcattg gaggagtatc    2820
cgctcactta ttcgccgtgt ttcaaggtct cctcaaagtc ctagccggta tcgacacaaa    2880
cttcacagtc acgtcaaaag cttcagacga agacggagac ttcgctgagc tctacttgtt    2940
caaatggaca acgcttctga ttccgccgac gacgctgctc attgtaaacc tcgtgggagt    3000
tgttgcggga ttctcgtacg caatcaacag tggataccaa tcttggggac cgctctttgg    3060
taagctgttc ttcgcgtttt gggtgattgt tcacttgtac cctttcctca agggtttgat    3120
ggggagacag aacaggactc ccaccattgt tgtggtctgg tctgttctct ggcttccat     3180 cttctccttg ttgtgggtta ggatcgatcc cttcactaaa agagtcactg gcccggacat    3240
actcgaatgt ggaatcaact gttgagaagt gagcaataat atgcttttg ggcttcaaaa     3300 gacgcagaaa atatataatt ttattgtttt atttgttaaa cggtttattt atcttgtttg    3360
tgtgtattgt cttgttcttg tttcgttttt tcatgtgtag aatatattac cctagttact    3420
ttggaaagat tattaagtca aaagcgaata tt                                  3452
```

<210> SEQ ID NO 37
<211> LENGTH: 3676
<212> TYPE: DNA
<213> ORGANISM: Brassica napus

<400> SEQUENCE: 37

```
aaaataggca aatcagattg gtgtttgaag tttaggatca agaaagaaa gaaagagagt       60 gtcagtgttg aacatctctc tgtcggtgtg tgatctgact catcagcatc aatggaggcc    120
agtgccggct tggtcgctgg ttcctaccgg agaaacgagc tcgttcggat ccgtcacgaa    180
tccgacggcg ggtccaaagc tatgaagaat atggatccac atacatgtca gatctgtggt    240
gataacgctg ggctcactga aactggagat cttttgtgg cttgcaatga atgtgccttc     300
cctgtctgcc gtccttgcta tgagtacgag aggaaagatg gaactcagtg ttgccctcaa    360
tgcaagacta gatacagacg tctcaggggt catcctcgtg ttgaagggga tgaagatgag    420
gatgatgttg atgatattga gaacgagttt aattacgctc aaggagctaa caagggaaga    480
```

```
cgccaacaac gtcatggtga agagttctct tcctcttcta gacatgaatc tcaaccaatt      540
cctcttctca ctcatggcca cacggtttca ggggaaattc gcacgcctga cacacaatct      600
gtgcgtacta catcaggtcc tttagggcct ggtgacagga atgccatttc atctccatat      660
attgacccac gccaacctgt acctgtgaga atcgtagacc cttcgaaaga tttgaactct      720
tatgggcttg gcaatgttga ctggaaagaa agggttgaag gctggaagct gaagcaggag      780
aagaatatgg tacagatgac tggtaaatac cacgaaggga aggtggaga aattgaaggc       840 actggttcca acggcgaaga actccaaatg gctgatgatt cgaggctgcc tatgagccgt      900
attgtgccta tcccgccttc tcatctcaca ccttaccggg ttgtgattat tctccggctt      960
atcatcttgg gattcttctt gcaatatcgt acaactcacc ctgtgaaaga tgcttatcca     1020
ttgtggttga cctcagttat ttgtgagatc tggtttgcat tttcttggct tctcgatcag     1080
tttcccaaat ggtaccctat taaccgagag acttatcttg accgtctcgc tataagatat     1140
gatcgagacg gtgaaccatc gcagcttact cctgttgacg tgtttgttag tacagtggac     1200
ccactgaaag agcctcctct tgtaacagca aacacagttc tctcgattct tgctgtggac     1260
tacccggtag acaaagtagc ctgttatgtt tcagacgatg gtgcagctat gctgacgttc     1320
gaatctcttt ctgaaactgc cgagttcgca aagaaatggg tgccattttg caagaagttt     1380
agcattgaac ccagagcccc tgagttctat tttgcacaga agatagatta cttgaaggac     1440
aagatccagc cttcttttgt aaagaacga cgagctatga agagagagta tgaagagttt      1500
aaggtgagga tcaatgcact tgttgctaaa gcacagaaga tccctgaaga aggatggacg     1560
atgcaggatg gtactccctg gcctggtaac aacactagat atcatcctgg aatgattcag     1620
gtgttcttag gccacagtgg aggtctagat actgatggaa atgagctgcc taggctcatc     1680
tatgtttctc gtgaaaagcg gcctggattt caacaccaca agaaggctgg agctatgaat     1740
gcattgatcc gtgtttctgc tgttctgacc aatggagctt atctattgaa cgtggattgt     1800
gatcattact tcaacaacag caaagctatt aaagaagcca tgtgtttcct gatggaccct     1860
gcttatggaa aaaatgctg ctacgtccag ttccctcagc gttttgatgg tattgacttg      1920
cacgatcgtt acgccaacag gaatatagtc ttcttcgata ttaacttgaa ggggttagat     1980
ggaatccagg gtccagtata tgtgggtact ggttgctgtt tcaataggca agctctatat     2040
gggtatgatc ctgttttgac tgaggaagat ctggaaccaa atattattgt caagagctgt     2100
tgtggctcaa ggaagaaagg aaagaaaagc aagaagtata actatgatca acagaggaga     2160
ggcatcaaca gaagtgactc caatgctcca cttttcaaca tggacgacat agaagagggt     2220
tttgaaggtt atgatgatga gaggtctatt ctaatgtccc agaagagtgt agagaagcgt     2280
tttggtcagt ccccagtgtt tattgcggct accttcatgg aacaaggtgg cattccacca     2340
acgaccaatc cagctactct tctcaaggag gctattcatg ttataagctg tggctacgag     2400
gacaagactg aatggggaaa agagattggt tggatctatg gttctgtgac agaagatatt     2460
cttactgggt tcaagatgca tgcccggggt tggatgtcca tctactgcaa tcctccacga     2520
cctgcgttca agggatctgc accaatcaat cttttctgatc gtttgaacca agttcttcga     2580
tgggcgttgg gatctattga gattctcctg agtagacatt gccctatctg gtatggctat     2640
acaggaaggt tgagactctt ggagagactc gcttacatca acaccattgt ctaccctatt     2700
acagctctcc cactcatcgc ctactgtatc cttcctgctt tttgcctcat cactgacaag     2760
ttcatcatac cagagataag caactacgcg agtatctggt ttattcttct cttcatctca     2820
atcgctgtga ctggagttct agagctgaga tggagcggcg tgagcattga ggactggtgg     2880
```

```
aggaacgagc agttctgggt catcggtgga acatctgctc atcttttcgc agtcttccaa    2940
ggtctactca aggttcttgc gggtatagac actaacttca ctgtcacatc caaagcctcg    3000
gacgaagatg gggatttcgc ggagctttac atcttcaaat ggacagctct tctcattcca    3060
ccgaccacag tgctagttgt gaacctcata ggcattgtgg ctggtgtctc ttacgctgtg    3120
aacagtgggt accagtcatg gggaccgctc tttgggaagc ttttcttcgc cttgtgggtc    3180
attgcccatc tctaccettt cttgaaaggt ctaatgggaa gacagaacag aacgccaacc    3240
atcgtcatcg tttggtctgt tcttctggcc tccatctttt cgttgctttg ggtcaggatc    3300
aatccttttg tctctgtcac tcccgaggcc aaccccactg ccgtcccagg aggtgtcttt    3360
tagaccctat tttatatata ttttgtaagc gcatatacgg aatgggagca ctctctaaat    3420
cttctaagcc tcaaaaccaa gtgaaccagg cggttagttt tctcttagcg gtcagagagt    3480
tatgaagtta ttggtacttg tcaccgttgt gatggtgtct ctcttttgaa acatagagcc    3540
acaagtaata ctttgttatt attatattat atttattaat tttgcttctc acctcaccttt   3600 gtaatgttgg agctttgttg ttgtcctaac gagtctatat atgcgctttc actataatac    3660 aaaagttta ttcaac                                                    3676

<210> SEQ ID NO 38
<211> LENGTH: 3660
<212> TYPE: DNA
<213> ORGANISM: Brassica napus

<400> SEQUENCE: 38
ggatatgatt tgttacaata tttaatatta ttgttttatg aattagaaga gtgacaagag      60
gcaaagagca gagacaaata gcagcttaca aatatctctc tctcttctag agaaagaatc    120
gcagattcat agagatctga agagtcacat cacaacgact ccatcttcag atctcatgat    180
ttgagctacc ccgacgattc ggtgatcgga gaaagtaagc gacgatggaa tccgatggag    240
aaaccgcggg gaagccgatg acgagcgtcg gtgggcagat atgccagatc tgcagcgaca    300
atgtcggcaa gactgttgac ggtgaccgtt tcgtggcctg tgatatctgt ggattccctg    360
tttgcaggcc ttgctatgaa tacgagagga agcacgggaa tcaatcttgt cctcagtgca    420
aaaccactta caagaggcac aagggtagtc ctgctattcc cggtgataag gatgaggatg    480
tcttcgctga tgaggccacc gttgagctca actaccegca gaaggagaag atttcggagc    540
ggatgcttgg atggcatctt acgcgtggga aaagtgagga gatggggcag cctgagtatg    600
acaaggaggt ttctcacaac catctccctc gtctcaccag tagacaagat acttcaggtg    660
agttttctgc tgcctcgcct gaacgtctct ctgtgtcttc tactatagct ggtggaaagc    720
gtcttcccta ttcatctgat atcaatcaat caccaaatag aaggatttcg gatcctgttg    780
gactagggaa tgtagcttgg aaggagagag ttgatggctg gaaaatgaag caggagaaga    840
ataatggtgg tcctgtgagc acccaggctg cttctgaaag aggtggagga gatattgatg    900
ctagcactga tatcctcgca gatgaggctt tgctgaatga cgaagcgagg cagcctctgt    960
caaggaaagt ttctattcct tcatcacgga tcaatcccta caggatggtt attatgttgc   1020
ggcttgttat cctgtgtctc ttcttgcact accgtataac aaatccagtg ccaaatgcct   1080
tcactctgtg gctgatctca gtgatatgtg agatctggtt tgccttttcc tggattttgg   1140
atcagtttcc caagtggttt cctgtgaacc gtgaaaccta cctcgacagg cttgctttaa   1200
gatatgatcg tgaaggtgag ccgtcacagt tagctgctgt ggacatcttc cgtgagtactg  1260
```

```
ttgacccttt gaaggagcca cctcttgtga cagccaacac agtgctctct attttggcgg    1320
ttgactaccc agttgacaag gtgtcttgct atgtttccga tgatggtgct gccatgttat    1380
catttgaagc acttgcagaa acatcagagt ttgctcgtaa atgggtacca ttctgcaaga    1440
aatatagcat tgagcctcgc gcaccagaat ggtattttgc tgcgaaaata gattacttga    1500
aggataaagt tcagacatca tttgtcaaag atcgtagagc catgaagagg gagtatgagg    1560
aatttaagat ccgaatcaat gcacttgttt ccaaggccct aaaatgtcct gaagaagggt    1620
gggttatgca agatggtaca ccatggcctg gaaataatac aagggaccat ccaggaatga    1680
tccaggtttt cttagggcaa aatggtggac ttgatgcgga gggcaatgag cttccacgtt    1740
tggtgtatgt ttctcgagaa aagagaccag gattccagca ccacaaaaag gctggtgcta    1800
tgaatgcact tgttagagtt tcagcagtac ttaccaatgg accttttcatc ttgaatcttg    1860
attgtgatca ttacataaat aacagcaagg ccttgagaga agcaatgtgc ttcctgatgg    1920
acccaaacct agggaagcaa gtttgttatg ttcagttccc acaaagattc gatggtattg    1980
ataagaacga tagatatgct aatcgtaata ccgtgttctt tgatattaac ttgagagagtt    2040
tggatgggat tcaaggacct gtatatgtgg gaactgggtg tgttttcaac agaacagcct    2100
tatatggtta tgaacctcca ataaaagtaa agcacaagaa gccaagtctc ttatctaagc    2160
tctgtggtgg atcaagaaag aagaattcca atctaagaa agattcggac aaaaagaaat    2220
caggcaggca tactgactca actgttcctg tattcaacct cgatgacata aagagggag    2280
ttgaaggtgc tggttttgac gatgaaaagg cgctcttgat gtcgcaaatg agcctggaga    2340
agcgatttgg acagtctgct gtttttgttg cttcaaccct aatggaaaat ggaggtgttc    2400
ctcctacaga aactccagaa aaccttctca agaggctat ccatgtcatt agttgtggtt    2460
acgaggataa gtctgattgg ggaatggaga ttggatggat ctatggttct gtgacagaag    2520
atattctaac tggggttcaaa atgcatgccc gtggatggag atccatttac tgtatgccaa    2580
aacttcccgc tttcaagggg tctgctccta tcaatctttc agaccgtctt aaccaagtcc    2640
tgaggtgggc tctaggttcg gttgagattc tcttcagtcg gcattgtcct atatggtatg    2700
gttacagtgg gaggcttaag tttcttgaga ggttgcgta tgtgaacaca accatctacc    2760
cactcacctc cgtccctctt ctcttttatt gtacattgcc cgccgtttgt ctcttcacca    2820
accagttcat cattcctcag atcagtaaca ttgcaagtat atggtttctg tctctctttc    2880
tgtctatttt cgccacgggt atactcgaaa tgaggtggag cggcgtaggg atagacgaat    2940
ggtggagaaa cgagcagttc tgggtcatcg gtggagtatc agctcacttg ttcgcggtgt    3000
ttcaaggtct cctcaaagtc ctagctggta tcgacacgaa cttcactgtc acgtcaaagg    3060
cttcagacga agacggagac ttcgcggagc tctacttgtt caaatggaca acgcttctga    3120
ttcctcccac cacgctgctc atcgtaaacc tcgtgggagt tgtcgcggga ttctcgtatg    3180
ctatcaacag tggataccag tcgtggggac cgctctttgg taagctgttc ttcgccttt    3240
gggtgattgt tcacttgtac ccattcctca agggtttgat ggggagacag aacaggactc    3300
ctactattgt tgtggtctgg tctgttctct tggcgtccat cttctccttg ttgtgggtta    3360
ggatcgatcc tttcactaaa agagtcactg gcccggacat tctggaatgt ggaatcaact    3420
gttgagatgt gagagcaatg atatgctttt gggtggttta agaaacacat aattataaag    3480
tttatattta ttattgtttt atttgtcttg tctattgtct gtttgtgtcg tgtaagatta    3540
aagagtattt ttgtttatgt gatgaagaag caagcagtgg atatagtttc atgttgtatt    3600
tttcaagaga tagaaaacat aaatctattg tttggaatga gaaatcattt agagactttg    3660
```

<210> SEQ ID NO 39
<211> LENGTH: 3705
<212> TYPE: DNA
<213> ORGANISM: Brassica napus

<400> SEQUENCE: 39

| | | | | | |
|---|---|---|---|---|---|
| cggaacacac | agacacagcg | attaaatagg | caaaagcaga | tttgttaaaa | aaactcaaat | 60 |
| cagacaaaga | gatacataga | gagagagagt | gtgtgtgtta | gtgtgaacat | cttcttttga | 120 |
| gttcgagaga | gaggttttc | gagatgccgt | attgaatcgg | ccaaagaatt | gaaattgcaa | 180 |
| tctctctgtc | tctgtgtgtt | tgtgtgtttg | tcggtggctc | gttgacttct | tcactcatca | 240 |
| gcgatggagg | ccagttccgg | cttggttgct | ggatcttacc | ggagaaacga | gctcgttcgt | 300 |
| atccgtcacg | aatctgacgg | cgggtccaaa | cctttgaaga | atatggaccg | tgagatatgc | 360 |
| cagatctgtg | gtgaccacgc | tggtctcacc | gaaactggag | atctctttgt | ggcttgcaat | 420 |
| gaatgtgcct | tccctgtgtg | tcgtccttgc | tatgattacg | agaggaaaga | tggaactcag | 480 |
| tgctgccctc | actgcaagac | tagatacaga | cggctcaggg | gtcatcctcg | tgttgaagga | 540 |
| gatgaggatg | aggatgatgt | tgatgatatc | gagaatgagt | tcagctacgc | ccagggagga | 600 |
| gctaacaagc | cgagacgccg | tgaagagttt | tcctcctcct | ctagacatga | ttctcagcca | 660 |
| attcctcttc | tcacccatgg | ccatggggtt | tctggagaga | ttcggacgcc | tgatacacaa | 720 |
| tctgtgcgaa | ctacatcagg | tcctttgggg | cctggtgaga | ggaacgccat | tcatcttca | 780 |
| tatattgacc | cacgccaacc | tgtccctgta | aggatcgtgg | accgtcaaa | agacttgaac | 840 |
| tcttacgggc | ttggaaacgt | tgactggaaa | gaaagagttg | aaggctggaa | gctgaaacag | 900 |
| gagaagaaca | tgttacagat | gactggtaaa | tatcatgaag | ggaaggagg | agagattgaa | 960 |
| gggactggtt | ccaatggcga | agaactccaa | atggctgatg | atacgcgact | tcctatgagc | 1020 |
| cgtattgtgc | ctatcccgcc | ttctcatctc | acaccttatc | gtgttgtgat | tattctccgg | 1080 |
| cttatcatct | tgggattctt | cttgcaatac | cgtacaactc | accctgtgaa | agatgcatat | 1140 |
| ccgttgtggt | tgacttcagt | tatttgtgag | atctggtttg | cattctcttg | gcttcttgat | 1200 |
| cagtttccca | aatggtaccc | cattaacaga | gagacttatc | ttgaccgtct | cgctataaga | 1260 |
| tatgatcgag | agggtgaacc | atctcagctt | actcctgttg | atgtgtttgt | tagtacggtg | 1320 |
| gacccactga | aagagccacc | tcttgtaacg | gcaaacacag | ttctctcgat | tcttgccgtg | 1380 |
| gactacccgg | tagataaagt | agcctgttat | gtttcagatg | atggtgcagc | gatgcttacc | 1440 |
| ttcgaatctc | tttctgaaac | tgctgagttc | gcaaagaaat | gggtgccttt | ttgcaagaaa | 1500 |
| ttcagcattg | aacccagggc | tcctgaattc | tattttcagc | agaagataga | ttacctgaag | 1560 |
| gacaagatcc | agccttcttt | tgttaaagag | cgacgagcta | tgaagagaga | gtatgaggag | 1620 |
| tttaaggtga | ggatcaatgc | acttgttgct | aaagcacaga | aaatccctga | agaaggctgg | 1680 |
| acgatgcagg | atggtactcc | ctggcctggt | aacaacacta | gagatcatcc | tggaatgatc | 1740 |
| caggtgttct | taggccacag | tggaggtcta | gataccgatg | gaaatgagct | gcctagactc | 1800 |
| atctatgttt | ctcgtgaaaa | gcggcctgga | ttccagcatc | acaaaaaggc | tggagctatg | 1860 |
| aatgccttga | tccgtgtttc | tgctgttctt | accaatggag | catatctttt | gaacgtggac | 1920 |
| tgtgatcatt | acttcaacaa | cagcaaggct | attaagaag | ccatgtgttt | cttgatggac | 1980 |
| cctgcttacg | gaaagaagtg | ctgctatgtc | cagttcccac | agcgtttcga | tggtattgat | 2040 |
| ttgcacgatc | gatatgccaa | caggaatatt | gtcttcttcg | atattaactt | gaagggttta | 2100 |

```
gatggtatcc aaggtccagt atatgtgggt actggatgtt gtttcaacag gcaagctcta    2160
tatggatatg atcctgtctt gacagaggaa gatttaaaac caaacatcat tgtcaagagc    2220
tgctgcggct caaggaagaa aggaaagaac agtaagaaat atagctatga tcaaaaaagg    2280
agaggcatca gcagaagtga ttccaatgct ccacttttca acatggacga catcgatgag    2340
ggtttcgaag gatatgatga tgataggtct attctaatgt cccagaagag tgtggagaag    2400
cgttttggtc agtcgccagt atttattgct gccacgttta tggaacaagg tggcattcca    2460
ccaacgacca atccagctac tcttctcaag gaggctattc atgttataag ctgtggttac    2520
gaggacaaga ctgagtgggg aaaagagatt ggttggatct atggttctgt tacagaagat    2580
attcttactg gattcaagat gcatgctcgt ggttggatgt ctatctactg caatcctcca    2640
cgacctgcgt tcaagggatc tgcaccaatc aatctttctg atcgtttgaa ccaagttctt    2700
cggtgggcgt tgggatctat cgagattctt ctgagtagac attgccctat ctggtatggc    2760
tatacaggaa ggttgagact cttggagagg ctcgcttaca tcaacaccat tgtctaccct    2820
attacagctc tccctctcat cgccattgt attcttccag cttttgcct catcactgac     2880
aagttcatca tacctgagat aagcaactac gcgagtattt ggttcattct tctcttcatc    2940
tccattgctg tgactggaat cctggagctg agatggagcg gtgtgagcat tgaggactgg    3000
tggagaaacg agcagttctg ggtcattgga ggcacatctg ctcatctttt tgcagtcttc    3060
caaggtctac tcaaggtact tgcgggcatc gacactaact tcaccgtcac atcaaaagcc    3120
tcagacgaag atggggactt cgcagagctt acatcttca aatggacagc tcttctcatt     3180
ccaccaacca cggtcctagt tgtgaacatg ataggcattg tggctggtgt ctcttacgct    3240
attaacagcg ggtaccagtc atggggtccg ctctttggga agcttttctt cgccttgtgg    3300
gtcattgccc atctctaccc gttcttgaaa ggtctgcttg aagacagaa cagaacacca     3360
accatcgtca ttgtttggtc tgttcttctc gcctccatct tttcgttgct ttgggtcagg    3420
atcaatccat ttgtctctgt cactccagct gccaacccca atgccgtccc tggtggtgtc    3480
ttttagaccc tatttttata tacattttgt gtgcatatta tggtgaaacc gagcggttat    3540
ggtgatgcag tgttagcttt ctctgtgtag caagagagtt atgaaactgt tggtggctgt    3600
cattgttgtg atgatcttaa ttattttggt atgttatagt ttttccagtg gagaagatgt    3660
gtaaaccaaa tgatacataa gtctacaaaa gataatcttt aattc                   3705
```